(12) United States Patent
Delgado et al.

(10) Patent No.: US 9,775,591 B2
(45) Date of Patent: Oct. 3, 2017

(54) SEALING DEVICES AND RELATED DELIVERY APPARATUSES

(71) Applicant: Edwards Lifesciences Corporation, Irvine, CA (US)

(72) Inventors: Sergio Delgado, Irvine, CA (US); Ralph Schneider, Trabuco Canyon, CA (US); Stanton J. Rowe, Newport Coast, CA (US); Ming H. Wu, Tustin, CA (US); Mohammad Jafari, Foothill Ranch, CA (US); Jon Boomgarden, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/549,444

(22) Filed: Nov. 20, 2014

(65) Prior Publication Data

US 2015/0142049 A1    May 21, 2015

Related U.S. Application Data

(60) Provisional application No. 61/907,180, filed on Nov. 21, 2013.

(51) Int. Cl.
*A61B 17/00* (2006.01)
*A61B 17/03* (2006.01)
(Continued)

(52) U.S. Cl.
CPC ...... *A61B 17/0057* (2013.01); *A61B 17/0401* (2013.01); *A61B 17/068* (2013.01); *A61B 17/0644* (2013.01); *A61B 17/3423* (2013.01); *A61B 17/3431* (2013.01); *A61B 17/3462* (2013.01); *A61B 17/3468* (2013.01); *A61B 17/3209* (2013.01); *A61B 17/3478* (2013.01);
(Continued)

(58) Field of Classification Search
CPC ...... A61B 17/0057; A61B 2017/00575; A61B 2017/00597; A61B 2017/00606; A61B 2017/00623; A61B 2017/00632; A61B 2017/00637; A61B 2017/00641; A61B 2017/00646; A61B 17/3423; A61B 17/3431; A61B 17/3462; A61B 2017/00592; A61F 2/24; A61F 2/2403; A61F 2/2406; A61F 2/95; A61F 2/2427
See application file for complete search history.

(56) References Cited

U.S. PATENT DOCUMENTS

| | | | | |
|---|---|---|---|---|
| 5,906,577 A | * | 5/1999 | Beane | A61B 17/0293 600/206 |
| 6,254,633 B1 | * | 7/2001 | Pinchuk | A61B 17/12022 606/200 |

(Continued)

OTHER PUBLICATIONS

Extended European Search Report issued for EP Patent Application No. 14863974.3, Completed Jul. 24, 2017.

*Primary Examiner* — Christopher L Templeton
(74) *Attorney, Agent, or Firm* — Michael Crapenhoft

(57) ABSTRACT

Embodiments of the present disclosure are directed to implantable sealing devices, delivery apparatuses, and methods of their use, for closing surgical openings or defects in a sidewall of a vessel in a subject. In several embodiments, the disclosed implantable sealing devices, delivery apparatuses, and methods can be used to close a surgical opening in a sidewall of the heart.

1 Claim, 93 Drawing Sheets

(51) Int. Cl.
  *A61B 17/34*     (2006.01)
  *A61B 17/04*     (2006.01)
  *A61B 17/064*    (2006.01)
  *A61B 17/068*    (2006.01)
  *A61B 17/3209*   (2006.01)

(52) U.S. Cl.
  CPC ............ *A61B 2017/00247* (2013.01); *A61B 2017/00252* (2013.01); *A61B 2017/00477* (2013.01); *A61B 2017/00526* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00668* (2013.01); *A61B 2017/00867* (2013.01); *A61B 2017/00986* (2013.01); *A61B 2017/0414* (2013.01); *A61B 2017/0427* (2013.01); *A61B 2017/0464* (2013.01); *A61B 2017/0641* (2013.01); *A61B 2017/0645* (2013.01); *A61B 2017/346* (2013.01); *A61B 2017/3425* (2013.01); *A61B 2017/3458* (2013.01); *A61B 2017/3464* (2013.01)

(56) References Cited

U.S. PATENT DOCUMENTS

| | | | |
|---|---|---|---|
| 6,391,036 B1* | 5/2002 | Berg | A61B 17/0057 606/151 |
| 6,440,063 B1* | 8/2002 | Beane | A61B 17/0293 600/206 |
| 6,599,303 B1 | 7/2003 | Peterson et al. | |
| 6,712,836 B1* | 3/2004 | Berg | A61B 17/0057 606/213 |
| 7,445,623 B2* | 11/2008 | Mialhe | A61B 17/0057 600/30 |
| 8,075,587 B2 | 12/2011 | Ginn | |
| 8,454,634 B2 | 6/2013 | Jahns et al. | |
| 8,777,893 B2 | 7/2014 | Malewicz | |
| 8,926,657 B2 | 1/2015 | Litvack et al. | |
| 2002/0091410 A1 | 7/2002 | Ben-David et al. | |
| 2003/0040772 A1* | 2/2003 | Hyodoh | A61F 2/90 606/200 |
| 2003/0120264 A1* | 6/2003 | Lattouf | A61B 17/00234 606/1 |
| 2003/0153935 A1* | 8/2003 | Mialhe | A61B 17/0057 606/157 |
| 2004/0054353 A1* | 3/2004 | Taylor | A61B 17/3423 606/1 |
| 2005/0090717 A1* | 4/2005 | Bonadio | A61B 17/0293 600/208 |
| 2005/0165344 A1* | 7/2005 | Dobak, III | A61F 2/01 604/8 |
| 2005/0283188 A1 | 12/2005 | Loshakove et al. | |
| 2006/0058820 A1 | 3/2006 | Mialhe | |
| 2006/0074484 A1* | 4/2006 | Huber | A61B 17/22004 623/2.11 |
| 2007/0078504 A1* | 4/2007 | Mialhe | A61B 17/0057 623/1.11 |
| 2008/0051830 A1* | 2/2008 | Eidenschink | A61B 17/0057 606/213 |
| 2008/0146884 A1* | 6/2008 | Beckman | A61B 17/3423 600/208 |
| 2009/0149847 A1 | 6/2009 | Yadin et al. | |
| 2010/0036504 A1* | 2/2010 | Sobrino-Serrano | A61F 2/04 623/23.68 |
| 2010/0228269 A1* | 9/2010 | Garrison | A61B 17/0057 606/139 |
| 2011/0071623 A1* | 3/2011 | Finch | A61B 17/0057 623/2.11 |
| 2012/0016411 A1 | 1/2012 | Tuval | |
| 2012/0083832 A1 | 4/2012 | Delaloye et al. | |
| 2012/0130391 A1* | 5/2012 | Sundt, III | A61M 1/10 606/108 |
| 2013/0289619 A1 | 10/2013 | Ben Hamou et al. | |
| 2014/0114345 A1 | 4/2014 | Ciobanu et al. | |
| 2015/0039084 A1* | 2/2015 | Levi | A61B 7/0057 623/2.38 |
| 2015/0112383 A1* | 4/2015 | Sherman | A61B 17/0057 606/213 |

\* cited by examiner

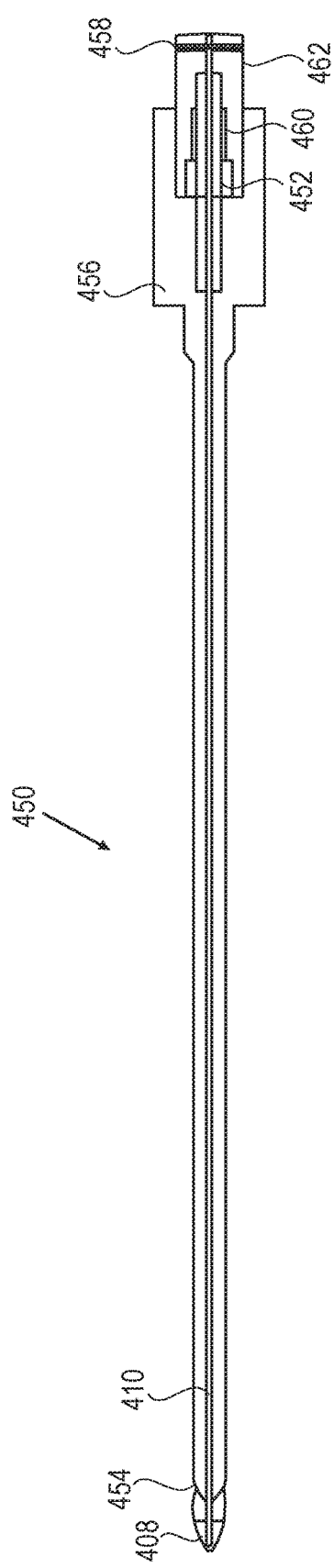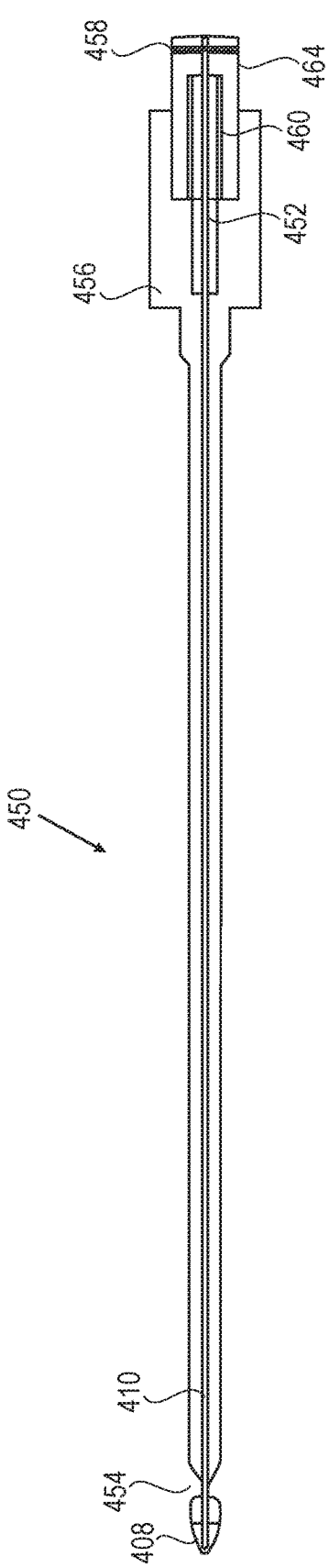

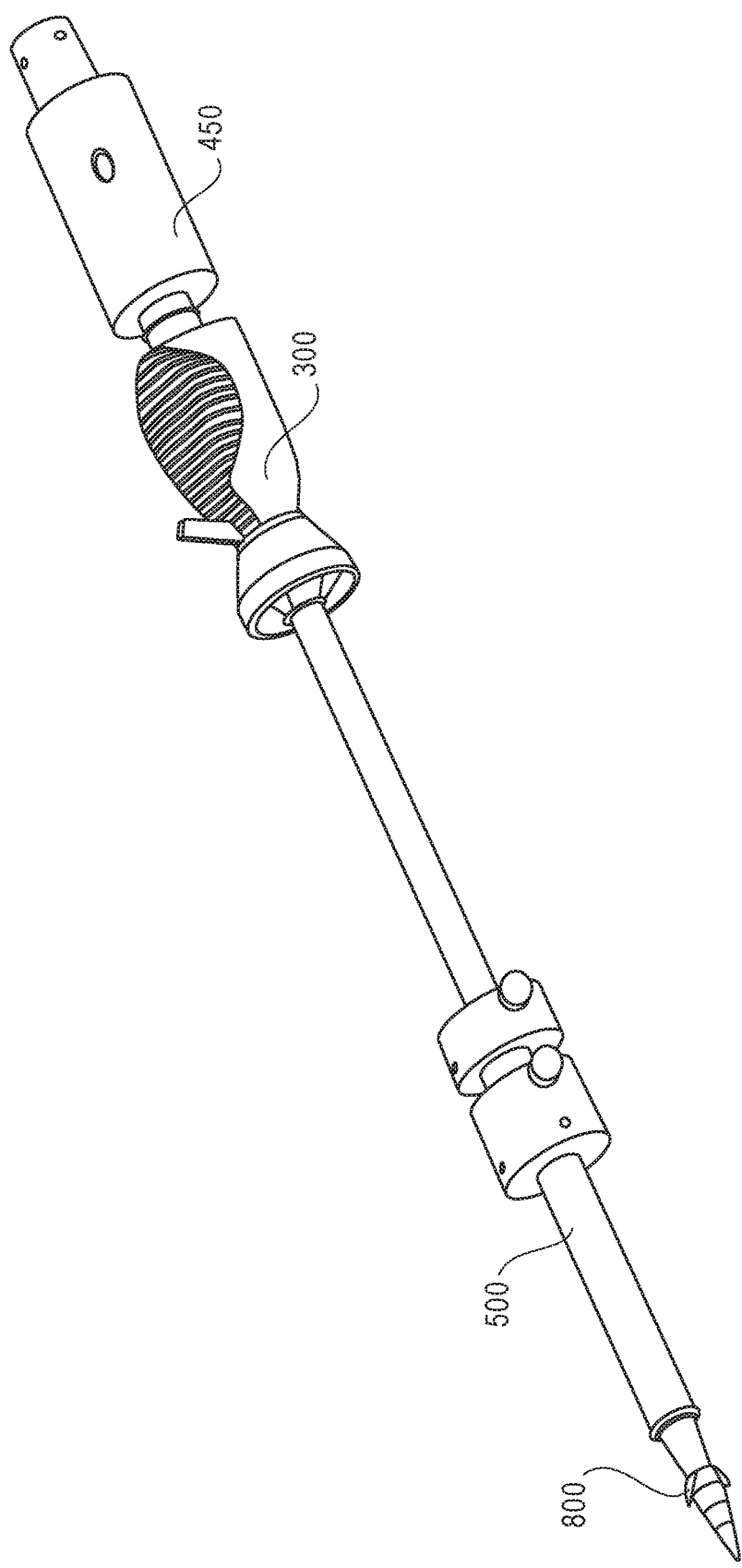

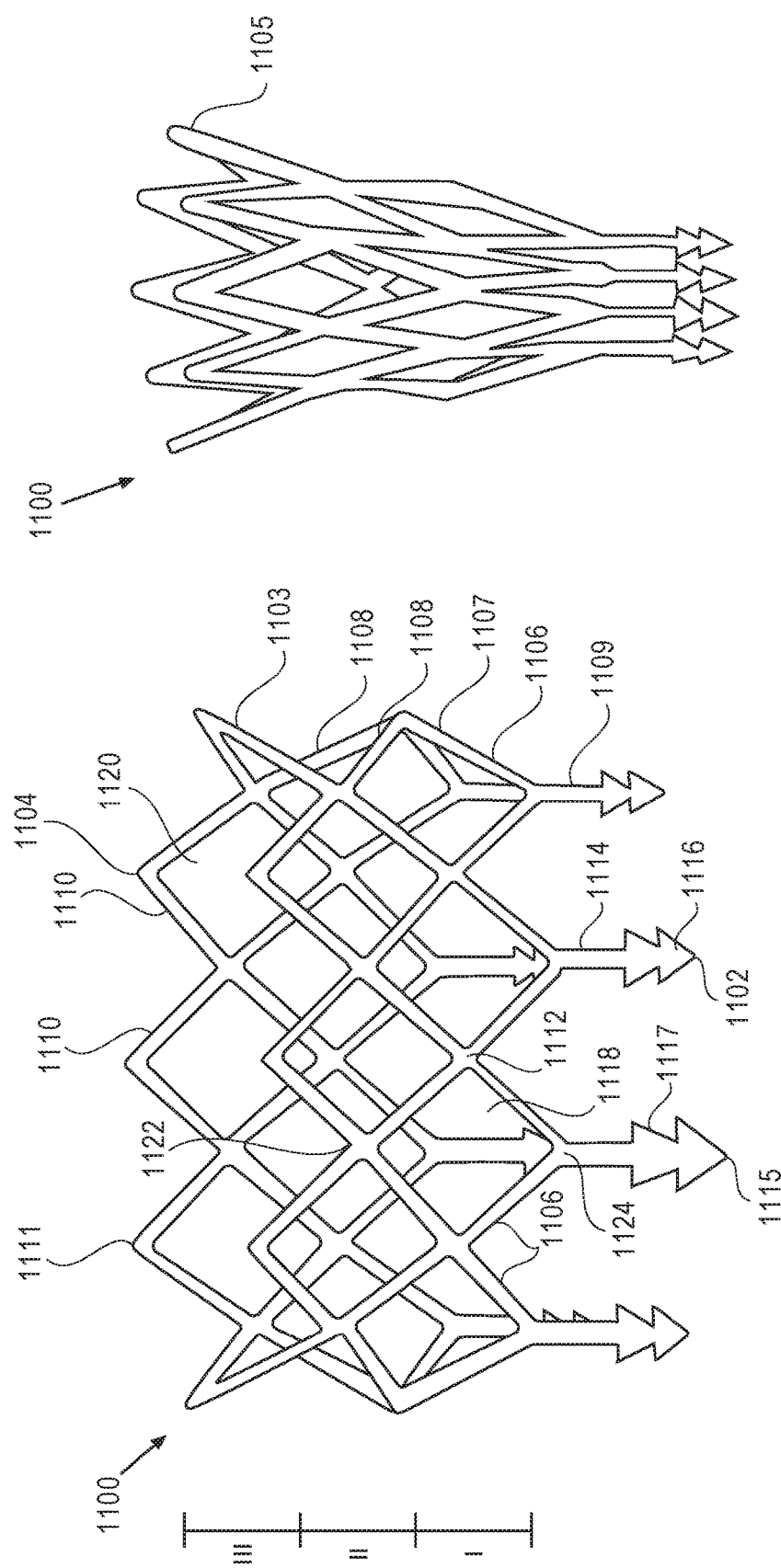

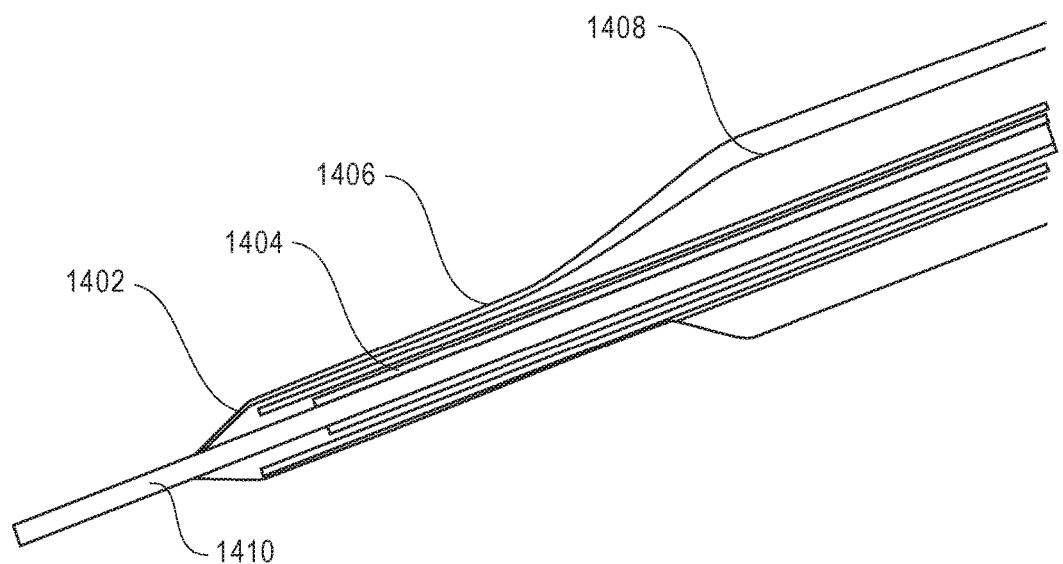
FIG. 127
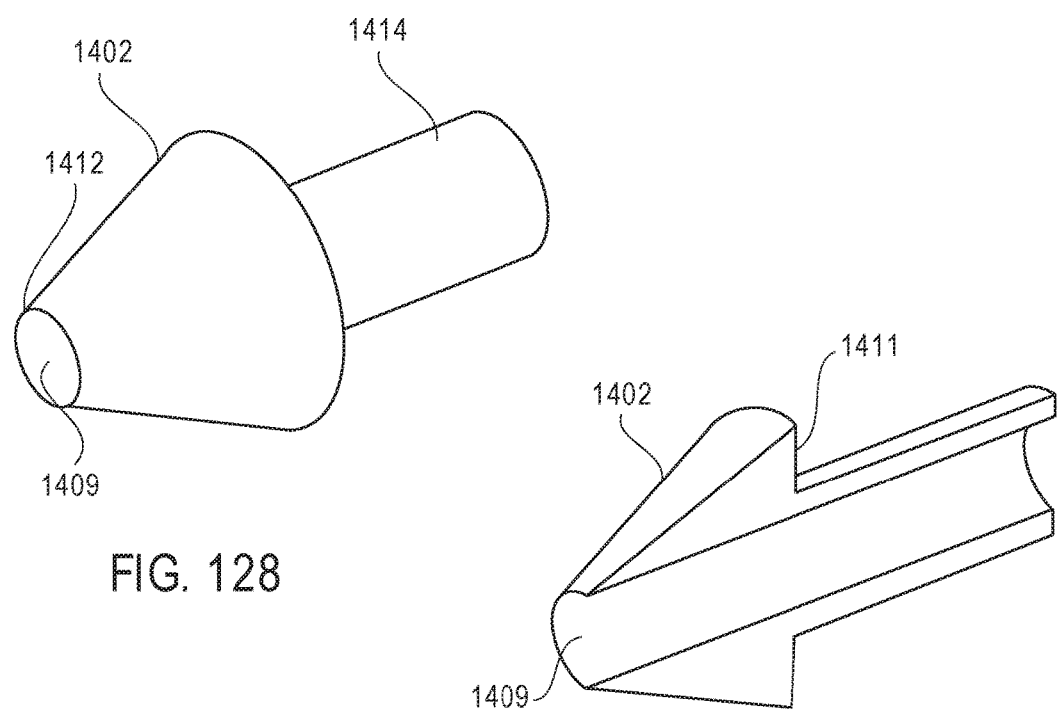
FIG. 128
FIG. 129

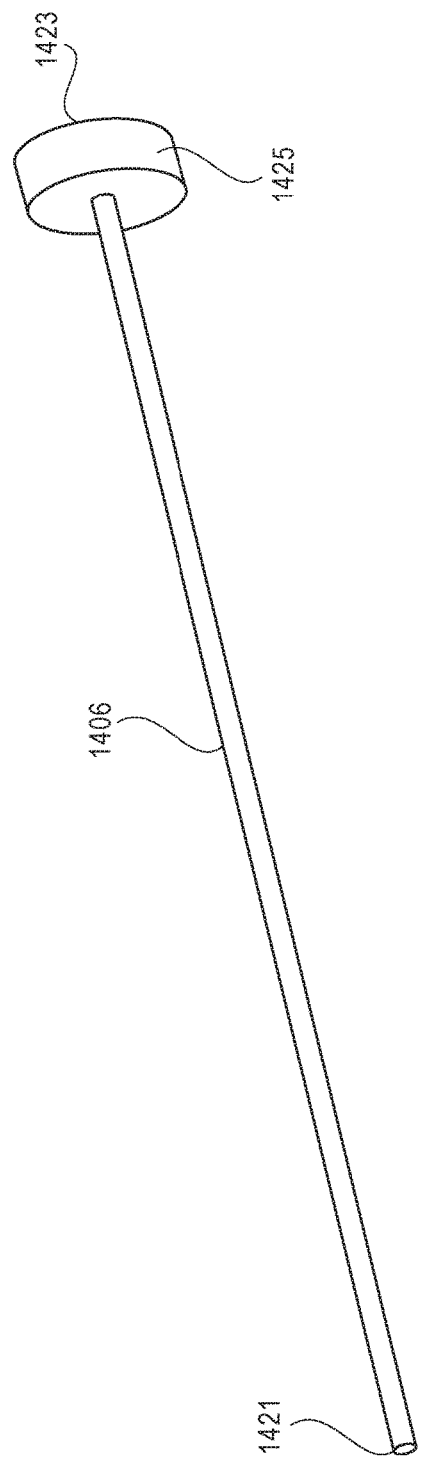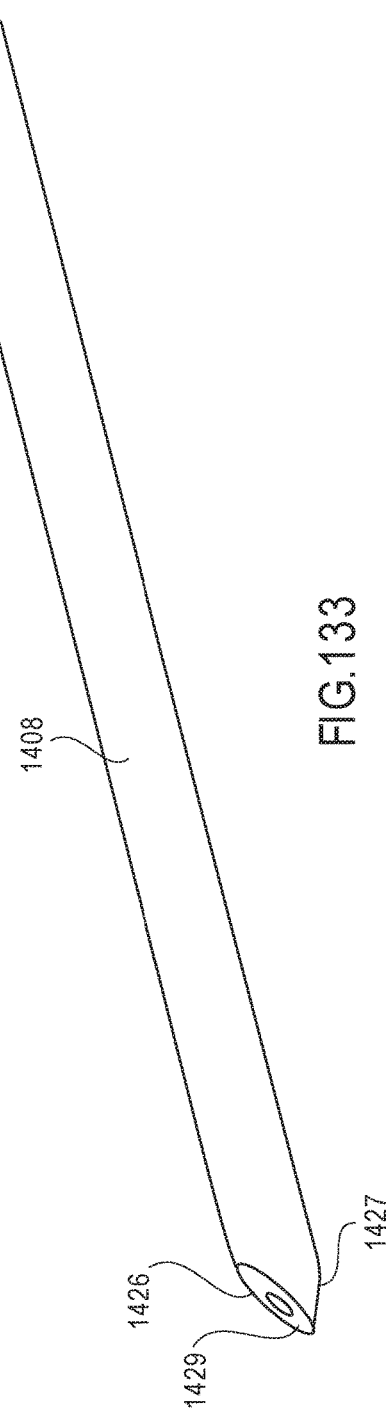

SEALING DEVICES AND RELATED DELIVERY APPARATUSES

CROSS REFERENCE TO RELATED APPLICATIONS

This application claims the benefit of U.S. Provisional Application No. 61/907,180, filed Nov. 21, 2013, which is incorporated by reference in its entirety.

FIELD

The present application concerns embodiments of devices for vessel access and/or closure, delivery apparatuses for implanting such devices, and methods of their use.

BACKGROUND

Open-heart surgical procedures typically are conducted under general anesthesia, during which the heart is stopped and blood flow is controlled by a heart-lung bypass machine. Such procedures are highly invasive and expose the patient to a number of potential risks, such as infection, stroke, renal failure, and adverse effects associated with use of the heart-lung machine, for example.

In contrast, using minimally invasive surgical approaches the heart is accessed through relatively small incisions, and without stopping the heart or use of a heart-lung machine. Difficulties concerning vessel opening, access, and closure involved with such procedures, however, have negatively impacted their utility. Thus, there is a need for improved methods and devices for vessel opening, access and closing for surgical procedures, including minimally invasive procedures on the heart.

SUMMARY

The present disclosure is directed to embodiments of implantable devices for vessel access and/or closure that can be used to hold open an aperture in the sidewall of a vessel to allow access to the lumen of the vessel, and/or can be used to seal the aperture after the lumen has been accessed. Delivery apparatuses for implanting such devices in the sidewall of a vessel and methods of their use are also disclosed.

In some embodiments, the sealing device can have an open state and a sealed or closed state, and is placed in the sidewall of the vessel prior to performance of an endoluminal procedure. The procedure is performed with the sealing device in the open state, and the device is moved to the sealed state following the procedure. Thus, the need for additional procedures to seal the aperture in the sidewall of the vessel following the endoluminal procedure is reduced. In several embodiments, the sealing device and delivery apparatus can be used to open and/or seal an aperture in a sidewall of the aorta in a patient during a surgical procedure, such as implantation of a prosthetic heart valve through a minimally invasive transaortic procedure.

In some embodiments, the sealing device comprises an annular puncture frame, a tubular sealing member, and a twisting frame. The annular puncture frame can comprise a longitudinal axis, a plurality of proximal fingers coupled to a proximal end of the frame, and a plurality of distal fingers coupled to a distal end of the frame. The proximal and distal fingers extend radially outward from the longitudinal axis when the annular frame is in a non-constrained state. The distal fingers can be moved to a constrained state pointing in a substantially axial direction for insertion through the aperture in the vessel sidewall and can self-extend to the non-constrained state, thereby pinching the vessel sidewall between the proximal and distal fingers. The tubular sealing member can comprise a distal end coupled to the puncture frame and a proximal end coupled to the twisting frame. The tubular sealing member comprises an open state that allows access to a lumen of the vessel via the aperture, and can be twisted to a sealed state by angular rotation of the twisting frame to close the aperture in the vessel sidewall.

In several embodiments, the twisting frame can be secured to the puncture frame to maintain the tubular sealing member in the sealed state.

In additional embodiments, the sealing device can comprise an annular puncture frame and a tubular sealing member. The annular puncture frame can comprise a longitudinal axis, a plurality of proximal fingers coupled to a proximal end of the frame, and a plurality of distal fingers coupled to a distal end of the frame. The proximal and distal fingers extend radially outward from the longitudinal axis when the annular frame is in a non-constrained state. The distal fingers can be moved to a constrained state pointing in a substantially axial direction for insertion through the aperture in the vessel sidewall and can self-extend to the non-constrained state, thereby pinching the vessel sidewall between the proximal and distal fingers.

The tubular sealing member can comprise a distal end coupled to the puncture frame and a proximal end coupled to a sleeve for holding a suture loop that can be tightened to radially collapse the tubular sealing member to a sealed state to close the aperture in the vessel sidewall.

In further embodiments, the sealing device can comprise an annular frame comprising a proximal end, a distal end, and a longitudinal axis, wherein the frame is radially compressible to a collapsed configuration and radially expandable to an expanded configuration. The frame is coupled to a plurality of tissue anchors extending axially in a distal direction, which comprise a first end coupled to the distal end of the annular frame and a second end comprising a shape configured for insertion and retention in the vessel sidewall. Methods of using such a sealing device include inserting the anchors into the tissue around the aperture in the vessel sidewall, and radially compressing the frame to the collapsed configuration to close the aperture in the sidewall. In some embodiments the frame is self-collapsible. In other embodiments, a suture loop can be secured around the frame, and tightened to compress the frame to the collapsed state.

In more embodiments, the sealing device includes an invertible annular frame, one of which is coupled to a plurality of tissue anchors that extend axially away from the frame in a first direction when the sealing device is in a non-constrained state. The tissue anchors comprise a shape configured for insertion and retention in a vessel sidewall. The sealing device can be inverted inside-out to a constrained state wherein the anchors extend axially away from the frame in a second direction that is substantially opposite the first direction, and will self-invert towards the non-constrained state. Methods of using such a sealing device comprise moving the sealing device to the constrained state, inserting the anchors into the tissue around the aperture in the vessel sidewall, and allowing the frame to self-invert towards the non-constrained state.

Delivery apparatuses designed for implantation of the disclosed sealing devices are also provided, as are methods of using the disclosed sealing devices and delivery apparatuses to open and/or close an aperture in a sidewall of a vessel in a subject.

The foregoing and other features and advantages of this disclosure will become more apparent from the following detailed description of several embodiments which proceeds with reference to the accompanying figures.

BRIEF DESCRIPTION OF THE DRAWINGS

FIGS. 22 and 23 show perspective views of a dilator for use with a delivery apparatus for implantation of a vessel opening and sealing device into a patient, according to another embodiment.

FIG. 51D is a side view of a delivery apparatus for implantation of a vessel opening and sealing device into a patient, with the sealing device loaded onto the delivery apparatus, and showing the puncture frame in a first delivery state.

FIG. 85 shows a perspective view of an expandable and collapsible sealing device for closing an aperture in a vessel sidewall, with the device in an expanded state, according to one embodiment.

FIG. 86 shows a perspective view of the expandable and collapsible sealing device of FIG. 85, with the device in a collapsed configuration.

FIG. 127 is a cut away view of a distal portion of the dilator and support structure subassembly of the delivery apparatus of FIG. 125.

FIGS. 128 and 129 are perspective and cut away views of the distal cap of the support structure of the delivery apparatus of FIG. 125.

FIGS. 132 and 133 are perspective views of the support sheath and dilator of the delivery apparatus of FIG. 125.

DETAILED DESCRIPTION

Embodiments of devices that can be used to seal an aperture in a vessel sidewall are disclosed. In several embodiments, the device can also be used to maintain an opening in the vessel sidewall, for example, for luminal access during a surgical procedure. Delivery apparatuses for implanting such devices in the sidewall of a vessel and methods of their use are also disclosed. In several embodiments, the device, delivery apparatus, and methods are useful for transaortic procedures in which an opening is created on the aorta, for example, for implanting a prosthetic heart valve in the aortic valve position. The devices and methods are also applicable for other locations, however, for example, the pulmonary artery, atrial wall (trans-atrial, for example, for implanting a prosthetic mitral valve), and/or ventricular wall (for example, for implanting a prosthetic mitral and/or aortic valve). The device, apparatus, and method also permit laparoscopic and/or robotic surgical procedures within organs, for example, the heart. The disclosed embodiments can provide a large opening (up to 26 F., up to 45 F., or even greater) for access to the interior of a vessel or chamber (such as the aorta or left atrium) in a patient.

A. Exemplary Sealing Device 2 with a Tubular Twisting Member

Figure 1:
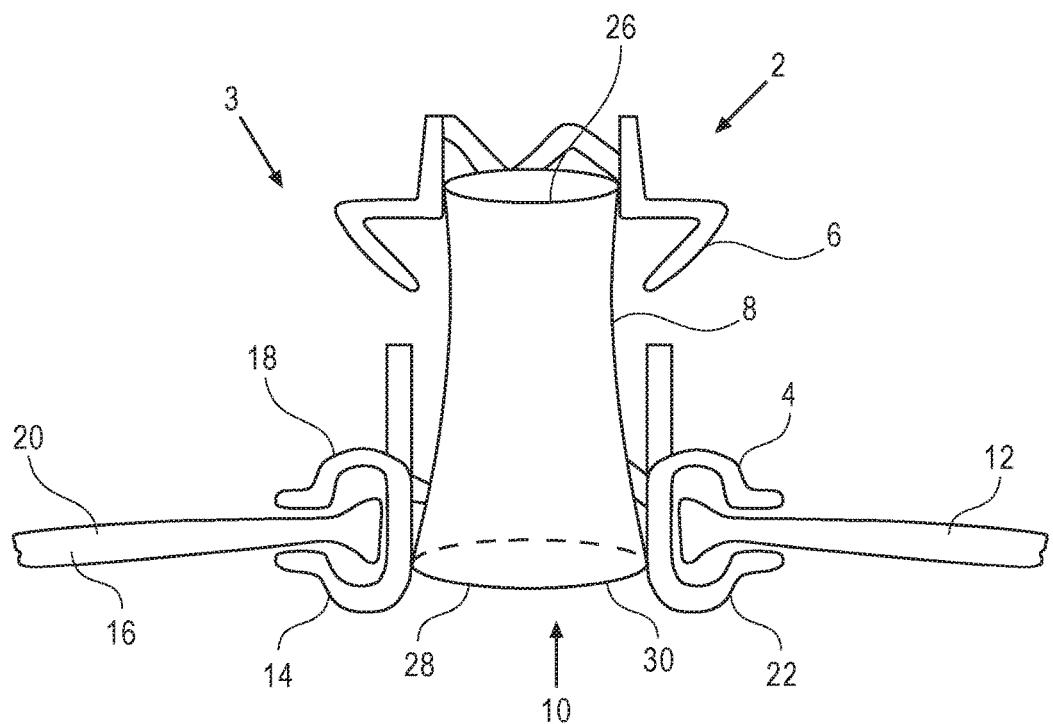
FIG. 1 is a perspective view of a vessel opening and sealing device in an open configuration that can be used to provide access to the lumen of a vessel, such as the aorta, according to one embodiment.

Referring first to FIG. 1, there is shown a cross sectional view of an open and deployed opening and sealing device 2, according to one embodiment. The vessel opening and sealing device 2 includes a puncture frame or stent 4, a twisting frame 6, and a tubular sealing member 8 that is secured to the puncture frame 4 and the twisting frame 8. The illustrated sealing device 2 is adapted to be deployed in the sidewall of the aorta, although it can also be used in other vessels of a subject. When deployed, the sealing device 2 has an open configuration 3 (see FIGS. 1, 11A, and 11B) and a sealed or closed configuration 5 (see FIGS. 2, 12A, and 12B). Following implantation of the vessel opening and sealing device 2, the open configuration provides for access to the interior of a blood vessel in a patient, for example access for performing a surgical procedure (e.g., heart valve replacement or repair). When placed in the sealed configuration, the sealing device 2 seals the opening used to access the interior of the vessel. Apparatus particularly suited for delivery and implantation of the sealing device 2, as well as methods of using the sealing device 2, are described in detail below.

Figure 29:
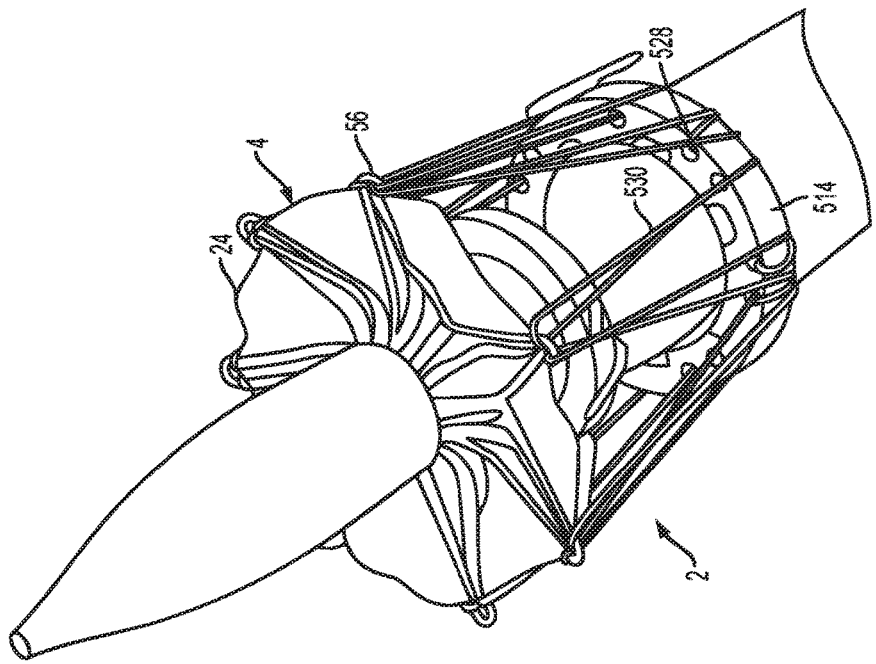
FIG. 29 is an exploded perspective view of a distal portion of the delivery apparatus of FIG. 14, with the sealing device loaded onto the delivery apparatus, and showing the puncture frame in the second delivery state.
Figure 28:
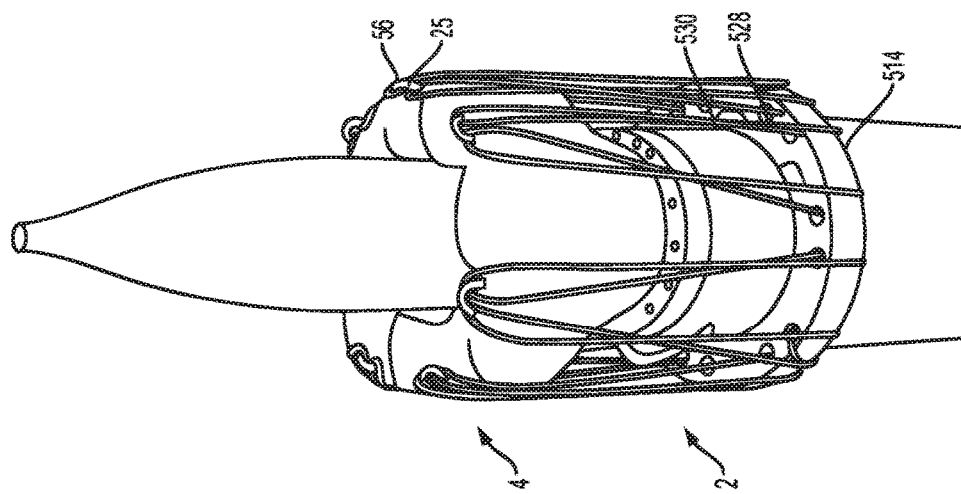
FIG. 28 is an exploded perspective view of a distal portion of the delivery apparatus of FIG. 14, with the sealing device loaded onto the delivery apparatus, and showing the puncture frame in the first delivery state.

Referring to FIG. 1, the puncture frame 4 can be inserted into a surgical opening or aperture 10 in a sidewall of a vessel or chamber 12 (e.g., a blood vessel) in a patient to maintain the aperture in an open state to allow for access to the interior of the vessel 12 via the aperture 10. The puncture frame 4 includes a distal portion 14 that engages a luminal side 16 of the vessel 12, and a proximal portion 18 that engages an exterior side 20 of the vessel 12. The puncture frame 4 becomes secured in the aperture 10 in the sidewall of the vessel 12 when the distal portion 14 and the proximal portion 18 of the puncture frame 4 have engaged the luminal side 16 and the exterior side 20 of the vessel 12, respectively. As discussed in more detail below, the puncture frame 4 is movable between at least a deployed state 22 (a clamped shape of the puncture frame when the proximal and distal portions are engaged with the sidewall of the vessel, as shown in FIG. 1), a second delivery state 24 (a shape of the puncture frame that allows insertion of the puncture frame 4 into the aperture 10 in the sidewall of the vessel 12, best shown in FIGS. 19 and 29), and a first delivery state 25 (a shape of the puncture frame when it is loaded on a delivery apparatus, best shown in FIGS. 18 and 28).

The tubular sealing member 8 can have a tubular shape and can be made of a flexible material that allows twisting of the sealing member 8, as described below. A proximal portion 26 of the tubular sealing member 8 can be secured to the twisting frame 6, and a distal portion 28 of the tubular sealing member 8 can be secured to the puncture frame 4. When untwisted, the tubular sealing member 8 assumes an open state 30 and access to the interior of vessel 12 can be achieved via the lumen of the open tubular sealing member 8.

The tubular sealing member 8 can be made of any suitable biological material (e.g., pericardial tissue, such as bovine or equine pericardium), bio-compatible synthetic materials, or other such materials, such as those described in U.S. Pat. No. 6,730,118, which is incorporated herein by reference. The tubular sealing member 8 desirably can be substantially impermeable to aqueous solutions, such as blood or plasma. In some embodiments, the tubular sealing member 8 can be a polymer or composite membrane or layer, for example, polytetrafluoroethylene (PTFE); or a woven, knit, or non-woven fabric material (e.g., a ripstop fabric) manufactured from natural and/or synthetic yarns or fibers, such as woven polyester (e.g., polyethylene terephthalate, PET, such as Dacron®), or cellulose (such as cotton or linen), silk, nylon, polyolefin, carbon fiber, and/or metal fibers. In additional embodiments, the tubular sealing member 8 can be made of a synthetic and/or natural material that is coated with a sealant (such as ePTFE, fluoropolymer, or gelatin (Vasutek® Gelatin Sealant, Terumo, UK); see, e.g., International Publication No. WO 2001/080918, which is incorporated by reference herein in its entirety). In more embodiments, the tubular sealing member 8 can be made of a bio-synthetic materials and composites (e.g., collagen-polyester composites, Omniflow®, Bio Nova, Melbourne, AU). Other embodiments use natural tissue, including intestinal submucosa, natural blood vessels (arteries or veins, e.g., from animal sources), and the like, which may be fixed (for example, using gluteraldehyde and/or formaldehyde). Other embodiments include artificial collagen or cellulose tubes.

In some embodiments, the tubular sealing member 8 is manufactured from sheet stock, two edges of which are brought together, for example, overlapped and/or abutted, and sealed or closed to form a tube comprising a seam. In some embodiments, the seam is linear, for example, extending along a longitudinal axis. In other embodiments, the seam has a different shape, for example, zig-zag or helical. The edges are closed using any suitable method, for example, suturing, welding, gluing, laminating, and/or bonding. In other embodiments, the tubular sealing member 8 does not comprise a seam, for example, when the tubular sealing member comprises a portion of a blood vessel, intestinal submucosa, or certain artificial tubular structures.

Figure 2:
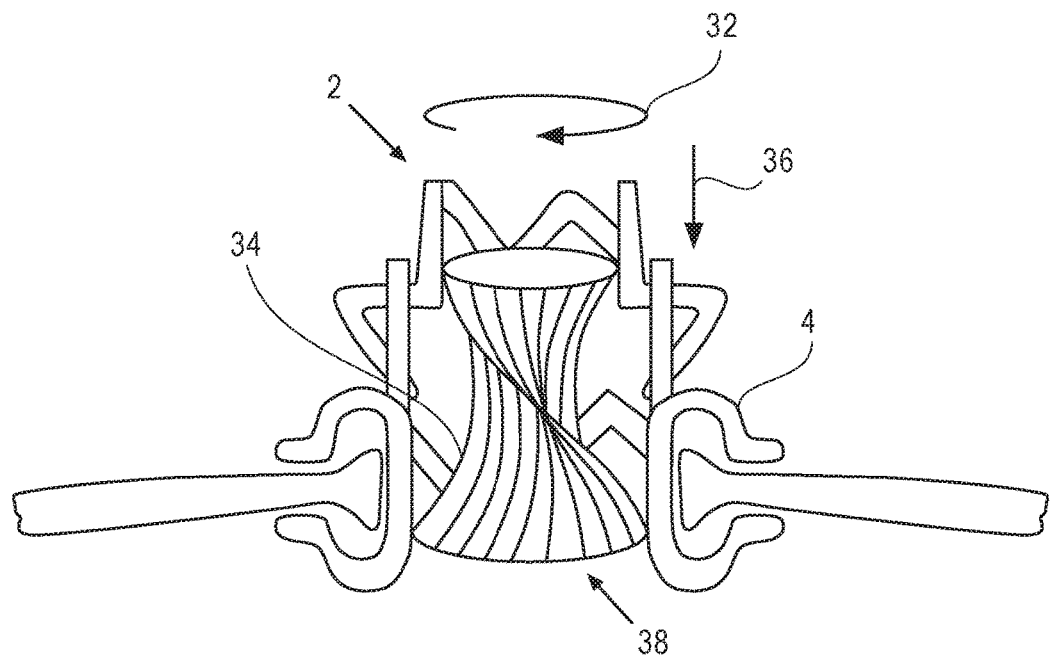
FIG. 2 is a perspective view of the vessel opening and sealing device of FIG. 1 shown in a closed or sealed state.
Figure 3:
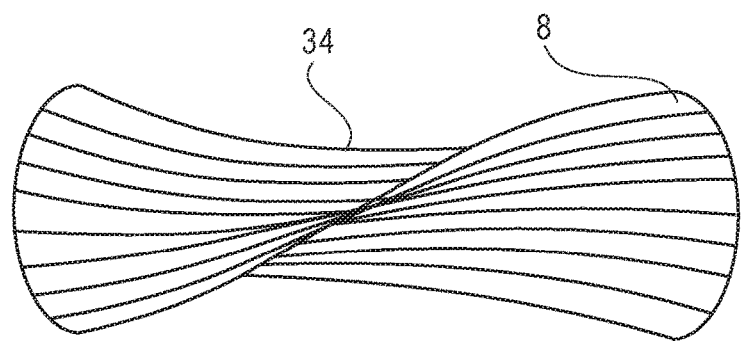
FIG. 3 is a perspective view of a sealing member of the sealing device of FIG. 1.

As shown in FIG. 2, rotating the twisting frame 6, in a clockwise direction 32 in the illustrated embodiment, causes twisting 34 of the tubular sealing member 8. FIG. 3 shows an additional view of the twisting 34 of the tubular sealing member 8. Referring to FIG. 2, as tubular sealing member 8 is twisted, its length along the longitudinal axis of the sealing device 2 is shortened, resulting in movement of the twisting frame toward the puncture frame in the direction of arrow 36. The tubular sealing member 8 can be twisted to a sealed or closed state 38 by rotating the twisting frame 6 in the clockwise direction 32. When sufficiently twisted, sealing member 8 forms a fluid-tight, sealed state and prevents access into or egress from the interior of vessel 12 via aperture 10.

Figure 4:
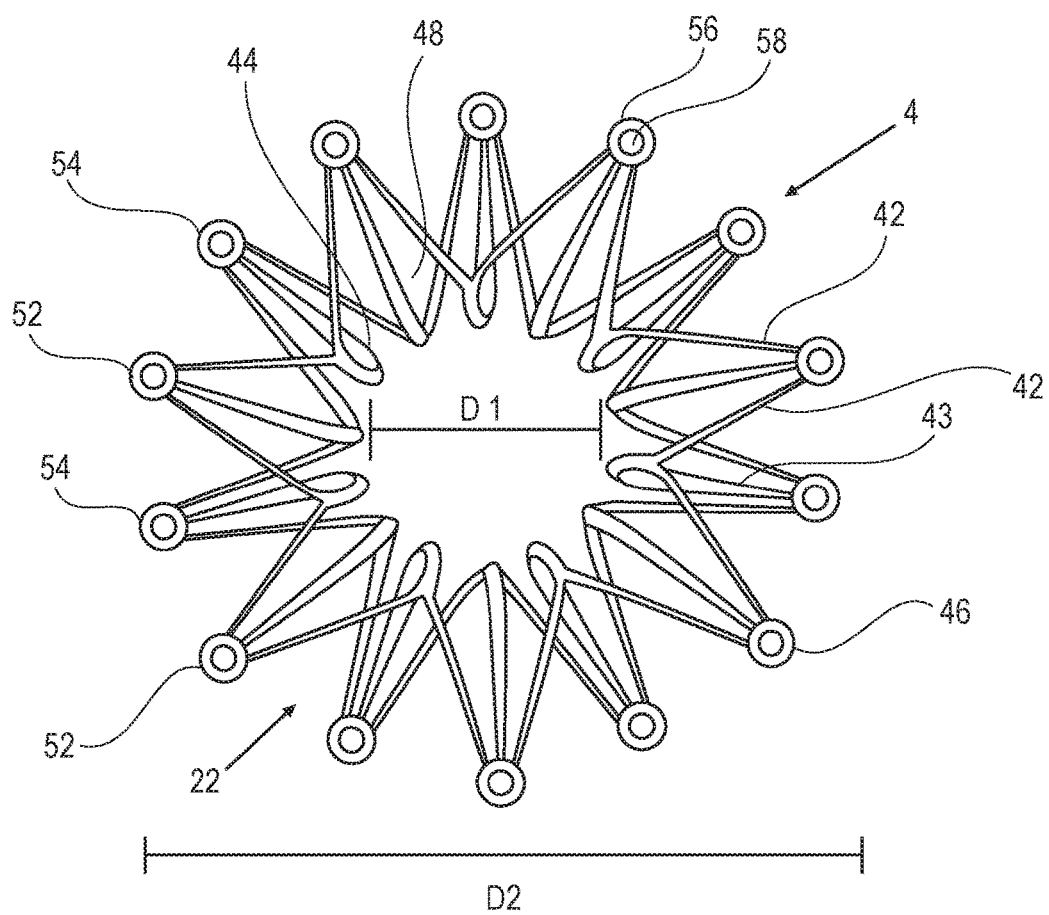
FIG. 4 is a perspective view of a puncture frame of the sealing device of FIG. 1.

FIG. 4 shows the puncture frame 4, without the other components of the vessel opening and sealing device for purposes of illustration. As shown, the puncture frame 4 can be formed from a plurality of lateral struts 42 and central struts 43. The struts 42, 43 are formed with alternating bends and are welded or otherwise secured to each other at nodes 44 and apices or vertices 46 to form a mesh structure having a plurality of trapezoidal- or parallelogram-shaped cells 48 between the struts 42, 43. In other embodiments, the struts define one or more different shapes. For example, in some embodiments, at least some of the struts comprise tabs and do not define cells at all. Alternatively, the puncture frame 4 can be laser cut, electrical-discharge machined, or otherwise formed from a cylindrical tube or from flat stock, for example, in a single piece. The struts 42, 43 can be made of a suitable shape-memory material, such as the nickel-titanium alloy known as nitinol, or from an elastic material, such as spring steel or cobalt-chromium alloy (Elgiloy®), which allows the puncture frame to be tensioned to one or more delivery states during delivery using a delivery apparatus and then allows the puncture frame to revert to the deployed state 22 when deployed from the delivery apparatus. In other embodiments, at least a portion of the puncture frame 4 comprises a plastically deformable material, for example, stainless steel.

The mesh structure formed by struts 42, 43 forms a plurality of proximal fingers 52 and a plurality of distal fingers 54 that can have a generally triangular shape and which extend radially outwardly from a longitudinal axis of the puncture frame 4. In other embodiments, at least some of the proximal fingers or distal fingers have a different shape, for example, straight or curved wires, rectangles, trapezoids, ovals, circles, or petal-shapes. The plurality of proximal fingers 52 and the plurality of distal fingers 54 can extend outwardly from the longitudinal axis at an angle of about 90° from a longitudinal axis when the puncture frame is in the deployed state 22. In some embodiments, the plurality of proximal fingers 52 can extend outwardly from the longitudinal axis at an angle of more than about 90° from the longitudinal axis and the plurality of distal fingers 54 can extend outwardly from the longitudinal axis at an angle of less than about 90° from the longitudinal axis, such that the plurality of proximal fingers 52 and the plurality of distal fingers 54 are sloped towards each other when the puncture frame is in the deployed state 22 (best shown in FIG. 10). The plurality of proximal fingers 52 is separated from the plurality of distal fingers 54 by length L1 (best shown in FIG. 10). L1 is appropriately sized for engagement of the sidewall of vessel 12 by the plurality of proximal fingers 52 and the plurality of distal fingers 54. Where the proximal fingers 52 meet the distal fingers 54 around the central opening, L1 can be twice the radius of curvature of the puncture frame 4. In the embodiment shown in FIG. 10, L1 can be larger towards the center of the puncture frame 4 and gets smaller towards the periphery thereof. In some embodiments, at least some of the proximal fingers 52 intersect or cross at least some of the distal fingers 54 at or near the outer rim of the puncture frame 4. That is, at least some apices 46 of the proximal fingers 52 are more distal than at least some apices 46 of the distal fingers 54 in the relaxed state illustrated in FIG. 4.

Referring again to FIG. 4, the puncture frame 4 includes a circular shape having an inner diameter D1 and an outer diameter D2. The inner diameter D1 is from slightly less to slightly greater than that the diameter of the aperture 10 in the sidewall of vessel 12. The inner diameter D1 is suitably sized to allow access to the intraluminal space of the vessel 12 by a treating physician, for example, for implantation of a heart valve. The outer diameter D2 is defined by the circumference formed from the apices of the proximal fingers 52 and the distal fingers 54 of the puncture frame 4. The distance between the inner diameter D1 and the outer diameter D2 generally sets the length of the proximal fingers 52 and the distal fingers 54. The lengths of the proximal fingers 52 and the distal fingers 54 desirably are sufficient for engaging the exterior side 20 and the interior side 16, respectively, of the sidewall of the vessel 12 in a manner that reduces or minimizes blood loss through the aperture 10 of vessel 12. In other embodiments, at least one of the inner diameter or outer diameter of the puncture frame 4 can have an elliptical- or oval-shape comprising two different diameters.

Figure 20A:
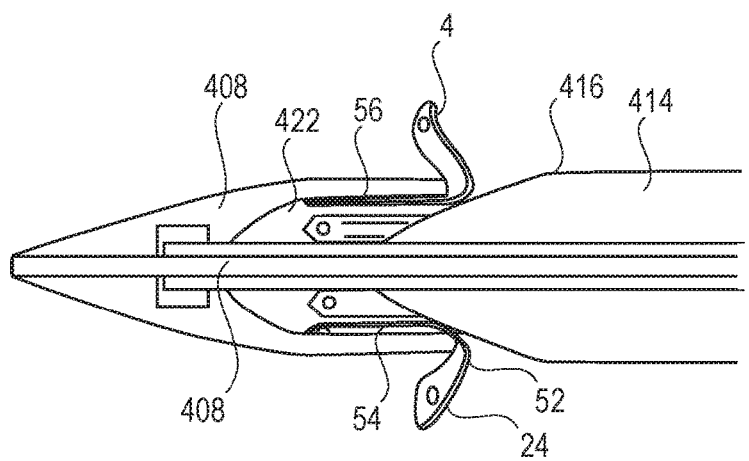
FIGS. 20A-20D are partial cross-sectional views illustrating the operation of the delivery apparatus for shifting the puncture frame from the second delivery state (FIG. 20A) to a deployed state (FIG. 20D).
Figure 20B:
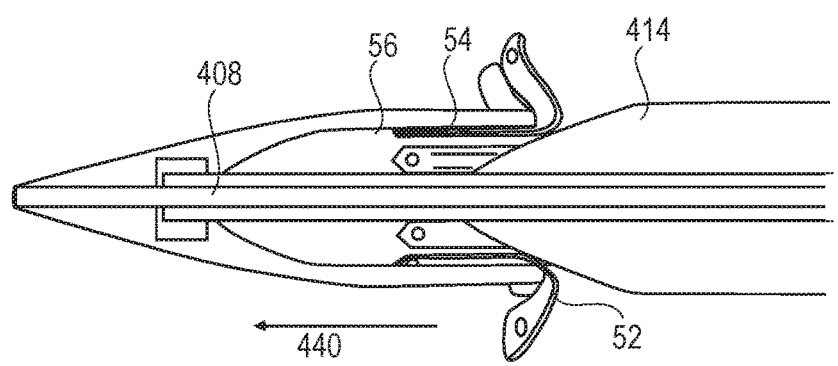
Figure 20C:
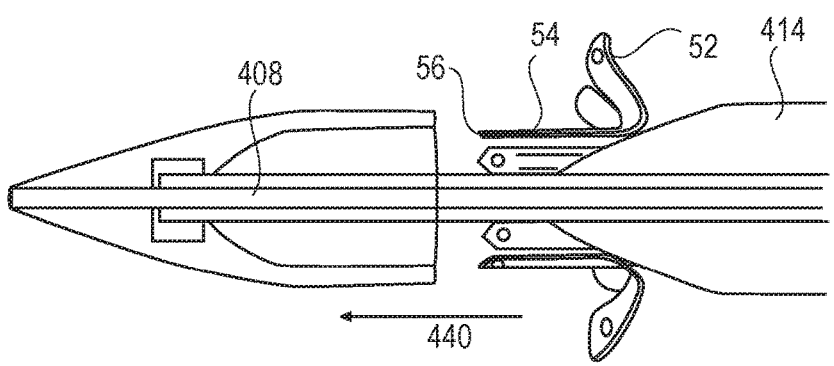
Figure 20D:
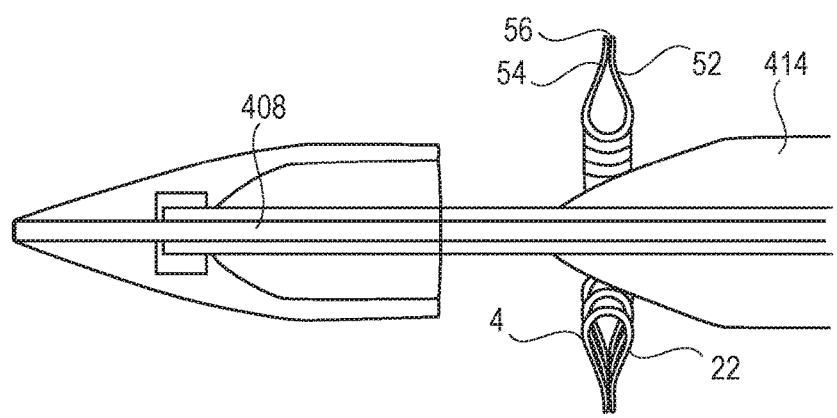

The apices 46 of the plurality of distal proximal fingers 52 and the distal fingers 54 can have a plurality of eyelets 56 extending outwardly from the longitudinal axis of puncture frame 4 when the puncture frame is in deployed state 22 (FIG. 20D). The eyelets 56 have respective apertures 58 that are sized to receive suture loops that are used to releasably secure and tension the puncture frame 4 to a delivery apparatus for delivering the vessel opening and sealing device to a subject (described below).

In the illustrated embodiment, each proximal finger 52 comprises two lateral struts 42 and a central strut 43 disposed therebetween, a first end of each lateral strut 42 and central strut 43 converging at an apex or vertex 46. A second end of each lateral strut 42 is coupled to the second end of a lateral strut 42 of an adjacent proximal finger 52 at each node 44. Consequently, the lateral struts 42 of the proximal fingers 52 together define a 7-pointed star in the deployed state 22 of the illustrated embodiment of the puncture frame 4. The arrangement of the distal fingers 54 is substantially identical in the illustrated embodiment.

A second end of the central strut 43 of each proximal finger 52 is coupled to the second ends of the lateral struts 43 of adjacent distal fingers 54 at each node 44, and vice versa. As a result, the apices 46 of the proximal fingers 52 and the apices 46 of the distal fingers 54 are staggered in the illustrated embodiment.

The puncture frame 4 is movable between at least the deployed state 22, the second delivery state 24, and the first delivery state 25. The deployed state 22 is described above. In the second delivery state 24, the plurality of distal fingers 54 can be substantially aligned with the longitudinal axis of the puncture frame 4 and the plurality of proximal fingers 52 extend outwardly from the longitudinal axis (see FIG. 19). This second delivery state 24 allows the distal fingers 54 to pass through the aperture 10 of the sidewall of vessel 12 to the interior of the vessel. When the puncture frame 4 is released during delivery, the puncture frame reverts to the deployed state 22, wherein the proximal fingers 52 and the distal fingers 54 engage the exterior side 20 and the luminal side 16 of the sidewall of vessel 12, respectively. The first delivery state 25 is utilized when the puncture frame 4 is loaded onto a delivery apparatus for implantation in a subject (as described below). In the first delivery state 25, the plurality of distal fingers 54 and the plurality of proximal fingers 52 can be substantially aligned with the longitudinal axis of the puncture frame 4 for loading on to the delivery apparatus (see FIG. 18).

Figure 5:
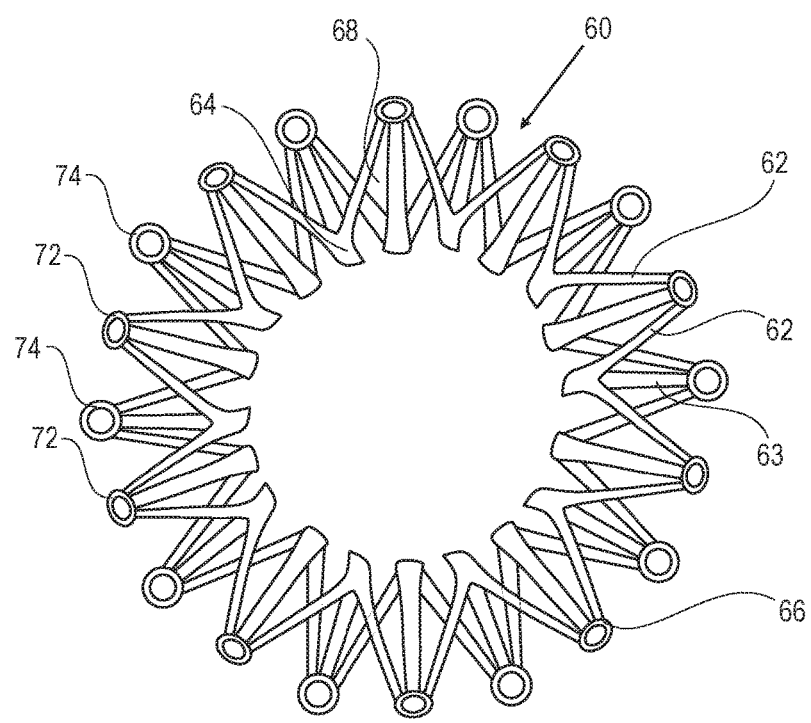
FIG. 5 is a perspective view of a puncture frame of a vessel opening and sealing device according to another embodiment.

FIG. 5 shows another embodiment of a puncture frame, generally indicated at 60, shown in a deployed state and without the other components of the vessel opening and sealing device for purposes of illustration. Similar to puncture frame 4, puncture frame 60 can be formed from a plurality of struts 62, 63 secured to each other at nodes 64 and apices 66 to form a mesh structure having a plurality of parallelogram- or trapezoidal-shaped cells 68 between the struts. The mesh structure formed by struts 62, 63 forms a plurality of proximal fingers 72 and a plurality of distal fingers 74 that can have a generally triangular shape and which extend outwardly from a longitudinal axis of the puncture frame 60. The illustrated embodiment of the puncture frame 60 is 10-fold rotationally symmetric. Also, similar to the puncture frame 4, the puncture frame 60 includes an inner diameter (D1) and an outer diameter (D2). The inner diameter D1 is from slightly less to slightly greater than that the diameter of the aperture 10 in the sidewall of vessel 12. The outer diameter D2 is defined by the circumference formed from the apices of the proximal fingers 72 and the distal fingers 74 of the puncture frame 60. The distance between the inner diameter D1 and the outer diameter D2 of puncture frame 60 generally sets the length of the proximal fingers 72 and the distal fingers 74. The inner diameter D1 and the outer diameter D2 can be varied as needed for particular applications of the puncture frame.

As illustrated by the puncture frames 4 and 60, the number of fingers included in the plurality of proximal fingers and the plurality of distal fingers, the length of the fingers, and the inner and outer diameter of the puncture frame can be varied as needed for particular applications of the puncture frame.

Figure 6:
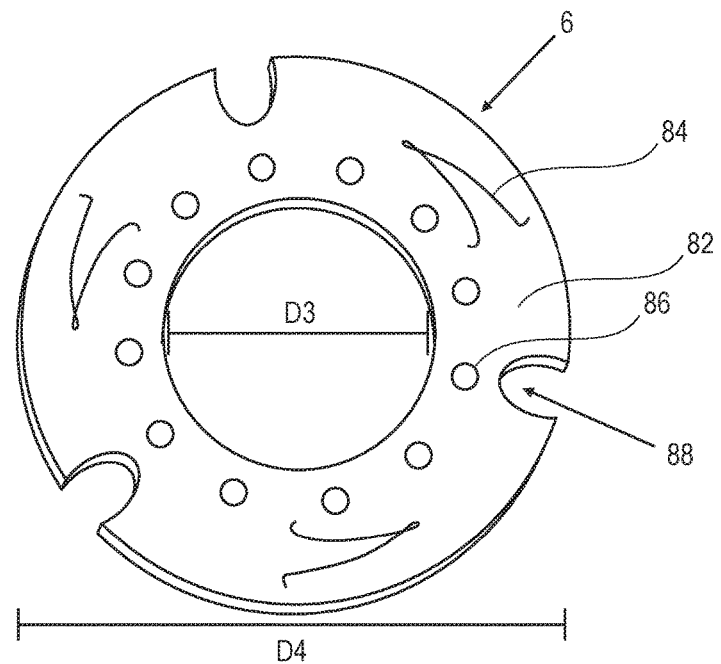
FIG. 6 is a perspective view of a twisting frame of the sealing device of FIG. 1.
Figure 8:
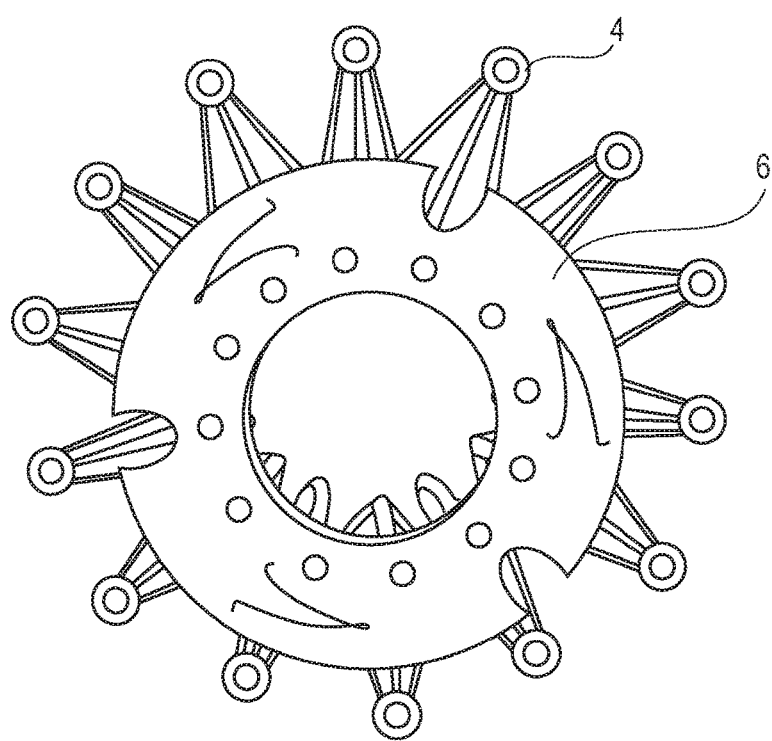
FIG. 8 is a perspective view of the puncture frame and the twisting frame of the sealing device of FIG. 1.

FIG. 6 shows the twisting frame or ring 6, without the other components of the vessel opening and sealing device for purposes of illustration. As shown, the twisting frame 6 can have a substantially ring like shape including an inner diameter D3 and an outer diameter D4. The inner diameter D3 can be substantially similar to the inner diameter D1 of the puncture frame 4 (FIG. 4). The outer diameter D4 can be slightly less than the outer diameter D2 of the puncture frame 4 (best shown in FIG. 8). The twisting frame 6 includes a proximal face 82 and a distal face 83 (not shown). The twisting frame 6 can be made of a suitable material, including metal (such as nitinol or stainless steel, polymer, or composites), and is suitably thick, to allow the twisting frame 6 to have sufficient stiffness for rotation during operation of the vessel opening and sealing device (such as described below). Where the twisting ring 6 is metal, it can be the same metal as the tissue clip 4 to avoid galvanic corrosion.

The twisting frame 6 can include a plurality of apertures 86 that are sized to allow for sutures to secure the twisting frame 6 to the proximal portion 26 of the tubular sealing member 8. Additionally, the twisting frame 6 can include one or more tines or prongs 84 that can extend distally from the twisting frame (best shown in FIG. 10) which can be used to secure the sealing device 2 in the sealed configuration. For example, the one or more tines 84 can engage the struts 42, 43 of the puncture frame 4 to secure the twisting frame in a rotationally stable position. In some embodiments, the puncture frame 4 includes a sealing skirt (such as the sealing skirt 100 described below), and the one or more tines 84 can engage the material of the sealing skirt to secure the twisting frame in a rotationally stable position. Further the twisting frame 6 can include one or more notches 88 that are appropriately sized for securing the twisting frame to a delivery apparatus during implantation of the sealing device in a patient (such as described below).

Figure 7:
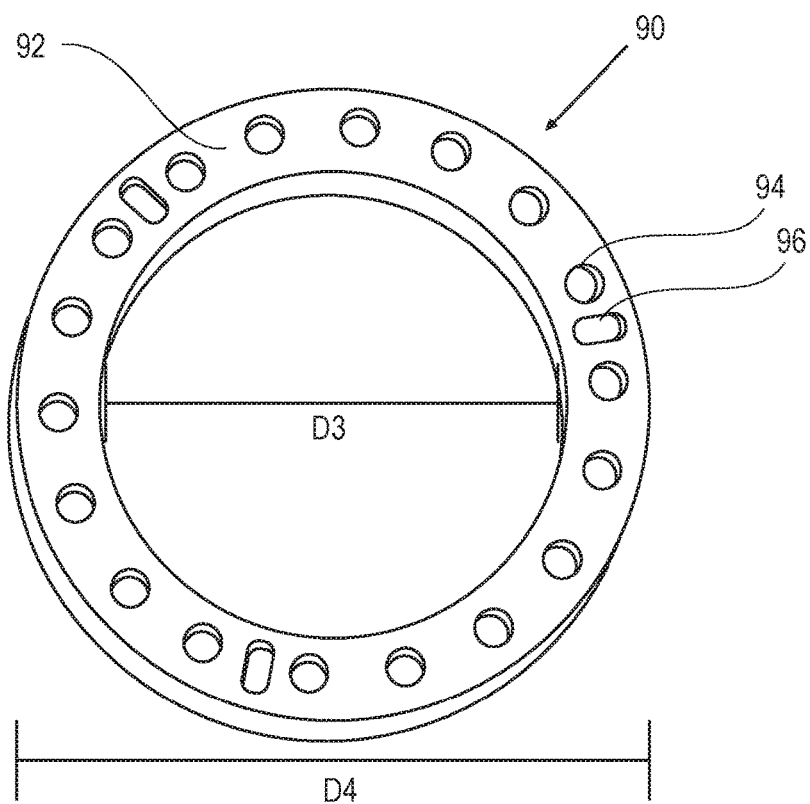
FIG. 7 is a perspective view of a twisting frame of a vessel opening and sealing device according to another embodiment.
Figure 9:
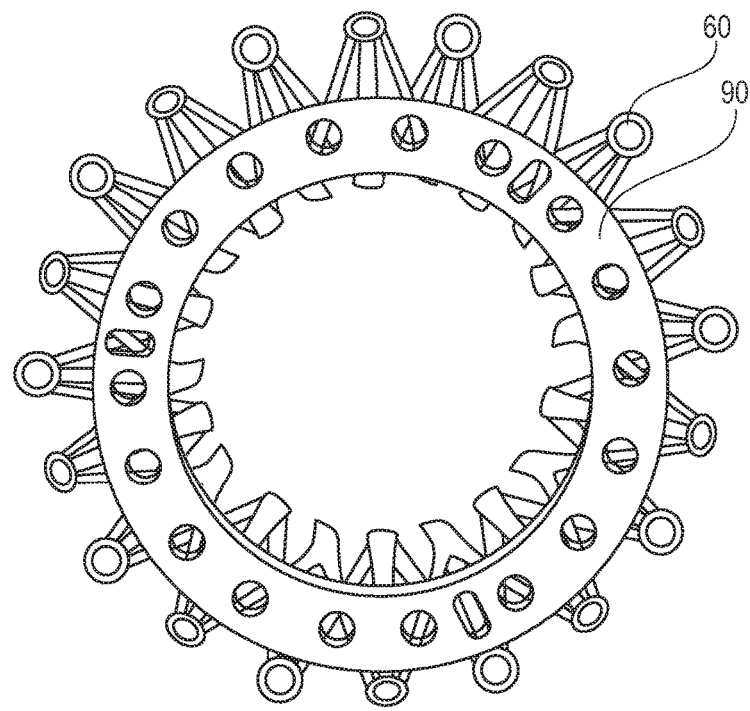
FIG. 9 is a perspective view of the puncture frame of FIG. 5 and the twisting frame of FIG. 7.

FIG. 7 shows a twisting frame 90 according to another embodiment, without the other components of the vessel opening and sealing device for purposes of illustration. As shown, the twisting frame 90 can have a substantially ring like shape including an inner diameter D3 and an outer diameter D4. The inner diameter D3 can be about the same size as the inner diameter D1 of the puncture frame 60 (FIG. 5). The outer diameter D4 can be slightly less than the outer diameter D2 of the puncture frame 60 (best shown in FIG. 9). The twisting frame 90 includes a proximal face 92 and a distal face 94 (not shown). The twisting frame 90 can be made of a suitable material, such as nitinol or stainless steel, and is suitably thick, to allow the twisting frame to have sufficient stiffness for rotation during operation of the vessel opening and sealing device (such as described below).

The twisting frame 90 can include a plurality of apertures 94 that are sized to allow for sutures to secure the twisting frame 90 to the proximal portion 26 of the tubular sealing member 8 of the vessel opening and sealing device. Additionally, the twisting frame 90 can include one or more oval shaped apertures 96 that are sized to allow for releasable sutures to secure the twisting frame 90 to a delivery apparatus during implantation of the sealing device in a patient (such as described below).

Figure 10:
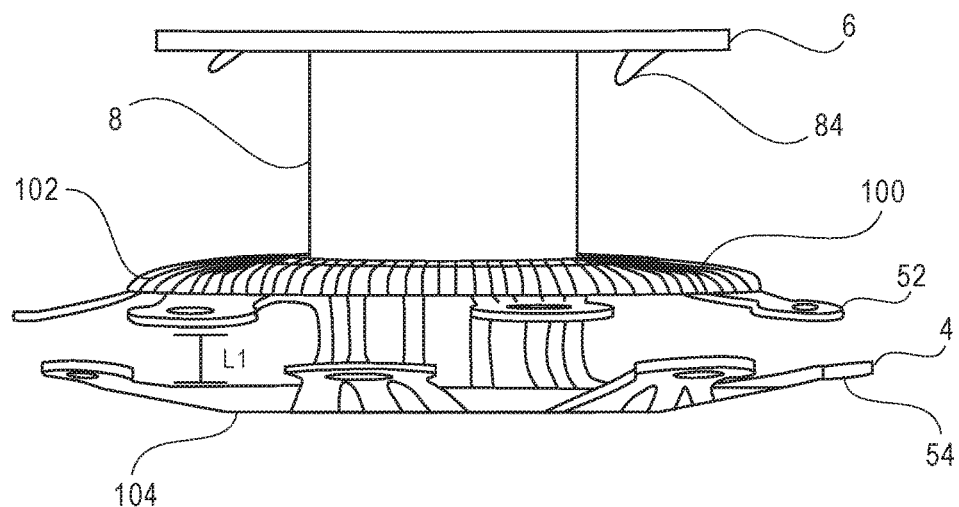
FIG. 10 is a side view of the sealing device of FIG. 1.

In several embodiments, the puncture frame 4 can include a sealing skirt 100 to seal openings in the puncture frame and to reduce leakage of fluids from the lumen of the vessel 12. As shown in FIG. 10, the sealing skirt 100 is secured to the puncture frame 4, and includes a proximal portion 102 and a distal portion 104. The sealing skirt is positioned such that the proximal fingers 52 of puncture frame 4 are positioned between the exterior side 20 of the sidewall of vessel 12 and the proximal portion 102 of the sealing skirt 100, and the distal fingers 54 of puncture frame 4 are positioned between the luminal side 16 of the sidewall of vessel 12 and the distal portion 104 of the sealing skirt 100, when the vessel opening and sealing device is implanted in a patient. The sealing skirt 100 can be secured to the puncture frame 4, for example, by a plurality of sutures 106 (best shown in FIGS. 11A-12B) that secure the sealing skirt 100 to the struts 42 of the puncture frame 4. The sealing skirt 100 can independently be made of any of the materials from which the tubular sealing member 8, for example, a bio-compatible synthetic material, such as polytetrafluoroethylene (PTFE), expanded polytetrafluoroethylene (ePTFE), or a woven, knit, or non-woven fabric material, such as woven polyester (e.g., polyethylene terephthalate) (PET)). In several embodiments, the sealing skirt is made of a napped, plush, or pile material, such as a loop-yarn, which functions as a filler material in that some fibers of the sealing skirt 100 can extend through the cells 48 of the puncture frame 4. In some embodiments, the sealing skirt 100 is made of a PET loop yarn or polyester 70/20 textured yarn. In some embodiments, the sealing skirt is coated, or impregnated, or includes an anti-hemorrhagic and/or clotting compound, such as chitosan (e.g., Celox™, MedTrade, UK). In some embodiments, at least a portion of the sealing skirt 100 is disposed around the outer perimeter of the central opening of the puncture frame 4 (not illustrated) for improving the seal between the puncture frame 4 and the sidewall of the vessel 12 around the opening 10 therein.

The sealing skirt 100 serves as a barrier to seal against fluid (e.g., blood or plasma) leakage between the frame 4 and the sidewall of vessel 12. Additionally, for embodiments utilizing a twisting frame 6 with tines, such as the twisting frame 6, the sealing skirt 100 provides a material that the tines of the twisting frame (such as tines 84 of twisting frame 6) can engage to secure the vessel opening and closing device in the sealed configuration 5.

FIGS. 10 and 11 illustrate an embodiment of the closure device 2 assembled using the puncture frame 4 illustrated in FIG. 4 and the twisting frame 6 illustrated in FIG. 6 in an open state, while FIGS. 12 and 13 illustrate the closure device 2 in a closed state.

Figure 11A:
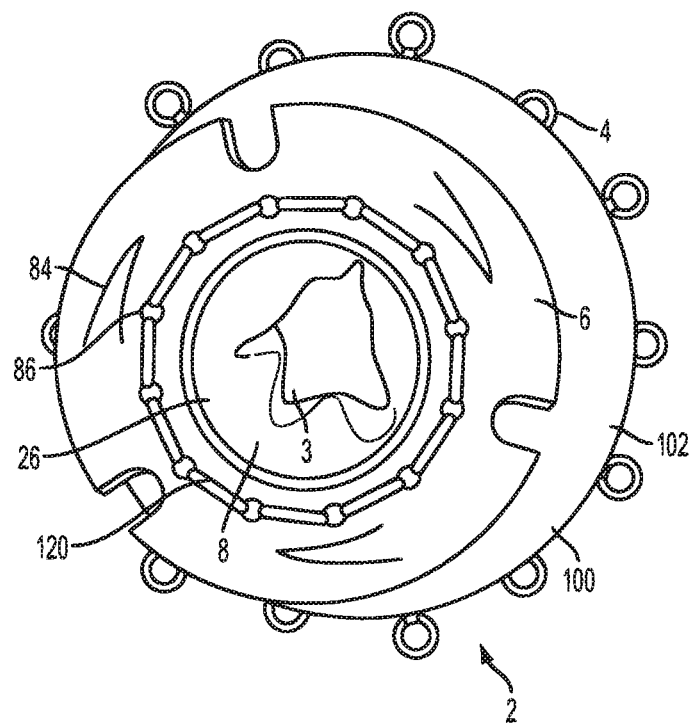
FIG. 11A is a proximal view of the sealing device of FIG. 1 in an open state.
Figure 11B:
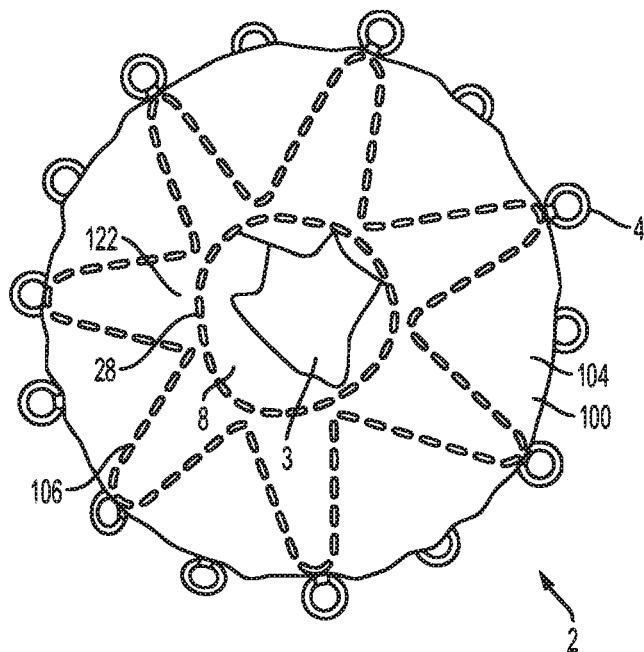
FIG. 11B is a distal view of the sealing device of FIG. 1 in an open state.
Figure 12A:
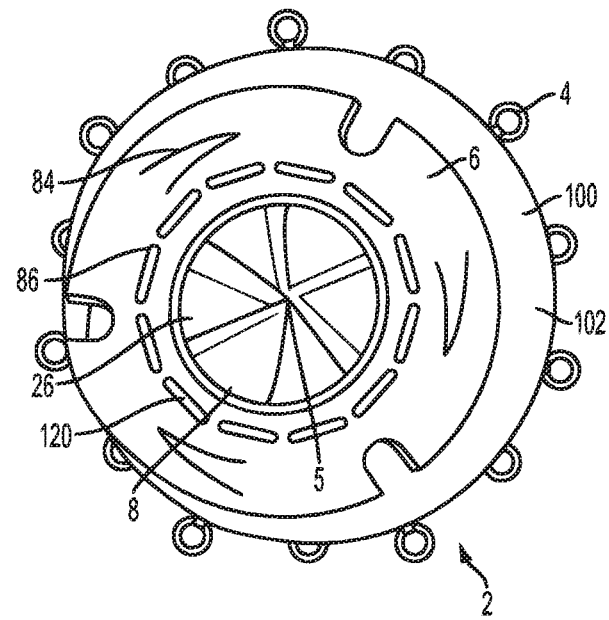
FIG. 12A is a proximal view of the sealing device of FIG. 1 in a closed state.
Figure 12B:
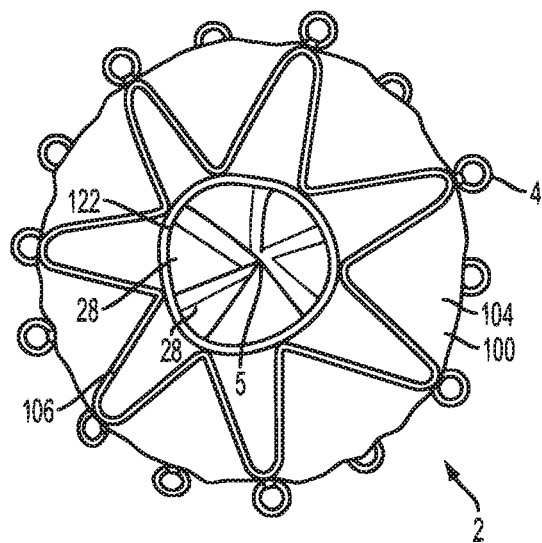
FIG. 12B is a distal view of the sealing device of FIG. 1 in a closed state.

FIG. 10 shows a sealing device 2 in the open configuration 3 that includes the puncture frame 4, the tubular sealing member 8, the twisting frame 6, and the sealing skirt 100. The proximal portion 26 of the tubular sealing member 8 can be secured to the twisting frame 6, and the distal portion 28 of the tubular sealing member 8 can be secured to the puncture frame 4, for example, by securing the distal portion 28 to the sealing skirt 100 on the puncture frame 4 and/or by securing the tubular sealing member 8 directly to the puncture frame 4. Referring to FIGS. 11A and 12A, the proximal portion 26 of the tubular sealing member 8 can be secured to the twisting frame 6 by sutures 120 that pass through the plurality of apertures 86 of twisting frame 6. Referring to FIGS. 11B and 12B, the distal portion 28 of the tubular sealing member 8 can be secured to the puncture frame 4 by sutures 122 that secure the distal portion 28 of the tubular sealing member 8 to the sealing skirt 100, which in turn can be secured to the puncture frame 4 by the sutures 106. In some embodiments, at least some of the sutures are replaced by another securing means, for example, clips, staples, adhesive, or the like.

Figure 13A:
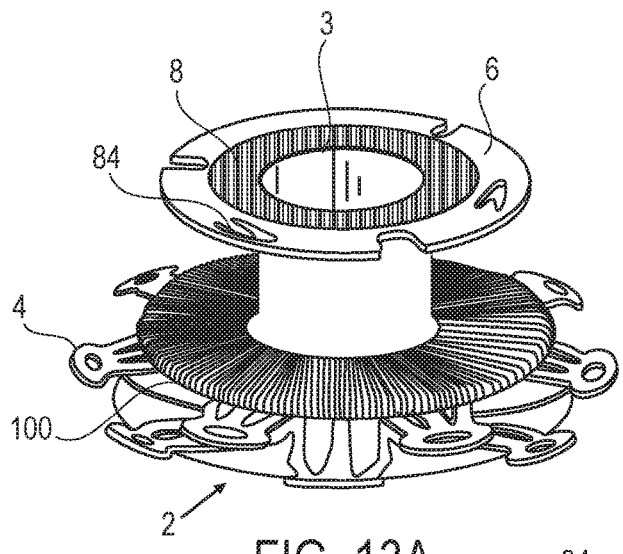
FIGS. 13A-13D show the sealing movement of the sealing device of FIG. 1 from an opened state (FIG. 13A) to a sealed state (FIG. 13D).
Figure 13B:
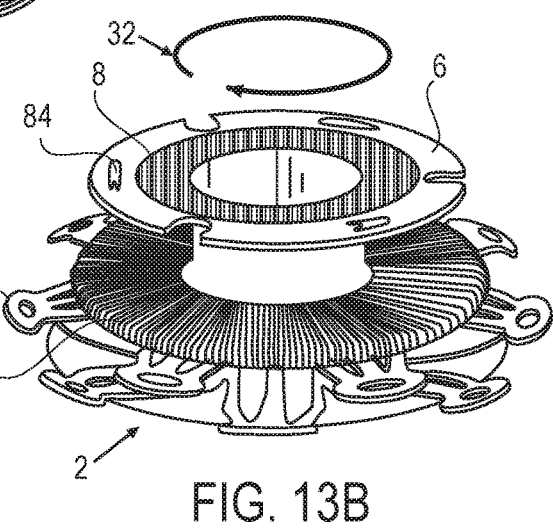
Figure 13C:
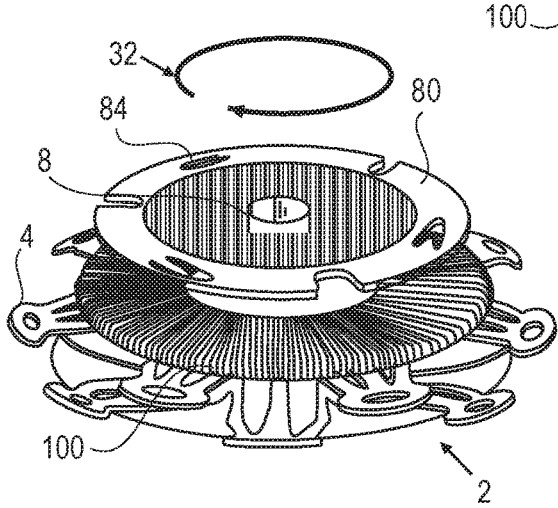
Figure 13D:
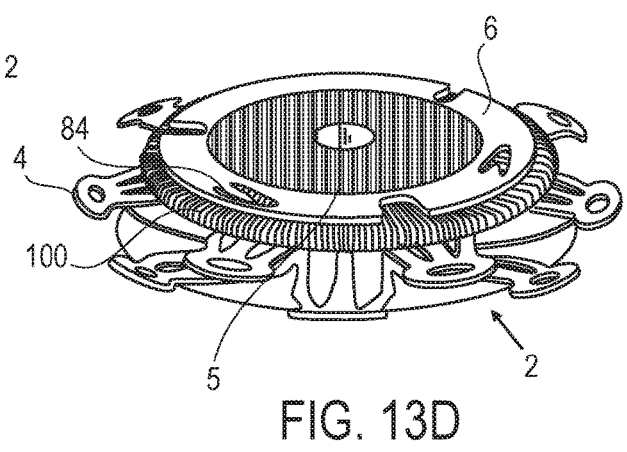

FIGS. 13A-13D illustrate operation of the sealing device 2 once implanted in the body. FIG. 13A shows the sealing device 2 in the open configuration 3. FIG. 13D shows the sealing device 2 in the sealed configuration 5. FIGS. 13B and 13C illustrate that the clockwise rotation 32 of the twisting frame 6 of the sealing device 2 causes twisting of the tubular sealing member 8. When sufficiently twisted, sealing member 8 forms a sealed state that prevents access to or egress from the interior of vessel 12 via aperture 10. As the tubular sealing member 8 is twisted, its length along the longitudinal axis of the sealing device 2 is shortened, until the distal face 83 of the twisting frame 6 contacts the sealing skirt 100, and the one or more tines 84 engage the material of the sealing skirt 100, thereby securing the sealing device 2 in the sealed configuration 5. Although the operation of the sealing device 2 is illustrated with clockwise rotation 32, counterclockwise rotation can also be utilized, for example by reversing the direction of the one or more tines 84 on twisting frame 6.

B. Exemplary Delivery Apparatus for Device 2

Figure 14:
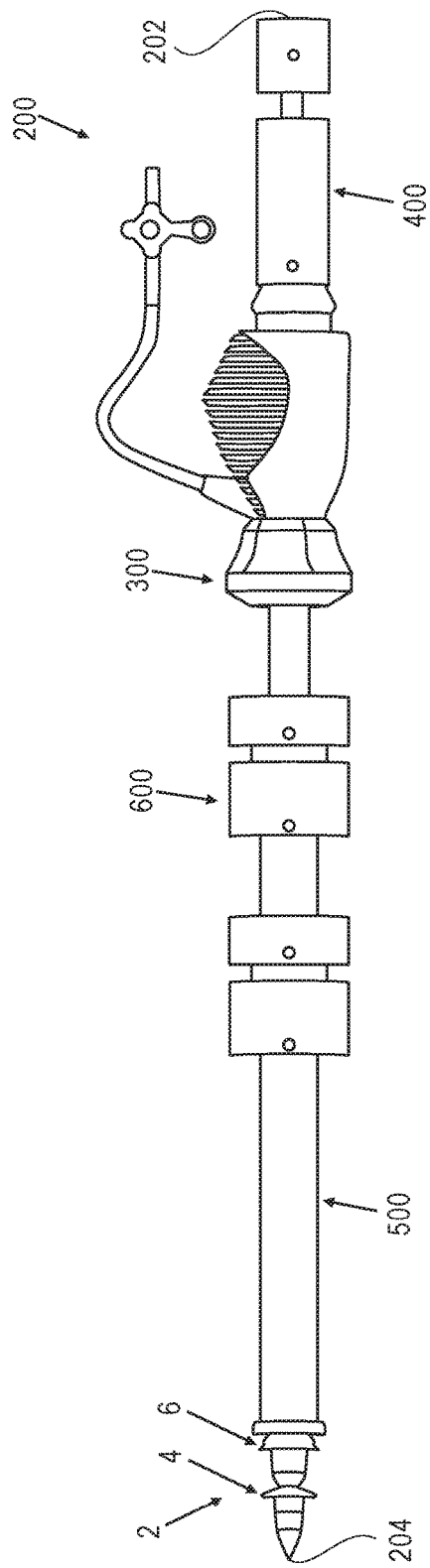
FIG. 14 is a side view of a delivery apparatus for implantation of a vessel opening and sealing device into a patient, with the sealing device loaded onto the delivery apparatus, and showing the puncture frame in a second delivery state.

FIG. 14 illustrates a delivery apparatus 200 for implanting the sealing device 2 in a subject, according to one embodiment. For illustration purposes, FIG. 14 shows the puncture frame 4 and the twisting frame 6, but the other components of the sealing device 2 have been omitted for clarity. The delivery apparatus 200 includes a proximal end 202 and a distal end 204, and includes a number of coaxial sleeves which are relatively axially slidable and angularly rotatable along a longitudinal axis extending from the proximal end 202 to the distal end 204. Preferably, the sleeves are actuatable by the physician from the proximal end portion of the instrument. The delivery apparatus 200 generally includes an introducer sheath 300, a dilator 400, a proximal finger actuator 500, and a twisting frame actuator 600, which are described in more detail below.

The components of the delivery apparatus, such as the introducer sheath 300, the dilator 400, the proximal finger actuator 500, and the twisting frame actuator 600, can include one or more locking mechanisms to releasably secure the position of the components with respect to each other and/or with respect to the vessel 12. Additional descriptions of exemplary locking mechanisms are provided below, however, the locking mechanisms can be manufactured in accordance with any type of mechanism known in the art, such as a releasable clamp or friction fitting, set screw, or bayonet mount. The components of the delivery apparatus, such as the introducer sheath 300, the dilator 400, the proximal finger actuator 500, and the twisting frame actuator 600, can be manufactured from any of various suitable materials known in the art, such as any of various metals or polymers, and combinations thereof.

Figure 15:
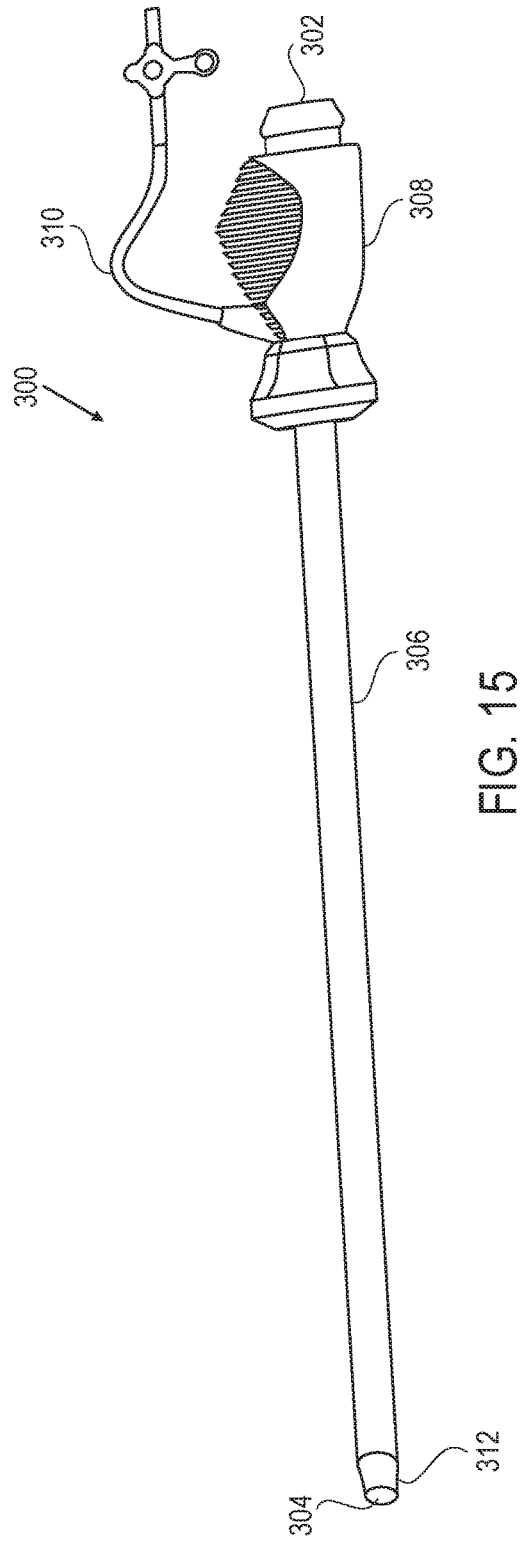
FIG. 15 is a perspective view of a delivery sheath of the delivery apparatus of FIG. 14.

FIG. 15 shows an embodiment of the introducer sheath 300. The introducer sheath 300 can be positioned axially inward from, and can be axially slidable and angularly rotatable relative to, the twisting frame actuator 600. Further, the introducer sheath 300 can be positioned axially outward from, and can be axially slidable and angularly rotatable relative to, the dilator 400. The introducer sheath 300 is configured to allow a proximal dilator 414 and a nose cone 408 (FIG. 16) to slide inside the introducer sheath 300, and be removable therefrom (discussed below). An inner diameter of the sheath 300 can vary based on the intended use, and can be suitably sized to allow access to the intraluminal space of the vessel 12 via the sheath 300 by a treating physician, for example, for implantation of a heart valve. The introducer sheath 300 includes an elongated sleeve 306, which can have a cone-shaped distal portion 312, designed for insertion through the aperture 10 in the sidewall of the vessel 12. A proximal portion of the sleeve 306 is secured to a handle 308. The handle 308 houses one or more seals configured to seal against the outer surface of a prosthetic-device-delivery-apparatus that is inserted through the introducer sheath 300, as known in the art. The handle 308 can optionally include a flush/suction port 310 for use during surgery as needed.

In several embodiments, the sheath 300 is designed for delivery of a prosthetic heart valve to a subject in need thereof. Several sheath materials, and configurations thereof are available (see, e.g., International Publication Nos. WO 2012/116368 and WO 2013/016665, and U.S. Patent Application Publication 2013/0274855, and U.S. Pat. Nos. 8,512,400, and 8,465,541, the disclosures of which are incorporated by reference). The sheath can be conventional. An example of a suitable introducer sheath includes the Edwards Ascendra® introducer sheath.

Figure 16:
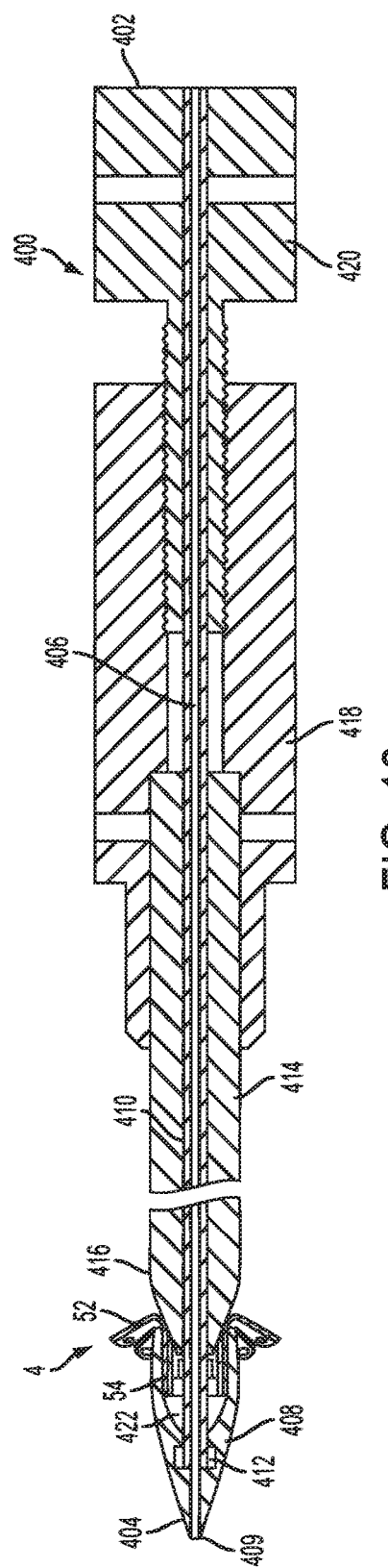
FIG. 16 is a cross-sectional view of a dilator of the delivery apparatus of FIG. 14, with the sealing device loaded onto the delivery apparatus, and showing the puncture frame in the second delivery state.
Figure 17:
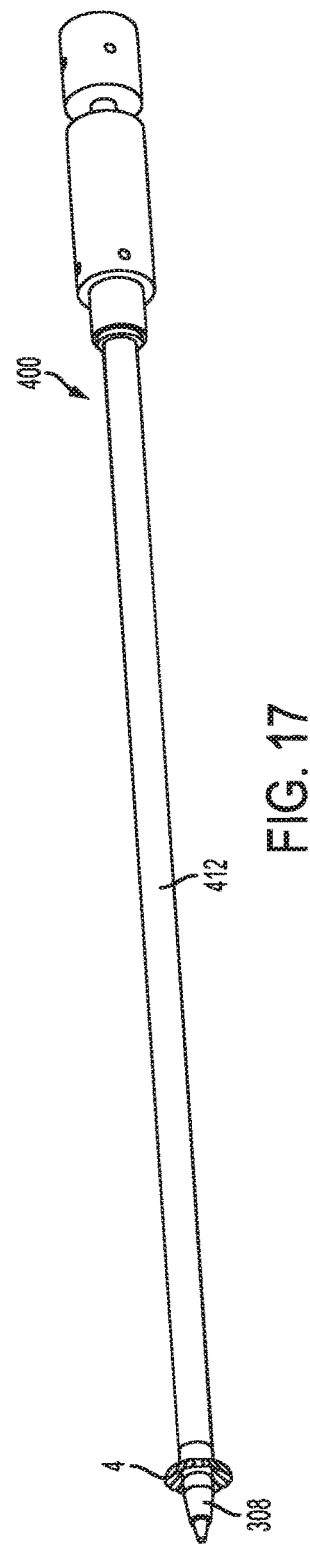
FIG. 17 is a perspective view of the dilator of FIG. 16.

FIG. 16 shows an embodiment of the dilator 400, which can be used to dilate an opening 10 in the side wall of vessel 12, and can also be utilized in the deployment of the puncture clip 4, for example, for causing the puncture clip 4 to transition from the first delivery state 25 to the second delivery state 24, and the second delivery state 24 to the deployed state 22, as discussed in greater detail below.

The dilator 400 is a multiple component subassembly that can have a proximal end portion positioned axially inward (proximally) from, and can be axially slidable and angularly rotatable relative to, the introducer sheath 300, the proximal fingers actuator 500, and the twisting frame actuator 600 of delivery assembly 200. As shown in FIG. 16, the dilator 400 can include the nose cone 408, the proximal dilator 414, a female dilator nut 418, and a dilator male screw 420. As shown, the dilator 400 includes a proximal end 402 and a distal end 404. Some embodiments of the dilator 400 further comprise a flush/suction port for use during deployment.

The dilator 400 is configured such that the proximal dilator 414 and nose cone 408 can slide inside the introducer sheath 300, and be removable therefrom. Thus, the proximal dilator 414 is positioned radially inward from the introducer sheath 300 and has an outer diameter slightly less than the inner diameter of the introducer sheath 300. The nose cone 408 also can have an outer diameter slightly less than the inner diameter of the introducer sheath 300. The female dilator nut 418 and the dilator male screw 420 can have diameters greater or less than the inner diameter of the introducer sheath 300.

As shown in FIG. 16, the moveable nosecone 408 can be secured to a hollow rod or shaft 410 at the distal end 404. The distal tip of the nose cone includes an aperture 409 configured to allow passage of a guide wire 411 and/or a hypodermic needle 413 from the lumen 406 of the hollow rod 410 (discussed below). The distal portion of the nose cone 408 can be curved or conical to facilitate insertion into an aperture in the side wall of the vessel 12. Movement of the hollow rod 410 in a distal or proximal direction causes corresponding distal or proximal movement of the moveable nose cone 408. In some embodiments the nosecone 408 is secured to the hollow rod 410 such that rotation of the hollow rod 410 causes corresponding rotation of the nosecone 408. In other embodiments, the moveable nosecone 408 includes a bearing assembly 412 for connection to the hollow rod 410 such that the hollow rod 410 can be freely rotatable without causing rotation of the moveable nosecone 408, but movement of the hollow rod 410 in a distal or proximal direction causes corresponding distal or proximal movement of the moveable nose cone 408.

As shown in FIG. 16, the exterior of the nose cone 408 does not include any cutting members, such as a blade. In alternative embodiments, a nose cone with one or more cutting members, such as one or more blades, can be used with a delivery apparatus for implanting a vessel opening and sealing device (such as sealing device 2) into a patient. The cutting members facilitate traversal of the vessel sidewall by the nose cone. In some embodiments, the one or more cutting members are deployable and/or retractable into the nose cone.

In some embodiments, the nose cone 408 has, for example, a concave or conical rather than a convex profile, or a combination of profiles. For example, in some embodiments, the nose cone 408 comprises at least one substantially cylindrical region, which is believed to allow the tissue in the wall of the vessel 12 to relax during the insertion process, thereby reducing tearing. At least a portion of the nose cone 408 can include a non-circular radial cross section, for example, oval, rectangular, or a parallelogram, and the nose cone 408 is also rotated during the dilation step.

In some embodiments, the nose cone 408 comprises a plurality of concentric elements. The central element is first advanced through the wall of the vessel 12. Each concentric element is then sequentially advanced over the central element while the dilator 400 is held stationary, thereby reducing the possibility of inadvertently pushing the nose cone 408 through the lumen of the vessel 12 and out an opposite wall thereof. In some embodiments, at least a portion of the nose cone 408 is expandable, for example, mechanically or through a hydraulic mechanism, for example, a balloon. Such controlled dilation techniques are also believed to reduce tearing in the vessel 12. Such methods also provide the user to control the shape of the opening 10 in the wall of the vessel 12, for example, towards greater roundness or ellipticity as desired. For example, in some procedures, an instrument enters a vessel wall at an off-normal angle. Consequently, an elliptical or oval access port in the vessel wall better accommodates the profile of an angled instrument. Furthermore, the mechanical properties of some vessel walls are anisotropic, for example, different in the circumferential and longitudinal directions. Embodiments of nose cones 408 with differing or controllable profiles in different radial directions improve control over the shape or geometry of the opening 10 in the vessel wall.

The hollow rod 410 is sleeve shaped and can include the lumen 406 configured for insertion of the guide wire 411 (FIG. 36) and/or the hypodermic needle 413 (FIG. 35) through the delivery apparatus 200 and into the vessel 12 of the patient (described in more detail below). In particular embodiments, the guide wire can be inserted through the sidewall of the vessel 12, and the nose cone 412 and proximal dilator 414 can be used to expand the puncture site from the diameter of the guide wire to about the diameter of the sleeve 306.

Proximal to the nosecone, the dilator 400 can include the proximal dilator 414. The proximal dilator 414 is sleeve shaped and can have a hollow conical shaped distal portion 416, designed for insertion into, and dilation of, the aperture 10 in the sidewall of the vessel 12. The proximal dilator 414 is secured to a female dilator nut 418, which is connected to a dilator male screw 420 by a screw interface. The hollow rod 410 extends through the proximal dilator 414, the dilator female nut 418 and the dilator male screw 420, thereby allowing access to the guide wire lumen 406 from the proximal end 402 of the dilator 400. The dilator male screw 420 can be fixedly secured to the hollow rod 410 such that rotating the male screw 420 to move the screw in a proximal or distal direction causes corresponding movement of the hollow rod 410 in a proximal or distal direction, respectively. As the distal portion of the hollow rod 410 is operably connected to the moveable nosecone 408, proximal or distal movement of the dilator male screw 420 causes corresponding proximal or distal movement of the nosecone 408.

Figure 18:
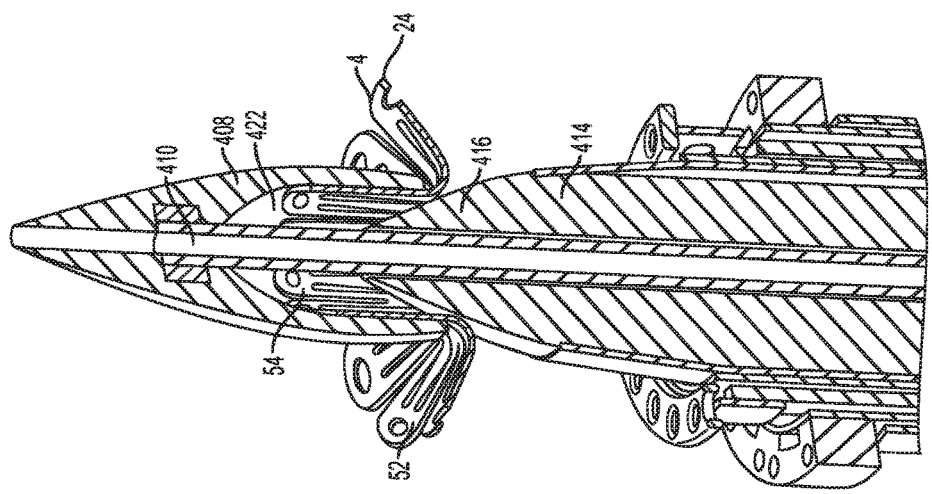
FIG. 18 is a partial cross-sectional view of the distal portion of the delivery apparatus of FIG. 14, with the sealing device loaded onto the delivery apparatus, and showing the puncture frame in a first delivery state.
Figure 19:
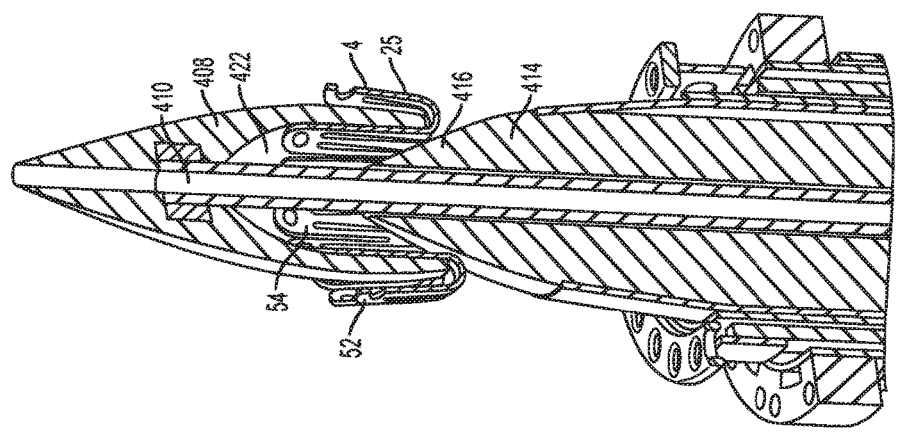
FIG. 19 is a partial cross-sectional view of the distal portion of the delivery apparatus of FIG. 14, with the sealing device loaded onto the delivery apparatus, and showing the puncture frame in the second delivery state.

FIGS. 18-19 illustrate the functionality of the nosecone 408 and proximal dilator 414 for transitioning the puncture frame 4 from the first delivery state 25 (FIG. 18) to the second delivery state 24 (FIG. 19). As shown in FIGS. 18 and 19, the nosecone 408 includes a hollow chamber 422 that is shaped to house the distal fingers 54 of the puncture frame 4 during delivery of the sealing device 2 to a patient. In referring to FIG. 18, the puncture frame 4 is securely positioned between the proximal end of the nosecone 408 and the distal end of dilator 414. FIG. 18 shows the puncture frame 4 in the first delivery state 25. In this state, the distal fingers 54 of the puncture frame 4 are "crimped" inside the hollow chamber 422, and both the proximal fingers 52 and the distal finger 54 of the puncture frame 4 are substantially aligned with the longitudinal axis of the delivery apparatus 200. The distal fingers 54 abut the interior of the nose cone 408, in the hollow chamber 422, and the proximal fingers 52 abut the exterior of the proximal portion of the nosecone 408. The puncture frame 4 can be loaded onto the nosecone in the first delivery state 24, for example, by a user.

FIG. 19 shows the puncture frame 4 in the second delivery state 24. In this state, the distal fingers 54 of the puncture frame 4 are still retained inside the hollow chamber 422, but the proximal fingers 52 of the puncture frame 4 extend radially outwardly from the longitudinal axis of the delivery apparatus 200. The puncture frame 4 is securely positioned between the proximal end of the nosecone 408 and the distal end of dilator 412. The second delivery state 24 of the puncture frame 4 is achieved by tensioning (pulling) the apices 46 of the proximal fingers 52 in a proximal direction along the longitudinal axis of the delivery apparatus 200. As discussed in more detail below, the tensioning force is applied by coupling the apices 46 of the proximal fingers 52 to the distal portion of the proximal apices actuator 500, and then moving the proximal apices actuator 500 proximally relative to the proximal dilator 414.

FIGS. 20A-20D illustrate the use of the nose cone 408 and dilator 412 for transitioning the puncture frame 4 from the second delivery state 24 to the deployed state 22. FIG. 20A shows the puncture frame 4 in the second delivery state 24. As discussed above, the nose cone 408 is secured to the hollow rod 410; therefore, moving the hollow rod distally causes corresponding distal movement of the nose cone 408 in the direction of arrow 440. FIGS. 20B and 20C show movement of the nose cone 408 in the direction of arrow 440. When the proximal end of the nose cone 408 extends distally beyond the apices 46 of the distal fingers 54 of the puncture frame 4 (FIG. 20C), the distal fingers 54 move toward the proximal fingers 52 due to the shape memory of the puncture frame 4, and the puncture frame adopts deployed state 22, shown in FIG. 20D.

Figure 21A:
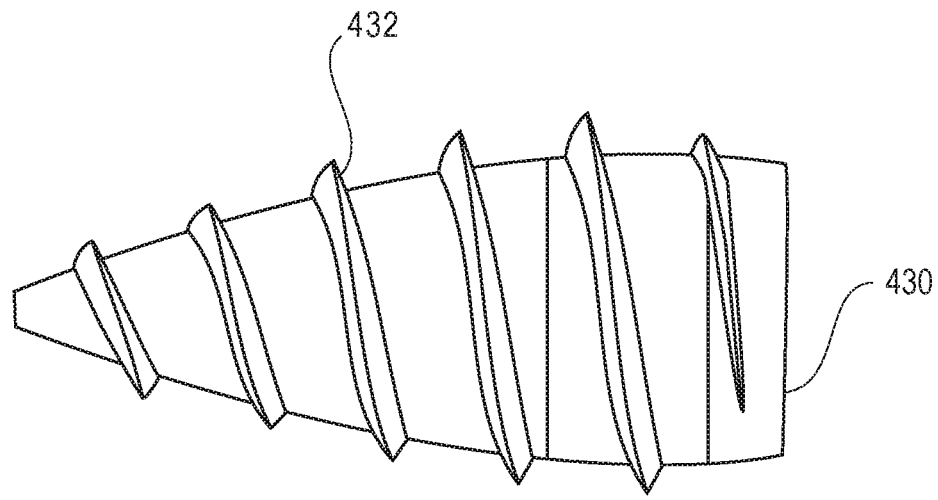
FIGS. 21A and 21B show perspective views of a nose cone of a dilator for use with a delivery apparatus for implantation of a vessel opening and sealing device into a patient, according to another embodiment.
Figure 21B:
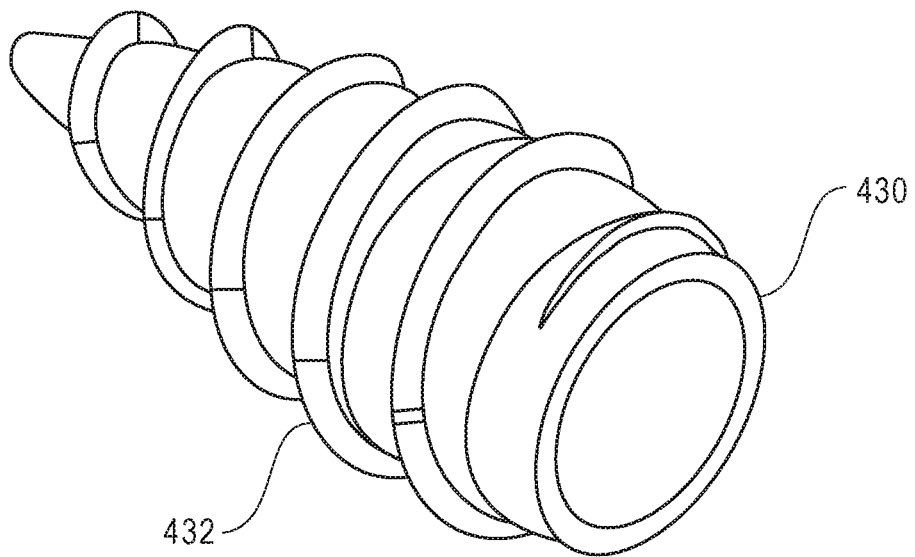

FIGS. 21A and 21B show an alternative threaded nosecone 430 for use with dilator 400. In such embodiments, the threaded nosecone 430 desirably is secured to the hollow rod 410 and rotation of the hollow rod 410 causes corresponding rotation of the nosecone 430. Similar to the nosecone 408, the nosecone 430 can include a hollow chamber 434 that is shaped to house the distal fingers 54 of the puncture frame 4 during delivery of the sealing device 2 to a patient. The threaded nosecone 430 includes a male thread 432 on its exterior surface. The thread 432 is suitably sized such that upon twisting the distal tip of the threaded nosecone 430 in an aperture in a vessel sidewall, the twisting will provide expansion of the aperture in the sidewall. Thus, the threaded nosecone 430 can the distribute outward force of the nosecone in an axial direction to enlarge the aperture in the vessel wall to minimize the force applied in a longitudinal direction, thereby reducing and/or preventing tearing of the vessel wall.

FIGS. 22 and 23 show an alternative proximal dilator 450 for use with the dilator 400. The proximal dilator 450 includes a biasing assembly 452 that can be used to induce longitudinal movement of nosecone 408 in a distal direction, for example, to drive the distal tip of nosecone through the sidewall of the vessel 12. The rapid movement of the nosecone through the sidewall of the vessel 12 minimizes tearing.

Similar to proximal dilator 414, the proximal dilator 450 is sleeve shaped and can have a cone shaped distal portion 454, designed for insertion into, and dilation of, the aperture 10 in the sidewall of the vessel 12. The distal portion 454 of proximal dilator 450 is shaped to suitably abut a nose cone, such as the nosecone 408 or the nose cone 430. The proximal portion of the proximal dilator 450 includes a housing 456 for housing the biasing assembly 452. The hollow rod 410 extends through the proximal dilator 450, and is secured at its distal end to the nosecone 408, and at its proximal end to a handle 458 of the biasing assembly 452. The biasing assembly includes at least a biasing element 460, such as the illustrated coil spring, that is secured at its proximal end to the handle 458. Pulling the handle proximally pulls against the biasing force of the biasing element 460. Release of the handle causes the handle to move in the direction of the biasing force, that is, distally. As the hollow rod 408 is secured to the handle 458 and the nosecone 408, movement of the handle 458 (due to the biasing force) causes corresponding movement of the hollow rod 410, which in turn causes movement of the nose cone 408. The biasing assembly 452 can be set in an activated state 362 (see FIG. 22) by tensioning proximally on the assembly against the biasing force. Release of the tension allows the biasing assembly to revert to a released state 464 (see FIG. 23). In alternative embodiments, the biasing element 460 can take other forms such as an elastic element.

Figure 24:
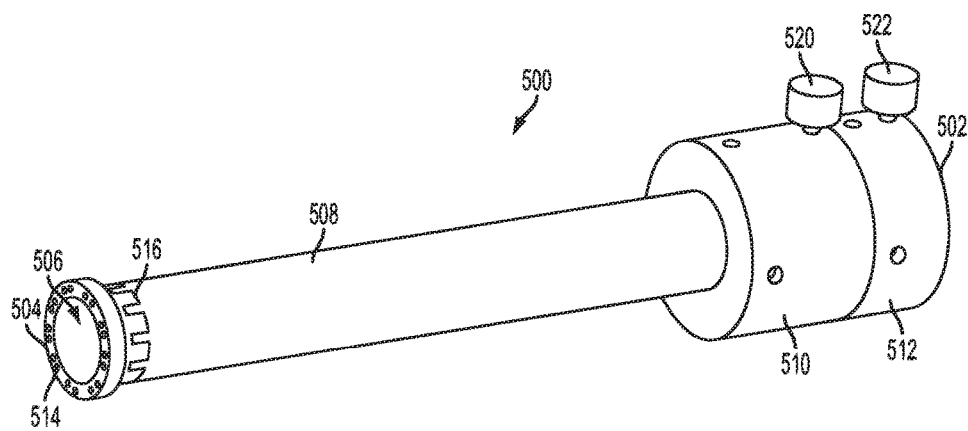
FIG. 24 is a perspective view of a proximal fingers actuator of the delivery apparatus of FIG. 14.

FIG. 24 shows an embodiment of the proximal fingers actuator 500, which can be used to cause the puncture frame 4 to transition from the first delivery state 25 to the second delivery state 24. As discussed below, the proximal fingers 52 of the puncture frame 4 can be releasably secured to a component of the proximal fingers actuator 500. Moving the proximal fingers actuator 500 proximally tensions the proximal fingers 52 to cause the puncture clip 4 to transition from the first delivery state 25 to the second delivery state 24.

The proximal fingers actuator 500 in the illustrated embodiment is a multiple component subassembly including multiple coaxial sleeves that are positioned axially outward from the introducer sheath 300, the twisting frame actuator 600, and the dilator 400 on delivery assembly 200. The fingers actuator 500 can be axially slidable and angularly rotatable relative to the introducer sheath 300, the twisting frame actuator 600, and the dilator 400. Referring to FIG. 24, the proximal fingers actuator 500 includes a proximal portion 502 and a distal portion 504, and can include an inner shaft 506, an outer shaft 508, an outer shaft handle 510, an inner shaft handle 512, and a suture ring 514.

The inner shaft 506 is positioned radially outwardly from an outer shaft 608 of the twisting frame actuator 600 (discussed below) and has an inner diameter slightly larger than the outer diameter of the outer shaft 608. The outer shaft 508 is positioned radially outward from the inner shaft 506 and has an inner diameter slightly larger than the outer diameter of the inner shaft 506. The proximal end of the outer shaft 508 can be secured to the outer shaft handle 512. The distal end portion of the outer shaft 508 can have a plurality of axially extending projections, or teeth 516 that are shaped to be inserted into a plurality of corresponding pockets 518 in the suture ring 514 (see FIGS. 26 and 27). The distal end of the inner shaft 506 can be secured to the suture ring 514 and the proximal end of the inner shaft 506 can be secured to the inner shaft handle 510. The inner and outer shafts can be axially slidable with respect to one another. The outer shaft handle 510 fits against the inner shaft handle 512. In some embodiments the inner shaft handle 512 includes a distal portion 524 that is slidable within a proximal portion 526 of the outer shaft handle 510 (best shown in FIG. 25).

Figure 25:
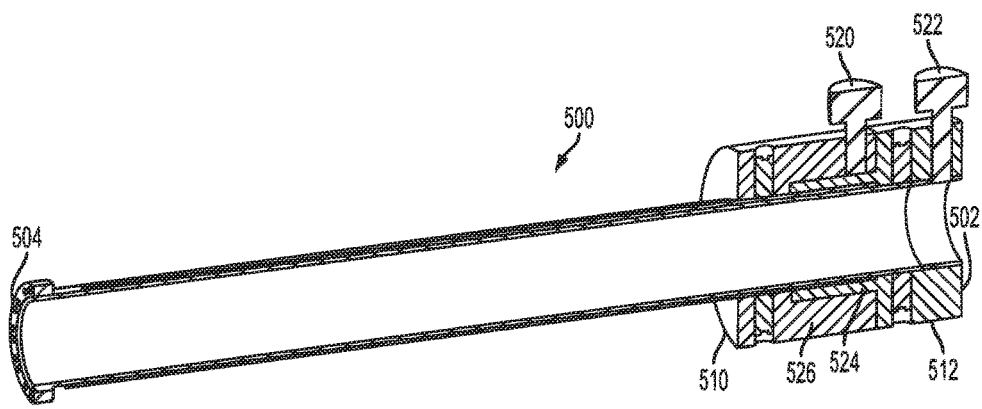
FIG. 25 is a cross sectional view of the proximal fingers actuator of FIG. 24.

The outer shaft handle 510 can include a locking mechanism 520 to releasably secure the inner shaft handle 512 to the outer shaft handle 510, to control axial sliding of the outer 508 and inner 506 shafts with respect with one another. Additionally, the inner shaft handle 512 can include a locking mechanism 522 to releasably secure the inner shaft handle 512 to the twisting frame actuator 600, for controlling angular rotation and/or axial sliding of the proximal fingers actuator 500 with respect to the twisting frame actuator 600. As shown in FIG. 25, the locking mechanism 520 can be a set screw that passes through the outer shaft handle 510 and is tightened against the inner shaft handle 512. The locking mechanism 522 can be a set screw that passes through the inner shaft handle 512 and is tightened against the twisting frame actuator 600. However, the locking mechanisms can be manufactured in accordance with any type of mechanism known in the art, such as a releasable clamp or friction fitting, set screw, spring latch, pin, or bayonet mount.

Figure 26:
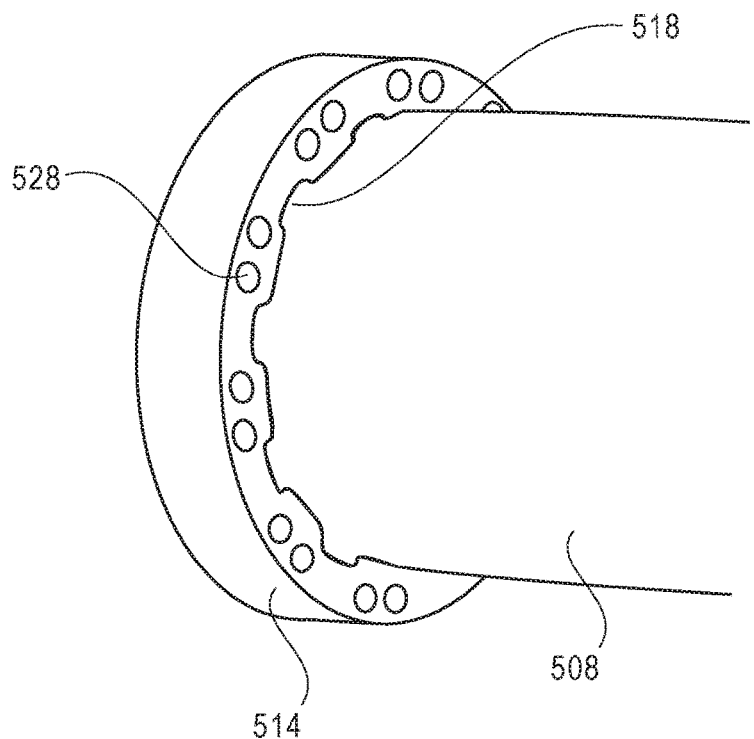
FIGS. 26 and 27 are perspective views of the distal portion of the proximal fingers actuator of FIG. 24.
Figure 27:
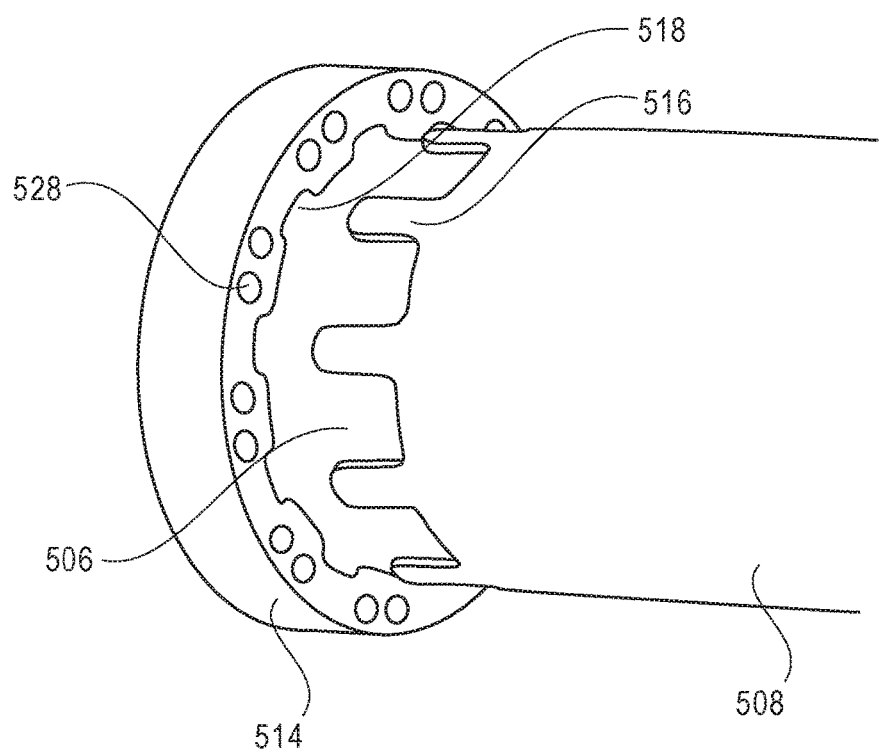

As shown in FIGS. 26 and 27, the suture ring 514 can be configured for connection to a plurality of suture loops 530 (best shown in FIGS. 28 and 29), which can be used to releasably secure the proximal fingers actuator 500 to the proximal fingers 52 of the puncture frame 4. The suture ring includes a plurality of apertures 528, to which the free ends of the suture loops 530 can be secured. The loops of the plurality of suture loops 530 can be passed through the eyelets 56 on the proximal fingers 52 of the puncture frame 4 (FIG. 4), and then looped under the teeth 516 of the outer shaft 508. The teeth 516 are inserted into the pockets 518 in the suture ring 514 to secure the suture loops 530 in place. Release of the suture loops from the teeth 516 can be accomplished by sliding the outer shaft 508 proximally to remove the teeth 516 from the pockets 518 in the suture ring 514, which frees the suture loops from the teeth 516. Moving the proximal finger actuator 500 proximally will pull the suture loops outwardly from the eyelets 56 on the proximal fingers 52 of the puncture frame 4, there by releasing the puncture frame 4 from its connection to the proximal finger actuator 500.

Figure 30A:
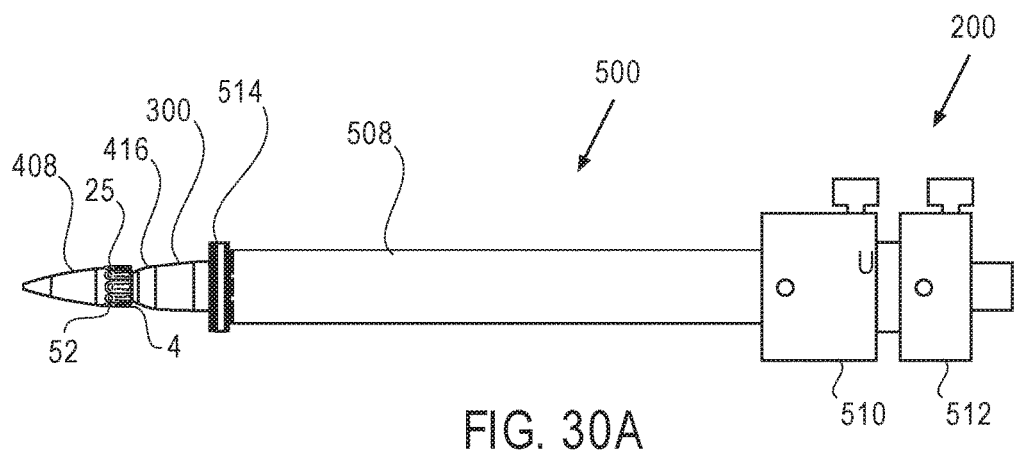
FIGS. 30A-30D are exploded cross-sectional views of a distal portion of the delivery apparatus of FIG. 14, illustrating the operation of the delivery apparatus for shifting the puncture frame from the first delivery state (FIG. 30A) to the second delivery state (FIG. 30D).
Figure 30B:
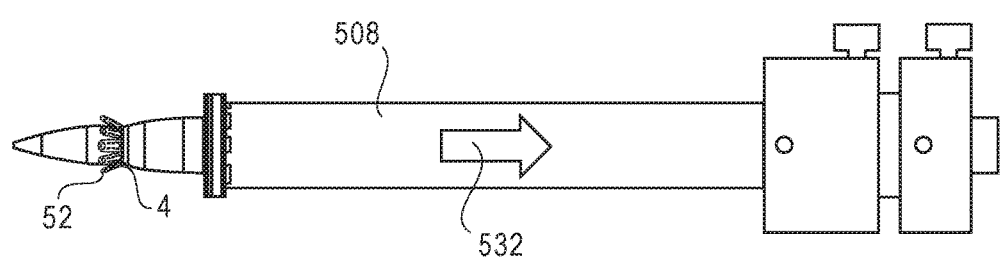
Figure 30C:
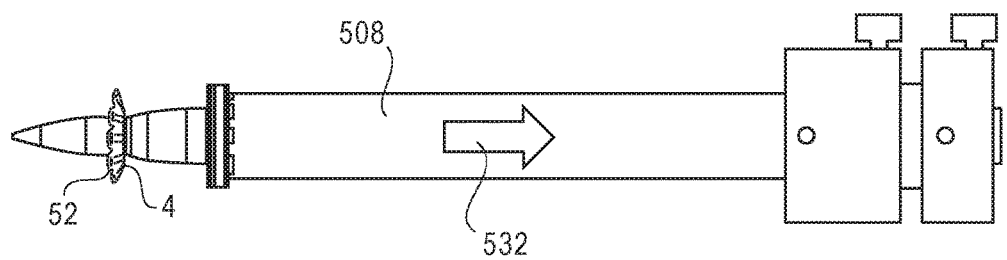
Figure 30D:
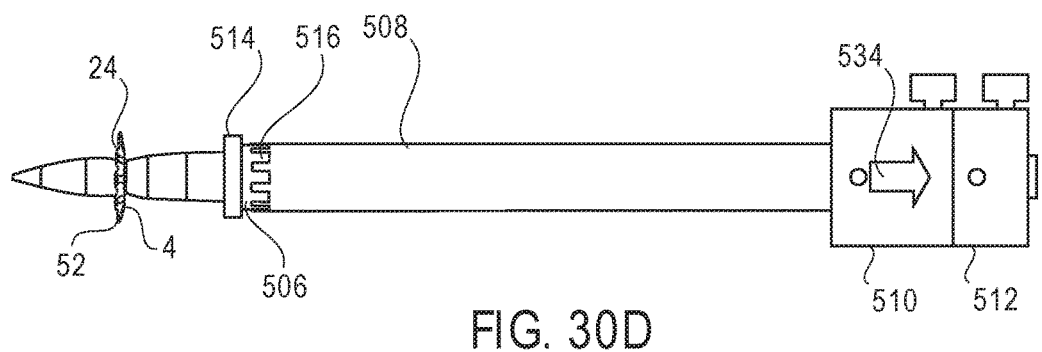

FIGS. 30A-30D further illustrate the use of the proximal fingers actuator 500 for shifting the puncture frame 4 from the first delivery state 25 to the second delivery state 24, and releasing the suture loops from the puncture frame 4. FIG. 30A shows the puncture frame 4 in the first delivery state 25 loaded onto the nose cone 408 of the dilator 400 of delivery assembly 200. For purposes of illustration the other components of the sealing device are not shown. The eyelets 56 on the proximal fingers 52 of the puncture frame 4 are secured to the suture ring 514 of the proximal fingers actuator 500 by suture loops 530 (not shown for purposes of illustration). Moving the proximal fingers actuator 500 proximally in the direction of arrow 532 pulls the suture loops 530 and attached proximal fingers 52 (FIGS. 30B and 30C) proximally, until the puncture frame 4 has transitioned from the first delivery state 25 to the second delivery state 24 (FIG. 30C). To release the suture loops from the puncture frame 4, the outer shaft 508 can be slidably moved proximally in the direction of arrow 534, while the inner shaft 506 is held stationary, retracting the teeth 516 from the pockets 518 in the suture ring 514, and disengaging the suture loops 530 from the teeth 516. The free ends of the suture loops 530 remain secured to the apertures 528. Therefore, slidably moving the proximal fingers actuator 500 proximally will pull the suture loops through the eyelets 56 and release the suture loops from the puncture frame 4 (FIG. 30D).

Figure 31:
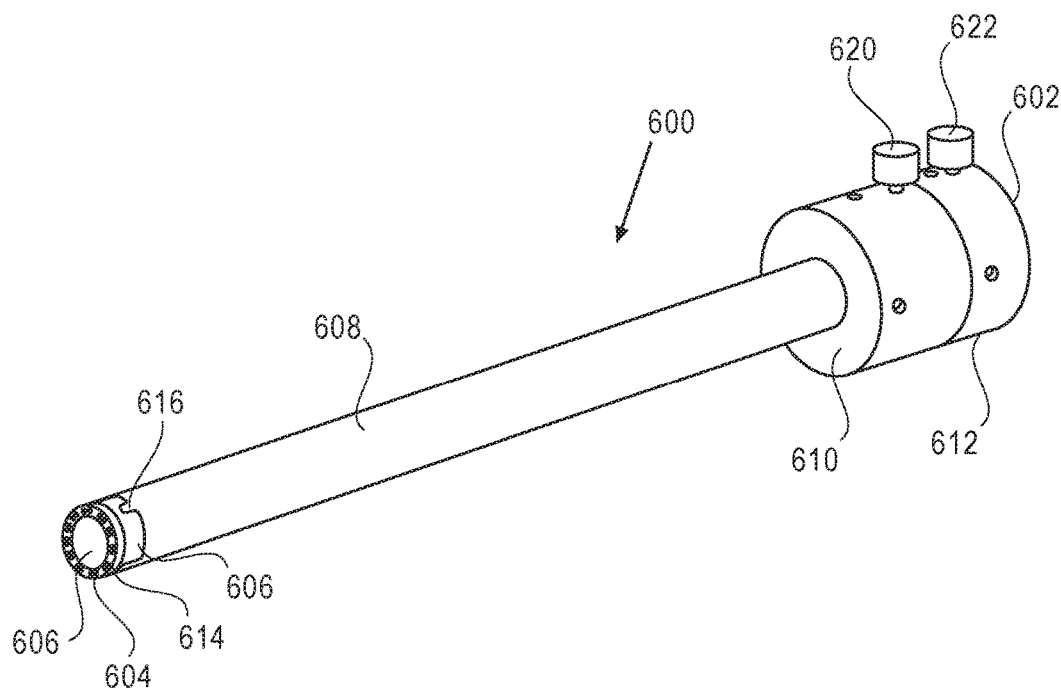
FIG. 31 is a perspective view of a twisting frame actuator of the delivery apparatus of FIG. 14.

FIG. 31 shows an embodiment of the twisting frame actuator 600, which can be used to rotate the twisting frame 6 (FIG. 6) and twist the sealing member 8 into a sealed or closed state 38. In some embodiments, the twisting frame actuator is also used to apply and/or maintain tension on the sealing member 8, which prevents the sealing member from bunching up, for example, when advancing the introducer 300 or other instrument therethrough. As discussed below, the twisting frame 6 can be releasably secured to a component of the twisting frame actuator 600. Rotating the twisting frame actuator 600 causes rotation of the twisting frame 6, which twists the sealing member 8 into its closed state 38.

The twisting frame actuator 600 is a multiple component subassembly including multiple coaxial sleeves that are positioned axially outward from (distal to) the handle 308 of the introducer sheath 300 and axially inward from (proximal to) the handles 510, 512 of the proximal fingers actuator 500, on delivery assembly 200. The twisting frame actuator 600 can be axially slidable and angularly rotatable relative to the introducer sheath 300, the proximal fingers actuator 500, and the dilator 400. Referring to FIG. 31, the twisting frame actuator 600 includes a proximal portion 602 and a distal portion 604, and can include an inner shaft 606, an outer shaft 608, an outer shaft handle 610 an inner shaft handle 612, and a suture ring 614.

The inner shaft 606 is positioned radially outwardly from the sleeve 306 of the introducer sheath 300 and has an inner diameter slightly larger than the outer diameter of the sleeve 306. The outer shaft 608 is positioned radially outward from the inner shaft 606, and has an inner diameter slightly larger than the outer diameter of the inner shaft 606. The outer shaft 608 is positioned radially inward from the inner shaft 506 of the proximal fingers actuator 500, and has an outer diameter slightly less than the inner diameter of the inner shaft 506.

The proximal end of the outer shaft 608 can be secured to the outer shaft handle 612. The distal end portion of the outer shaft 608 can have a plurality of projections or teeth 616 that are shaped to be inserted into a plurality of corresponding pockets 618 in the suture ring 614 (see FIGS. 33 and 34). The distal end of the inner shaft 606 can be secured to the suture ring 614 and the proximal end of the inner shaft 606 can be secured to the inner shaft handle 610. The inner 606 and outer 608 shafts are axially slidable with respect to one another. The outer shaft handle 610 fits against the inner shaft handle 612. In some embodiments the inner shaft handle 612 includes a distal portion 624 that is slidable within a proximal portion 626 of the outer shaft handle 610 (best shown in FIG. 32).

Figure 32:
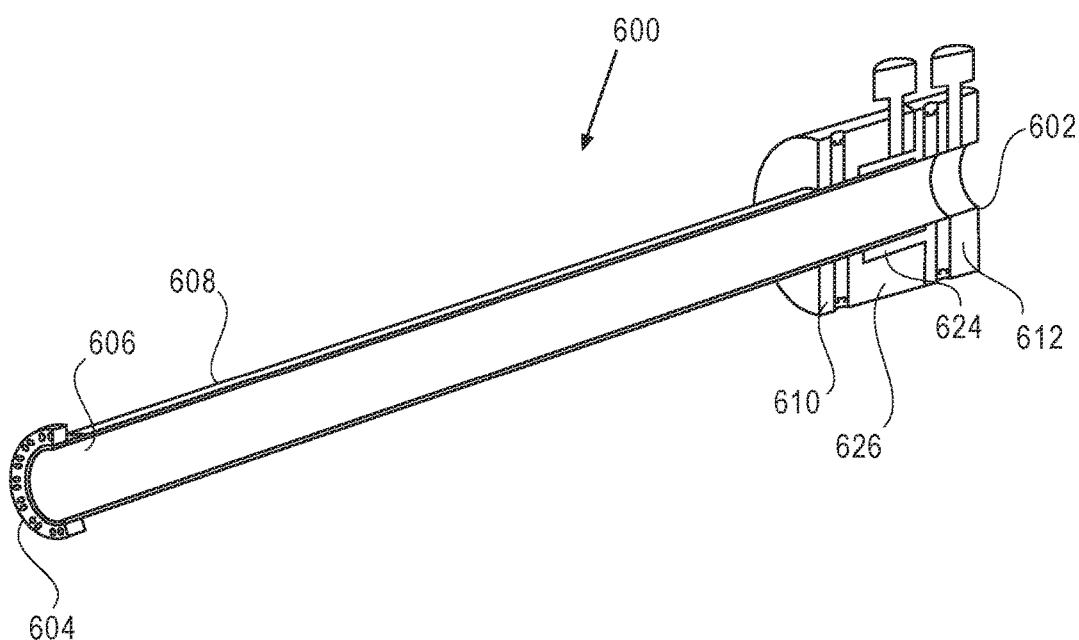
FIG. 32 is a cross sectional view of the twisting frame actuator of FIG. 31.

The outer shaft handle can include a locking mechanism 620 to releasably secure the inner shaft handle 612 to the outer shaft handle 610, to control axial sliding of the outer 606 and inner 608 shafts with respect with one another. Additionally, the inner shaft handle 612 can include a locking mechanism 622 to releasably secure the inner shaft handle 612 to the introducer sheath 300, to control angular rotation and/or axial sliding of the twisting frame actuator 600 with respect to the introducer sheath 300. As shown in FIG. 32, the locking mechanism 620 can be a set screw that passes through the outer shaft handle 610 and is tightened against the inner shaft handle. The locking mechanism 622 can be a set screw that passes through the inner shaft handle 612 and is tightened against the introducer sheath 300. However, the locking mechanisms can be manufactured in accordance with any type of mechanism known in the art, such as a releasable clamp or friction fitting, set screw, spring latch, pin, or bayonet mount.

Figure 33:
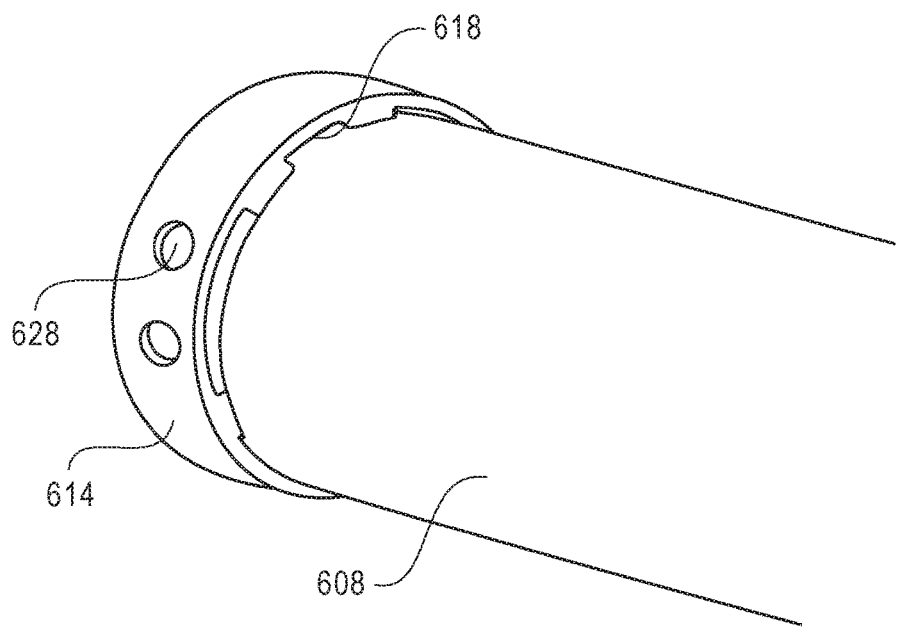
FIGS. 33 and 34 are exploded perspective views of the distal portion of the twisting frame actuator of FIG. 31.
Figure 34:
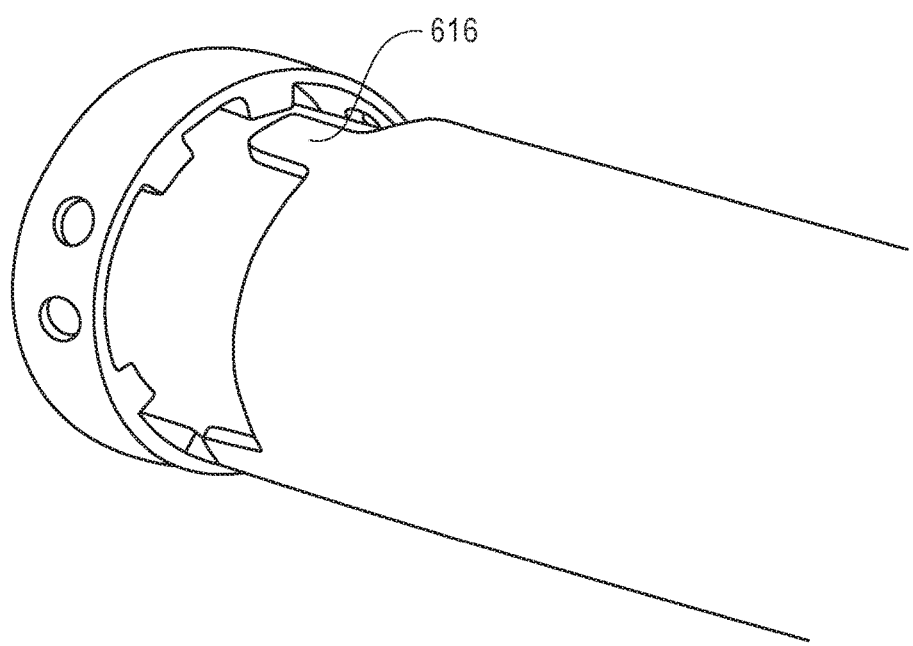

As shown in FIGS. 33 and 34, the suture ring 614 can be configured for connection to a plurality of suture loops 630 (best shown in FIG. 29), which can be used to releasably secure the twisting frame actuator 600 to the twisting frame 6 of the sealing device 2. The suture ring 614 includes a plurality of apertures 628, to which the free ends of the suture loops 630 can be secured. The loops of the plurality of suture loops 630 can be passed through openings 86 on the twisting frame 6 (FIG. 6), and then looped under the teeth 616 of the outer shaft 608. The teeth 616 are inserted into the pockets 618 in the suture ring 614 to secure the suture loops 630 in place. When secured, the suture loops 630 secure the twisting frame 6 to the twisting frame actuator 600. Therefore, rotating the twisting frame actuator 600 causes corresponding rotation of the twisting frame 6, and the sealing member 8, to which the twisting frame 6 is secured. Thus, angular rotation of the twisting frame actuator 600 can be used to rotate the sealing member 8 into its closed state 38. Release of the suture loops from the teeth 616 is accomplished by sliding the outer shaft 608 proximally to remove the teeth 616 from the pockets 618 in the suture ring 614 which frees the suture loops from the teeth 616. Moving the twisting frame actuator 600 proximally will pull the loops of the suture loops 630 from the openings 86 on the twisting frame 6, thereby releasing the twisting frame 6 from its connection to the twisting frame actuator 600.

C. Exemplary Method of Using Sealing Device 2

FIGS. 35-44 illustrate an exemplary method of using a disclosed vessel opening and sealing device and a delivery apparatus for accessing the lumen of a vessel (such as the aorta) for performing an endoluminal procedure via an aperture in the sidewall of the vessel, and then sealing the aperture following the endoluminal procedure. The illustrated method utilizes the delivery apparatus 200 and the sealing device 2; however, other embodiments of a sealing device and/or a delivery apparatus (for example, as described herein) can be used to perform the disclosed method. In several embodiments, the disclosed method is used to create and seal an aperture in a sidewall of the aorta in a patient during a surgical procedure, such as implantation of a prosthetic heart valve.

Figure 35:
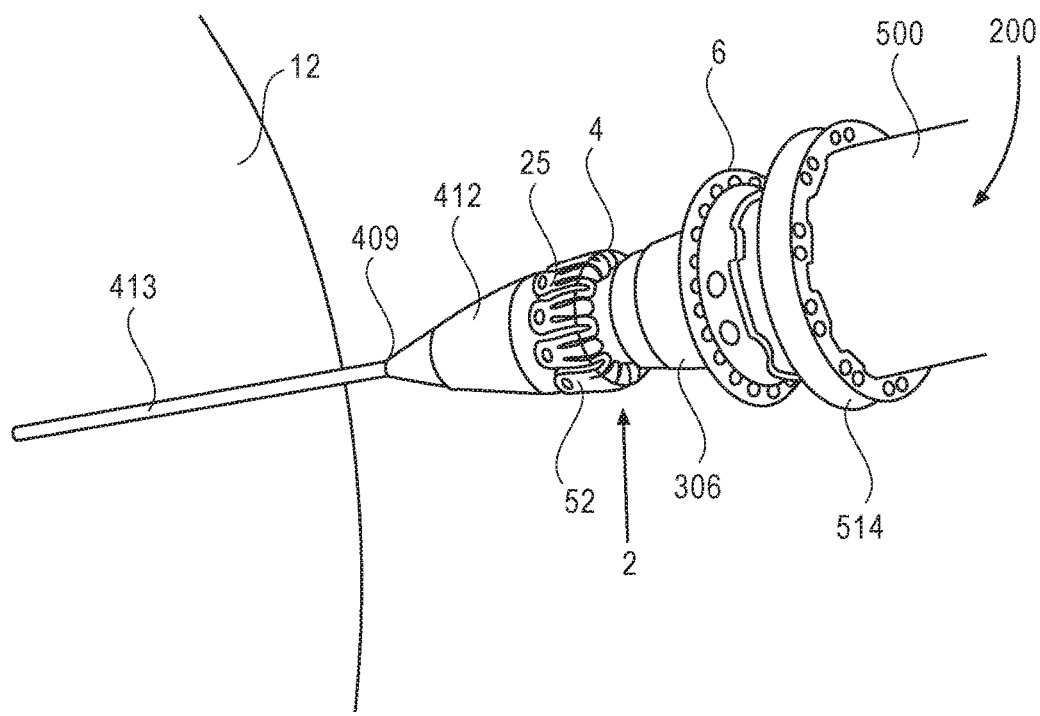
FIGS. 35-44 illustrate an exemplary method of using a disclosed vessel opening and sealing device and a delivery apparatus for accessing the lumen of a vessel for performance of an endoluminal procedure via an aperture in the sidewall of the vessel, and then sealing the aperture following the endoluminal procedure.

FIG. 35 shows delivery apparatus 200 with sealing device 2 loaded onto the distal portion of the delivery apparatus. For illustration purposes, the puncture frame 4 and the twisting frame 6, but not the other components of the sealing device 2, are shown. The puncture frame 4 initially is in the first delivery state 25, with the distal fingers 54 positioned inside the nose cone 412, and the proximal fingers 52 positioned outside and folded against the nose cone 412. The sidewall of the vessel 12 is shown. In particular embodiments, the hypodermic needle 413 can be advanced through the lumen 406 and aperture 409 at the distal tip of the nose cone 412 and the hollow rod 410 (FIG. 16), respectively, and inserted through the sidewall of the vessel 12. The guide wire 411 can then be inserted through the hypodermic needle 413 and into the lumen of the vessel 12, and placed as needed for the endoluminal procedure. After placement of the guide wire 411, the hypodermic needle 413 is retracted from the sidewall of the vessel 12.

Figure 36:
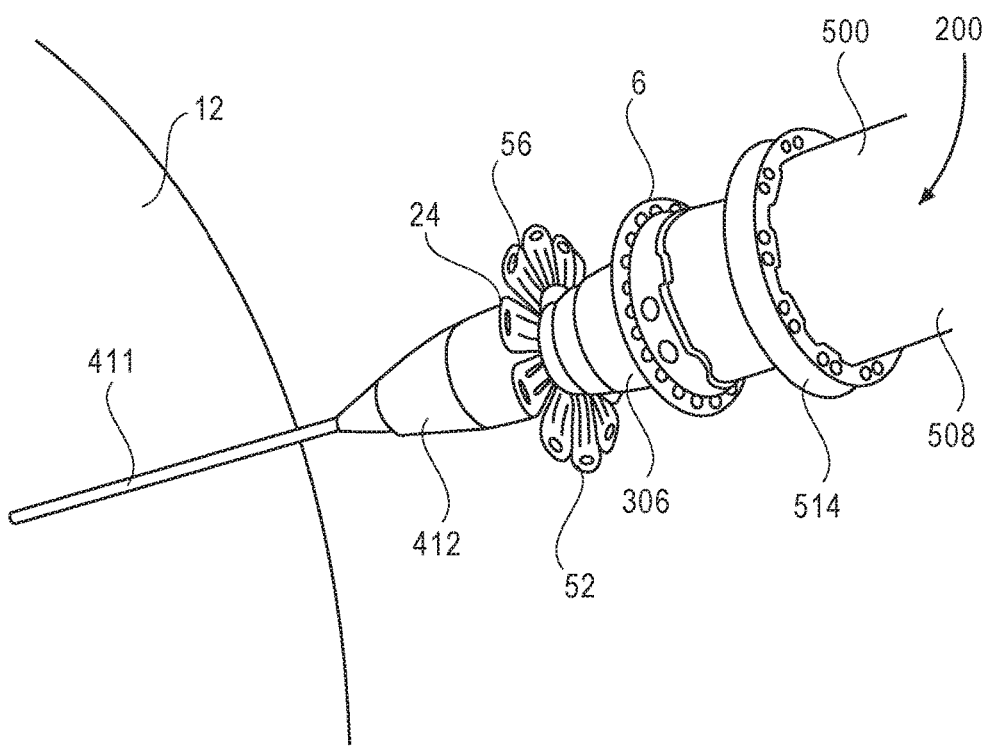

After placement of the guide wire 411, the puncture frame 4 is transitioned from the first delivery state 25 to the second delivery state 24 (FIG. 36). As noted above, the eyelets 56 on the proximal fingers 52 of the puncture frame 4 are secured to the suture ring 514 of the proximal fingers actuator 500 by suture loops 530 (FIGS. 28 and 29; for purposes of illustration, the suture loops 530 are not shown in FIGS. 35-44). The proximal fingers actuator 500 is moved proximally causing corresponding proximal movement of the proximal fingers 52, until the puncture frame 4 has transitioned from the first delivery state 25 to the second delivery state 24.

Figure 37:
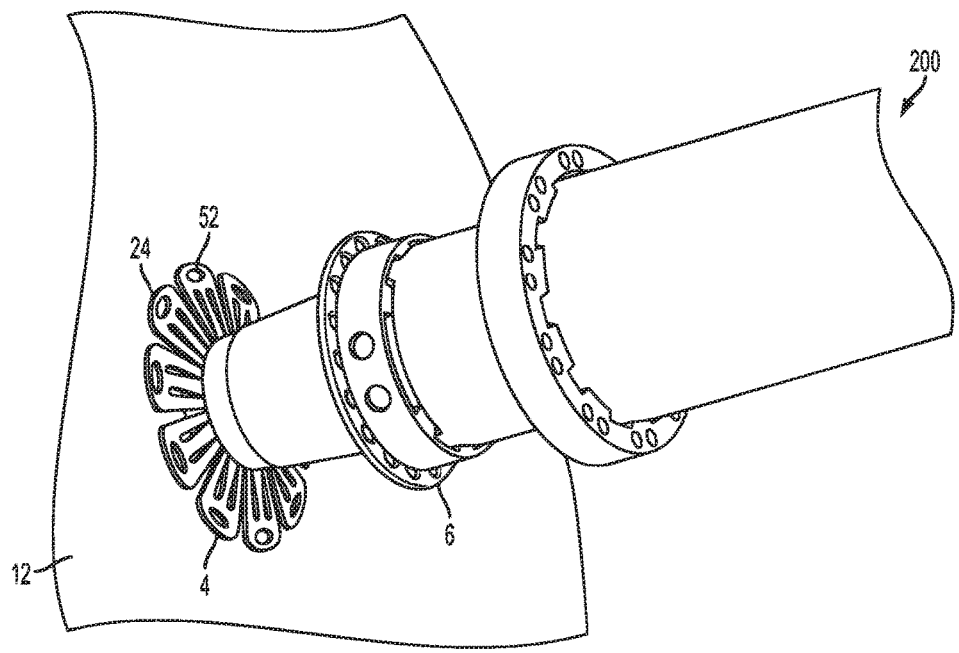
Figure 38:
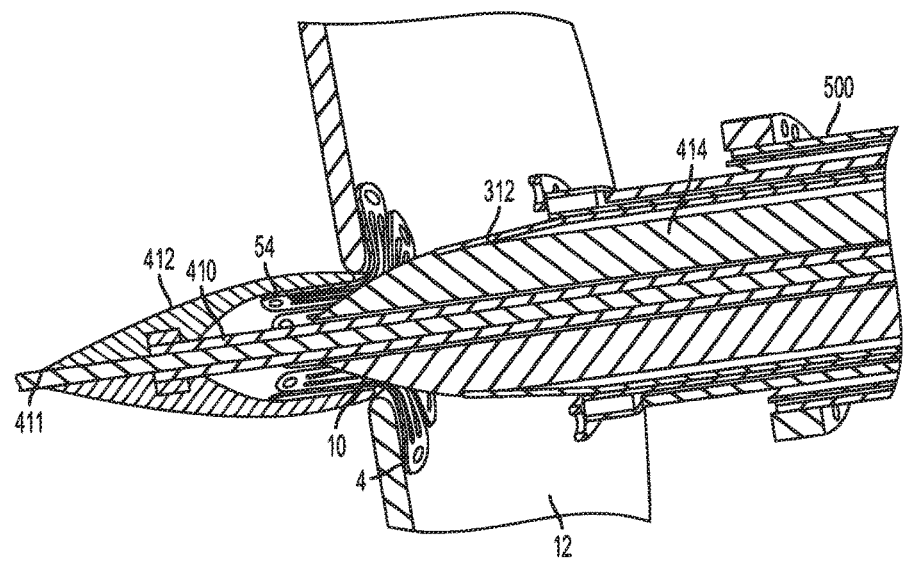

After the puncture frame 4 is moved to the second delivery state 24, the delivery apparatus 200 can be advanced distally until the nose cone 412 penetrates the sidewall of the vessel 12, and the proximal fingers 52 of the puncture frame 4 are flush with the exterior side 20 of the sidewall of the vessel 12 (FIGS. 37 and 38). The suture loops 530 are released from the eyelets 56 on the proximal fingers 52 of the puncture frame 4 by sliding the outer shaft 508 proximally, while the inner shaft 506 is held stable (best shown in FIG. 42). This retracts or removes the teeth 516 from the pockets 518 in the suture ring 514, and frees the suture loops 530 from the teeth 516. The free ends of the suture loops 530 remain secured to the suture ring 514. The proximal fingers actuator 500 can be slid proximally to pull the suture loops through the eyelets 56 and release the suture loops from the puncture frame 4. In some embodiments, the proximal fingers 52 are released at a different stage of the deployment, for example, after pushing the introducer sheath 300 through the puncture frame 4.

Optionally, an incision in vessel wall 12 can be performed prior to advancing the nose cone 412 through the sidewall of the vessel. The incision can be circular or X-shaped (or another shape). In some embodiments, placement of the incision reduces tearing of the side wall of the vessel 12 when penetrated with the nose cone 412. The reduction in tearing can reduce leakage between the sidewall of the vessel 12 and the puncture frame 4.

Figure 39:
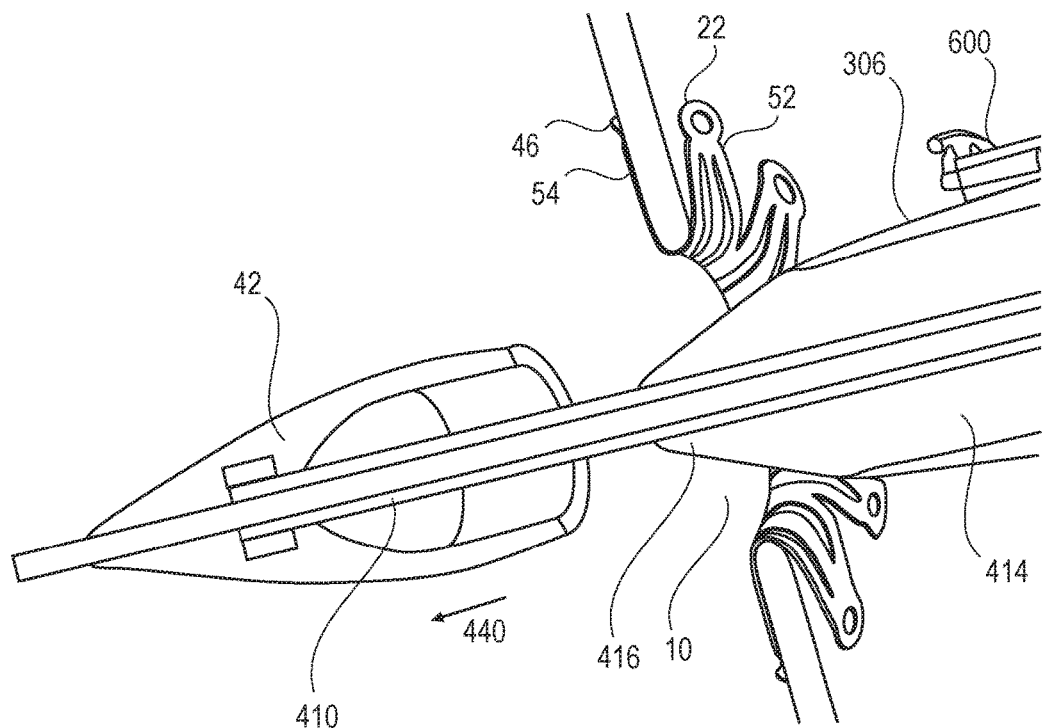
Figure 40:
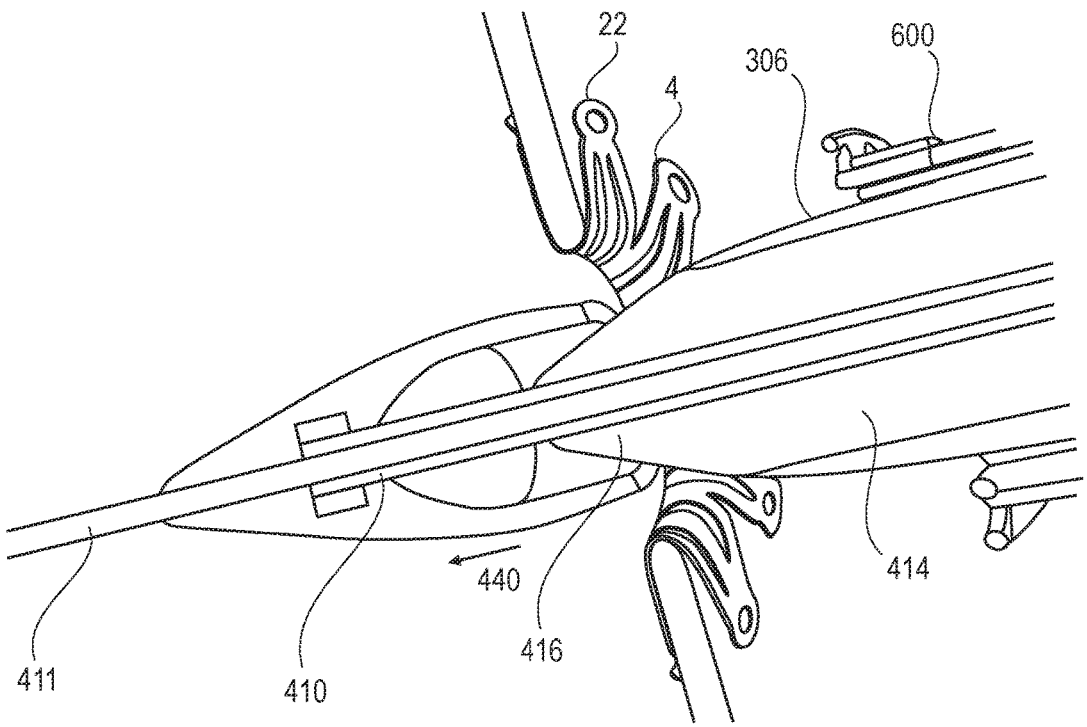

After the proximal fingers 52 are flush with the exterior side 20 of the sidewall of the vessel 12, the nose cone 408 can be advanced distally to transition the puncture frame 4 from the second delivery state 24 to the deployed state 22 (FIG. 39). The hollow rod 410 is advanced distally, causing corresponding movement of the nose cone 408 in the direction of arrow 440. When the proximal end of the nose cone 408 extends distally beyond the apices 46 of the distal fingers 54 of the puncture frame 4, the distal fingers 54 move toward the proximal fingers 52 due to the shape memory of the puncture frame 4, and the puncture frame adopts deployed state 22 around the sidewall of the vessel 12. The proximal and distal fingers 52, 54, respectively, bear against the outer and inner surfaces of the vessel wall so as to secure the frame 4 within the opening 10. In the illustrated embodiment, the transition from the second delivery state 24 to the deployed state 22 is accompanied by an increase in the inner diameter D1 of the puncture frame 4, resulting in the puncture frame 4 applying an outward radial force against the opening 10 in the wall of the vessel 12, thereby improving the seal therewith. The nose cone 408 can then be retracted proximally in the direction opposite that of arrow 440 (FIG. 40).

Figure 41:
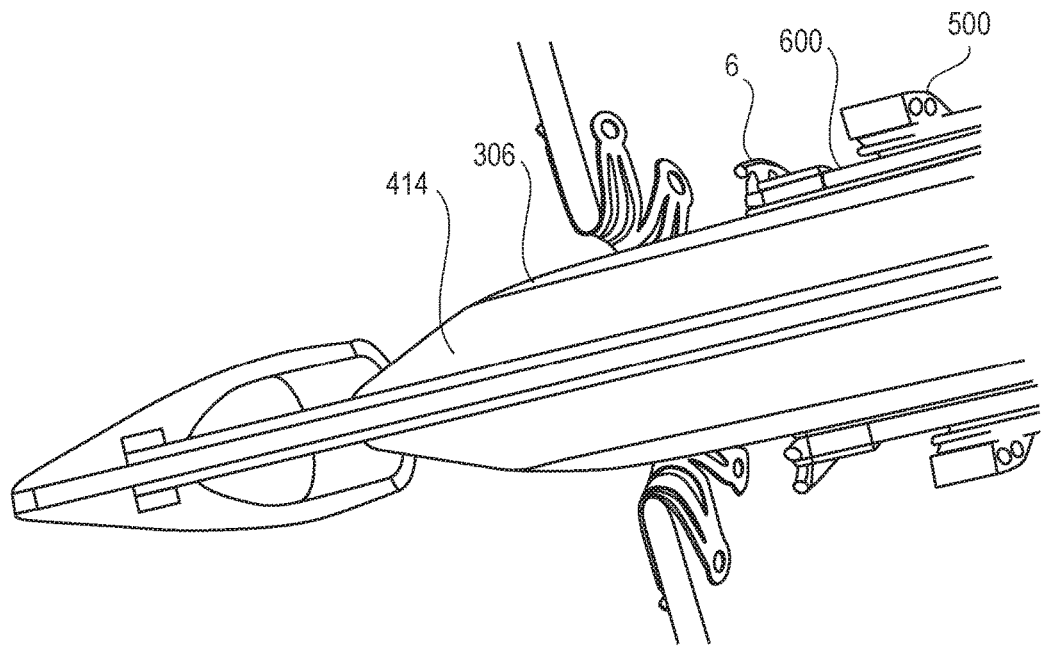
Figure 42:
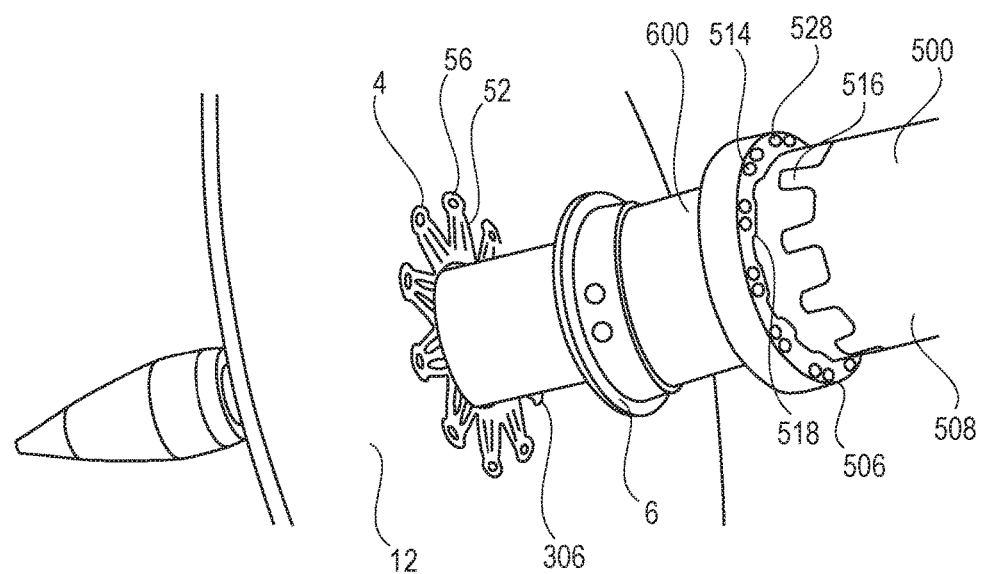

Following deployment of the puncture frame 4, the introducer sheath 300 and the dilator 500 can be advanced distally until the sleeve 306 traverses the aperture 10 in the sidewall of the vessel 12 (FIGS. 41 and 42). The twisting frame actuator 600 optionally can be rotated angularly to cause twisting of the sealing member 8 (not pictured for illustration purposes). Twisting of the sealing member 8 tightens the sealing member 8 around the sleeve 306, thereby providing hemostasis or a seal that reduces and/or prevents bleeding between the sleeve 306 and the sealing member 8, and/or provides for immobilization of the sleeve 306.

Figure 43:
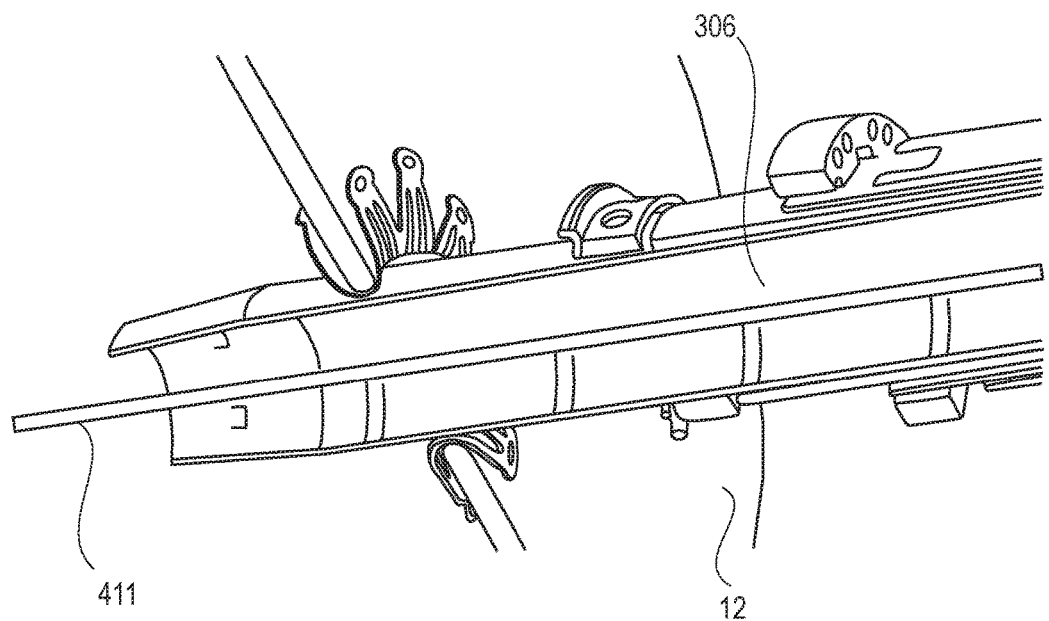

The dilator 500 can then be retracted proximally and removed from the delivery assembly 200 leaving the sleeve 306 and guide wire in place, extending through the sealing device 2 (FIG. 43). The introducer sheath can be advanced as needed for performing the endoluminal procedure. In some embodiments, the endoluminal procedure includes advancing one or more tools and/or instruments through the introducer sheath 300, such as a prosthetic heart valve delivery apparatus. Exemplary endoluminal procedures include, but are not limited to, placing or repairing a prosthetic heart valve, placing or repairing a vascular stent, placing or repairing of an abdominal aortic aneurysm graft, repairing a natural valve, repairing a cardiac defect, and the like).

Figure 44:
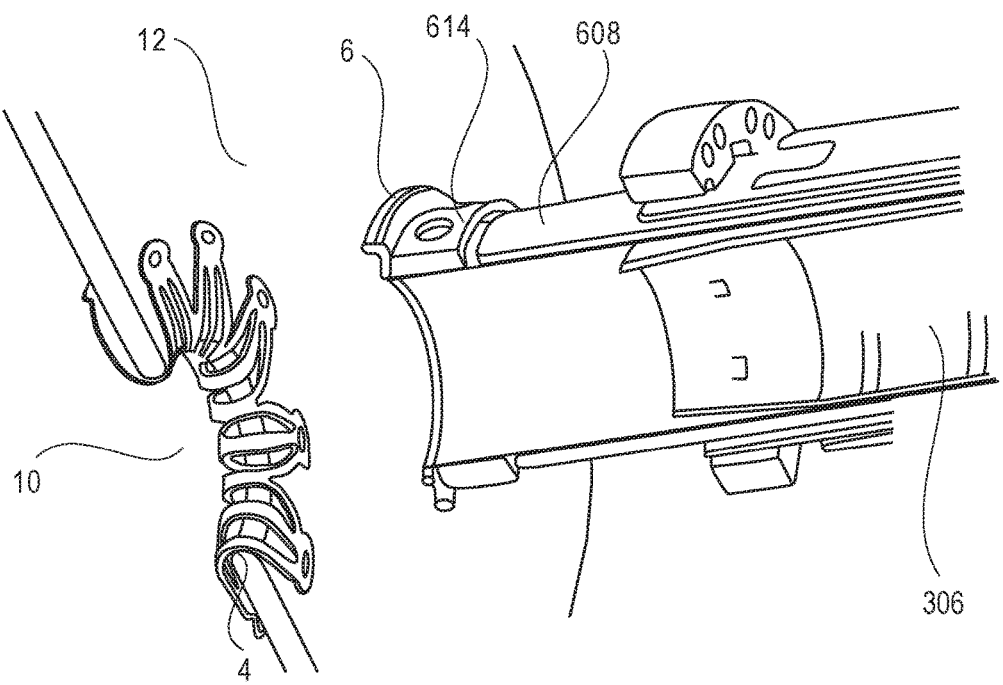

Following the endoluminal procedure, the guide wire 411 is removed, and the sleeve 306 is retracted proximally within the twisting frame actuator 600 (FIG. 44).

Figure 45:
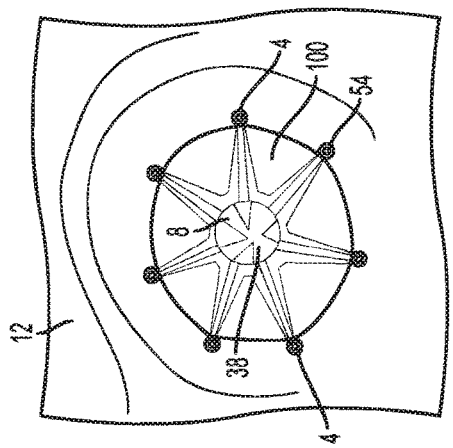
FIGS. 45 and 46 show distal and proximal views of the sealing device of FIG. 1 implanted into the sidewall of a blood vessel.
Figure 46:
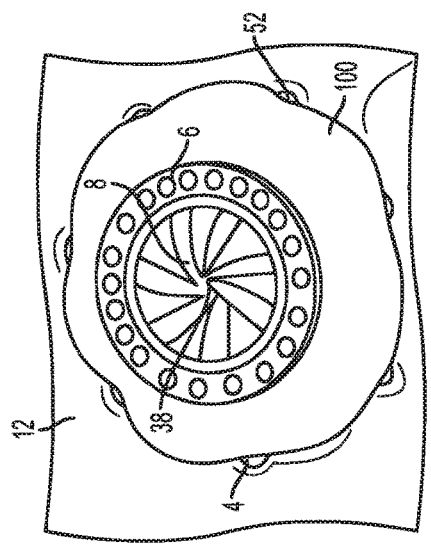

The sealing member 8 can then be moved the closed state 38 (see FIGS. 44-46). As noted above, the openings 86 on the twisting frame 6 are secured to the suture ring 614 of the twisting frame actuator 600 by suture loops 630 (for purposes of illustration, the suture loops 630 are not shown). The twisting frame 600 can be rotated around the longitudinal axis to cause corresponding rotation of the twisting frame 4, which is secured to the sealing member 8. Thus, the angular rotation of the twisting frame actuator 600 rotates the sealing member 8 into its closed state 38. FIG. 45 shows a distal view of the implanted sealing device with the sealing member 8 in the closed state 38, and FIG. 46 shows a proximal view of the implanted sealing device with the sealing member 8 in the closed state 38. The suture loops 630 are released from the twisting frame actuator 600 by sliding the outer shaft 608 proximally to retract or remove the teeth 616 from the pockets 618 in the suture ring 614, thereby freeing the suture loops 630 from the teeth 616. The twisting frame actuator 600 is then retracted proximally, pulling the loops of the suture loops 630 from the openings 86 on the twisting frame 6, thereby releasing the twisting frame 6 from its connection to the twisting frame actuator 600. The delivery apparatus 200 can then be removed from the patient.

D. Additional Exemplary Embodiments

Figure 47:
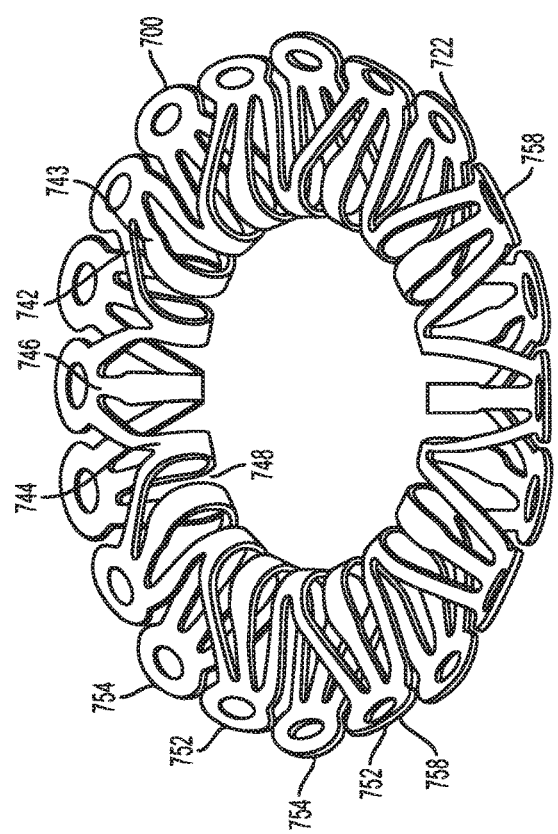
FIG. 47 shows a perspective view of an embodiment of a puncture frame for use with a sealing device.

FIG. 47 illustrates a puncture frame 700 according to another embodiment. The puncture frame 700 is substantially the same as the puncture frame 4. Similar to puncture frame 4, the puncture frame 700 can be formed from a plurality of struts 742, which are formed with alternating bends and are welded or otherwise secured to each other at nodes 744 and apices 746 to form a mesh structure having a plurality of trapezoidal shaped cells 748 between the struts. The mesh structure formed by struts 742 forms a plurality of proximal fingers 752 and a plurality of distal fingers 754 that can have a generally triangular shape and which extend radially outwardly from a longitudinal axis of the puncture frame 700. The puncture frame 700 can transition from a first delivery state 725 to a second delivery state 724 to a deployed state 722, corresponding to the first delivery state 25, the second delivery state 24 and the deployed state 22 of the puncture frame 4.

The apices of the plurality of proximal fingers 752 can have a plurality of angled eyelets 758 extending outwardly from the longitudinal axis of puncture frame 700 and angled proximally, away from the sidewall of vessel 12, when the puncture frame is in deployed state 722 (best shown in FIG. 47). The apices of the plurality of distal fingers 754 can have a plurality of eyelets 756 extending outwardly from the longitudinal axis of puncture frame 700 when the puncture frame is in deployed state 722 (similar to the eyelets 56 on the plurality of distal fingers 54 of puncture frame 4).

Figure 48:
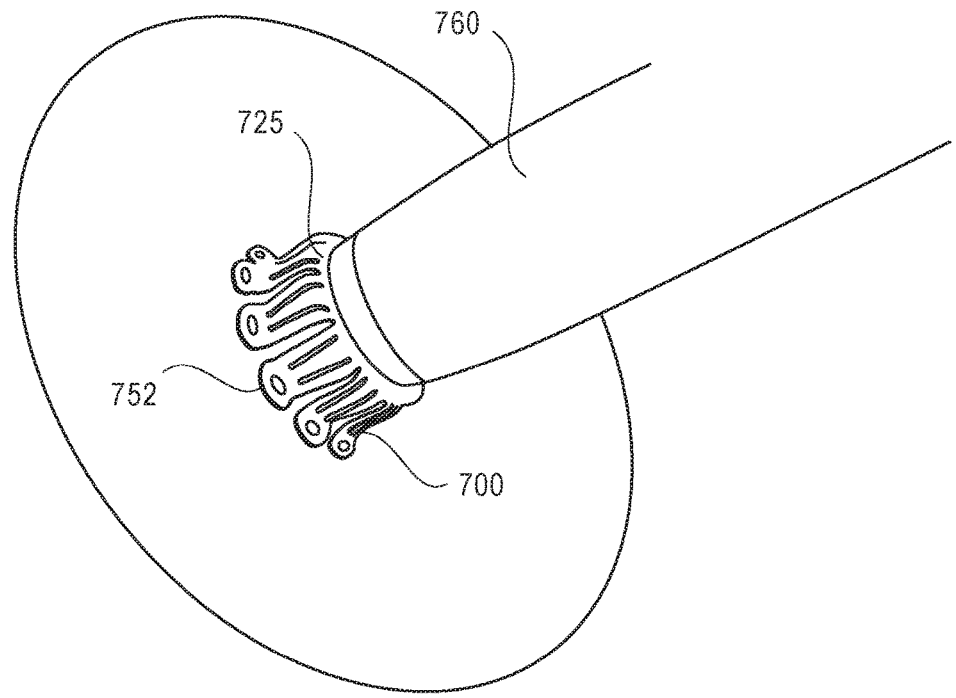
FIGS. 48 and 49 shows a perspective views illustrating the operation of the puncture frame of FIG. 47 for implantation into the side wall of a blood vessel.
Figure 49:
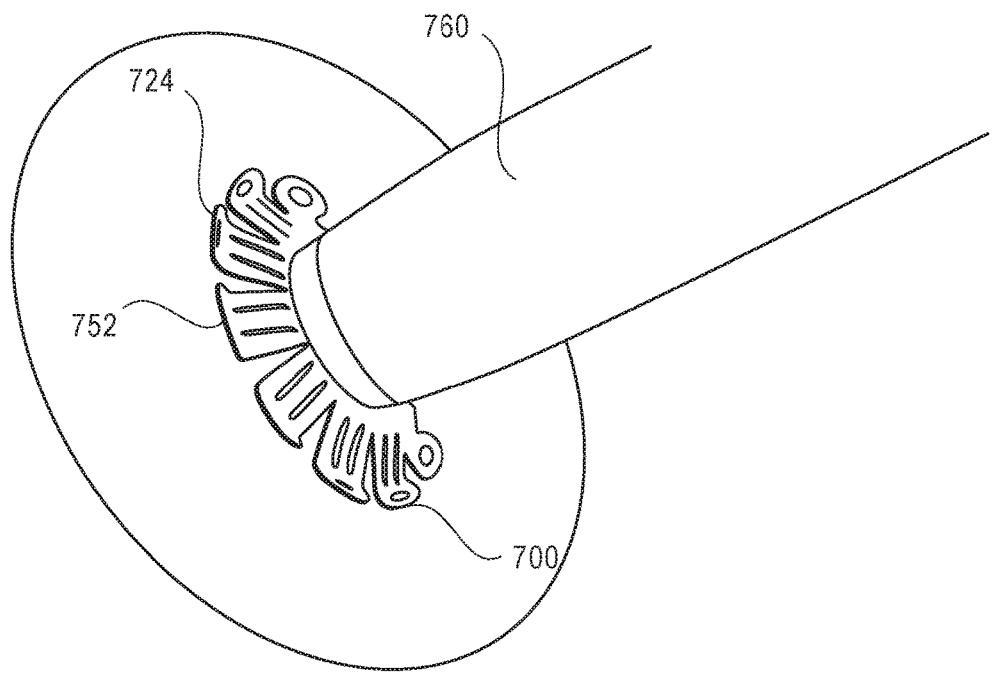

The function of the angled eyelets 758 is illustrated in FIGS. 48 and 49. FIG. 48 shows a delivery apparatus 760 (similar to delivery apparatus 200) with puncture frame 700 loaded onto the distal portion of the delivery apparatus. When a distal portion of the delivery apparatus 760 is placed through the sidewall of vessel 12, the angled eyelets 758 contact the sidewall of vessel 12 (best shown in FIG. 48, which shows the puncture frame 700 loaded onto the delivery apparatus 760 and in the delivery state 725). As the distal portion of the delivery apparatus 760 is advanced further through the sidewall of the vessel 12, the plurality of proximal fingers 752 are pushed outwards by the sidewall of the vessel 12, and the puncture frame 700 adopts the second delivery state 724 (FIG. 49). Thus, the puncture frame 700 can be transitioned to the second delivery state 724 without use of sutures secured to the plurality of eyelets 758, or a proximal fingers actuator (such as proximal fingers actuator 500) to pull the proximal fingers 752 into the second delivery state 724.

Figure 50:
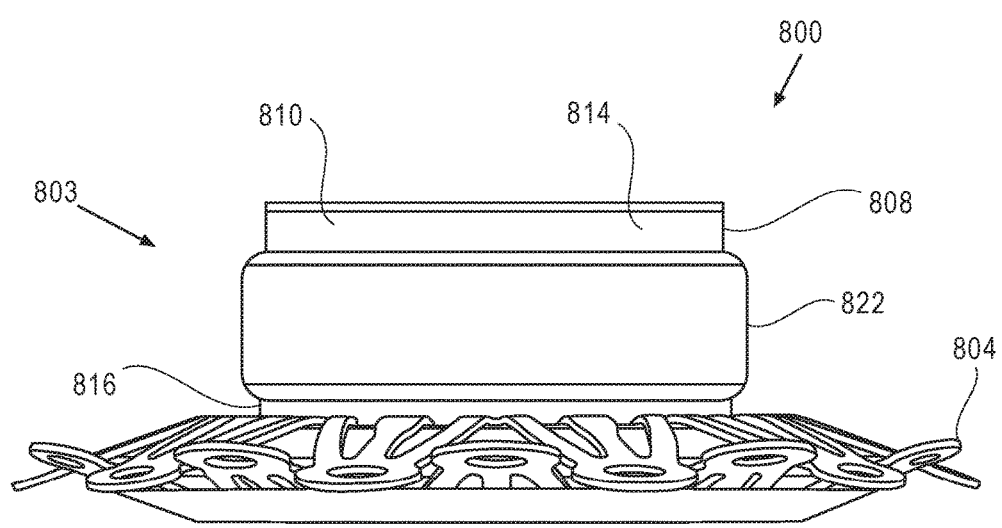
FIG. 50 shows a side view of a sealing device, in one embodiment.

In FIG. 50, there is shown a sealing device 800, according to another embodiment. Similar to the sealing device 2, the sealing device 800 is adapted to be deployed in the sidewall of the aorta, although it can also be used in other vessels of a subject. When deployed, the sealing device 800 has an open configuration 803 (see FIGS. 50 and 51A) and a sealed or closed configuration 805 (see FIG. 51C). Following implantation of the vessel opening and sealing device, the open configuration provides for access to the interior of a blood vessel in a patient, for example access for performing a surgical procedure (e.g., heart valve replacement or repair). When placed in the sealed configuration, the sealing device seals the opening 10 used to access the interior of the vessel.

The sealing device 800 includes a puncture frame or stent 804, and a tubular sealing member 808 that is secured to the puncture frame 804. The sealing member 808 can have an open state 810 and a closed state 812, and can be transitioned from the open state 810 to the closed state 812 by use of a suture loop 818 (described below). Thus, a twisting frame (similar to the twisting frame 6 of the sealing device 2) is not required for transitioning the sealing member 808 to the closed state 812. Sealing member 808 includes a proximal portion 814 and a distal portion 816. The distal portion 816 is secured to the puncture frame 804.

Figure 51A:
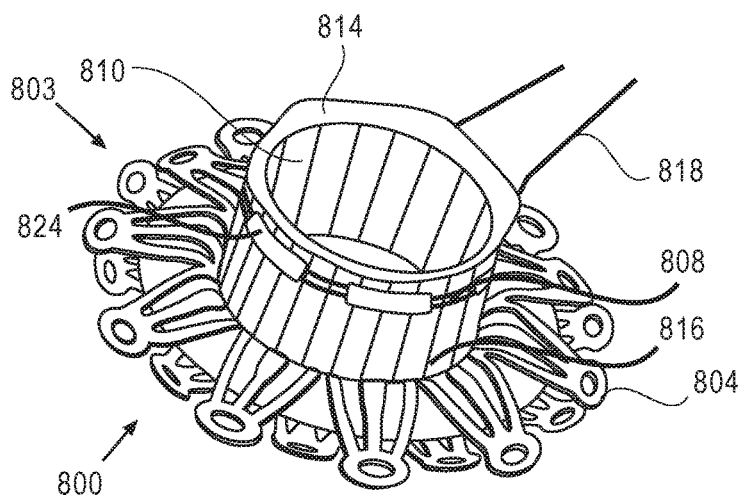
FIGS. 51A-51C show perspective views illustrating the operation of the sealing device of FIG. 50.
Figure 51B:
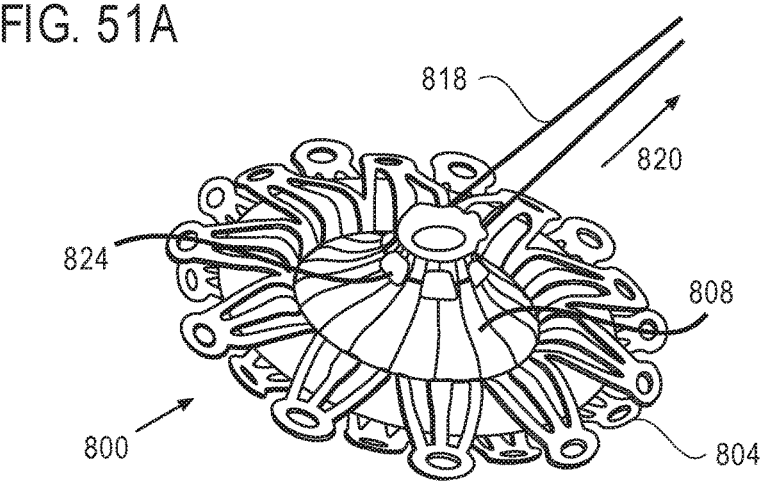
Figure 51C:
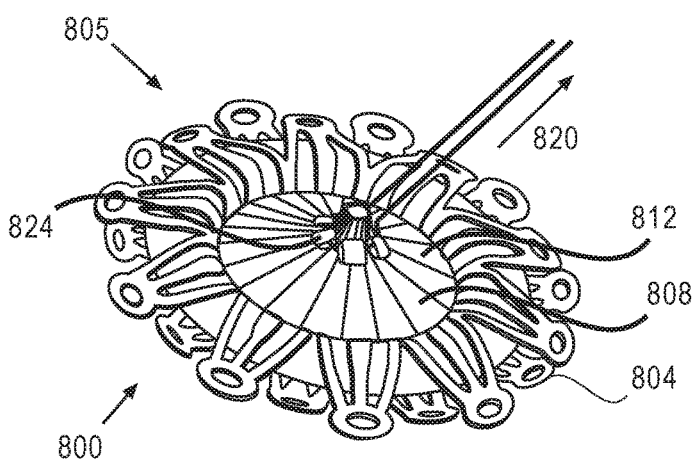

The suture loop 818 is used to transition the sealing member 808 from the open state 810 to the closed state 812. The suture loop generally operates as a purse-string closure for the sealing member 808. As such, the sealing device 800 can be described as a prosthetic, prefabricated purse-string suture. As illustrated by FIGS. 51A-51C, the suture loop 818 is secured around the outer surface of the sealing member 808. In some embodiments, the suture loop 818 can be secured by a sleeve. The sleeve can be a continuous sleeve 822 (as depicted in FIG. 50), where the ends of the suture loop 818 are passed through a sidewall of the sleeve, or a non-continuous sleeve 824 similar to a set of belt loops (as depicted in FIGS. 51A-51C), wherein the ends of the suture loop 818 are passed through a gap in the sleeve. In another embodiment, the sealing member 808 is constructed of two layers of material, and the suture loop 818 is secured to the sealing member 808 by running the suture loop between the two layers of material. In some embodiments, the two layers of material are formed by folding or doubling over at least a portion of the sealing member 808. In another embodiment, the suture loop 818 is sewn through the wall of the sealing member 808, in a fashion similar to a typical purse-string suture placed on a vessel wall.

Some embodiments include a plurality of suture loops 818, for example, as a backup in case of failure of one suture loop 818, for providing a more secure closure, and/or with tails exiting from circumferentially spaced positions of the sealing member 808 for providing additional control of sealing member. In some embodiments, at least two of the plurality of suture loops 818 are positioned at substantially the same longitudinal position of the sealing member 808, for example, the proximal end thereof. In some embodiments, a first suture loop 818 is disposed on the sealing member distally of a second suture loop 818.

The suture loop 818 wraps around the perimeter of the sealing member 808, and the free ends of the suture loop 818 can be pulled (e.g., in the direction of arrow 820) to cinch the suture loop 818, thereby transitioning the sealing member 808 from the open state 810 to the closed state 812. The suture loop can have any suitable configuration that allows tightening of the loop to transition the sealing member 808 to the closed state 812. For example, the suture loop 818 can be looped around the perimeter of the sealing member 808 with two free ends extending away from the sealing member 808, which can be pulled to transition the sealing member 808 to the closed state 812 (as shown in FIGS. 51A-51C). The suture loop can be wrapped around the perimeter of the sealing member 808 multiple times (such as twice). Alternative configurations include securing one of the ends of the suture loop 818 to the sealing member 808 such that the remaining end of the suture loop 818 can be pulled to tighten the suture loop. Alternatively, the suture loop 818 can be tied using any suitable known method that can be tightened, for example, using a knot or hitch such as a bowline, a clove hitch, a taught-line hitch, or cow hitch. In some embodiments, the suture loop 818 is locked, tied, or fastened using locking mechanism or device, for example, a clasp, a cord lock, a ratchet, a line tensioner, a clip, or the like. Some embodiments of the locking mechanism include a one-way feature, which permits the suture loop 818 to move in a first direction therethrough, but prevents movement in a second direction opposite the first direction. In some embodiments, the locking mechanism is controllable, for example, using another suture line that controls the locking and/or unlocking of the suture loop 818 by locking mechanism. In some embodiments, the locking mechanism is secured to the sealing device 800, for example, the sealing member 808, while in other embodiments, the locking mechanism is urged from the free end(s) of the suture loop 818 towards the sealing member 808 in the sealing step. Some embodiments include both features, for example, in a two-component locking mechanism. In a non-limiting example, the suture loops 818 can be tightened and held closed using a suture clip that is pushed down the suture loop, for example as described in U.S. Patent Pub. No. 2014/0031864, which is incorporated by reference herein in its entirety.

In some embodiments, the suture loop 818 is partially tightened around an introducer sheath or other instrument to maintain hemostasis. In some embodiments, the suture loop 818 is also used to apply and/or maintain tension on the sealing member 808, for example, when advancing an introducer sheath or other instrument therethrough. Keeping the sealing member 808 taut reduces or prevents the sealing member 808 from bunching-up, thereby reducing drag on and improving user control of the introducer sheath or other instrumentation.

Sealing devices including a sealing member that closes by use of a suture loop (such as the sealing device 800) can be used in place of the sealing device 2 for any application for which sealing device 2 has utility. In some embodiments, a suture loop (such as suture loop 818) can be secured to the sealing member of any of the disclosed sealing devices (such as the sealing device 2), for example as a secondary closure mechanism to the twisting closure of the sealing device 2.

FIG. 51D illustrates a delivery apparatus for implanting the sealing device 800 in a subject, according to one embodiment. The delivery apparatus illustrated in FIG. 51D is the same as delivery apparatus 200, except that the twisting frame actuator 600 has been eliminated. The twisting frame actuator 600 is not needed because the sealing device 800 does not include a twisting frame, and instead includes a sleeve on the tubular sealing member through which a suture loop can be tightened to seal the tubular sealing member. For illustration purposes, FIG. 51D shows the puncture frame 804, but the other components of the sealing device 800 have been omitted for clarity.

In another alternative embodiment (not illustrated), a first set of the distal fingers of the puncture frame are biased towards the center of the puncture frame in their relaxed or default positions, while a second set of distal fingers are biased away from the center in their relaxed or default positions. For example, starting from the embodiment illustrated in FIG. 5, every other distal finger 66 points radially inwardly instead of outwardly. The first set of distal fingers is sufficiently flexible to extend longitudinally in an open configuration when an instrument is inserted through the puncture frame. After withdrawing the instrument from the puncture frame, the first set of distal fingers pivots to the relaxed or closed configuration, thus defining a gate or valve. In some embodiments, at least some portion of the first set of distal fingers overlap or interlock in the closed or relaxed configuration, for example, edges and/or apices, thereby providing a more robust closure. Some embodiments of at least a portion of the first set of distal fingers have a different shape, for example, rectangular, trapezoidal, saw-tooth, or curved. In some embodiments, the apices of at least a portion of the first set of distal fingers are configured to interlock in the closed or relaxed configuration, for example, including a stepped-, a tabbed-, and/or a notched-shape. Some embodiments comprise 2n distal fingers, where n is an odd number, and where the first set of distal fingers comprises every other distal finger. In some of these embodiments, no distal finger in the first set is diametrically opposite another distal finger in the first set, reducing interference therebetween in transforming into the closed or relaxed configuration.

A portion of the sealing skirt secured to and covering the first set of distal fingers is movable with the distal fingers. In the open configuration, the sealing skirt assumes a tubular configuration, for example, cylindrical or frustoconical. In other embodiments, the sealing skirt is not circumferentially continuous in the open configuration, for example, comprising gaps between adjacent distal fingers. In the closed configuration, the sealing skirt occludes the central opening in the puncture frame. In some embodiments, portions of the sealing skirt extend past the apices of at least some of the first set of distal fingers, thereby improving sealing around the apices at the center of the puncture frame. In some embodiments, a purse string is placed through the extended portions of the sealing skirt and/or apices of the first set of distal fingers, which can be pulled closed to urge the first set of distal fingers into the closed configuration and/or to improve the seal in the closed configuration. Some embodiments of the sealing skirt are pre-pleated, resulting in a flatter configuration in the closed configuration, for example, pleated in a manner used in certain types of foldable or collapsible coin purses. In some embodiments, the sealing skirt has some rigidity and the pleats are live hinges. In some embodiments, the sealing skirt comprises an elastomeric or stretchable fabric. For example, in some embodiments, the entire portion of the sealing skirt attached to the first set of distal fingers is elastomeric or stretchable, while other embodiments comprise elastomeric or stretchable panels between adjacent distal fingers. Some embodiments of the distal fingers in the first set are partially or completely solid rather than skeletal and do not include a sealing skirt over the solid portions.

Embodiments of the alternative puncture frame can be used in embodiments of both the twisting frame and prosthetic purse-string suture devices described above. In the closed configuration, the sealing skirt and first set of distal fingers close or occlude the access opening in the puncture frame, thereby creating a secondary seal in addition to the twisting or purse-string seal of the tubular sealing member. Moreover, the blood pressure inside the vessel forces the sealing skirt and associated first set of distal fingers proximally, that is away from the center line of the vessel, thereby enhancing this secondary seal in some embodiments. In some embodiments, the seal created by the sealing skirt and first set of distal fingers is sufficient for the puncture frame to be used alone as an access and closure device, that is, without a tubular sealing member. In particular, embodiments of puncture frames with overlapping apices, interlocking apices, and/or extended sealing skirts exhibit enhanced sealing characteristics.

E. Exemplary Sealing Device 900 with a Tubular Twisting Member

Figure 52:
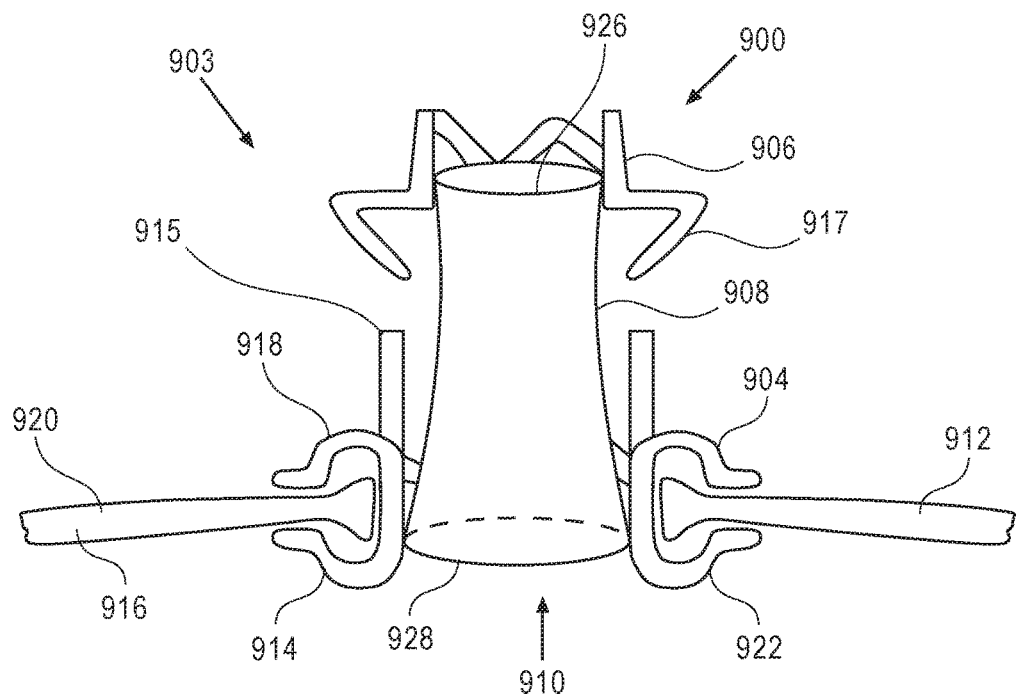
FIG. 52 is a perspective view of an opening and sealing device in an open configuration that can be used to provide access to the lumen of a vessel, such as the aorta, according to one embodiment.

In FIG. 52, there is shown a vessel opening and sealing device 900, according to another embodiment. Similar to the sealing device 2, the sealing device 900 is adapted to be deployed in the sidewall of the aorta, although it can also be used in other vessels or organs of a subject, such as a wall of the heart or aorta. When deployed, the sealing device 900 has an open configuration 903 or a sealed or closed configuration 905 (see FIG. 53). Following implantation of the vessel opening and sealing device, the open configuration 903 provides for access to the interior of a blood vessel in a patient, for example access for performing a surgical procedure (e.g., heart valve replacement or repair). When placed in the sealed configuration 905, the sealing device seals the opening 910 used to access the interior of the vessel.

Referring to FIG. 52, the puncture frame 904 is inserted into a surgical opening or aperture 910 in a sidewall of a vessel or chamber 912 (e.g., a blood vessel) in a patient to allow for access to the interior of the vessel 912 via the aperture 910. Similar to puncture frame 4, the puncture frame 904 includes a distal portion 914 that engages a luminal side 916 of the vessel 912, and a proximal portion 918 that engages an exterior side 920 of the vessel 912. The puncture frame 904 becomes secured in the aperture 910 in the sidewall of the vessel 912 when the distal portion 914 and the proximal portion 918 of the puncture frame 904 have engaged the luminal side 916 and the exterior side 920 of the vessel 912, respectively. The proximal portion 918 includes one or more connection features, such as in the form of posts 915, that are shaped to interlock with corresponding connection features, such as posts 917, on the puncture frame 904, thereby securing the twisting frame to the puncture frame. As discussed in more detail below, the puncture frame 904 is movable between at least a deployed state 922 (a clamped shape of the puncture frame when the proximal and distal portions are engaged with the sidewall of the vessel, as shown in FIG. 52) and a delivery state 924 (a shape of the puncture frame that allows insertion of the puncture frame 904 into the aperture 910 in the sidewall of the vessel 912, best shown in FIG. 68).

Figure 53:
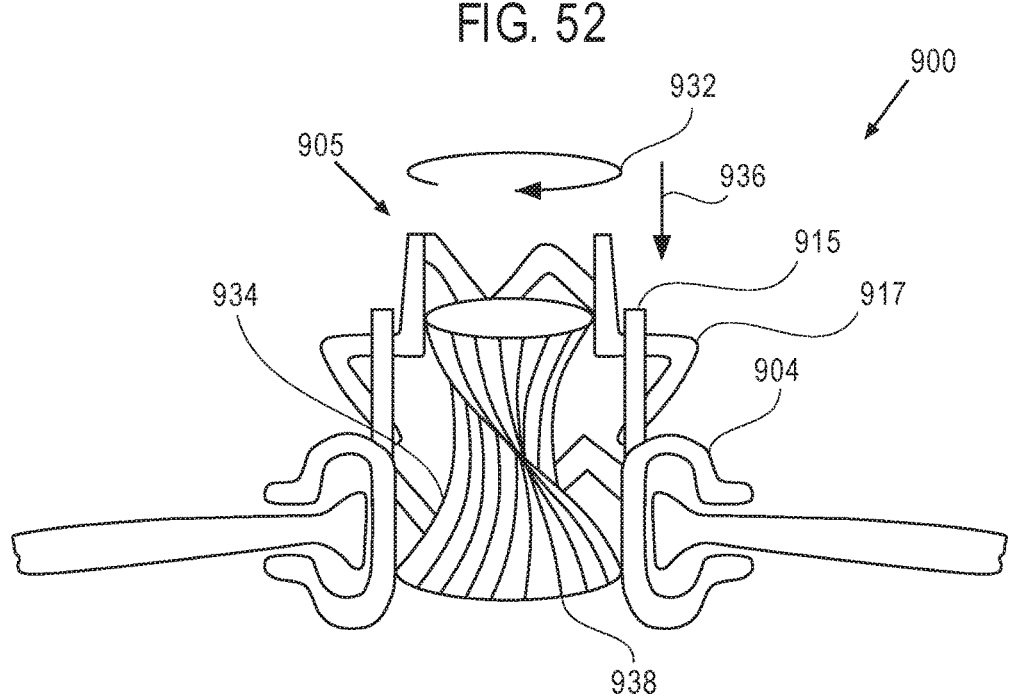
FIG. 53 is a perspective view of the vessel opening and sealing device of FIG. 52 shown in a closed or sealed state.

The tubular sealing member 908 is substantially the same as sealing member 8, and can have a tubular shape and can be made of a flexible and suitable material that allows twisting of the sealing member 908, and desirably is substantially impermeable to aqueous solutions, such as blood or plasma. When sufficiently twisted, sealing member 908 forms a fluid-tight, sealed state and prevents access into or egress from the interior of vessel 912 via aperture 910. As shown in FIG. 53, rotating the twisting frame 906, in a clockwise direction 932 in the illustrated embodiment, causes twisting 934 of the tubular sealing member 908. As tubular sealing member 908 is twisted, its length along the longitudinal axis of the sealing device 900 is shortened, resulting in movement of the twisting frame toward the puncture frame in the direction of arrow 936. When sufficiently close to each other, the connection posts 915 on the puncture frame engage the connection posts 917 on the twisting frame; thereby, securing the twisting frame to the puncture frame, and stabilizing the tubular sealing member in the sealed or closed state 938. In the illustrated embodiment, the connection posts 915 on the puncture frame have a female shape and interlock with the male shape on the corresponding connection posts on the twisting frame. However, any suitable interlocking shapes can be used for the connection posts 915 and 917, for example, the connection posts on the twisting frame can have a female shape and the connection posts 915 on the puncture frame can have a male shape.

Figure 54:
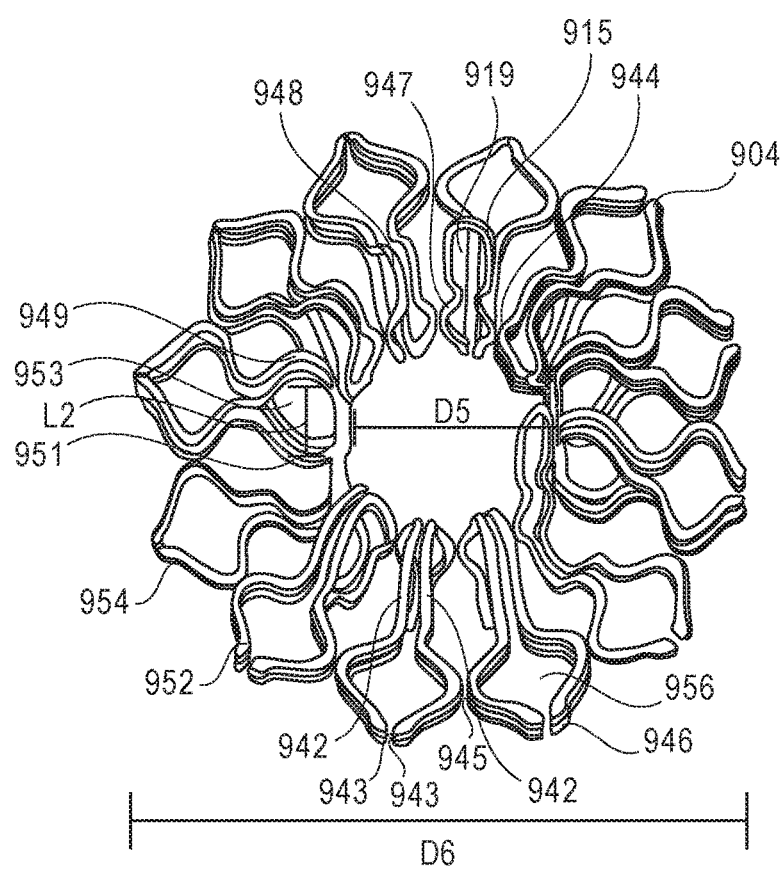
FIGS. 54 and 55 are perspective and side views of a puncture frame of the sealing device of FIG. 52.

FIG. 54 shows the puncture frame 904, without the other components of the vessel opening and sealing device for purposes of illustration. Similar to puncture frame 4, the puncture frame 904 can be formed from a plurality of struts 942. The struts 942 are formed in a mesh structure with alternating bends to form a plurality of proximal fingers 952 and a plurality of distal fingers 954 that terminate in proximal and distal apices or vertices 946, and which extend outward from the longitudinal axis of the frame in deployed state 922. The struts 942 also form central folds 947 at the inner diameter of the frame 904. As illustrated in FIG. 54, the distal fingers can align with the proximal fingers such that the proximal and distal apices 946 are aligned when the frame is in deployed state 922.

As shown in FIG. 54, the puncture frame 904 can include multiple connection posts 915 that extend proximally relative to the longitudinal axis of the frame 904 in deployed state 922. Each connection post can be formed from the struts 942 and can be included on a continuous loop of material that also includes a distal finger; or, alternatively, can be formed by struts 946 that can be welded or otherwise secured at a node 943 on the distal finger or the connection post, or on both the distal finger and the connection post. The connection posts 915 on the puncture frame are shaped to interlock with the connection posts 917 on the twisting frame. In the illustrated embodiment, each connection post 915 on the puncture frame includes an aperture 919 sized to receive and retain the connection posts 917 of the twisting frame.

In the illustrated embodiment, each of the proximal and distal fingers comprise two lateral struts 942, which converge at a respective apex or vertex 946 of the proximal or distal finger. Each aligned proximal and distal finger can be formed by a pair of struts 942 that are connected side-by-side in a continuous loop, which can be laser cut or otherwise formed from a tubular piece of material or from flat stock. Alternatively, aligned proximal and distal fingers can be formed by a pair of struts 946 that can be welded or otherwise secured at a single node 943 on a proximal or distal finger, or by a node 943 on each proximal and distal finger. Each pair of proximal and distal fingers can be welded or otherwise secured to adjacent pairs at nodes 944 and 945 to form a mesh structure having a plurality of rectangular and oval-shaped cells 948 between the struts 942. In other embodiments, the struts define one or more different shapes. For example, in some embodiments, at least some of the struts comprise tabs and do not define cells at all.

Similar to the puncture frame 4, the struts 942 can be made of a suitable shape-memory material (such as Nitinol) that allows the puncture frame to be tensioned to one or more delivery states during delivery using a delivery apparatus and then allows the puncture frame to revert to the deployed state 922 when deployed from the delivery apparatus.

The plurality of proximal fingers 952 and a plurality of distal fingers 954 can have a general petal shape, and can extend radially outwardly from a longitudinal axis of the puncture frame 904. In other embodiments, at least some of the proximal fingers or distal fingers have a different shape, for example, straight or curved wires, rectangles, trapezoids, ovals, circles, or triangular (such as in puncture frame 4) shapes. In the illustrated embodiment, each finger in the plurality of proximal fingers 952 and the plurality of distal fingers 954 includes an aperture 956 formed from the struts 942. However, solid fingers (or tabs) are also possible.

The plurality of proximal fingers 952 and the plurality of distal fingers 954 can extend outwardly from the longitudinal axis at an angle of about 90° from a longitudinal axis when the puncture frame is in the deployed state 922. In some embodiments, the plurality of proximal fingers 952 can extend outwardly from the longitudinal axis at an angle of more than about 90° from the longitudinal axis and the plurality of distal fingers 954 can extend outwardly from the longitudinal axis at an angle of less than about 90° from the longitudinal axis, such that the plurality of proximal fingers 952 and the plurality of distal fingers 954 are sloped or angled towards each other when the puncture frame is in the deployed state 922.

In the illustrated embodiment, the lateral struts 942 of the distal fingers 952 together define a 12-pointed star in the deployed state 922 of the puncture frame 904. The lateral struts 942 of the proximal fingers 954 together define a 9-pointed star in the deployed state 922 of the puncture frame 904, with a connection post 915 alternating between every three points of the star. In other embodiments, the puncture frame can include more or fewer proximal or distal fingers, or connection posts.

Figure 55:
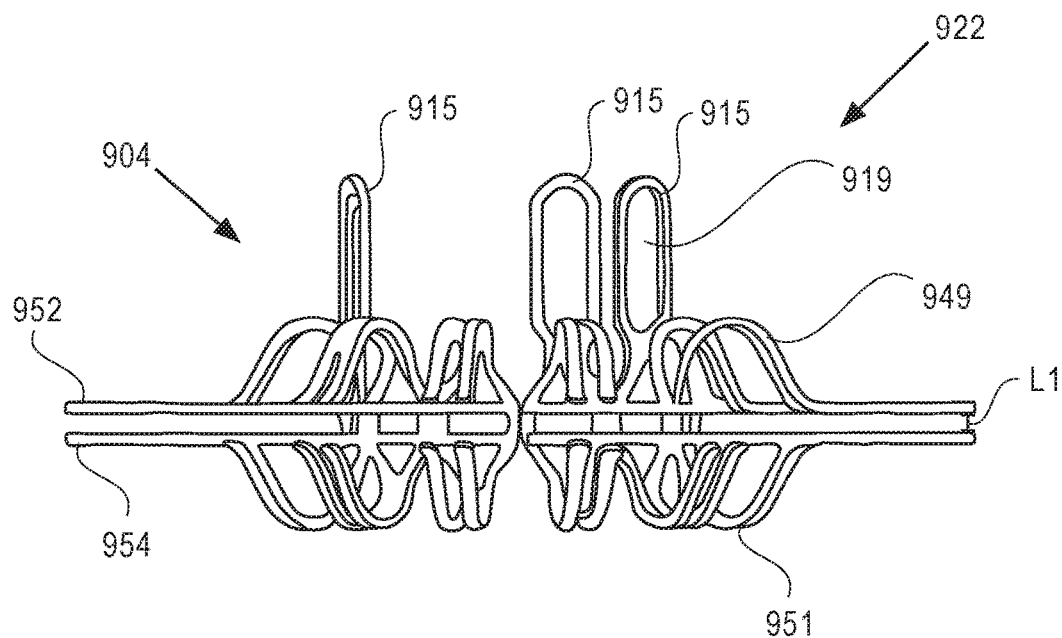

The plurality of proximal fingers 952 is separated from the plurality of distal fingers 954 by length L2 (shown in FIGS. 54 and 55) adjacent the central aperture of the frame 904. L2 is appropriately sized for engagement of the sidewall of vessel 912 by the plurality of proximal fingers 952 and the plurality of distal fingers 954. Where the proximal fingers 952 meet the distal fingers 954 around the central opening, L2 can be twice the radius of curvature of the puncture frame 904. In the embodiment shown in FIGS. 54 and 55, L2 is larger towards the center of the puncture frame 904 and gets smaller towards the center portion of the proximal and distal fingers. For example, as shown in FIG. 54, the struts 942 of the plurality of proximal fingers 952 and the plurality of distal fingers 954 can have mirrored curves 949 and 951, respectively, such that in the deployed state 922, the proximal and distal fingers form a plurality of oval-shaped pockets 953. These pockets can provide space for a sealing skirt or other material to be included on the puncture frame and engage the vessel sidewall to reduce leakage from the vessel lumen.

Referring again to FIG. 54, the puncture frame 904 has a circular shape having an inner diameter D5 and an outer diameter D6. The inner diameter D5 is from slightly less to slightly greater than that the diameter of the aperture 910 in the sidewall of vessel 912. The inner diameter D5 is suitably sized to allow access to the intraluminal space of the vessel 912 by a treating physician, for example, for implantation of a heart valve. The outer diameter D6 is defined by the circumference formed from the apices of the proximal fingers 952 and the distal fingers 954 of the puncture frame 904. The distance between the inner diameter D5 and the outer diameter D6 generally sets the length of the proximal fingers 952 and the distal fingers 954. The lengths of the proximal fingers 952 and the distal fingers 954 desirably are sufficient for engaging the exterior side 920 and the interior side 916, respectively, of the sidewall of the vessel 912 in a manner that reduces or minimizes blood loss through the aperture 910 of vessel 912. In other embodiments, at least one of the inner diameter or outer diameter of the puncture frame 904 can have an elliptical- or oval-shape comprising two different diameters.

The puncture frame 904 is movable between at least the deployed state 922, and the delivery state 924. The deployed state 922 is described above. In the delivery state 924, the plurality of distal fingers 954 and the plurality of proximal fingers 952 can be substantially aligned with the longitudinal axis of the puncture frame 904, with the distal and proximal fingers extending in opposite directions (see FIG. 68). The delivery state 924 allows the distal fingers 954 to pass through the aperture 910 of the sidewall of vessel 912 to the interior of the vessel. When the puncture frame 904 is released during delivery, the puncture frame reverts to the deployed state 922, wherein the proximal fingers 952 and the distal fingers 954 engage the exterior side 920 and the luminal side 916 of the sidewall of vessel 912, respectively, and the connection posts 915 extend proximally relative to the longitudinal axis of the puncture frame 904.

Figure 56:
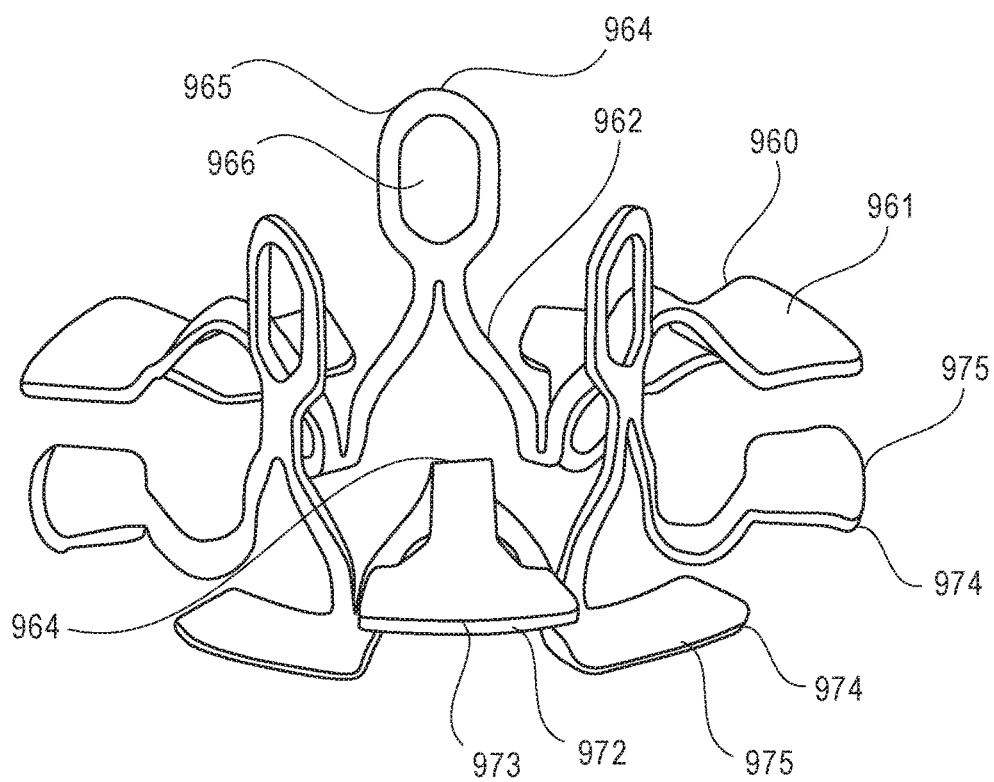
FIG. 56 is a perspective view of a puncture frame of a vessel opening and sealing device according to another embodiment.

FIG. 56 shows another embodiment of a puncture frame for use with device 900, generally indicated at 960, shown in a deployed state 961 and without the other components of the vessel opening and sealing device for purposes of illustration. Similar to puncture frame 904, the puncture frame 960 can be formed from a plurality of struts 962. The struts 962 are formed in a mesh structure with alternating bends to form a plurality of proximal fingers 972 and a plurality of distal fingers 974 that terminate in proximal tabs 973 and distal tabs 975, respectfully, and which extend outward from the longitudinal axis of the frame in the deployed state 961.

As shown in FIG. 56, the puncture frame 960 can include multiple connection posts 964 that extend in a proximal direction parallel to the longitudinal axis of the frame 960 in the deployed state. Similar to the aligned proximal and distal fingers, each connection post can be formed from the struts 962 and can terminate with an eyelet 965 including an aperture 966. The connection posts 964 on the puncture frame 960 are shaped to interlock with the connection posts (such as connection posts 917) on a corresponding twisting frame. In the illustrated embodiment, each aperture 966 is sized to receive and retain a respective connection post 917 of the twisting frame.

Similar to the puncture frame 904, the puncture frame 960 includes an inner diameter that can be from slightly less to slightly greater than that the diameter of the aperture 910 in the sidewall of vessel 912. The outer diameter is defined by the circumference formed from the apices of the proximal and distal fingers 972, 974 of the puncture frame 960 in the deployed state 961. The distance between the inner and outer diameters generally sets the length of the proximal and distal fingers 972, 974.

The illustrated embodiment of the puncture frame 960 includes three proximal fingers, six distal fingers, and three connection posts. As illustrated by the puncture frames 904 and 960, the number of proximal fingers and distal fingers, the length of the fingers, the number of connection posts 964, and the inner and outer diameter of the puncture frame can be varied as needed for particular applications of the puncture frame.

Figure 57:
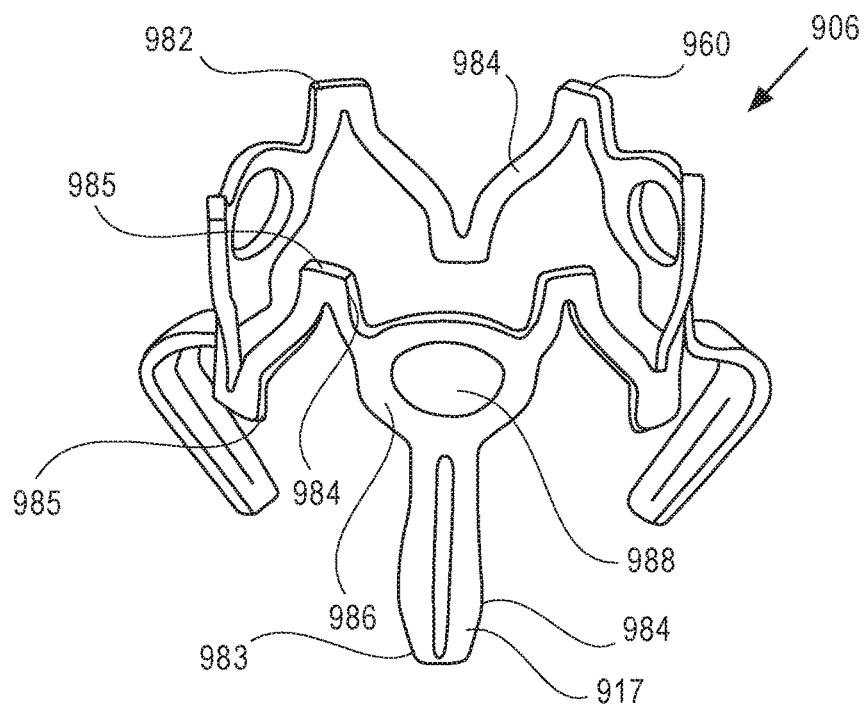
FIGS. 57 and 58 are perspective and top views of a twisting frame of the sealing device of FIG. 52.
Figure 58:
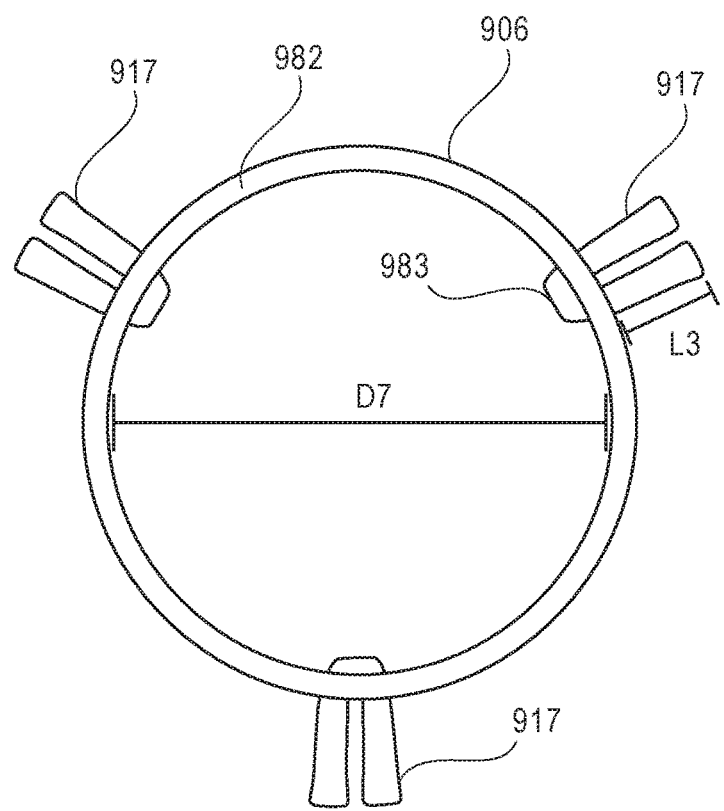

FIG. 57 shows the twisting frame 906, without the other components of the vessel opening and sealing device 900 for purposes of illustration. The twisting frame 906 includes a proximal end 982 and a distal end 983, and can have a substantially annular shape formed from a plurality of struts 984. The struts 984 are formed in a zigzag structure with alternating bends to form the annular shape of the twisting frame 906 and with proximal and distal apices or vertices 985. The struts 984 also form one or more eyelets 986 (three are shown in the illustrated embodiment). The eyelets 986 form apertures 988 that can be appropriately sized for securing the twisting frame to a delivery apparatus during implantation of the sealing device in a patient (such as described below). The struts 984 can be welded or otherwise secured to each other to form the structure of the twisting frame 906. Alternatively, the twisting frame 906 can be laser cut, electrical-discharge machined, or otherwise formed from a cylindrical tube or from flat stock, for example, in a single piece. As shown in FIG. 58, the twisting frame 906 can have an inner diameter D7 that can be substantially similar to the inner diameter D5 of the puncture frame 904 (FIG. 54).

The twisting frame 906 can be made of a suitable material, including metal (such as Nitinol or stainless steel, polymer, or composites), and is suitably thick, to allow the twisting frame 906 to have sufficient stiffness for rotation during operation of the vessel opening and sealing device (such as described below). Where the twisting ring 906 is metal, it can be the same metal as the puncture frame 904 to avoid galvanic corrosion.

As shown in FIG. 58, the twisting frame 906 can include one or more connection posts 917 that can extend distally from the twisting frame, and which can bow outwardly by a length L3 from the eyelets 986. The posts 917 are shaped to be suitable for interlocking with the apertures 919 of the connection posts 915 of the puncture frame 904, to secure the sealing device 902 in the sealed configuration. The connection posts 917 can flex or deflect inwardly relative to eyelets 986 and the struts 984 to engage the apertures 919 of the connection posts 915 when the twisting frame is rotated.

Figure 59:
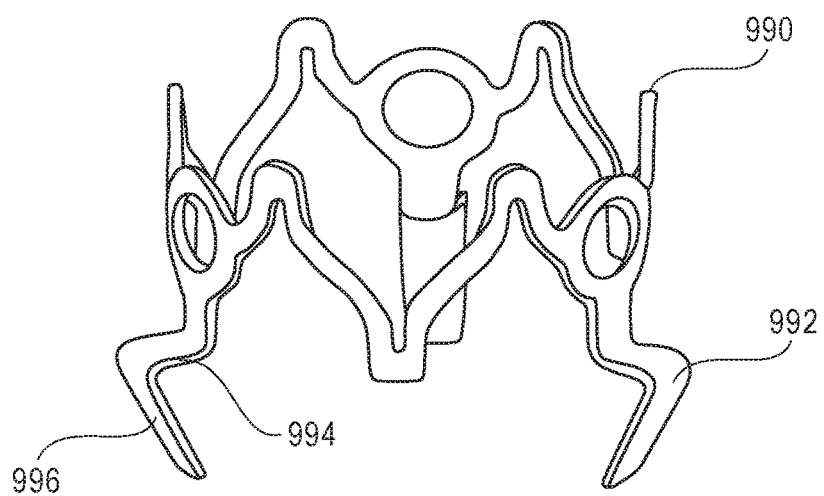
FIG. 59 is a perspective view of a twisting frame of an opening and sealing device according to another embodiment.

FIG. 59 shows a twisting frame 990 according to another embodiment. As shown, the twisting frame 990 can be substantially the same as the twisting frame 906, but includes differently shaped connection posts for securing to the puncture frame. Twisting frame 990 includes connection posts 992, which can be shaped to include a proximal portion 994 that extends radially outwardly at an angle of about 90° from the longitudinal axis. The connection post then bends back and includes a distal portion 996 that extends radially inwardly toward the longitudinal axis. The "ledge" formed by this shape of the connection post 992 can engage the aperture 919 of a connection post 915 of the puncture frame to secure the twisting frame in a rotationally stable position.

Figure 60:
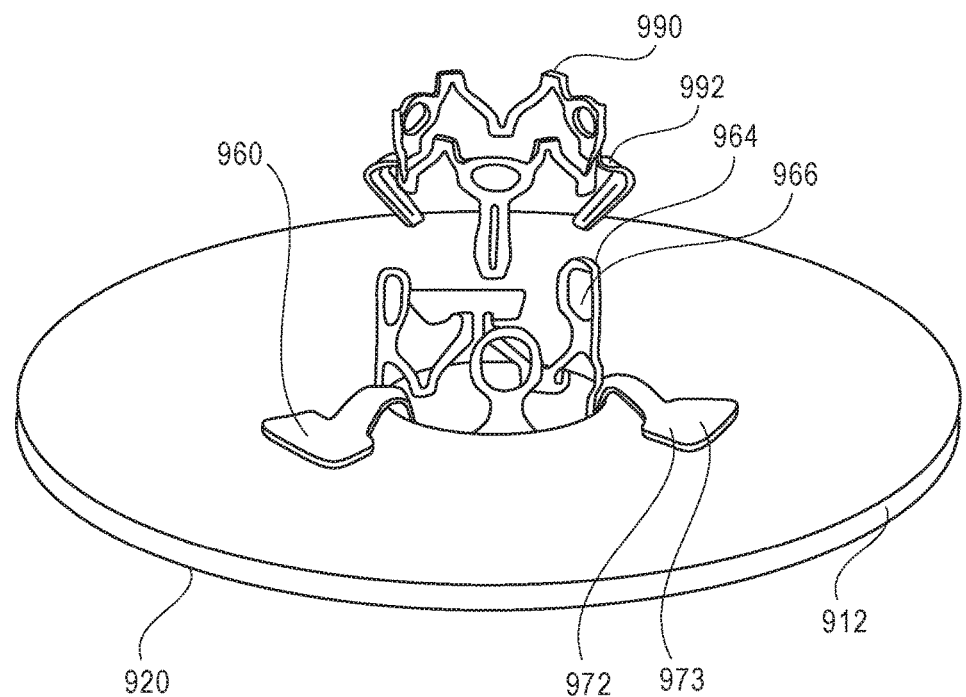
FIGS. 60 and 61 show exterior and luminal perspective views, respectively, of an embodiment of an opening and sealing device implanted in an aperture in a vessel sidewall. In the illustrated embodiment, the twisting frame is not interlocked with the puncture frame. For clarity, the tubular sealing member of the device is not shown.
Figure 61:
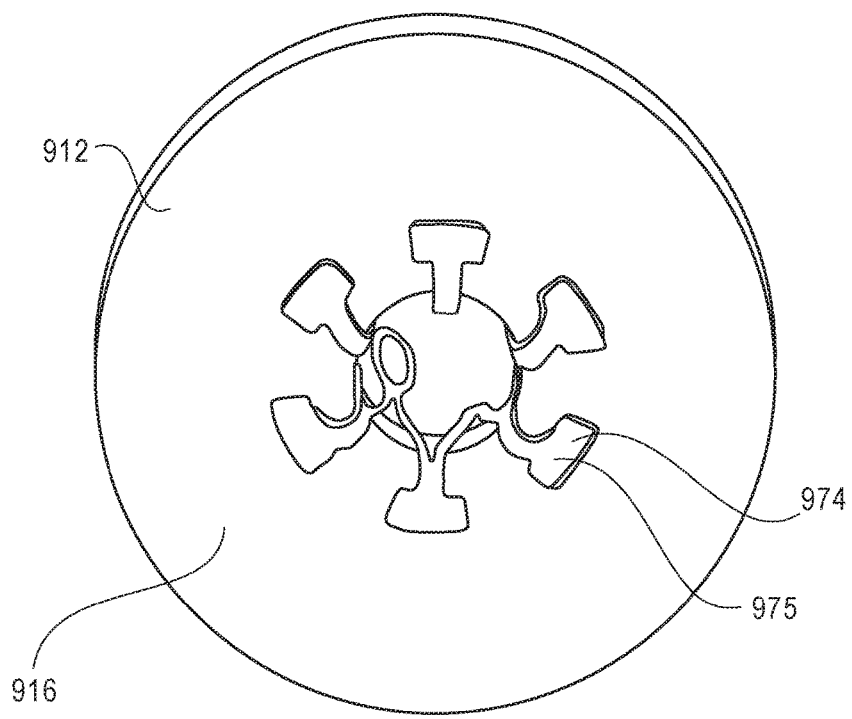
Figure 62:
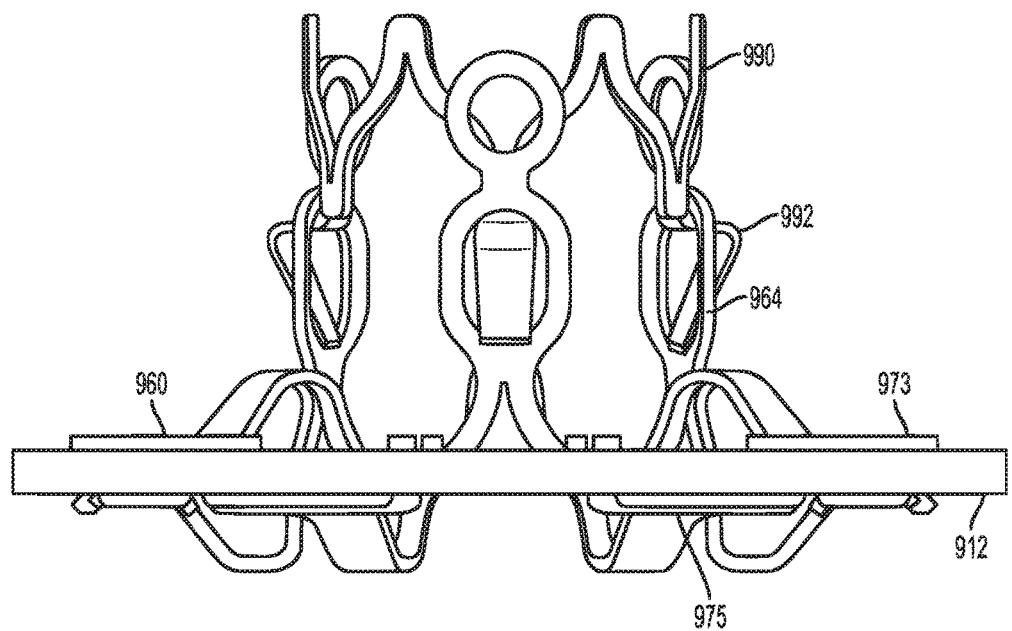
FIG. 62 shows a side view of an embodiment of an opening and sealing device implanted in an aperture in a vessel sidewall. In the illustrated embodiment, the twisting frame is interlocked with the puncture frame. For illustration purposes, the tubular sealing member of the device is not shown.

FIGS. 60-62 illustrate the puncture frame 960 in the deployed state and engaged with a vessel sidewall 912 and the twisting frame 990 before (FIG. 60) and after (FIG. 62) the connection posts 964 of puncture frame 960 are engaged by the connection posts 992 of twisting frame 990. For purposes of illustration, the remaining components of the vessel opening and sealing device are not shown.

The puncture frame 960 can include a sealing skirt to seal openings in the puncture frame and to reduce leakage of fluids from the lumen of the vessel 912. The sealing skirt can be substantially similar to the sealing skirt 100 (FIG. 10) included with the vessel opening and sealing device 2. Similar to sealing skirt 100, the sealing skirt of the present embodiment can be secured to the inside of the puncture frame 962, and is positioned such that the proximal fingers 972 of puncture frame 960 are positioned between the exterior side 920 of the sidewall of vessel 912 and a proximal portion of the sealing skirt, and the distal fingers 974 of puncture frame 904 are positioned between the luminal side 916 of the sidewall of vessel 912 and the distal portion of the sealing skirt, when the vessel opening and sealing device is implanted in a patient. Similar to sealing skirt 100, the sealing skirt on the puncture frame 960 serves as a barrier to seal against fluid (e.g., blood or plasma) leakage between the frame 904 and the sidewall of vessel 912. The puncture frame 904 (FIG. 55) also can have a sealing skirt configured in the same manner. In alternative embodiments, any of the puncture frames described herein can have a sealing skirt secured to the outside of the puncture frame.

F. Exemplary Delivery Apparatus for Use with Device 900

Figure 63:
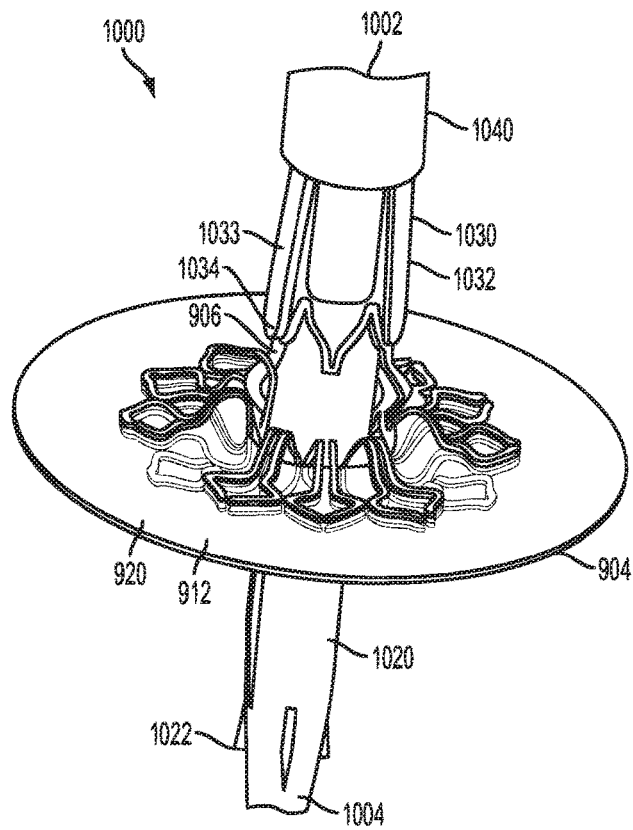
FIG. 63 shows a perspective view of an embodiment of an opening and sealing device mounted on a delivery apparatus and implanted in an aperture in a vessel sidewall.

FIG. 63 illustrates the sealing device 900 in a deployed state and still loaded on a delivery apparatus 1000 for implantation in a subject, according to one embodiment. For illustration purposes, FIG. 63 shows the puncture frame 904 and the twisting frame 906, but the other components of the sealing device 900 have been omitted for clarity. The delivery apparatus 1000 includes a number of coaxial sleeves which are relatively axially slidable and angularly rotatable along a longitudinal axis extending from the proximal end to the distal end of the apparatus. Preferably, the sleeves are actuatable by the physician from the proximal end portion of the instrument. The delivery apparatus 1000 generally includes an introducer sheath (not shown, the introducer sheath can be substantially similar to introducer sheath 300), a dilator 1020, a twisting frame actuator 1030, and an outer cylinder or sleeve 1040, which are described in more detail below.

The dilator 1020 can include a nose cone portion 1021 (see FIG. 65), which can be curved or conical to facilitate insertion into an aperture in the side wall of the vessel 912. The dilator 1020 can optionally include extendable and retractable cutting members 1022 (e.g., blades) on the nose cone portion 1021 of the dilator, and proximal to the distal tip of the dilator, that are substantially similar to the extendable and retractable cutting members 1082 of dilator 1080 (discussed below). The distal tip of the dilator includes an aperture configured to allow passage of a guide wire 1023 and/or a hypodermic needle from a guide wire lumen extending longitudinally through the dilator.

Figure 68:
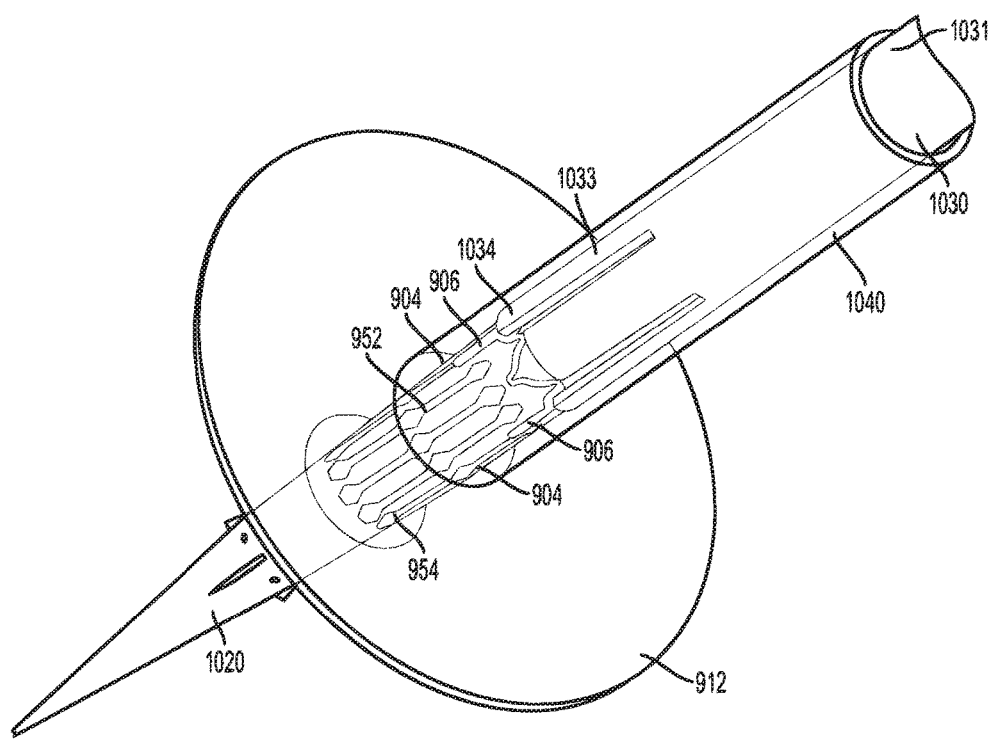

Referring to FIGS. 63 and 68, the twisting frame actuator 1030 in the illustrated embodiment includes a coaxial sleeve or shaft 1031 that is positioned between the dilator 1020 and the outer cylinder 1040 on delivery assembly 1000. The twisting frame actuator 1030 can be axially slidable and angularly rotatable relative to the dilator 1020 and the outer cylinder 1040. The twisting frame actuator 1030 includes a proximal portion and a distal portion 1032. The proximal portion can be secured to a handle or other suitable member for operation by a treating physician. The distal portion 1032 can have a plurality of arms or projections 1033 that extend distally from the distal end of the shaft 1031. Each projection 1033 can have a distal tip 1034 with a suitably shaped tab or tooth 1035 that can releasably engage the aperture 988 of an eyelet 986 on the twisting frame (see FIG. 73) to releasably secure the twisting frame to the twisting frame actuator 1030. When secured, the projections 1033 secure the twisting frame 906 to the twisting frame actuator 1030. Therefore, rotating the twisting frame actuator 1030 causes corresponding rotation of the twisting frame 906 (FIG. 63), and the sealing member 908, to which the twisting frame 906 is secured. Thus, angular rotation of the twisting frame actuator 1030 can be used to rotate the sealing member 908 into its closed state 938. In some embodiments, the twisting frame actuator can be used to apply and/or maintain tension on the sealing member 908, which prevents the sealing member from bunching up, for example, when advancing the introducer sheath or other instrument therethrough.

Figure 72:
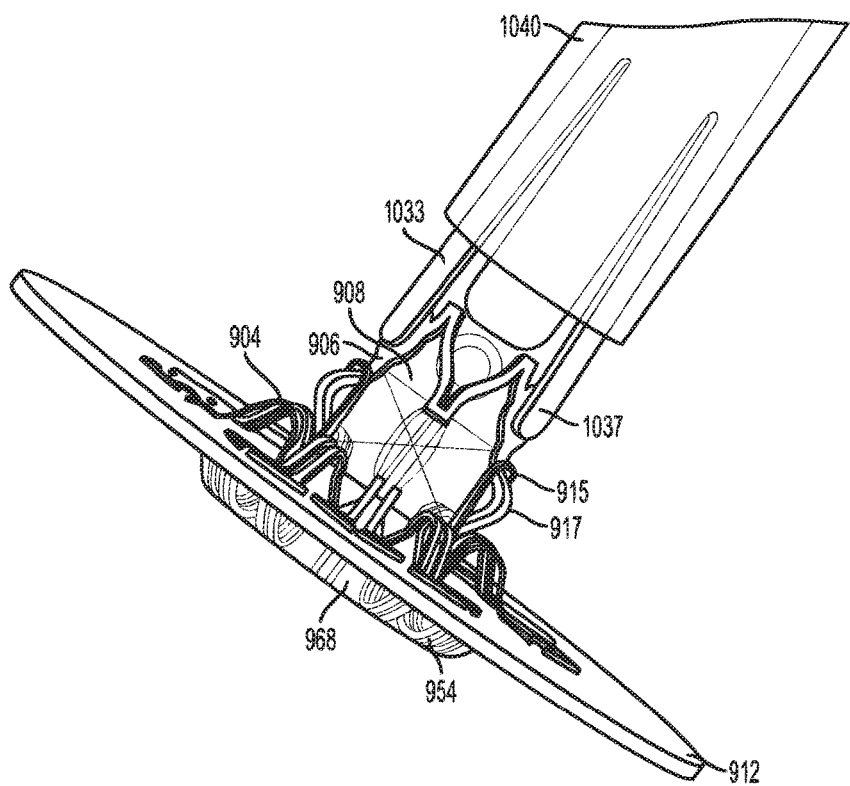
Figure 73:
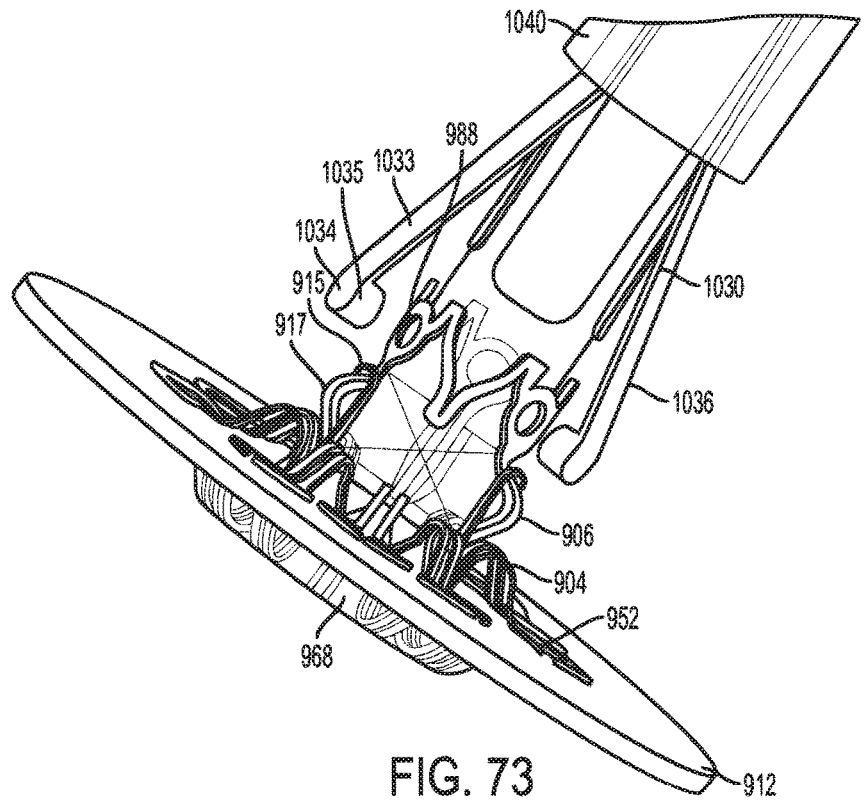

The projections 1033 of the twisting frame actuator can be made of a memory material that has a non-constrained state 1036 where the projections project radially outwardly from the longitudinal axis of the twisting frame actuator (shown in FIG. 73). In the non-constrained state 1036, the teeth 1035 do not engage with the apertures 988 of the twisting frame; thus the twisting frame can be released from the twisting frame actuator by moving the projections 1033 to their non-constrained state 1036. The projections 1033 can be radially collapsed to a constrained state 1037 where the projections extend substantially axially as shown in FIG. 72. When in the constrained state 1037, and properly positioned relative to the twisting frame, the teeth 1035 of the projections engage respective apertures 988 of the twisting frame, thereby releasably securing the twisting frame actuator to the twisting frame.

In several embodiments, the projections 1033 of the twisting frame actuator can be moved between the constrained and non-constrained states 1037, 1036, by use of the outer cylinder 1040. As shown in FIG. 72, the distal end of the outer cylinder 1040 can be positioned over all or a sufficient portion of the projections 1033 to collapse the projections to the constrained state 1037. By moving the outer cylinder 1040 proximally, the distal end of the outer cylinder 1040 will no longer retain the projections 1033 in their constrained state, allowing the projections to self-expand radially to the non-constrained state 1036, thereby releasing the twisting frame (FIG. 73).

FIG. 68 shows the puncture frame 904 in the delivery state 924. In this state, the distal fingers 954 and the proximal fingers 952 of the puncture frame 904 are held in the delivery state between the sleeve portion 1023 of dilator 1020 and the outer cylinder 1040, with the plurality of distal fingers 954 and the plurality of proximal fingers 952 extending in opposite directions and substantially parallel to the longitudinal axis of the puncture frame 904. The puncture frame 904 can be loaded onto the delivery apparatus 1000 in the delivery state 924, for example, by a user.

Figure 70:
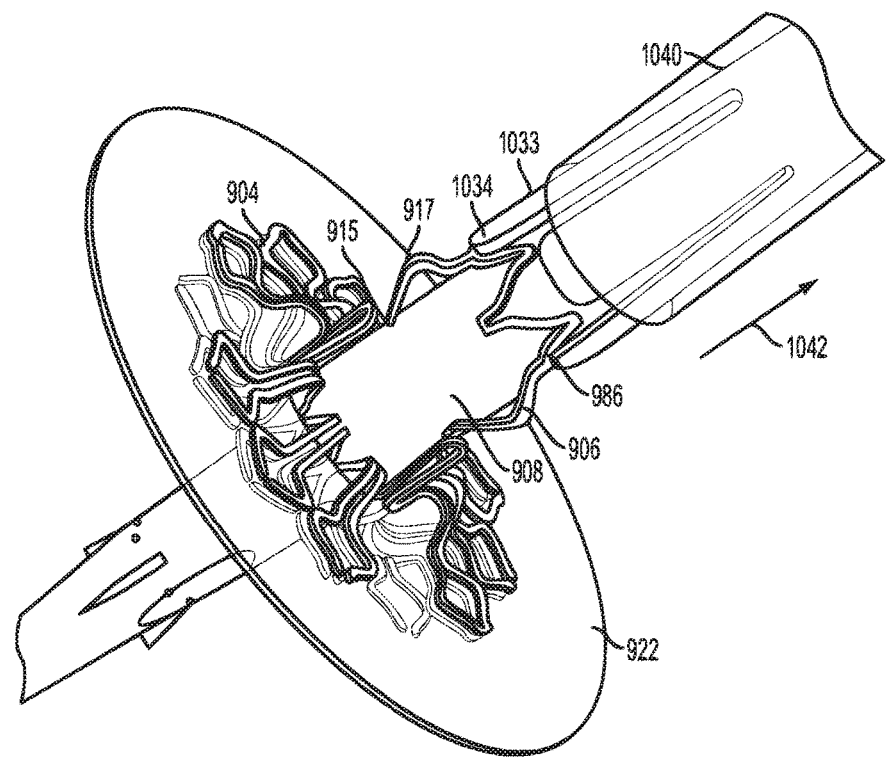

FIG. 70 shows the puncture frame in the deployed state 922 following proximal retraction of the outer cylinder 1040 in the direction of arrow 1042. When the distal end of the outer cylinder 1040 is moved proximally beyond the distal fingers 954 of the puncture frame 904, the distal fingers 954 move toward the luminal side of the vessel wall 910 due to the shape memory of the puncture frame 904. As the outer cylinder 1040 is moved farther proximally beyond the proximal fingers 952 of the puncture frame 904, the proximal fingers 952 move toward the outer side of the vessel wall 910 due to the shape memory of the puncture frame 904, and the puncture frame adopts deployed state 922, shown in FIG. 70.

G. Exemplary Method of Using Device 900

FIGS. 64-80 illustrate an exemplary method of using a disclosed vessel opening and sealing device and a delivery apparatus for accessing the lumen of a vessel (such as the aorta) for performing an endoluminal procedure via an aperture in the sidewall of the vessel, and then sealing the aperture following the endoluminal procedure. The illustrated method utilizes the delivery apparatus 1000 and the sealing device 900; however, other embodiments of a sealing device and/or a delivery apparatus (for example, any of the embodiments described herein) can be used to perform the disclosed method. In several embodiments, the disclosed method is used to create and seal an aperture in a sidewall of the aorta in a patient during a surgical procedure, such as implantation of a prosthetic heart valve (e.g., a prosthetic aortic valve).

Prior to initiation of the method, the sealing device 900 is loaded onto the delivery apparatus 1000, with the puncture frame and twisting frame held in a constrained, delivery state between the dilator 1020 and the outer cylinder 1040. The puncture frame is not secured to the twisting frame by the connection posts of each frame, but the sealing member 908 is secured to the puncture frame and the twisting frame, for example, by securing the distal portion of the sealing member to the puncture frame (e.g., by suturing the sealing member to the struts of the puncture frame or to a sealing skirt secured to the puncture frame) and securing the proximal portion of the sealing member to the twisting frame (e.g., by suturing the sealing member to the struts of the twisting frame).

Figure 64:
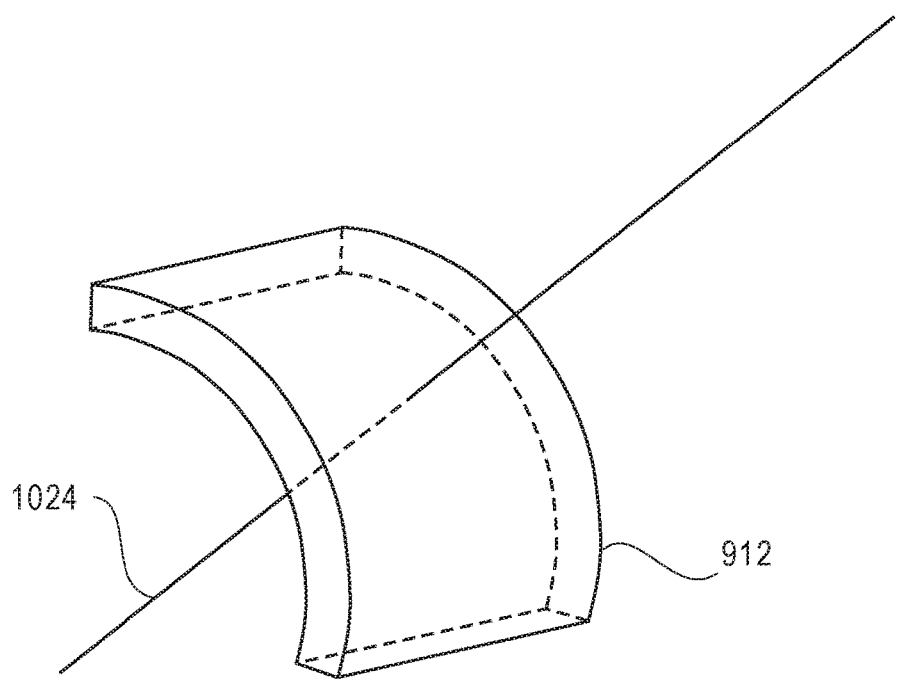
FIGS. 64-77 illustrate an exemplary method of using a disclosed opening and sealing device and a delivery apparatus for accessing the lumen of a vessel for performance of an endoluminal procedure via an aperture in the sidewall of the vessel, and then sealing the aperture following the endoluminal procedure.

In particular embodiments, a hypodermic needle can be advanced through the lumen and aperture at the distal tip of the nose cone 1021 of the dilator 1020 and inserted through the sidewall of the vessel 912. The guide wire 1024 can then be inserted through the hypodermic needle and into the lumen of the vessel 912, and placed as needed for the endoluminal procedure. After placement of the guide wire 1024, the hypodermic needle can be retracted from the sidewall of the vessel 912, leaving the guide wire in place (FIG. 64).

Figure 65:
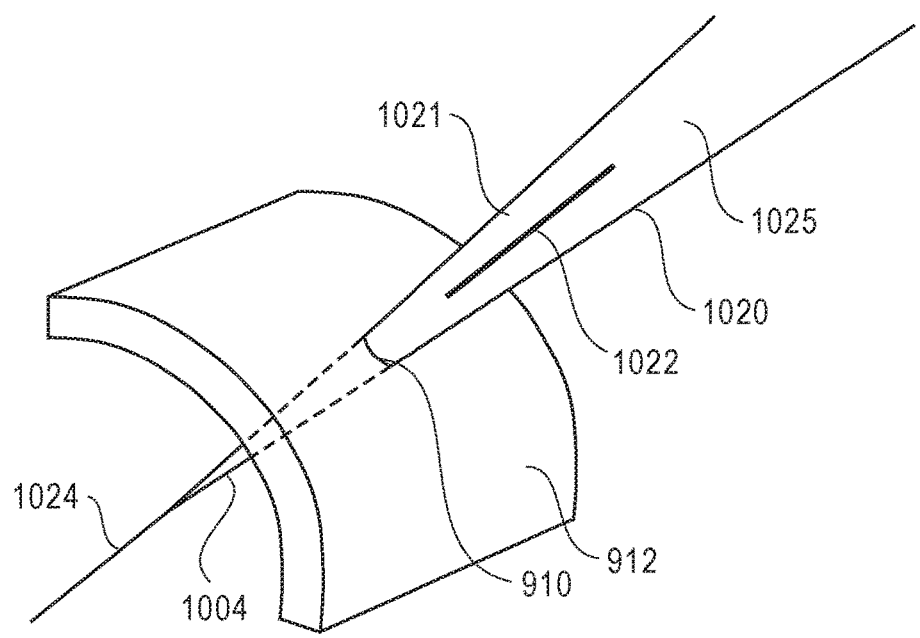
Figure 66:
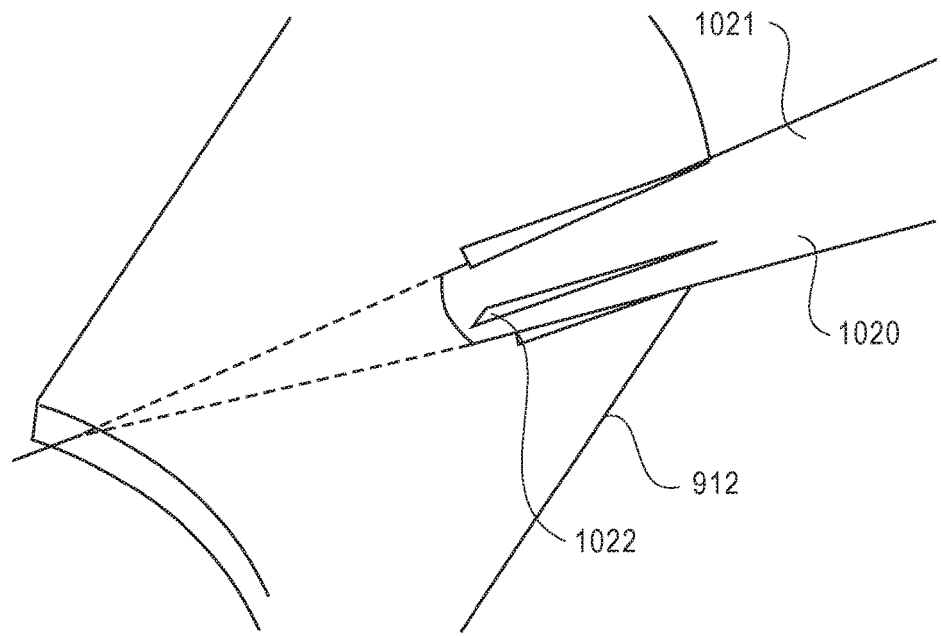
Figure 67:
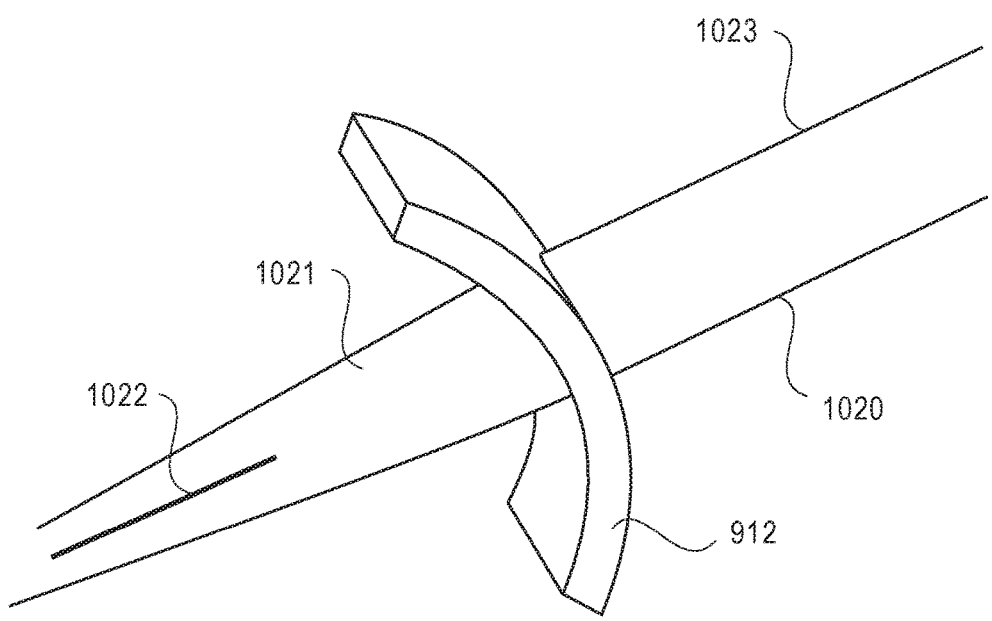

After placement of the guide wire 1024, the delivery apparatus 1000 can be advanced distally over the guide wire until the distal tip of the nose cone 1021 penetrates the sidewall of the vessel 912 (FIG. 65). In the illustrated embodiment, the dilator 1020 includes extendable and retractable cutting members 1022, which can be extended from the dilator body to facilitate traversal of the vessel sidewall 912 by the nose cone and for widening of the aperture 910 (FIG. 66). After the cutting members 1022 have traversed the vessel sidewall 912, they can be retracted into the body of the nosecone 1002 (FIG. 67). Optionally, an incision in vessel sidewall 912 can be performed prior to advancing the nose cone 1021 through the sidewall of the vessel, for example, to reduce tearing of the side wall of the vessel 912 as discussed herein.

Figure 69:
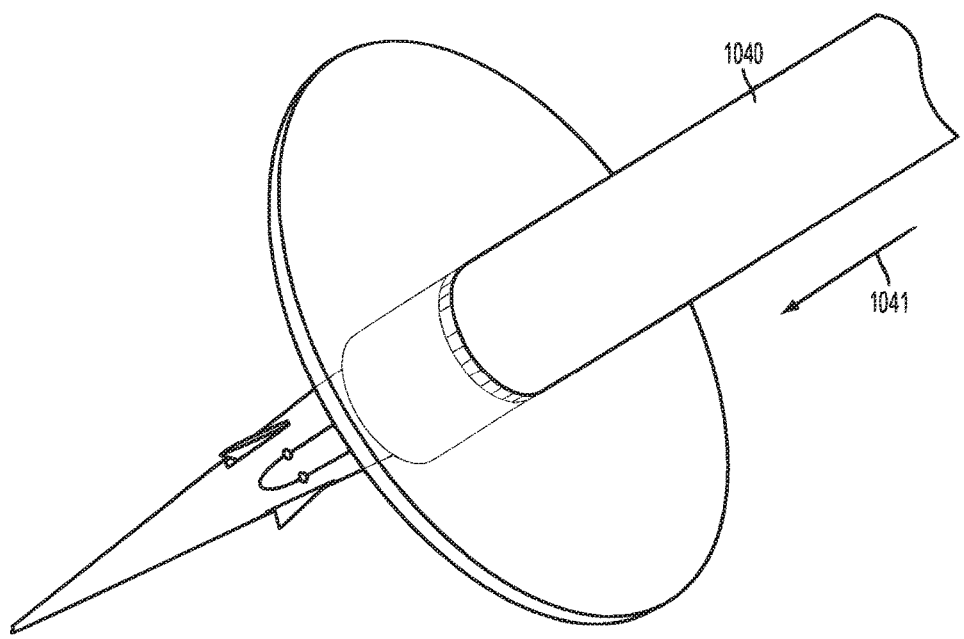

As shown in FIGS. 68 and 69, the delivery apparatus can be advanced distally (in the direction of arrow 1041) until the outer cylinder 1040 passes through the opening 910 in the vessel sidewall 912 to a point where the distal fingers 954 of the puncture frame 904 are on the luminal side of the vessel sidewall 912 and the proximal fingers 952 are on the outer side of the vessel 912.

As shown in FIG. 70, the outer cylinder 1040 is next moved proximally in the direction of arrow 1042 to deploy the puncture frame 904, as discussed above. At this step the outer cylinder 1040 is moved to a position that allows deployment of the puncture frame 904, but does not allow release of the projections 1033 from the twisting frame 906. Thus, the twisting frame 906 remains secured to the twisting frame actuator 1030.

Figure 71:
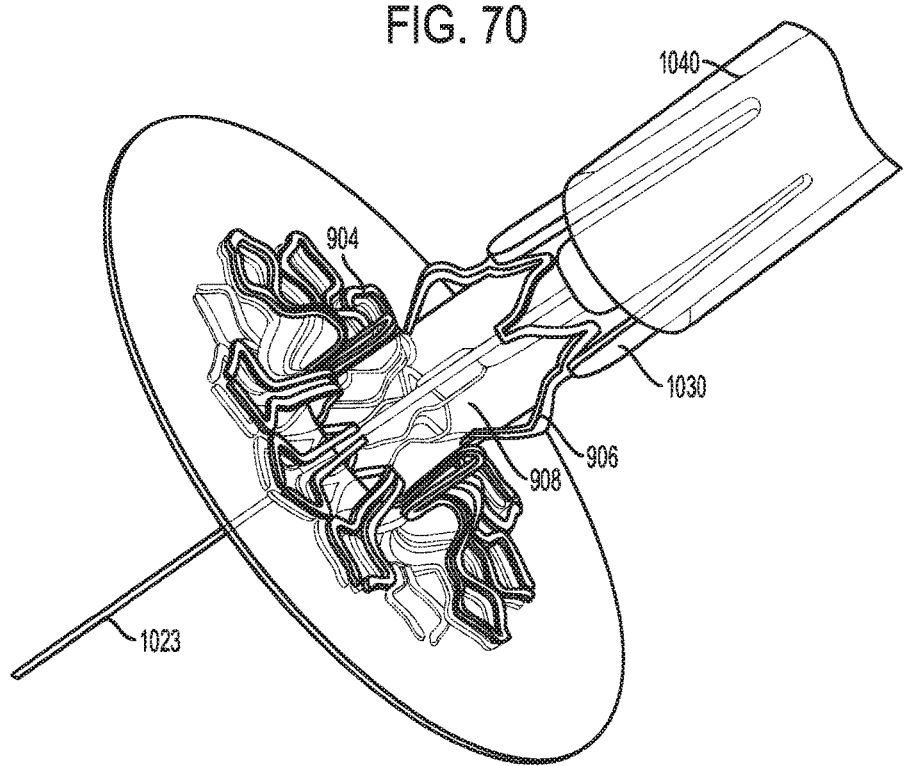

After deployment of the puncture frame, the dilator 1020 can then be retracted proximally and removed from the body (FIG. 71).

Following deployment of the puncture frame 904, an introducer sheath (not shown) can be advanced distally over the guide wire until the sleeve of the introducer sheath traverses the aperture 910 in the sidewall of the vessel 912 (not shown). The twisting frame actuator 1020 optionally can be rotated angularly to cause twisting of the sealing member 908. Twisting of the sealing member 908 tightens the sealing member 908 around the sleeve of the introducer sheath, thereby providing hemostasis or a seal that reduces and/or prevents bleeding between the sleeve of the introducer sheath and the sealing member 908, and/or provides for immobilization of the sleeve of the introducer sheath.

One or more medical devices or tools can be inserted into the body via the introducer sheath as needed for performing the endoluminal procedure. For example, a prosthetic, transcatheter heart valve mounted on a delivery apparatus can be inserted through the introducer sheath and deployed within one of the native heart valves.

Following the endoluminal procedure, the guide wire 1023 is removed, and the introducer sheath is retracted proximally within the twisting frame actuator 1030 and optionally removed from the body. The sealing member 908 can then be moved to the closed state 938 (see FIGS. 72-77) by rotation of the twisting frame 1030. As the tubular sealing member 908 is twisted, its length along the longitudinal axis of the sealing device shortens, until the connection posts 915 on the puncture frame engage the connection posts 917 on the twisting frame, thereby securing the puncture frame to the twisting frame and the tubular sealing member in the sealed or closed state 938 (see FIG. 72).

Figure 74:
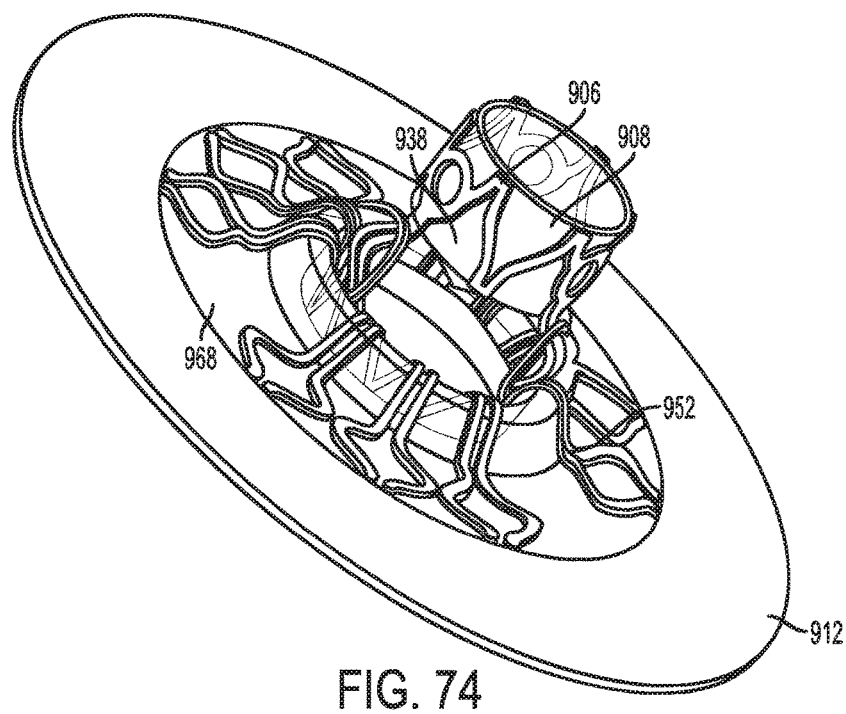

To release the twisting frame from the twisting frame actuator, the outer cylinder 1040 is moved proximally, which allows the projections 1033 to move to their memory shape and to release the teeth 1035 from the apertures 988 of the eyelets 986 on the twisting frame 906. (FIG. 73). The twisting frame actuator is then retracted proximally and any excess material of the sealing member 908 that extends proximally beyond the twisting frame 906 can be removed (FIG. 74). The delivery apparatus 1000 can then be removed from the patient.

Figure 75:
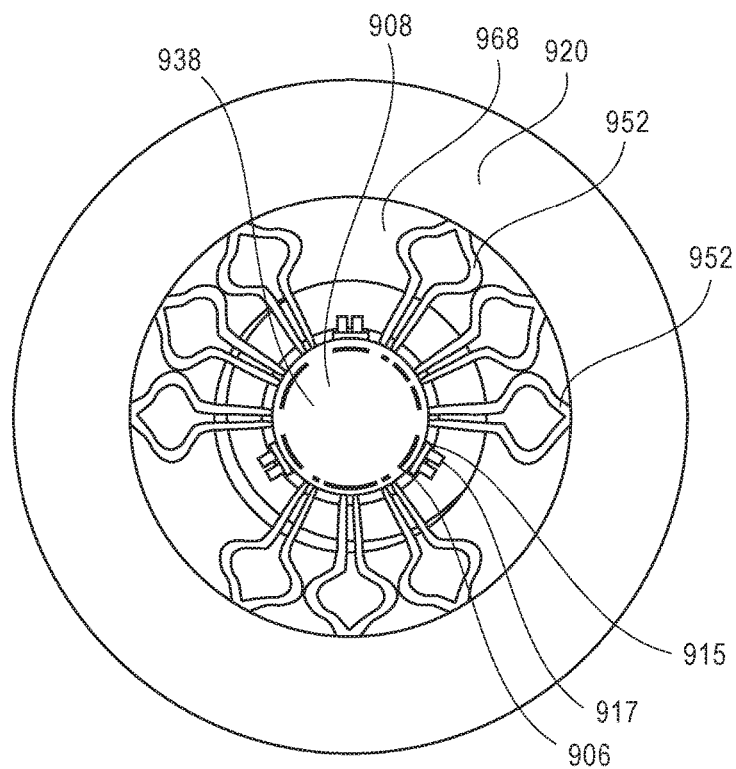
Figure 76:
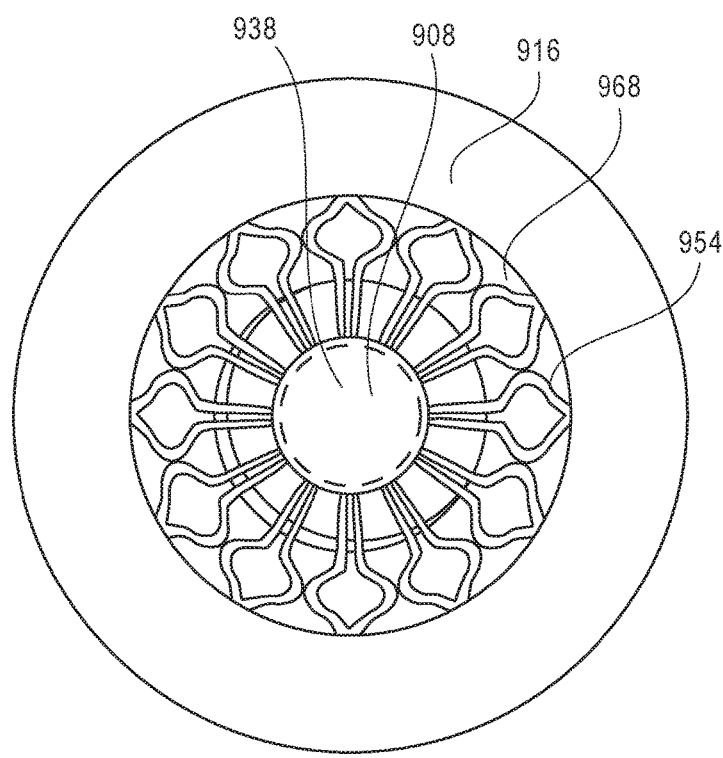
Figure 77:
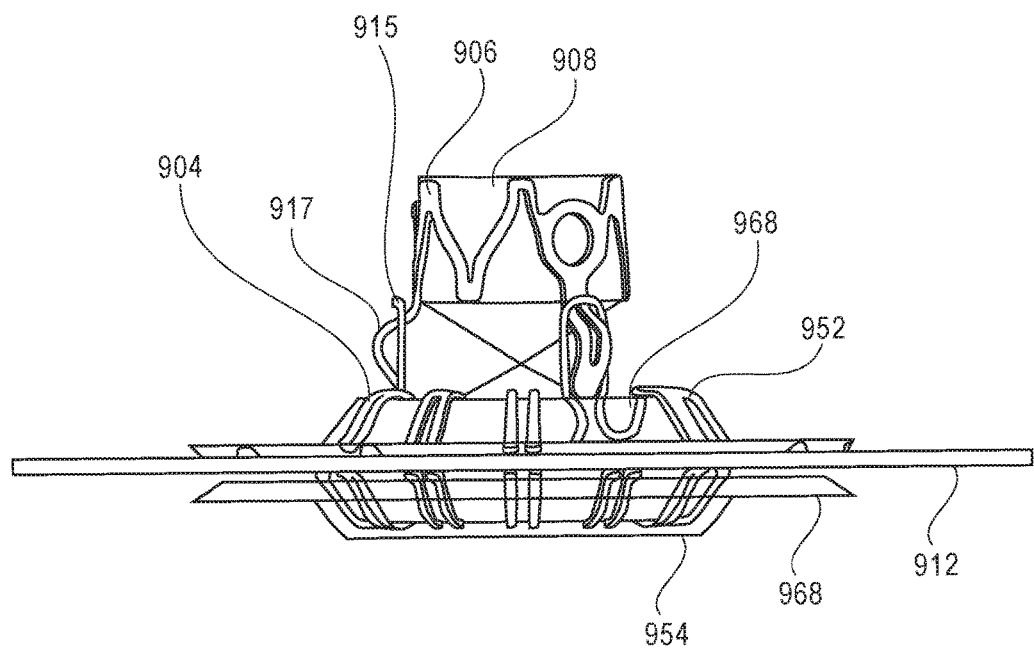

FIGS. 75-77 show proximal, distal, and side views, respectfully, of the implanted sealing device with the sealing member 908 in the closed state 938 following removal of the delivery apparatus 1000. FIGS. 75 and 76 also show a sealing 968 skirt of the sealing device 900, which is shown between the proximal fingers 952 and the outer side 920 of the vessel sidewall 912 (FIG. 75) and between the distal fingers 954 and the luminal side 916 of the vessel sidewall 912 (FIG. 76).

Figure 78:
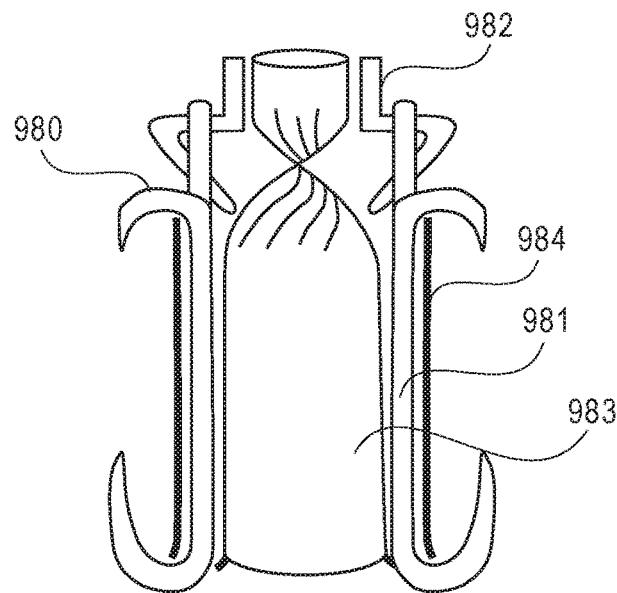
FIG. 78 shows a side view of a sealing device for implantation in an apical aspect of the heart, in one embodiment.
Figure 79:
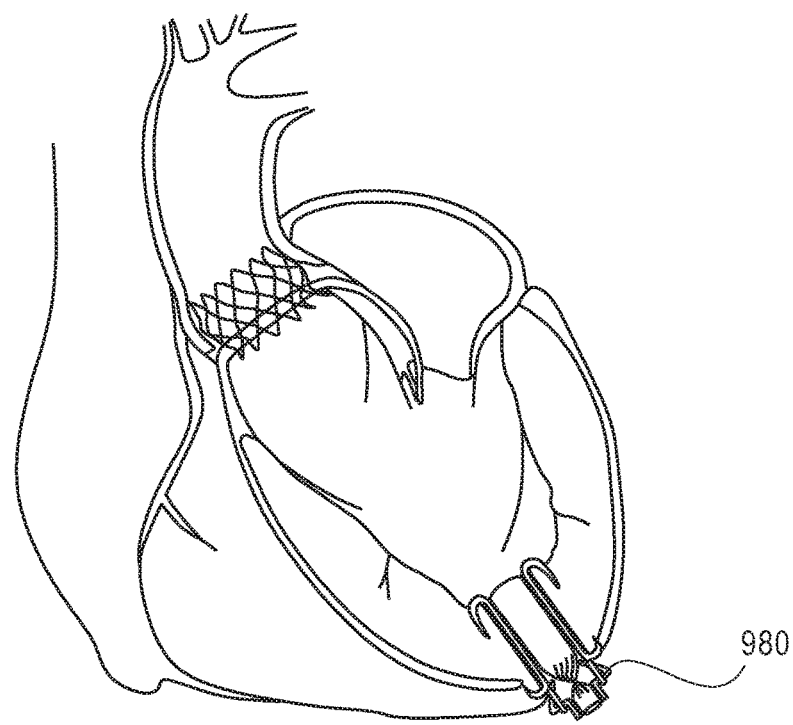
FIG. 79 shows a side view of an implanted and closed sealing device of FIG. 78.

FIGS. 78 and 79 illustrate that the opening and sealing devices described above can be modified for use in a variety of vessel or organ sidewalls for access to luminal space, including for access to lumen the heart. For example, FIG. 78 shows opening and sealing device 980, which is substantially similar to opening and sealing device 900 (including a puncture frame 981, a twisting frame 982, a tubular sealing member 983 and a sealing skirt 984), but wherein the puncture frame 981 is substantially longer in the axial direction for placement in a bare spot on the lower anterior ventricle wall of the heart.

FIGS. 80-84 illustrate an exemplary dilator, dilator 1080, for example for use with delivery assembly 1000. The dilator 1080 can be used to dilate an opening in the side wall of a vessel. The dilator 1080 is configured to slide inside an introducer sheath (such as the introducer sheath 300), and be removable therefrom. A sleeve or shaft portion 1085 of the dilator 1080 can have an outer diameter slightly less than the inner diameter of the introducer sheath.

Figure 80:
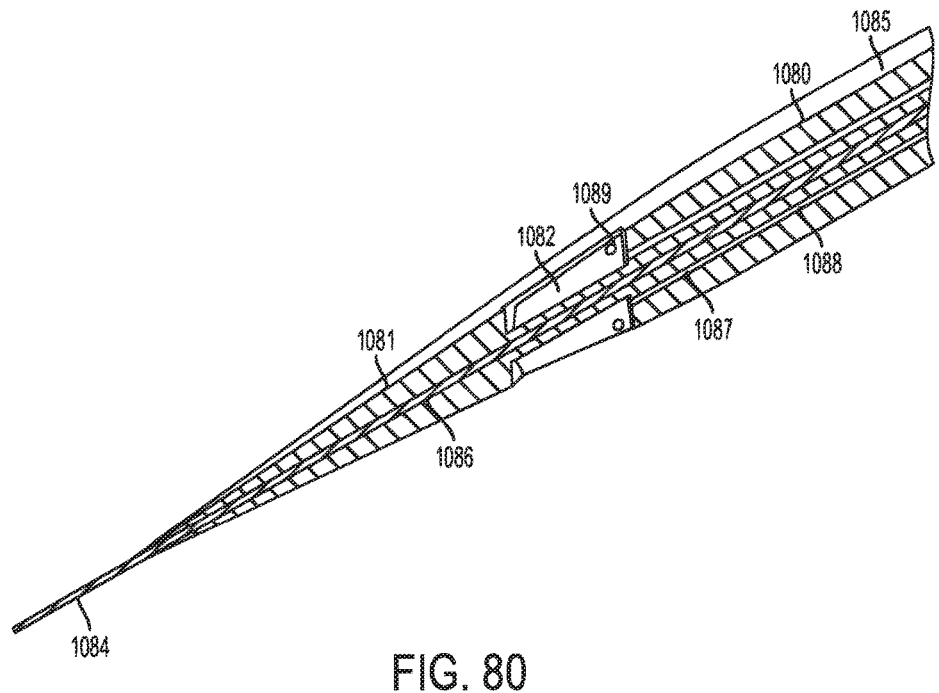
FIGS. 80-84 show views of a dilator nose cone with extendable and retractable cutting members, according to one embodiment.
Figure 81:
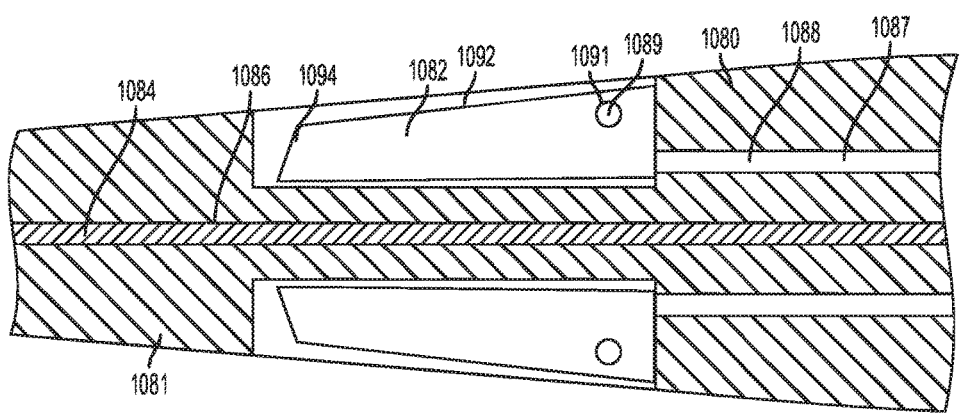
Figure 82:
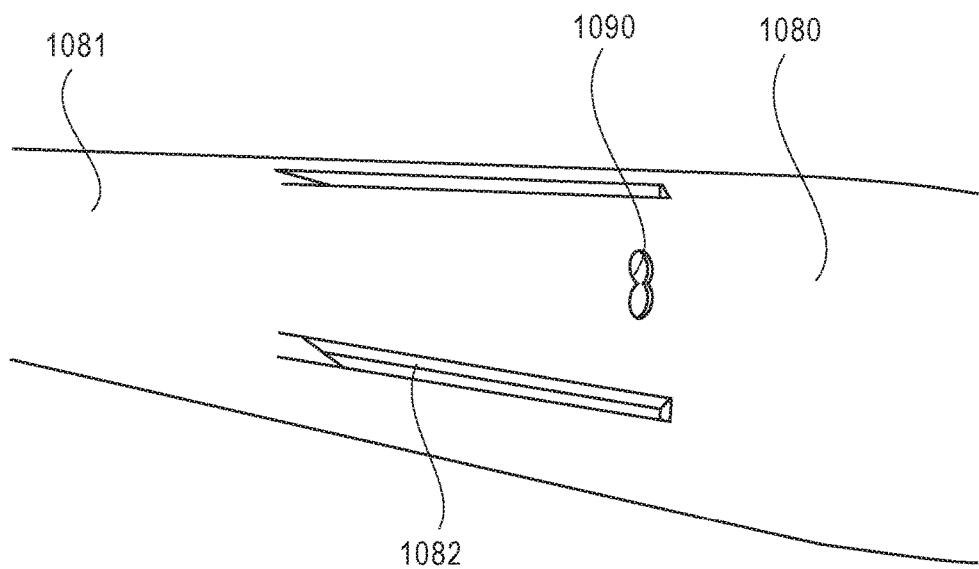
Figure 83:
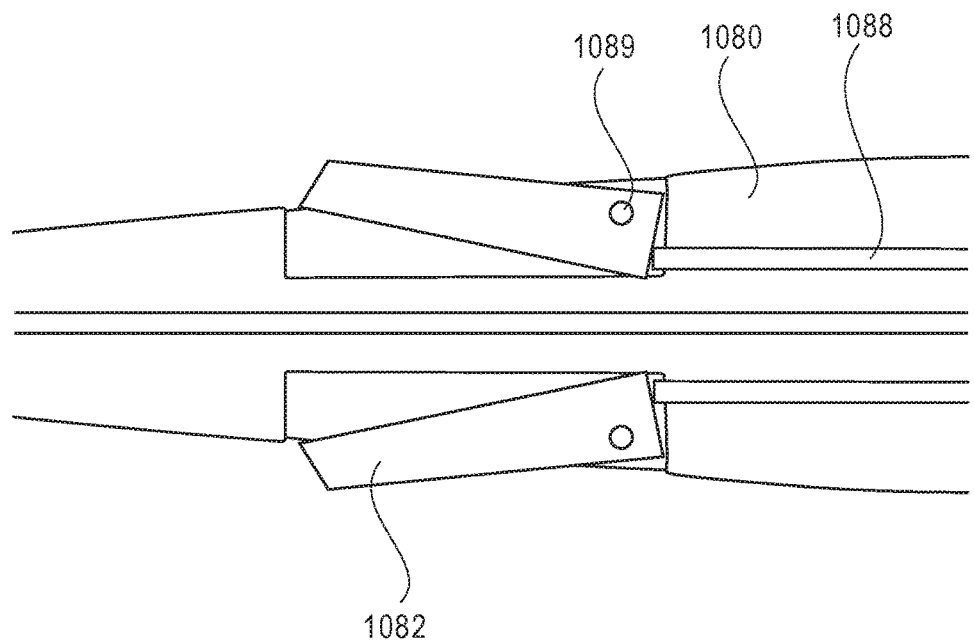
Figure 84:
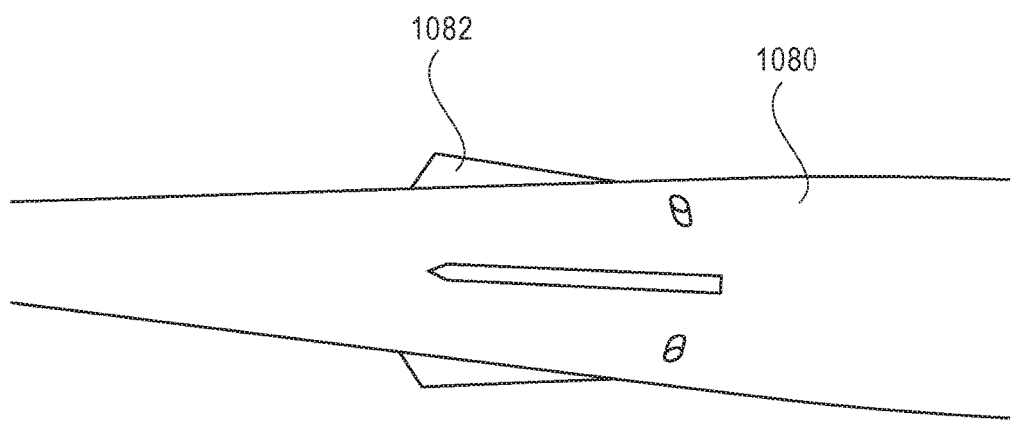

As shown in FIG. 80, the dilator 1080 can include a nose cone portion 1081, which can be tapered or conical to facilitate insertion into an aperture in the side wall of the vessel. The dilator 1080 includes extendable and retractable cutting members 1082 (e.g., blades) on the nose cone portion 1081 of the dilator, and proximal to the distal tip of the dilator. In specific embodiments, the dilator 1080 can include three or four cutting members 1082 that can be equally spaced around the dilator nose cone 1081; however, any suitable number of cutting members 1082 can be included on the dilator 1080. In the illustrated embodiment, the cutting members 1082 have a cutting edge 1092 that extends lengthwise of the cutting member and is generally parallel to the longitudinal axis of the dilator. Each cutting members can also have a cutting edge 1094 at its free end that extends generally perpendicular with respect to the length of the cutting member. Further, in the illustrated embodiment, the cutting members are blades. In alternate embodiments, the cutting members can be ultrasonic, harmonic or electric cutting members. The cutting members 1082 can be extended from the dilator body to facilitate traversal of the vessel sidewall by the nose cone for widening an aperture (such as the aperture 910) in a vessel sidewall, and fully retracted into the dilator body when not in use.

Each cutting member 1082 can be secured to the nose cone 1081 using any suitable means, for example by a securing member 1089 (e.g., a pivot pin or rod) that extends through an aperture 1091 in the proximal portion of the cutting member, around which the cutting member can be rotationally movable for extension and retraction from the nose cone 1081. In examples where the securing member 1089 is a pin or rod, the securing member can extend through a lumen 1090 formed in the nose cone 1081 of the dilator 1080 (see FIG. 82). Extension of each cutting member from the nose cone 1081 can be accomplished by any suitable means, for example, by cutting member actuator 1088 which can be a rod positioned within a cutting member actuator lumen 1087 that can be extended distally to push against the proximal portion of the cutting member 1082 to cause rotation of the cutting member around the securing member 1089 and extension of the cutting member 1082 from the nose cone 1081 of the dilator (see FIG. 83). The cutting member 1082 can be further secured to the nose cone 1081 by a retraction member (e.g., a spring) that causes the cutting member to retract into the nose cone 1081 when the cutting member actuator 1088 is moved proximally to withdrawing the pressure on the proximal portion of the cutting member.

The distal tip of the dilator includes an aperture configured to allow passage of a guide wire 1084 and/or a hypodermic needle from a guide wire lumen 1086 within the dilator. In particular embodiments, the guide wire can be inserted through the sidewall of a vessel, and the nose cone portion 1081 of the dilator can be used to expand the puncture site from the diameter of the guide wire to about the diameter of the sleeve portion 1083 of the dilator.

Some embodiments of the dilator further comprise a flush/suction port for use during deployment.

H. Exemplary Collapsing Sealing Device 1100

FIG. 85 shows a sealing device 1100, for use in sealing an aperture or opening in a vessel side wall, for example following opening of an aperture 910 in a wall of the aorta for implantation of a prosthetic heart valve.

The illustrated sealing device 1100 is adapted to be deployed in the sidewall of the aorta, although it can also be used in other vessels of a subject. The sealing device 1100 has an open configuration 1103 (see FIG. 85) and a sealed or closed configuration 1105 (see FIG. 86). The sealing device 1100 can be initially deployed in the open configuration around a puncture or aperture in a vessel sidewall that was created for access to the interior of a blood vessel in a patient, for example access for performing a surgical procedure (e.g., heart valve replacement or repair). When placed in the sealed configuration, the sealing device 1100 seals the opening used to access the interior of the vessel. Apparatuses particularly suited for delivery and implantation of the sealing device 1100, as well as methods of using the sealing device 1100, are described in detail below.

In several embodiments, the sealing device 1100, delivery apparatus, and methods are useful for transaortic procedures in which an opening is created on the aorta, for example, for implanting a prosthetic heart valve in the aortic valve position. The sealing device 1100 and methods are also applicable for other locations, however, for example, the pulmonary artery, atrial wall (trans-atrial, for example, for implanting a prosthetic mitral valve), and/or ventricular wall (for example, for implanting a prosthetic mitral and/or aortic valve). The sealing device 1100, apparatus, and method also permit laparoscopic and/or robotic surgical procedures within organs, for example, the heart. The embodiments can provide a large opening (up to 26 F., up to 45 F., or even greater) for access to the interior of a vessel or chamber (such as the aorta or left atrium) in a patient.

The sealing device 1100 can be made of any of various suitable plastically-collapsible materials (e.g., stainless steel, etc.) or shape-memory, self-collapsing materials (e.g., Nitinol) as known in the art. When constructed of a plastically-collapsible material, the sealing device 1100 can be crimped to a radially collapsed configuration to seal the opening used to access the interior of the vessel, as discussed in more detail below. When constructed of a self-collapsible material, the sealing device 1100 can be restrained in the open configuration by insertion onto a sheath or equivalent mechanism of a delivery apparatus. During implantation, the sealing device 1100 can be advanced from the delivery sheath, which allows the sealing device to collapse to the closed configuration.

Suitable plastically-collapsible materials that can be used to form the sealing device 1100 include, without limitation, stainless steel, a nickel based alloy (e.g., a cobalt-chromium or a nickel-cobalt-chromium alloy), polymers, or combinations thereof. In particular embodiments, the sealing device 1100 is made of a nickel-cobalt-chromium-molybdenum alloy, such as MP35N™ (trade name of SPS Technologies), which is equivalent to UNS R30035 (covered by ASTM F562-02). MP35N™/UNS R30035 comprises 35% nickel, 35% cobalt, 20% chromium, and 10% molybdenum, by weight. In particular, when MP35N is used as the frame material, less material is needed to achieve the same or better performance in radial and crush force resistance, fatigue resistances, and corrosion resistance.

In some embodiments, the sealing device 1100 can be made of a biodegradable material, such as a biodegradable polymer, that is absorbed by the body over time.

Referring to FIG. 85, the sealing device 1100 in the illustrated embodiment comprises a distal end 1102 and a proximal end 1104; a distal row of axially extending anchors 1109 including struts 1114 and barbs 1116, and a upper portion 1107 including a first row I of circumferentially extending, angled struts 1106 arranged end-to-end and extending circumferentially; a second row II of circumferentially extending, angled struts 1108; a third row III of circumferentially extending, angled struts 1110 at the proximal end of the frame. The struts of rows I, II, and III can be connected at nodes or junctions 1111, 1112, and 1122 (discussed below). Alternatively, a plurality of substantially straight axially extending struts can be used to interconnect the struts of the row I with the struts of the row II, and/or the struts of the row II and the struts of the row III.

The struts and frame portions of the sealing device 1100 collectively define a plurality of open cells of the frame. At the distal end 1102 of the sealing device 1100, struts 1106 and struts 1108 define a lower row of cells defining openings 1118. The second and third rows of struts 1108 and 1110 define a proximal row of cells defining openings 1120. In the illustrated embodiment, the opening 1118 and 1120 are substantially the same size and shape; however, openings of different size and shape are also possible.

As shown in FIG. 85, the distal end of two adjacent struts 1106 are connected to each other at a single strut 1114 at a node or junction 1124. The distal end of two adjacent struts 1108 are connected to the proximal end of two adjacent struts 1106 at a node or junction 1112, and the proximal end of two adjacent struts 1108 are connected to two adjacent struts 1110 at a node or junction 1122. Further, two adjacent struts 1110 are connected at a node or junction 1111 at the proximal end 1103 of the sealing device 1100.

The distal ends of struts 1114 are connected to barbs 1116, which can be shaped to include a sharp tip 1115 and a serrated edge 1117 that can be inserted through the vessel sidewall and resist removal in the opposite direction.

When the sealing device 1100 is deployed around an opening in a vessel sidewall, the frame can have an open cylindrical shape shown in FIG. 85. The anchors 1109 are inserted through the sidewall of the vessel around the opening. When the frame 1100 moves to the closed configuration as shown in FIG. 86, the anchors 1109, which are inserted through the sidewall of the vessel, pull the vessel tissue around the opening closed, thereby sealing the opening in the sidewall of the vessel.

The sealing device 1100 in the open configuration comprises a diameter suitable for insertion around an aperture in a vessel sidewall, for example, in some embodiments, the sealing device 1100 can be expanded up to a diameter of 10-15 mm in the open configuration and can contract to a diameter of 3-5 mm in the closed configuration. In particular embodiments, the thickness of the frame 1100 measured between the inner diameter and outer diameter is about 0.45 mm or less. In additional embodiments, the height of the device 1100 measured from the distal end 1102 to the proximal end 1104 can be from about 8 to about 10 mm. In more embodiments, the anchors 1109 can have a height of about 3 to about 4 mm.

As shown in FIG. 86, the sealing device 1100, when in the closed configuration, can assume an overall tapered shape that tapers from a maximum diameter at the proximal end of the frame to a minimum diameter at the distal end of the frame.

Figure 96:
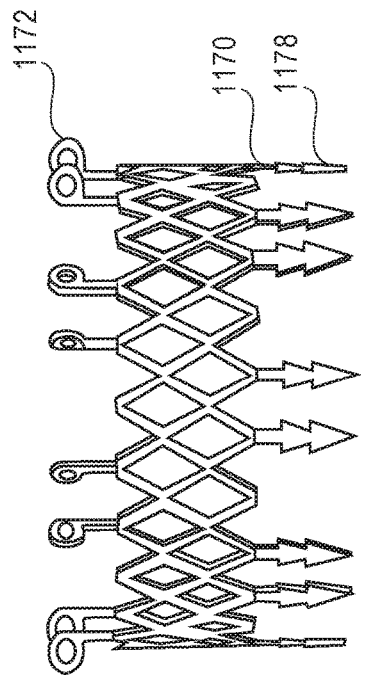
FIGS. 95-98 show perspective and side views of additional embodiments of an expandable and collapsible sealing device.
Figure 95:
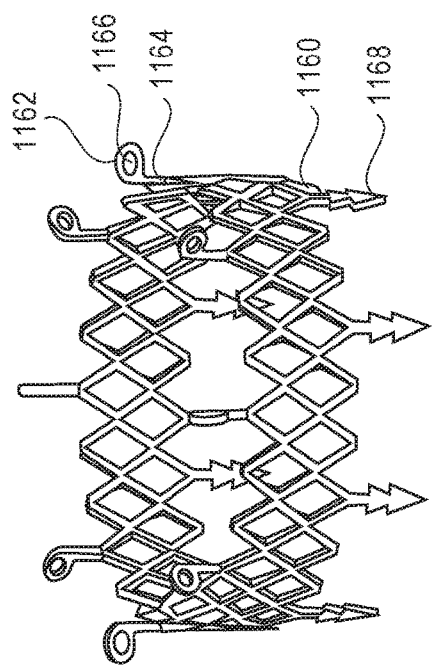

In some embodiments, the sealing device can include circumferentially spaced loops or eyelets through which a suture can be threaded to facilitate moving the sealing device to the closed configuration. For example, FIG. 95 shows a perspective view of alternate sealing device 1160 which is substantially the same as the sealing device 1100, but includes eyelets 1162 comprising apertures 1166 through which a suture can pass, and which are secured to the proximal end of the sealing device by struts 1164. In the illustrated embodiment, the sealing device 1160 includes eight eyelets 1162; however, more or fewer of such eyelets can be included on the sealing device. Additionally, sealing device 1160 includes eight anchors 1168; however, more or fewer of such anchors can be included on the sealing device. For example, FIG. 96 shows a side view of a sealing device 1170, which includes eight eyelets 1172, and sixteen anchors 1178.

Figure 98:
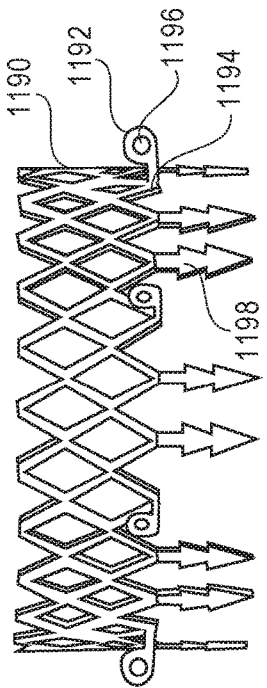
Figure 97:
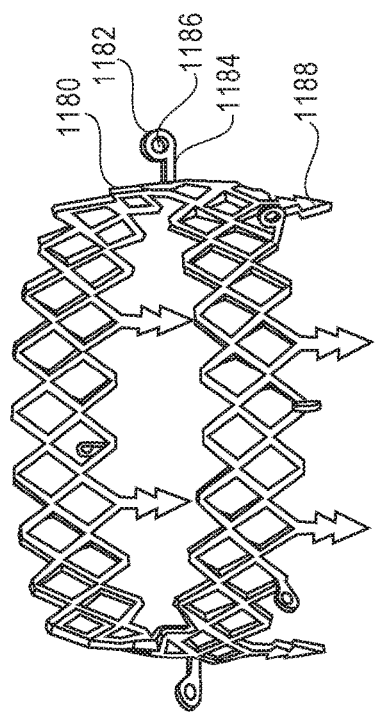

In another alternate embodiment of the sealing device, the circumferentially spaced loops or eyelets can be positioned on the distal portion of the sealing device. For example, FIG. 97 shows a perspective view of alternate sealing device 1180 which is substantially the same as the sealing device 1100, but includes eyelets 1182 comprising apertures 1186 through which a suture can pass, and which are secured to the distal end of the sealing device by struts 1184. In the illustrated embodiment, the sealing device 1180 includes eight eyelets 1182; however, more or fewer of such eyelets can be included on the sealing device. Additionally, sealing device 1180 includes eight anchors 1188; however, more or fewer of such anchors can be included on the sealing device. For example, FIG. 98 shows a side view of sealing device 1190, which includes eight eyelets 1192 positioned on the distal portion of the sealing device, and sixteen anchors 1198.

I. Exemplary Delivery Apparatus for Sealing Device 1100

Figure 87:
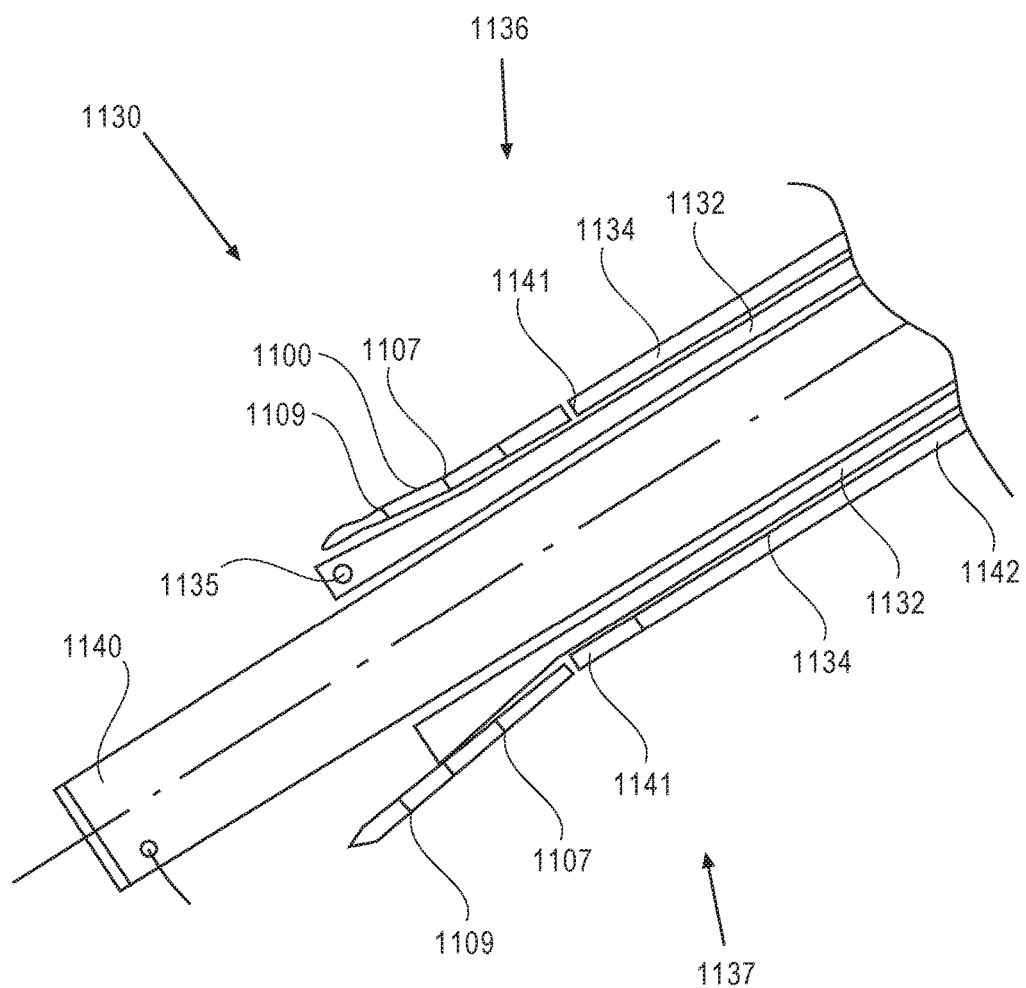
FIG. 87 shows a cross-sectional view of a delivery apparatus for implantation of expandable and collapsible sealing device, according to one embodiment.

FIG. 87 illustrates a delivery apparatus 1130 that can be used for surgical procedures (e.g., implantation of a prosthetic heart valve) that involve opening an aperture in a vessel sidewall (e.g., a sidewall of the aorta) and then sealing that aperture with sealing device 1100. The delivery apparatus 1130 includes a number of coaxial sleeves which are relatively axially slidable and angularly rotatable along a longitudinal axis extending from the proximal end to the distal end of the deliverer apparatus. Preferably, the sleeves are actuatable by the physician from the proximal end portion of the instrument. As shown in FIG. 87, the delivery apparatus 1130 can include a carrier 1132 on which the sealing device 1100 can be mounted, a sealing device pusher 1134, and an introducer sheath 1140 (for example, similar to introducer sheath 300). In several embodiments, the delivery apparatus 1130 can also include a dilator 1150 (FIG. 88), which can be substantially the same as the dilator 1080 described above, although any suitable dilator can be used with delivery assembly 1130.

In the illustrated embodiment (and for ease of illustration), the delivery apparatus 1130 is in a straight configuration. However, the delivery apparatus can include a curved or angled configuration to facilitate access to a vessel if needed.

Additionally, the introducer sheath 1140 can include one or more deployable members at its distal end (for example, similar to dilator 1080) that can be deployed inside the lumen of the accessed vessel to act as a counter support for the sidewall of the vessel 1154 to facilitate engagement of the sealing device anchors 1109 with the sidewall of the vessel.

In additional embodiment, the distal end of the introducer sheath 1140 can include an absorbent material (such as Dacron) to act as a pledget that contacts the sidewall of the vessel when the introducer sheath is inserted through the aperture in the vessel.

FIG. 87 shows a cross-sectional view of the delivery apparatus 1130, and illustrates the delivery apparatus in both a retracted configuration 1136 and an insertion configuration 1137. In the retracted configuration, the anchors 1109 of the sealing device 1100 do not extend distally beyond the distal end 1135 of the carrier 1132. In the insertion configuration 1136, the anchors 1109 of the sealing device 1100 extend distally beyond the distal end 1135 of the carrier 1132. The delivery apparatus 1130 can be moved to the insertion configuration by moving the pusher 1134 distally, thereby pushing the anchors 1109 of the sealing device 1100 distally beyond the distal end 1135 of the carrier 1132. When used in a surgical procedure, the distal end 1135 of the carrier can be placed against the vessel sidewall. Thus, when the anchors 1109 are pushed distally beyond the distal end 1135 of the carrier 1132, the anchors can penetrate into the vessel sidewall and are held in place by the barbs 1116 of the sealing device.

The components of the delivery apparatus 1130, such as the introducer sheath 1140, the dilator 1150, the carrier 1132, and the sealing device pusher 1134, can include one or more locking mechanisms to releasably secure the position of the components with respect to each other and/or with respect to the sidewall of the vessel, for example, as described herein or as known in the art. The components of the delivery apparatus can be manufactured from any of various suitable materials known in the art, such as any of various metals or polymers, and combinations thereof.

The introducer sheath 1140 (FIG. 88) can be substantially the same as the introducer sheath 300 used for embodiments described above. Similar to introducer sheath 300, the introducer sheath 1140 can be positioned axially inward from, and can be axially slidable and angularly rotatable relative to, the carrier 1132. Further, the introducer sheath 1140 can be positioned axially outward from, and can be axially slidable and angularly rotatable relative to, the dilator 1150. The introducer sheath 1150 can be configured to allow the dilator 1150 to slide inside the introducer sheath, and be removable therefrom. An inner diameter of the sheath 1130 can vary based on the intended use, and can be suitably sized to allow access to the intraluminal space of the vessel 912 via the sheath 1140 by a treating physician, for example, for implantation of a prosthetic heart valve. The introducer sheath 1140 can include an elongated sleeve, which can have a cone-shaped distal portion designed for insertion through the sidewall of a vessel and a proximal portion secured to a handle. The handle can house one or more seals configured to seal against the outer surface of a prosthetic-device-delivery-apparatus that is inserted through the introducer sheath, as known in the art, and can optionally include a flush/suction port for use during surgery as needed. An example of a suitable introducer sheath includes the Edwards Ascendra® introducer sheath.

The carrier 1132 in the illustrated embodiment includes a coaxial sleeve that is positioned between the introducer sheath 1140 and the pusher 1134 on delivery assembly 1130. The carrier 1132 can be axially slidable and angularly rotatable relative to the introducer sheath 1140 and the pusher 1132. Referring to FIG. 87, the carrier 1132 includes a distal portion 1135 and a proximal portion. The proximal portion of the carrier 1132 can be secured to a handle or other suitable member for operation by a treating physician. The distal portion 1135 of the carrier extends distally beyond a distal end 1141 of the pusher and is shaped to allow mounting of the sealing device 1100. In some embodiments, the distal end 1135 of the carrier 1132 can angle or flare outward (see FIG. 87), thereby causing the sealing device 1100 to angle or flare outward as it is pushed into the deployed configuration 1137 by distal movement of the pusher 1134. This in turn causes the anchors 1109 of the sealing device 1100 to penetrate insert into the vessel sidewall at an angle.

The pusher 1134 in the illustrated embodiment includes a coaxial sleeve that is positioned radially outward from the carrier 1134. The pusher 1134 can be axially slidable and angularly rotatable relative to the introducer sheath 1140 and the carrier 1132. Referring to FIG. 87, the pusher includes the distal end 1141 and a proximal portion. The proximal portion of the pusher 1134 can be secured to a handle or other suitable member for operation by a treating physician. The distal end 1141 of the pusher is configured to contact the proximal end of the sealing device 1100 when it is mounted on the carrier 1132. When the pusher 1134 is moved distally, the distal end 1141 of the pusher contacts that proximal end of the sealing device 1100 and pushes the sealing device into the deployed configuration 1137 of the delivery apparatus 1130.

J. Exemplary Method of Using Sealing Device 1100

FIGS. 88-94 illustrate an exemplary method of using the delivery apparatus 1130 for accessing the lumen of a vessel 1152 (such as the aorta) for performing an endoluminal procedure via an aperture 1154 in the sidewall of a vessel, and then sealing the aperture following the endoluminal procedure with a sealing device such as sealing device 1100. The illustrated method utilizes the delivery apparatus 1130 and the sealing device 1100; however, other embodiments of a sealing device and/or a delivery apparatus (for example, any of the embodiments described herein) can be used to perform the disclosed method. In several embodiments, the disclosed method is used to create and seal the aperture 1154 in a sidewall of the aorta in a patient during a surgical procedure, such as implantation of a prosthetic heart valve.

Prior to initiation of the method, the sealing device 1100 is loaded onto the delivery apparatus 1130, with the sealing device mounted on the distal portion of the carrier 1132.

In the illustrated embodiment of the method, the delivery apparatus includes the dilator 1150, which can be substantially the same as the dilator 1080 described above. A hypodermic needle can be advanced through the lumen and aperture at the distal tip of the nose cone of the dilator and inserted through the sidewall of the vessel 1152. The guide wire can then be inserted through the hypodermic needle and into the lumen of the vessel 1152, and placed as needed for the endoluminal procedure. After placement of the guide wire, the hypodermic needle can be retracted from the sidewall of the vessel, leaving the guide wire in place. After placement of the guide wire, the delivery apparatus 1130 can be advanced distally until the distal tip of the nose cone penetrates the sidewall of the vessel 1152. The dilator can include extendable and retractable cutting members, which can be extended from the dilator body to facilitate traversal of the sidewall of the vessel 1154 by the nose cone and for widening of the aperture 1152, for example, as discussed above for cutting members 1082 of dilator 1080. Optionally, an incision in the sidewall of the vessel 1152 can be performed prior to advancing the nose cone through the sidewall of the vessel.

Figure 88:
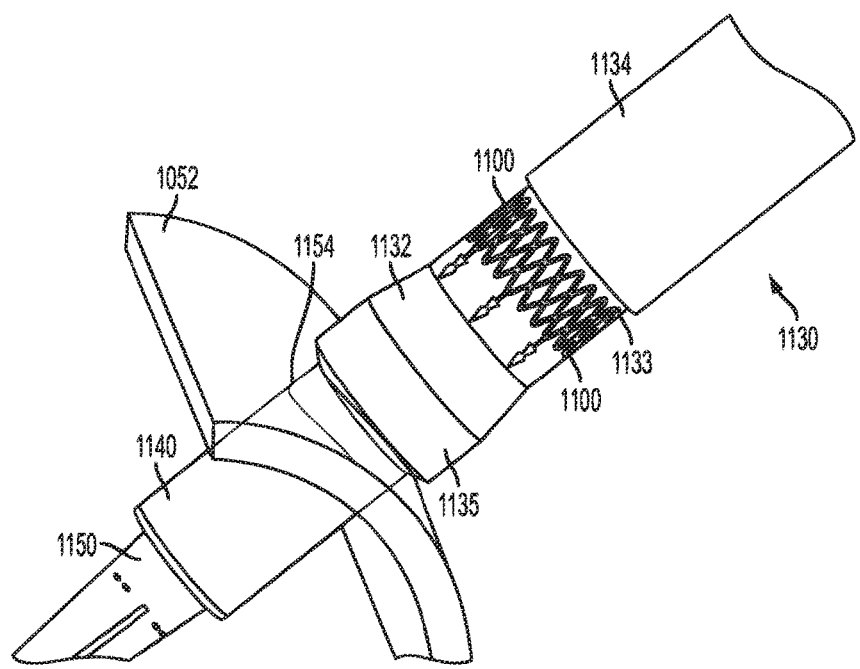
FIGS. 88-94 illustrate an exemplary method of using a disclosed sealing device and related delivery apparatus for accessing the lumen of a vessel for performance of an endoluminal procedure via an aperture in the sidewall of the vessel, and then sealing the aperture following the endoluminal procedure.
Figure 89:
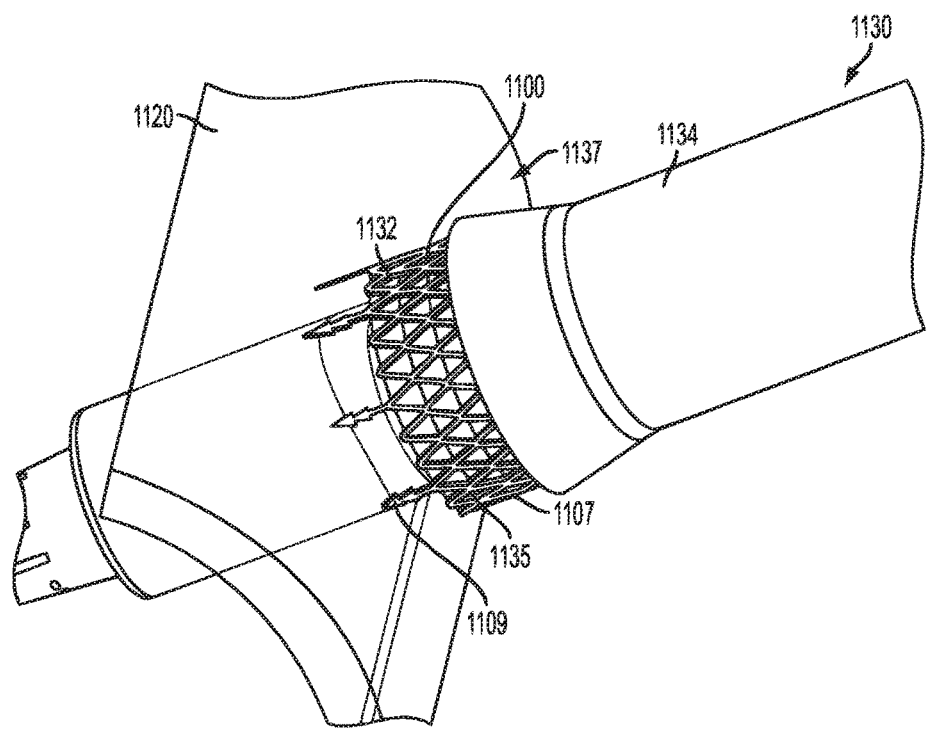
Figure 90:
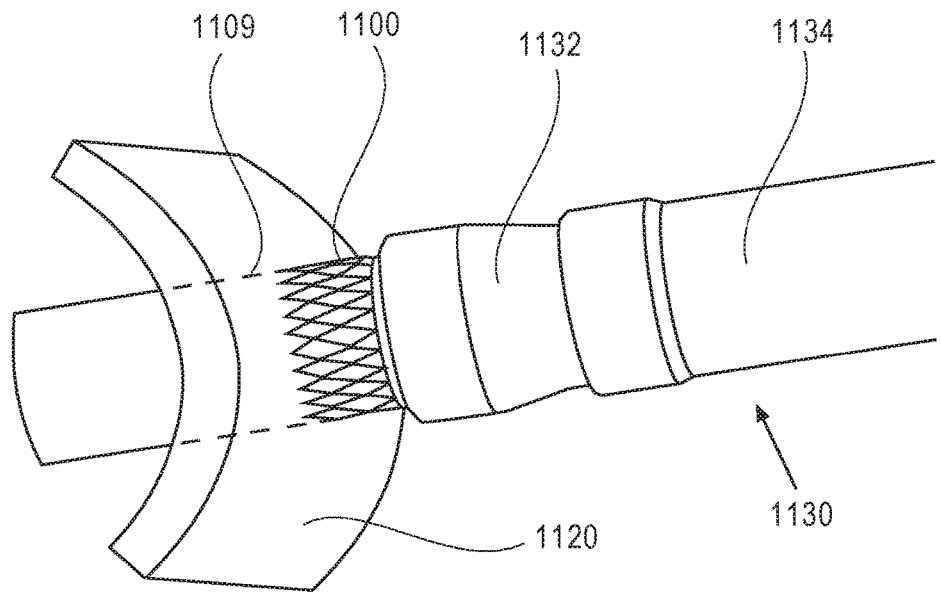

As shown in FIG. 88, the introducer sheath 1140 can be advanced distally until the distal portion of the sleeve of the introducer sheath 1140 advances through the aperture 1152, and the carrier 1132 is advanced distally until the distal end 1135 of the carrier contacts or is adjacent the sidewall of the vessel 1154. In the illustrated embodiment of the method, the pusher 1134 is then moved distally to push the sealing device 1100 into the deployed configuration and the anchors 1109 penetrate into the sidewall of the vessel 1154 (FIG. 89). The carrier 1132 can then be retracted proximally. As the carrier is retracted, the anchors 1109 of the sealing device 1100 will remain secured to the sidewall of the vessel 1154. At this point of the method, the carrier can be retracted proximally until the distal end 1135 of the carrier 1132 passes proximally beyond the proximal end of the sealing device 1100, leaving the sealing device 1100 positioned on the outer surface of the introducer sheath (FIG. 90).

In embodiments where the sealing device 1100 is self-contracting (e.g., is made of Nitinol) the sealing device 1100 tightens around the introducer sheath 1140, thereby providing hemostasis or a seal that reduces and/or prevents bleeding between the sleeve of the introducer sheath and the aperture 1154 in the sidewall of the vessel 1152, and/or provides for immobilization of the sleeve of the introducer sheath. In embodiments where the sealing device 1100 is not self-contracting, the sealing device can be tightened around the introducer sheath by mechanical means (e.g., by tying a cord around the sealing device), if needed.

Figure 91:
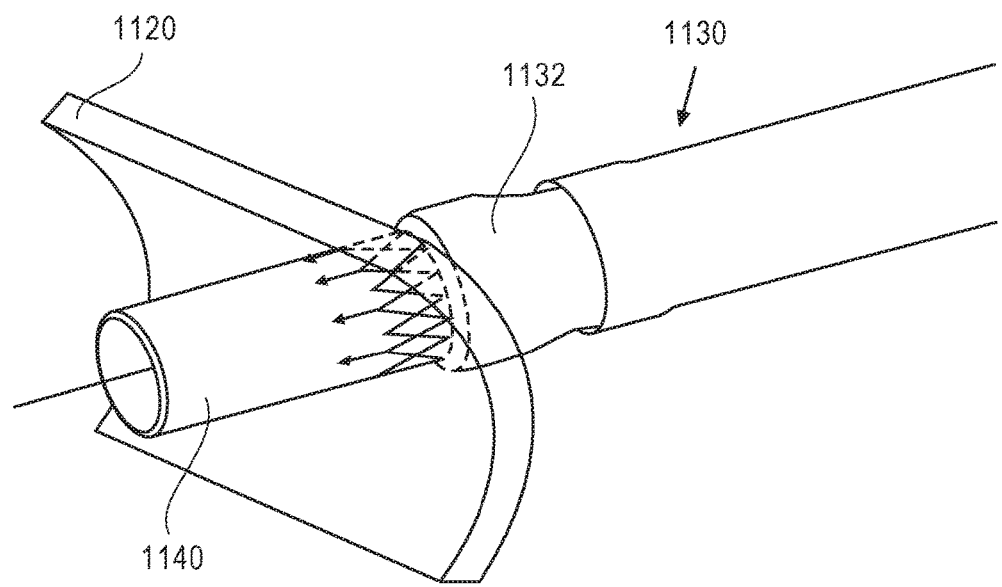

The dilator 1150 can then be retracted proximally and temporarily removed from the delivery assembly 1130 (FIG. 91). The endoluminal procedure can then be performed. In some embodiments, the endoluminal procedure includes advancing one or more tools and/or instruments through the introducer sheath, such as a prosthetic heart valve delivery apparatus. Exemplary endoluminal procedures include, but are not limited to, placing or repairing a prosthetic heart valve, placing or repairing a vascular stent, placing or repairing of an abdominal aortic aneurysm graft, repairing a natural valve, repairing a cardiac defect, and the like).

Figure 92:
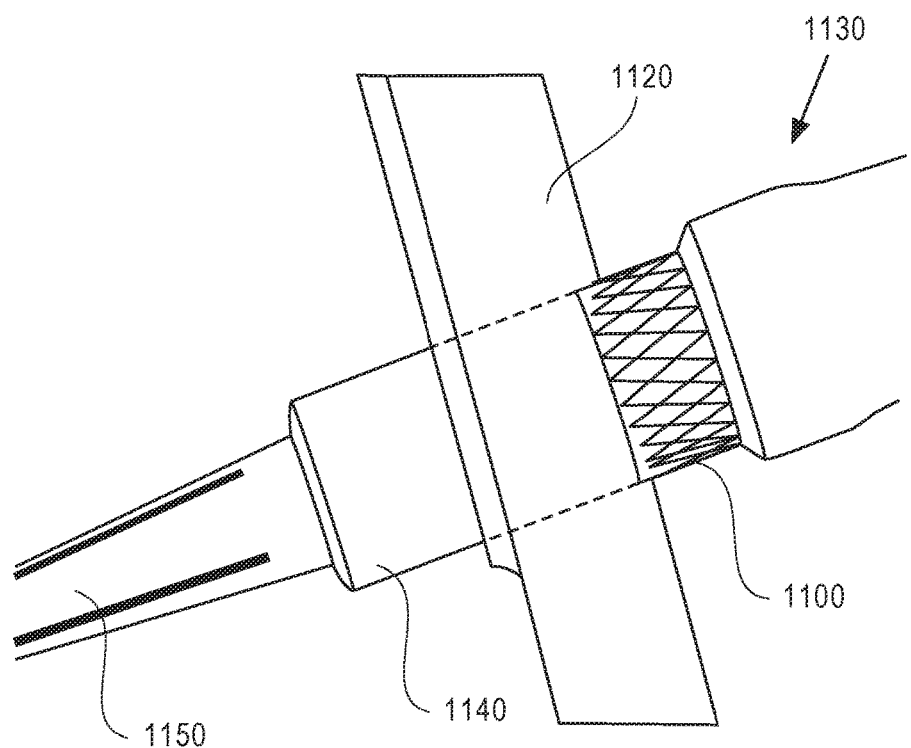

Following the endoluminal procedure, the dilator 1150 can be reinserted through the introducer sheath until the distal portion of the dilator advances through the aperture 1152 in the sidewall of the vessel 1154, and the guide wire can be removed (FIG. 92).

Figure 93:
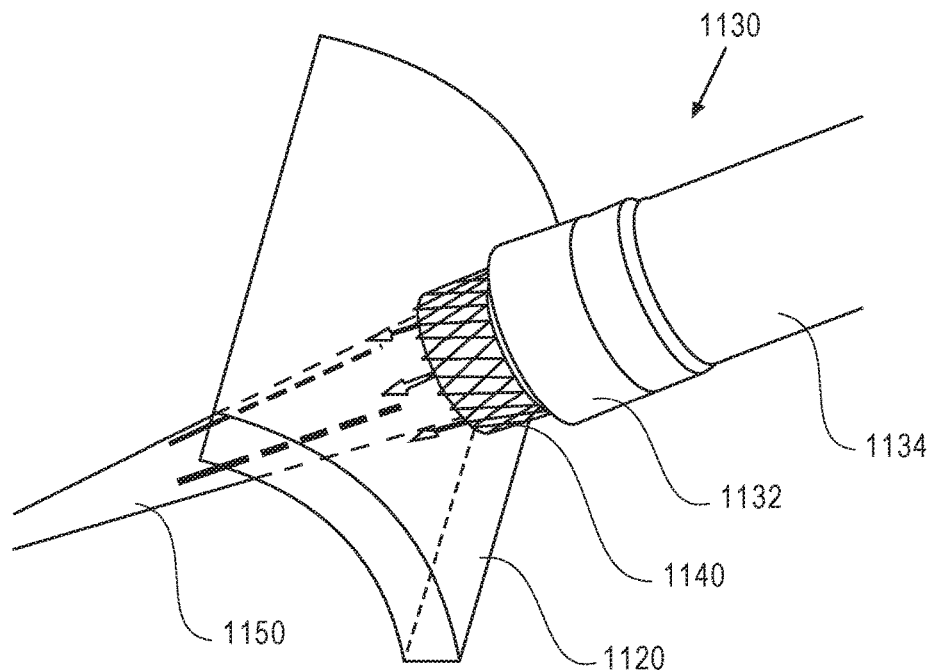
Figure 94:
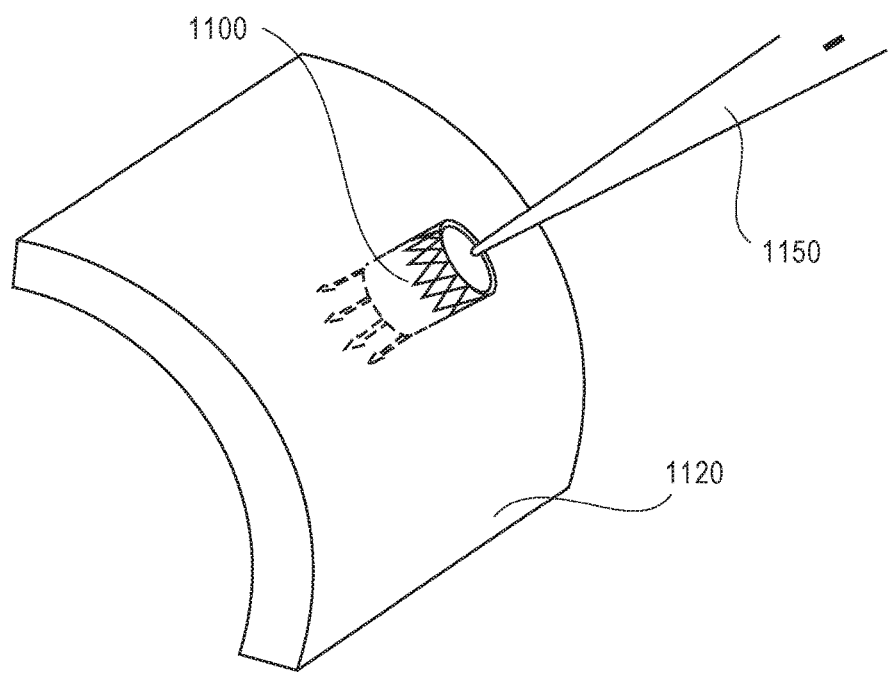

The introducer sheath 1140 and dilator 1150 are then retracted proximally while the carrier 1132 is held in place to stabilize the sealing device 1100 while the introducer sheath and dilator are retracted (FIG. 93). As the dilator 1150 is retracted from the aperture 1152, the sealing device 1100 contracts (e.g., the sealing member self-contracts, or is contracted by mechanical means) to the sealed configuration 1105. When the frame 1100 moves to the closed configuration, the anchors 1109, which are inserted through the sidewall of the vessel 1154, pull the vessel tissue around the aperture 1152 closed, thereby sealing the aperture 1152 in the sidewall of the vessel (FIG. 94).

In the illustrated embodiment, the sealing device 1100 is deployed into the sidewall of the vessel 1054 prior to performance of the endoluminal procedure. In alternate embodiments, the sealing device 1100 can be deployed into the sidewall of the vessel 1054 after performance of the endoluminal procedure.

K. Exemplary Self-Inverting Sealing Device 1200

Figure 99:
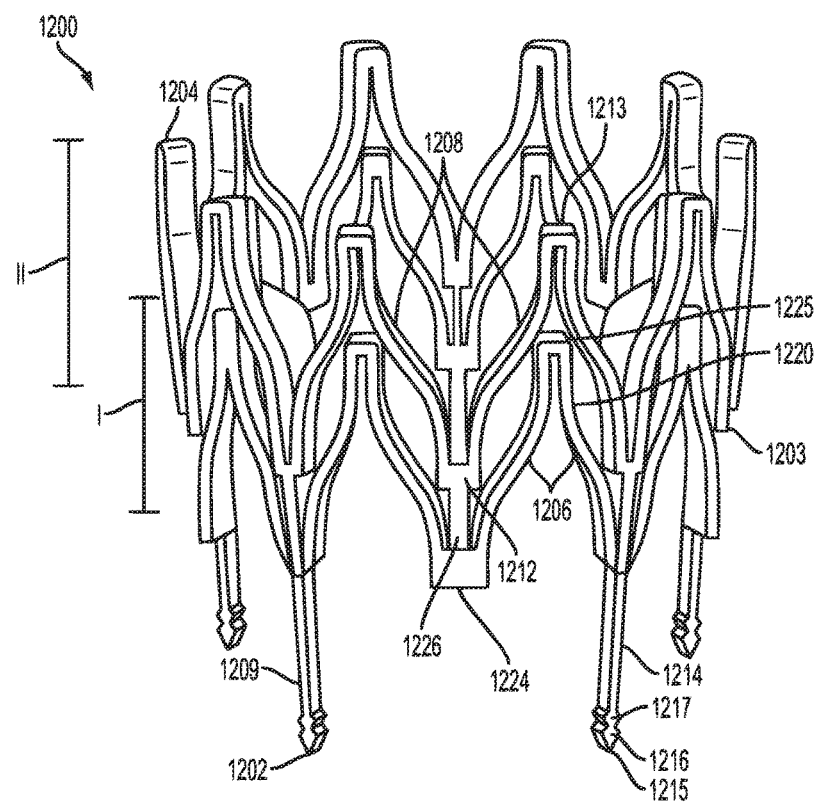
FIG. 99 shows a perspective view of an invertible sealing device in a non-constrained state, according to one embodiment.

FIG. 99 shows a sealing device 1200, for use in sealing an aperture or opening in a vessel side wall, for example following opening of an aperture 910 in a wall of the aorta for implantation of a prosthetic heart valve. The illustrated sealing device 1200 is adapted to be deployed in the sidewall of the aorta, although it can also be used in other vessels or organs of a subject. The sealing device 1200 has an open configuration 1203 (see FIG. 99) and a sealed or closed configuration 1205 (see FIG. 103). The sealing device 1200 can be deployed around a puncture or aperture in a vessel sidewall that was created for access to the interior of a blood vessel in a patient, for example access for performing a surgical procedure (e.g., heart valve replacement or repair). When placed in the sealed configuration 1205, the sealing device 1200 seals the opening used to access the interior of the vessel. As discussed in more detail below, unlike known sealing devices, the sealing device 1200 is made of a shape memory material and is in a constrained state when in sealed configuration 1205. In several embodiments, the constraint applied in the sealed configuration 1205 is advantageous because the stress applies a constant force on the tissue, which permits the sealing device 1200 to close larger opening than other devices without excessive leaking from the luminal space. Apparatus particularly suited for delivery and implantation of the sealing device 1200, as well as methods of using the sealing device 1200, are described in detail below.

In several embodiments, the sealing device 1200, delivery apparatus, and methods are useful for transaortic procedures in which an opening is created on the aorta, for example, for implanting a prosthetic heart valve in the aortic valve position. The sealing device 1200 and methods are also applicable for other locations, however, for example, the pulmonary artery, atrial wall (trans-atrial, for example, for implanting a prosthetic mitral valve), and/or ventricular wall (for example, for implanting a prosthetic mitral and/or aortic valve). The sealing device 1200, apparatus, and method also permit laparoscopic and/or robotic surgical procedures within organs, for example, the heart. The embodiments can seal a large opening (up to 26 F., up to 45 F., or even greater) that was opened for access to the interior of a vessel or chamber (such as the aorta or left atrium) in a patient.

The sealing device 1200 can be made of any of various suitable memory shape materials (e.g., Nitinol) as known in the art.

Figure 100:
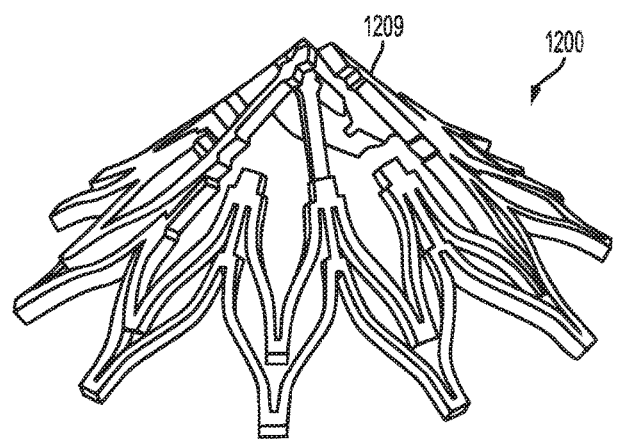
FIG. 100 shows a perspective view of the invertible sealing device of FIG. 99, in a constrained state.
Figure 101:
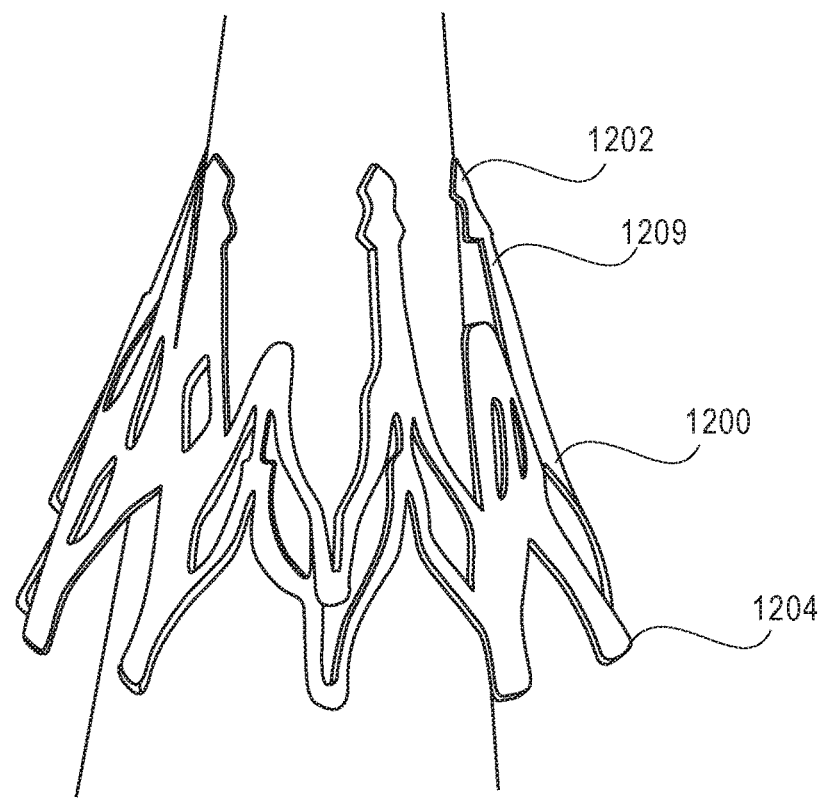
FIGS. 101 and 102 show side views of the invertible sealing device of FIG. 99 in a constrained state and mounted on a conical or tubular expansion member, respectively.
Figure 102:
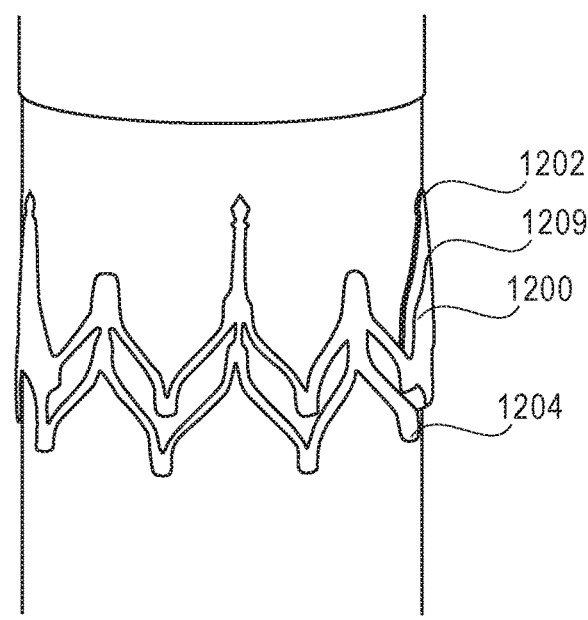
Figure 103:
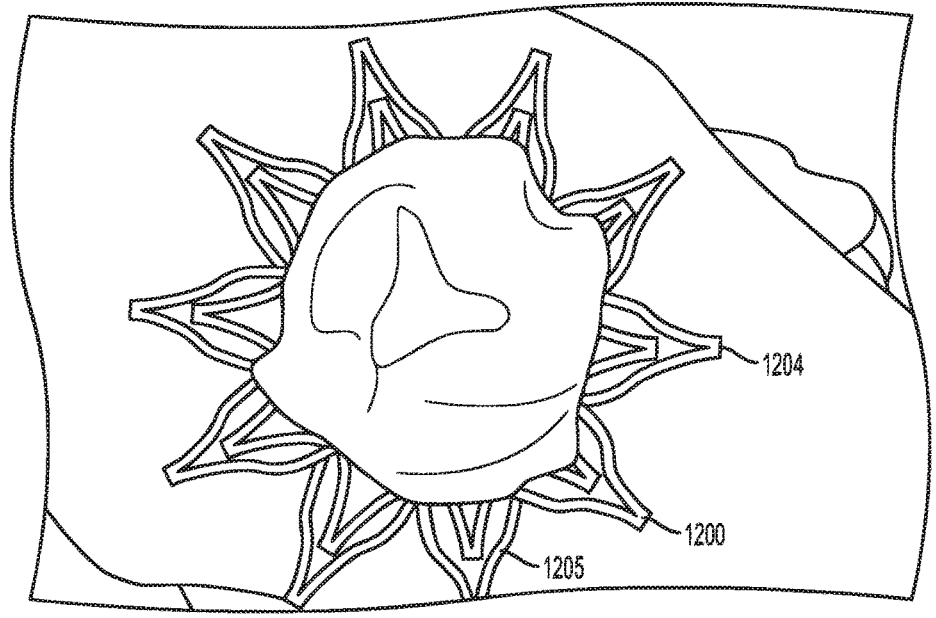
FIG. 103 shows a top view of the invertible sealing device of FIG. 99 implanted in a vessel sidewall and in a deployed state.
Figure 104:
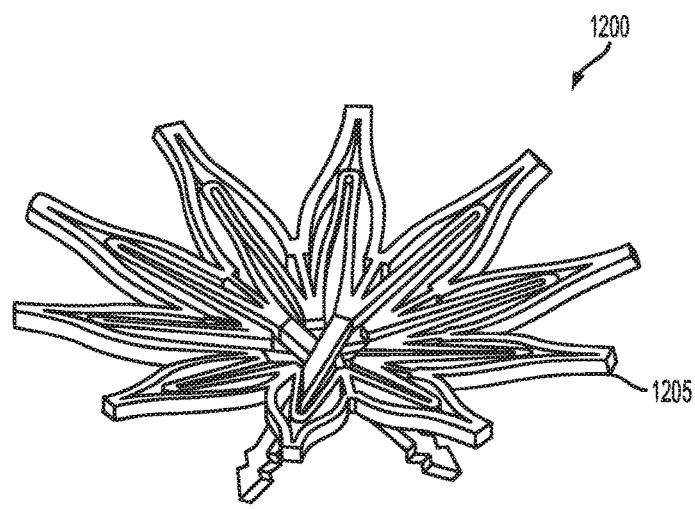
FIG. 104 shows a perspective view of the invertible sealing device of FIG. 99 in a deployed state. For illustration purposes, the vessel sidewall is not shown.

FIG. 99 illustrates the sealing device 1200 in its memory shape. For use to seal an aperture in a vessel wall, the sealing device 1200 is first inverted about 180 degrees (for example, flipped inside out) such as by flipping or rotating axially extending struts or anchors 1209 from the position shown in FIG. 99 to the position shown in FIG. 100 such that the anchors are generally extending in the opposite direction. In particular embodiments, the sealing device 1200 can be inverted by rotating the anchors 1209 inwardly through the lumen of the sealing device to the position shown in FIG. 100. The sealing device can then can be further expanded toward a cylindrical shape by inserting a conical mandrel or similar apparatus through the sealing device (such as the nosecone of a delivery apparatus; FIG. 101) and then retained in a cylindrical shape by sliding the sealing device onto a cylindrical shaft of a delivery apparatus or device (FIG. 102) that is used to implant the sealing device in the vessel wall. Upon deployment, the anchors 1209 of the sealing device 1200 are inserted into the vessel wall around an aperture, as further described below. Once deployed and released from the delivery apparatus, the sealing device 1200 will strive to return to its memory shape thus forcing the tissue around the aperture to close together (FIG. 103). However, due to the interference of the anchors and the tissue of the vessel wall, the deployed sealing device 1200 does not fully return to its memory shape, but instead moves to the closed configuration 1205 (FIG. 103). For illustration purposes, FIG. 104 shows the sealing device 1200 in the closed configuration 1205 without the tissue of the vessel wall.

Referring to FIG. 99, the sealing device 1200 in the illustrated embodiment comprises an distal end 1202 and a proximal end 1204; a distal row of axially extending anchors 1209 including struts 1214 and barbs 1216, and a upper portion including a first row I of circumferentially extending, angled struts 1206 arranged end-to-end and extending circumferentially; and a second row II of circumferentially extending, angled struts 1208 at the proximal end of the frame. In the illustrated embodiment, the struts of rows I and II can be connected at nodes or junctions 1212 (discussed below).

The struts and frame portions of the sealing device 1200 collectively define a plurality of open cells 1220 of the frame. In the illustrated embodiment, the opening 1220 are substantially the same size and shape; however, openings of different size and shape are also possible.

As shown in FIG. 99, the distal end of two struts 1206 can be connected at a node or junction 1224 (forming a distal apex) and the proximal end of two struts 1206 can be connected at a node or junction 1225 (forming a proximal apex). The distal end of two struts 1208 can be connected at a node or junction 1212 (forming a distal apex), and the proximal end of two struts 1208 can be connected at a node or junction 1213 (forming a proximal apex). As shown in the illustrated embodiment, the distal apices 1212 and 1224 can be connected by a longitudinally extending strut 1226.

The struts 1214 can be connected to selected distal apices 1224, such as every other distal apex 1224, as shown. The distal end of each strut 1214 can be connected to a barb 1216, which can be shaped to include a sharp tip 1215 and a serrated edge 1217 that can be inserted through the vessel sidewall and secured therein. The struts 1214 and barbs 1216 form the anchors 1209 of the sealing device 1200. In the illustrated embodiment, the sealing device includes five anchors 1209, with a single anchor 1209 connected to alternating distal apices 1224. However, more or fewer anchors can be included on the sealing device, and the spacing of the anchors 1209 on the sealing device can vary.

The sealing device 1200 comprises a diameter suitable for insertion around an aperture in a vessel sidewall, for example, in some embodiments, the sealing device 1100 can expand up to a diameter of 10-15 mm and can contract to a diameter of 3-5 mm. In particular embodiments, the thickness of the frame 1200 measured between the inner diameter and outer diameter is about 0.45 mm or less. In additional embodiments, the height of the device 1200 can be from about 8 to about 10 mm. In more embodiments, the anchors 1209 can have a height of about 3 to about 5 mm.

L. Exemplary Delivery Apparatus 1230 for Implanting Sealing Device 1200

Figure 105:
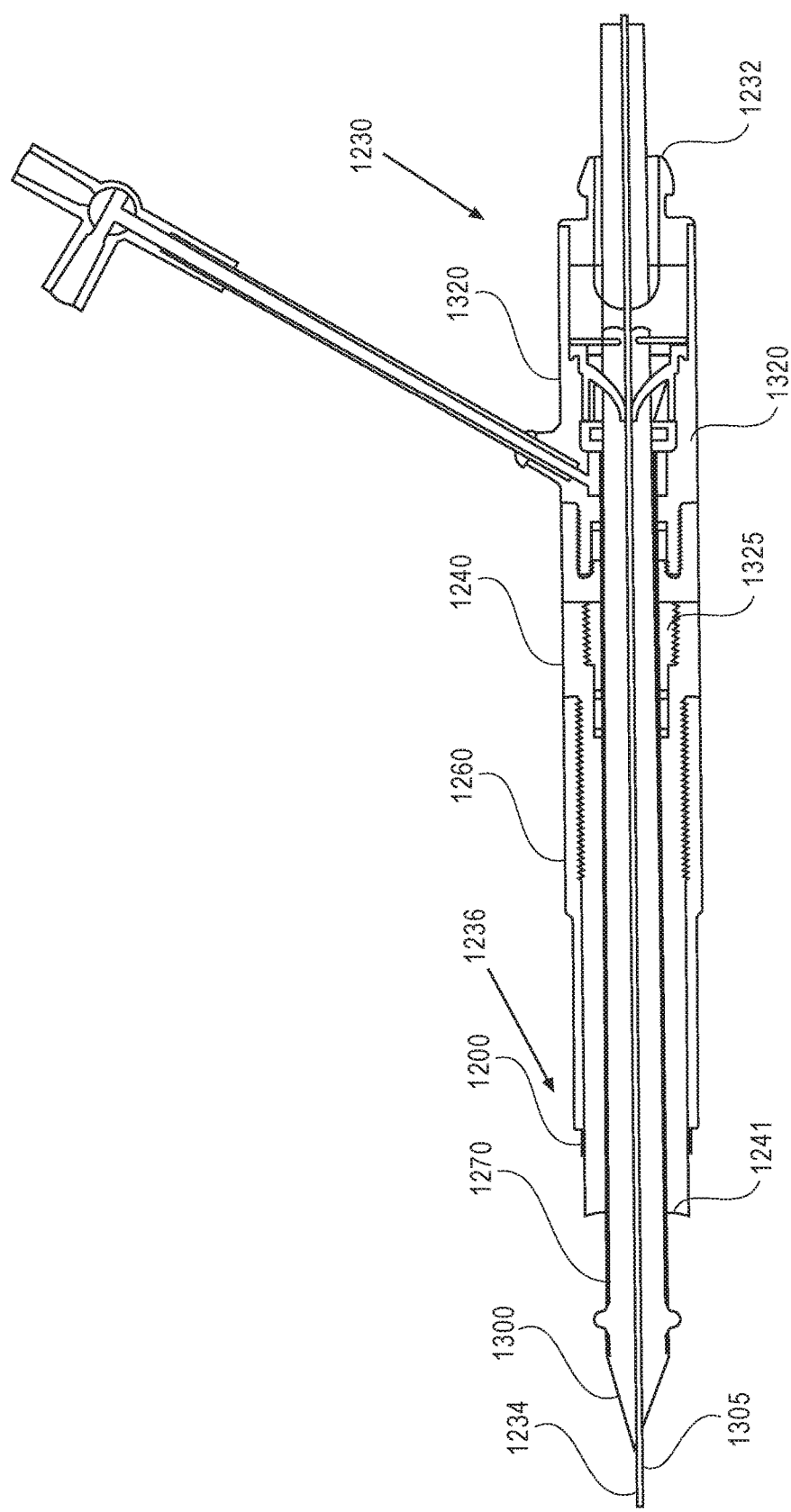
FIG. 105 is a cross-sectional view of a delivery apparatus for implantation of a vessel sealing device into a patient, with the sealing device 1200 loaded onto the delivery apparatus.

FIG. 105 illustrates a delivery apparatus 1230 that can be used for surgical procedures (e.g., implantation of a prosthetic heart valve) that involve opening an aperture in a vessel sidewall (e.g., a sidewall of the aorta) and then sealing that aperture with sealing device 1200. As illustrated in FIGS. 113-124, the delivery apparatus 1230 can be used to open an aperture 1238 in a sidewall of vessel 1239 for intra-luminal access, and then seal the aperture 1238 with sealing device 1200. The delivery apparatus 1230 includes a proximal end 1232 and a distal end 1234, and includes a number of coaxial sleeves which are relatively axially slidable and angularly rotatable along a longitudinal axis extending from the proximal end to the distal end of the deliverer apparatus. Preferably, the sleeves are actuatable by the physician from the proximal end portion of the instrument. As shown in FIG. 105, the delivery apparatus 1230 generally includes a carrier 1240 on which the sealing device 1200 can be mounted, a pusher 1260, a duel sheath balloon assembly 1270, a dilator 1300, an introducer housing 1320 (also referred to as a hemostasis valve and filling port).

In the illustrated embodiment (and for ease of illustration), the delivery apparatus 1230 is in a straight configuration. However, the delivery apparatus can include a curved or angled configuration to facilitate access to a vessel if needed.

FIG. 105 shows a cross-sectional view of the delivery apparatus 1230, and illustrates the delivery apparatus in a retracted configuration 1236. In the retracted configuration, the anchors 1209 of the sealing device 1200 do not extend distally beyond the distal end 1241 of the carrier 1240. The delivery apparatus 1230 can be moved from the retracted configuration to a insertion configuration 1237 by moving the pusher 1260 distally, thereby pushing the sealing device 1200 distally, and the anchors 1109 of the sealing device 1200 beyond the distal end 1241 of the carrier 1240 (see FIGS. 106 and 107). When used in a surgical procedure, the distal end 1241 of the carrier can be placed against or adjacent the vessel sidewall. Thus, when the anchors 1109 are pushed distally beyond the distal end 1241 of the carrier 1240, the anchors can penetrate into the vessel sidewall and are held in place by the barbs 1216 of the sealing device.

The components of the delivery apparatus 1230, such as the duel sheath balloon assembly 1270, the dilator 1300, the carrier 1240, and the pusher 1260, can include one or more locking mechanisms to releasably secure the position of the components with respect to each other and/or with respect to the sidewall of the vessel, for example, as described herein or as known in the art. The components of the delivery apparatus can be manufactured from any of various suitable materials known in the art, such as any of various metals or polymers, and combinations thereof.

Figure 107:
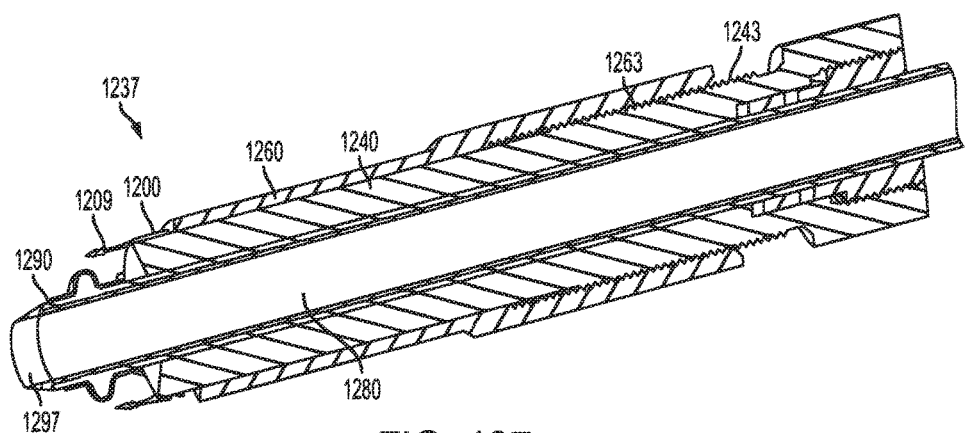
FIG. 107 is a cross-sectional view of a distal portion of the delivery apparatus of FIG. 105.
Figure 108:
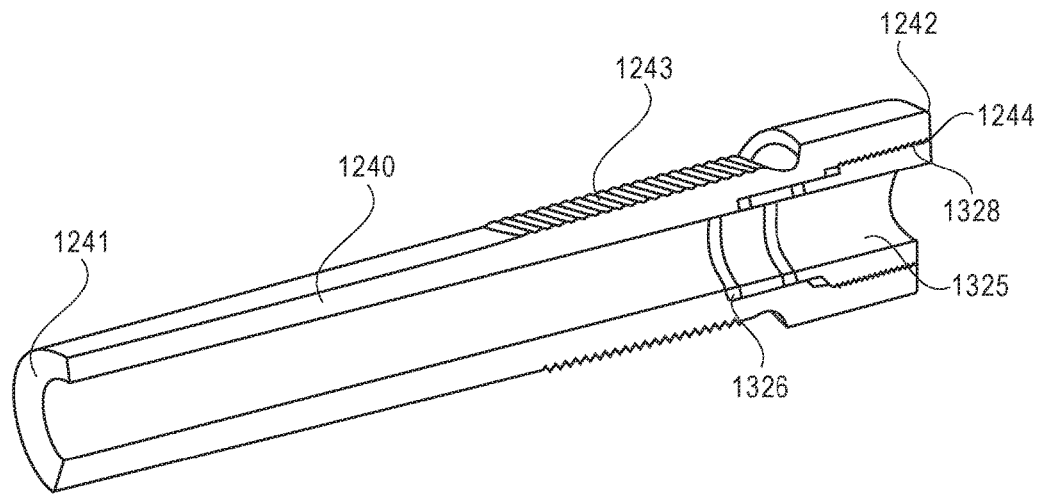
FIGS. 108 and 109 are cross-sectional views of the sealing device carrier and pusher of the delivery apparatus of FIG. 105, respectively.

As shown in FIG. 105, the carrier 1240 in the illustrated embodiment includes a coaxial sleeve that is positioned between the duel sheath balloon assembly 1270 and the pusher 1260 on delivery assembly 1230. The carrier 1240 can be axially slidable and angularly rotatable relative to the duel sheath balloon assembly 1270 and the pusher 1260. Referring to FIG. 108, the carrier 1240 includes a distal end 1241 and a proximal end 1242. The proximal portion of the carrier 1240 can be secured to the pusher 1260 by any suitable means, for example by use of interlocking threads on the outer surface of the carrier. In the illustrated embodiment, the proximal portion of the carrier 1240 includes threads 1243 that can engage with corresponding threads 1263 on the proximal portion of the pusher (FIG. 107). When the pusher 1260 is rotated (clockwise) relative to the carrier, the threaded connection with the carrier will advance the pusher in the distal direction, thus advancing the sealing device and exposing its anchors. Additionally, when the carrier 1240 is rotated (counterclockwise in this example) relative to the pusher, the threaded connection with the pusher will retract the carrier in the proximal direction, thus releasing the sealing device from the circumferential constraint of the carrier, at which point the sealing device can collapse onto the introducer sheath, and will grab the vessel tissue with it, if the anchors 1209 of the sealing device are inserted into the vessel tissue.

The distal end 1241 of the carrier extends distally beyond a distal end 1261 of the pusher and is shaped to allow mounting of the sealing device 1200. In some embodiments, the distal end 1241 of the carrier 1240 can angle or flare outwardly (for example, similar to carrier body 1132), thereby causing the sealing device 1200 to angle radially outwardly as it is pushed into the deployed configuration 1237 by distal movement of the pusher 1260. This in turn causes the anchors 1209 of the sealing device 1200 to penetrate into the vessel sidewall at an angle.

Figure 109:
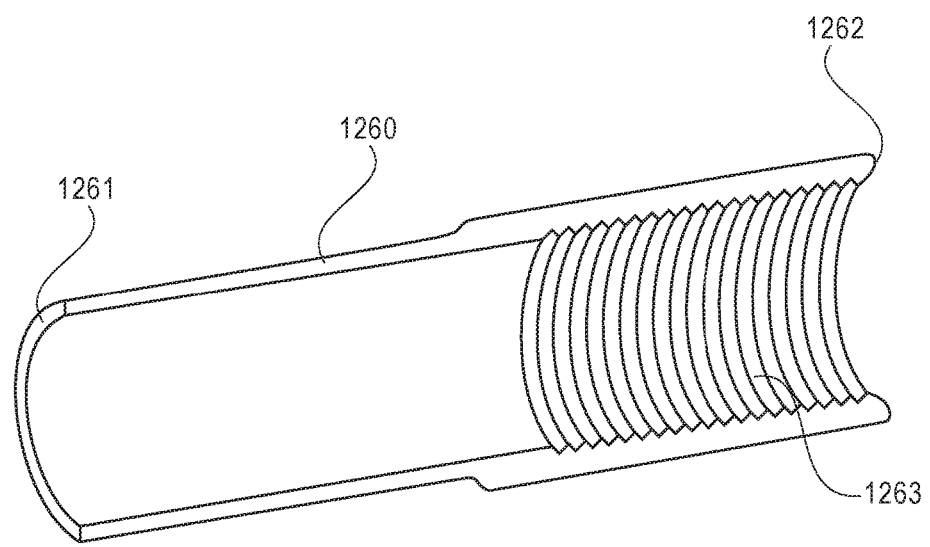

The pusher 1260 in the illustrated embodiment includes a coaxial sleeve that is positioned radially outwardly from the carrier 1240. The pusher 1260 can be axially slidable and angularly rotatable relative to the duel sheath balloon assembly 1270 and the carrier 1240. Referring to FIG. 109 the pusher includes the distal end 1261 and a proximal end 1262. The proximal portion of the pusher 1260 includes threads 1263 that can engage with corresponding threads 1243 on the proximal portion of the carrier, as noted above. The distal end 1261 of the pusher is configured to contact the proximal end of the sealing device 1200 when it is mounted on the carrier 1240. When the pusher 1260 is moved distally, the distal end 1261 of the pusher contacts that proximal end of the sealing device 1200 and pushes the sealing device into the deployed configuration 1237 of the delivery apparatus 1230.

In several embodiments, the proximal portion of the carrier 1240 can be coupled to the introducer housing 1320, or to a connector or adapter linking the carrier and the housing, by any suitable means. In the illustrated embodiment, as best shown in FIG. 108, the proximal portion of the carrier 1240 includes internal threads 1244 that can engage with corresponding external threads 1328 on a connector 1325, which in turn can be secured to introducer housing 1320 (FIG. 105). The axially position of the carrier 1240 relative to the introducer sheath can be adjusted by rotating the carrier 1240 relative to the connector 1325. As discussed in more detail below, the introducer housing 1320 and/or the connector 1325 include one or more seals (such as an O-ring) that contact the outer diameter of the duel sheath balloon assembly.

Figure 110:
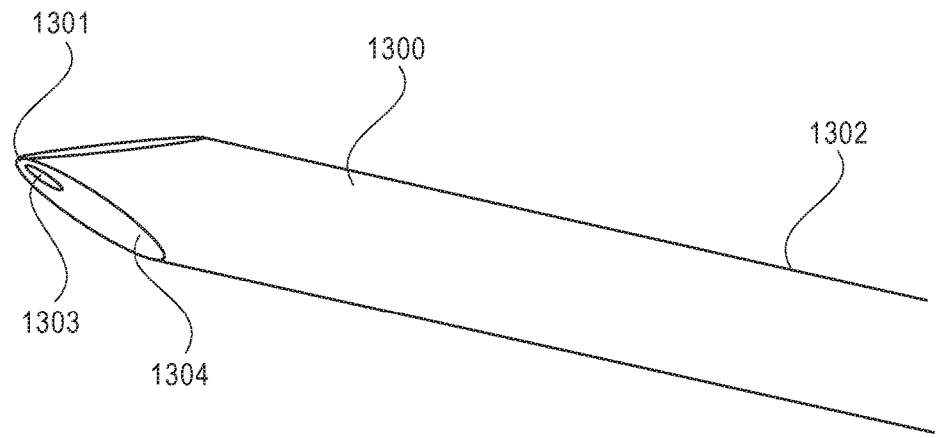
FIG. 110 is a perspective view of a distal portion of the dilator of the delivery apparatus of FIG. 105.

With reference to FIG. 110, the dilator 1300 can include a distal portion 1302 having a distal end 1301. The distal portion 1302 of the dilator includes a nose cone portion 1304, which can be tapered or conical to facilitate insertion into an aperture in the side wall of the vessel 1239. The dilator 1300 can optionally include extendable and retractable cutting members (e.g., blades) on the nose cone portion 1304 of the dilator, and proximal to the distal tip of the dilator, that are substantially similar to the extendable and retractable cutting members 1082 of dilator 1080 (discussed above), and which can be used to facilitate traversal of the vessel sidewall. Some embodiments of the dilator further comprise a flush/suction port for use during deployment.

The distal tip of the dilator includes an aperture configured to allow passage of a guide wire 1305 and/or a hypodermic needle from a guide wire lumen 1303 within the dilator. In particular embodiments, the guide wire can be inserted through the sidewall of the vessel 1239, and the nose cone portion 1304 of the dilator can be used to expand the puncture site from the diameter of the guide wire to about the outer diameter of the portion of the dilator proximal to the nose cone portion.

Figure 111:
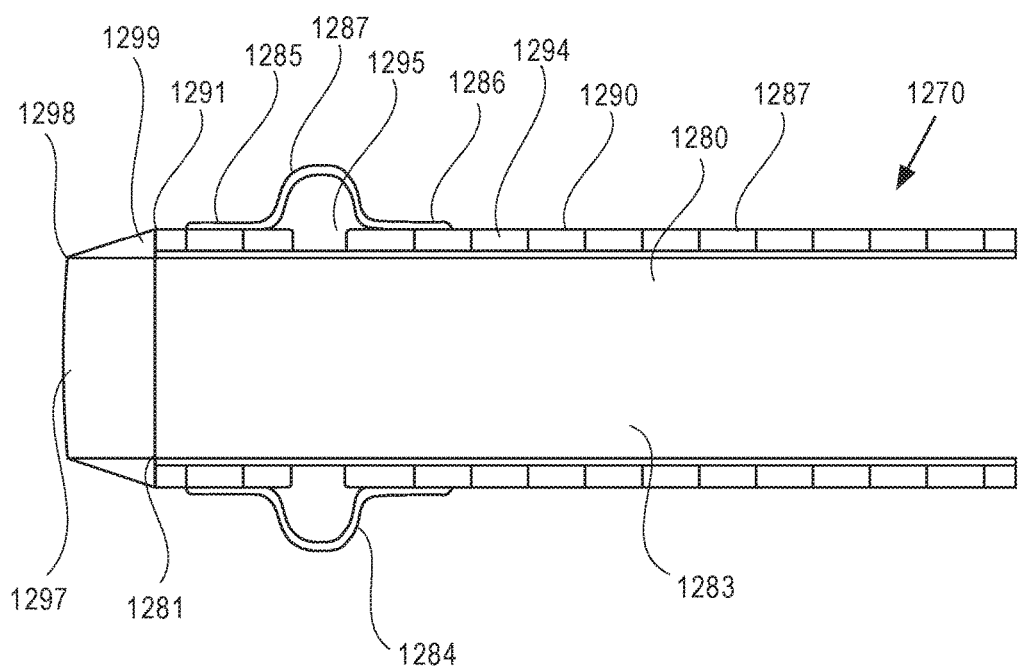
FIG. 111 is a cross-sectional view of a distal portion of the balloon sheath of the delivery apparatus of FIG. 105.

FIG. 111 shows an embodiment of the duel sheath balloon assembly 1270, which is a multi-component assembly. The duel sheath balloon assembly 1270 includes a nose cone 1297 designed for insertion through the aperture 1238 in the sidewall of the vessel 1239, an introducer sheath 1280 and a balloon sheath 1290, which encompass an inter-sleeve lumen 1294, and a distally located balloon 1284, which can be inflated or deflated by injecting or suctioning fluid through the inter-sleeve lumen from the proximal portion of the delivery apparatus.

Figure 112:
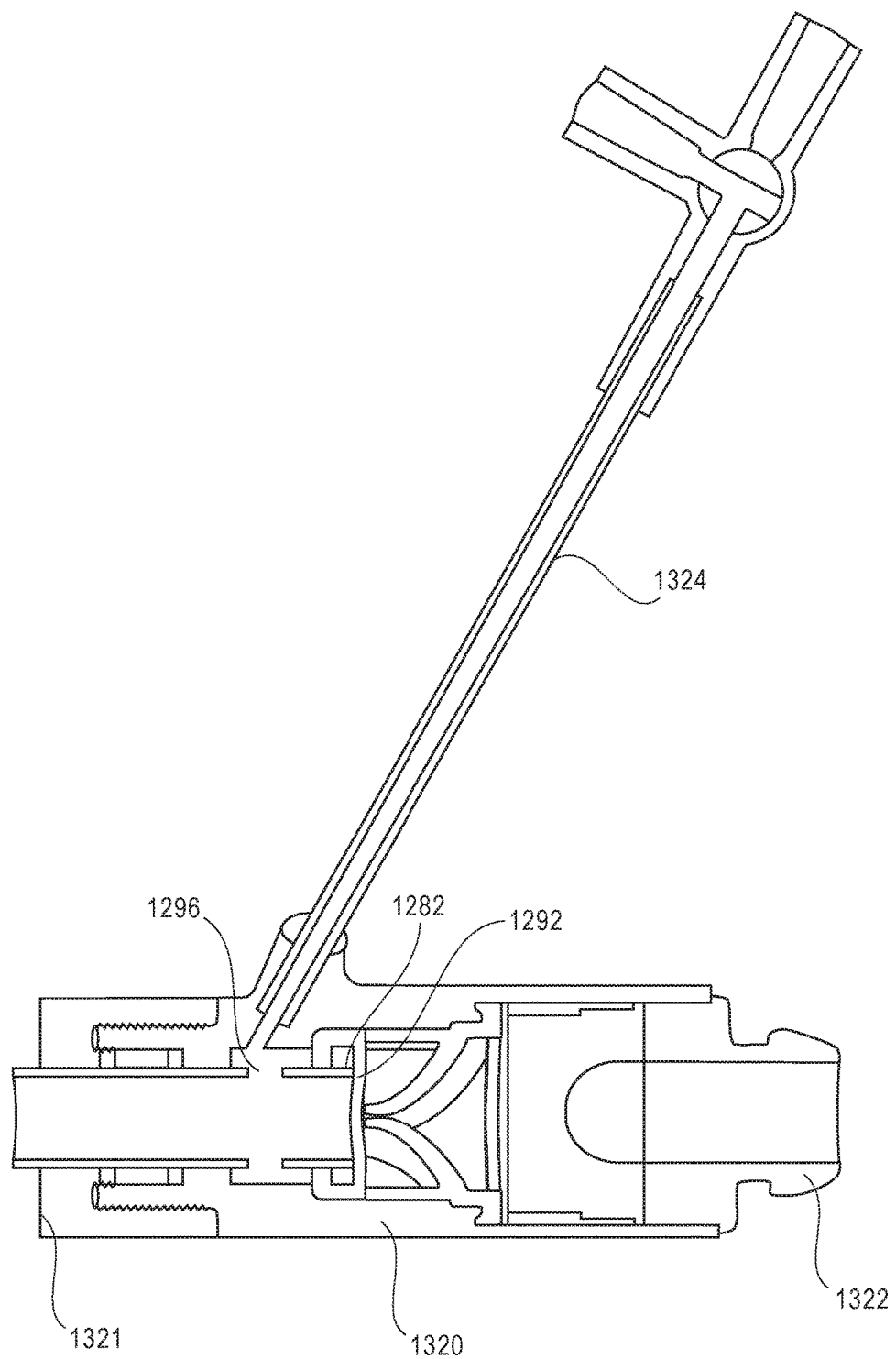
FIG. 112 is a cross-sectional view of the hemostasis valve assembly of the delivery apparatus of FIG. 105.

The introducer sheath 1280 in the illustrated embodiment comprises a sleeve or shaft 1283 extending from an introducer housing 1320. The sleeve 1283 is positioned radially inwardly from the balloon sheath 1290 on delivery assembly 1230 (see FIG. 111), the sleeve 1283 including a distal end 1281 and a proximal end 1282. In the illustrated embodiment, the distal end 1281 of the introducer sheath is coupled to the nose cone 1297, and the proximal end 1282 is secured within the introducer housing 1320 (FIGS. 111 and 112).

The introducer sheath 1280 is configured to allow the dilator (and delivery devices for delivering a prosthetic implant) to slide inside, and be removable therefrom. An inner diameter of the introducer sheath can vary based on the intended use, and can be suitably sized to allow access to the intraluminal space of the vessel 1239 via the sheath 1280 by a treating physician, for example, for implantation of a heart valve. In several embodiments, the sheath 1280 is designed for delivery of a prosthetic heart valve to a subject in need thereof. The introducer sheath 1280 can be substantially the same as other embodiments of introducer sheaths described herein or known in the art. An example of an introducer sheath includes the Edwards Ascendra® introducer sheath.

Figure 106:
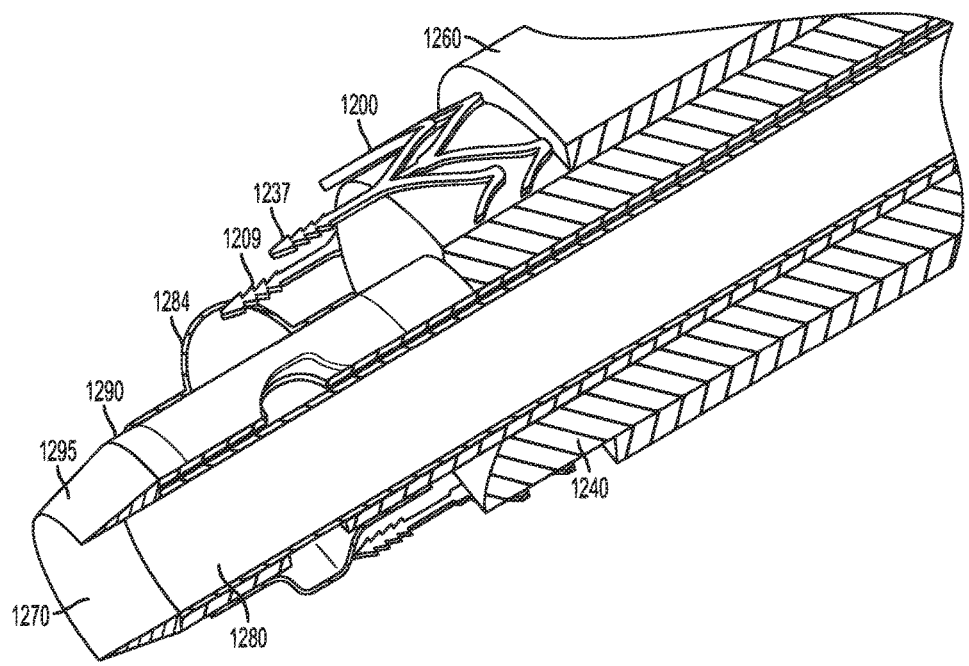
FIG. 106 is an exploded cut away view of a distal portion of the delivery apparatus of FIG. 105.

The balloon sheath 1290 in the illustrated embodiment comprises a coaxial sleeve or shaft that is positioned between the shaft 1283 of the introducer sheath 1280 and the pusher 1260 on delivery assembly 1230 (see FIGS. 106 and 107). The balloon sheath 1290 includes a distal end 1291 and a proximal end 1292 (see FIGS. 111 and 112). In the illustrated embodiment, the distal end 1211 of the balloon sheath is coupled to the nose cone 1297, and the proximal end 1292 is secured within the introducer housing 1320.

The inter-sheath lumen 1294 is the annular space located between the introducer and balloon sheaths (see FIG. 111), and extends from the proximal opening 1296 (FIG. 112) in the balloon sheath to the distal opening 1295 in the balloon sheath (FIG. 111).

Referring to FIG. 111, the balloon 1284 is secured to the distal portion of the balloon sheath. A distal portion 1285 and a proximal portion 1286 of the balloon 1284 are secured to the balloon sheath, with an inflatable portion 1287 of the balloon in between the proximal and distal portions. The balloon can be secured to the balloon sheath by any suitable means known in the art, for example by adhesive bonding, and can be made of any suitable inflatable and bio-compatible material, such as silicone.

The inflatable portion 1287 of the balloon can be located in fluid communication with the distal opening 1295 in the balloon sheath which is in fluid communication via the inter-sheath lumen 1294 to a proximal opening 1296 in the balloon sheath. The proximal opening in the balloon sheath can be located in fluid communication with one or more inflation-fluid ports on the introducer housing. Thus, inflation and deflation of the balloon can be accomplished by altering the pressure of fluid (e.g., liquid or gas) within the inter-sleeve lumen 1294 by injecting or suctioning liquid or gas through the port on the hemostasis valve.

The balloon 1284 is located at the distal portion of the duel sheath balloon assembly 1270 that is inserted into the lumen of a vessel during use of the delivery apparatus 1230 (discussed in more detail below). The balloon 1284 can be inflated after insertion into the vessel lumen, and deflated prior to remove of the introducer sheath from the vessel lumen. Once inflated, the balloon can provide a seal against the luminal side of the vessel to reduce or prevent leakage of blood or other fluids. The inflated balloon also provides support for the vessel tissue when the anchors 1209 of the sealing device 1200 are inserted into the sidewall of the vessel. When inflated, the balloon 1284 extends radially outwardly from the balloon sheath 1290. In some embodiments, the balloon 1284 can extend by about up to 5 mm radially. In some embodiments, the balloon 1284 can extend by about 5-10 mm from the introducer sheath. When deflated, the balloon can lie substantially flat against the outer surface of the balloon sheath 1290.

A proximal portion of the sleeve 1283 and the balloon sheath 1290 can be secured within the introducer housing 1320, which can house one or more seals or valves (e.g., slit valves or duck-bill valves) configured to seal against the outer surface of a prosthetic-device-delivery-apparatus that is inserted through the introducer sheath 1280, as known in the art. As shown in FIG. 112, the introducer housing 1320 includes a distal end 1321 and a proximal end 1322. The introducer housing 1320 can include one or more ports for pressurizing or depressurizing fluid in the inter-sleeve lumen 1294 of the introducer sheath to inflate or deflate the balloon 1284. The introducer housing 1320 can optionally include one or more flush/suction ports 1324 for use during surgery as needed (see FIG. 112).

M. Exemplary Method of Implanting Sealing Device 1200 with Apparatus 1230

FIGS. 113-124 illustrate an exemplary method of using the delivery apparatus 1230 for accessing the lumen of a vessel 1239 (such as the aorta) to perform an endoluminal procedure via an aperture 1238 in the sidewall of a vessel, and then sealing the aperture following the endoluminal procedure with a sealing device such as sealing device 1200. The illustrated method utilizes the delivery apparatus 1230 and the sealing device 1200; however, other embodiments of a sealing device and/or a delivery apparatus (for example, as described herein) can be used to perform the disclosed method. In several embodiments, the disclosed method is used to create and seal the aperture 1238 in a sidewall of the aorta in a patient during a surgical procedure, such as implantation of a prosthetic heart valve.

Prior to initiation of the method, the sealing device 1200 is loaded onto the delivery apparatus 1230, with the sealing device mounted on the distal portion of the carrier 1240 (FIG. 105).

Figure 113:
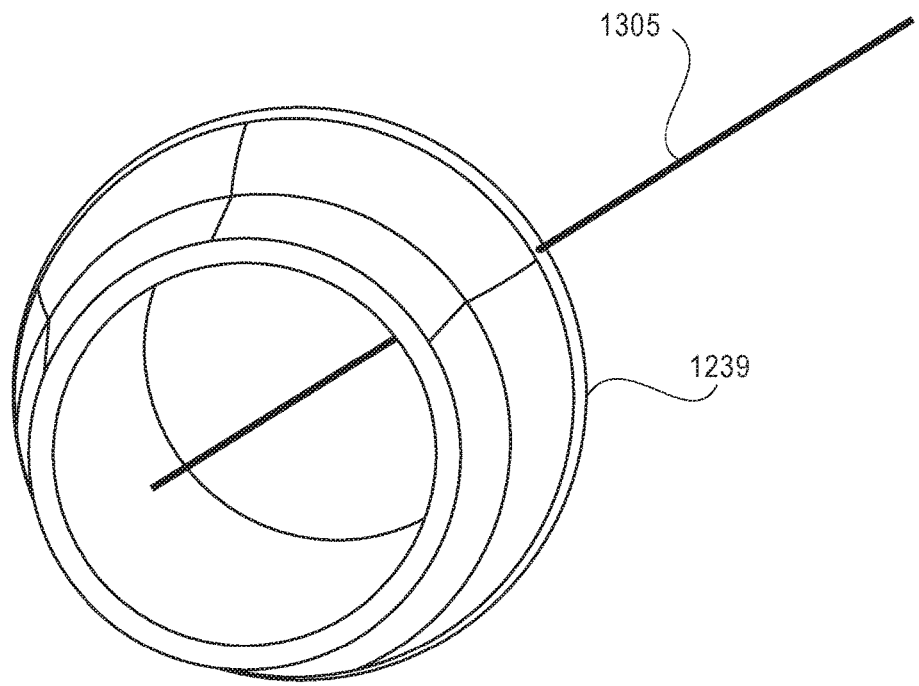
FIGS. 113-124 illustrate an exemplary method of using a disclosed sealing device and related delivery apparatus for accessing the lumen of a vessel for performance of an endoluminal procedure via an aperture in the sidewall of the vessel, and then sealing the aperture following the endoluminal procedure.
Figure 114:
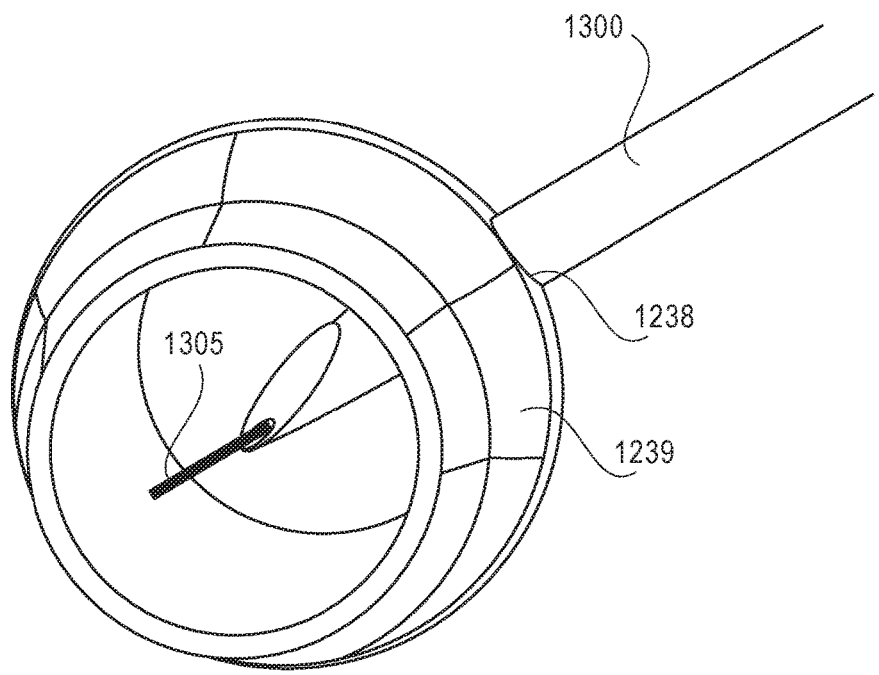

In the illustrated embodiment of the method, the delivery apparatus includes the dilator 1300, which can be substantially the same as the dilator 1080 described above. A hypodermic needle can be advanced through the lumen and aperture at the distal tip of the nose cone of the dilator and inserted through the sidewall of the vessel 1239. The guide wire 1305 can then be inserted through the hypodermic needle and into the lumen of the vessel 1239, and placed as needed for the endoluminal procedure. After placement of the guide wire, the hypodermic needle can be retracted from the sidewall of the vessel, leaving the guide wire 1305 in place (FIG. 113). After placement of the guide wire, the delivery apparatus 1230 can be advanced distally until the distal tip of the nose cone of the dilator 1300 penetrates the sidewall of the vessel 1239 (FIG. 114). The dilator can include extendable and retractable cutting members, which can be extended from the dilator body to facilitate traversal of the sidewall of the vessel 1239 by the nose cone and for widening of the aperture 1238, for example, as discussed above for dilator 1080. Optionally, an incision in the sidewall of the vessel 1239 can be performed prior to advancing the nose cone through the sidewall of the vessel.

Figure 115:
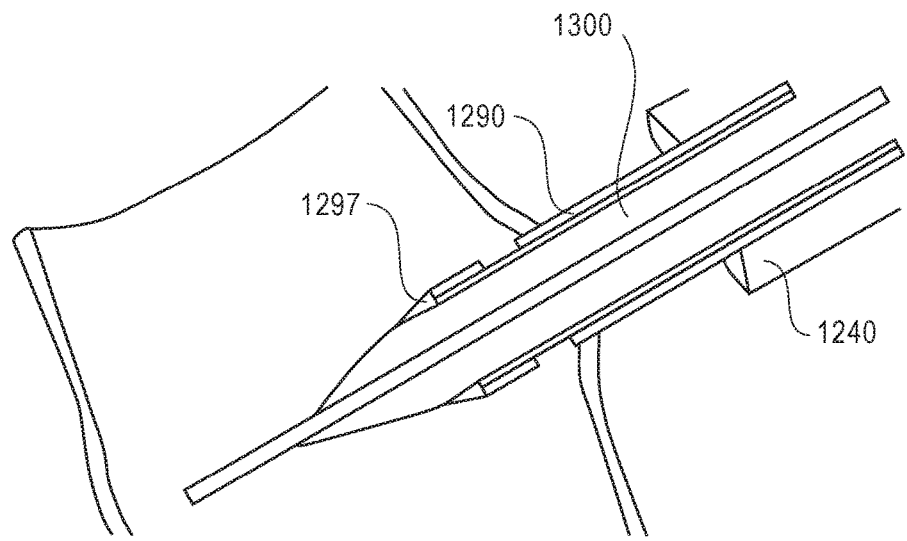
Figure 116:
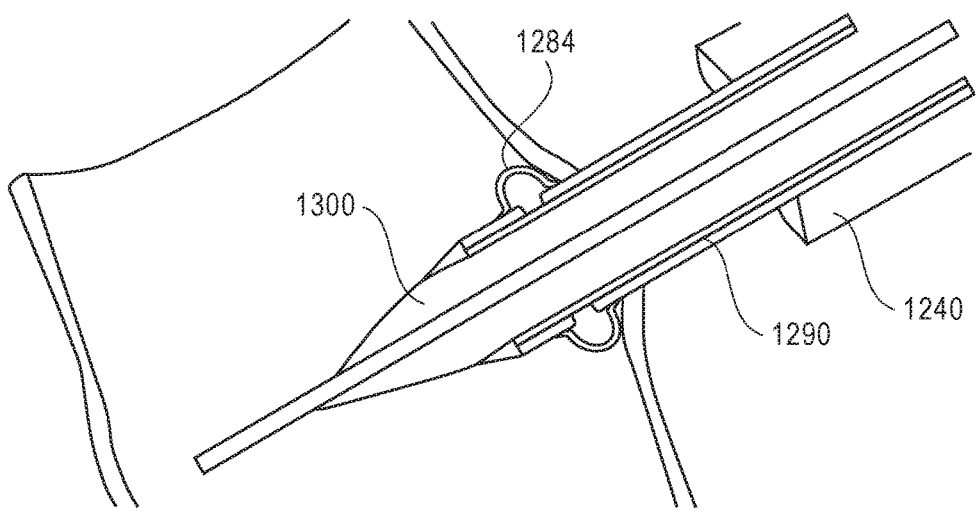

As shown in FIG. 115, the introducer sheath 1280 can be advanced distally until the nose cone 1297 of the duel lumen balloon assembly 1270 advances through the aperture 1238. The duel lumen balloon assembly 1270 is advanced further distally, until the balloon 1284 (deflated) advances through the aperture 1238 and is within the lumen of the vessel 1239. The balloon can then be inflated, and the introducer sheath 1280 is moved proximally so the inflated balloon engages the luminal side of the vessel 1389 (FIG. 116).

Figure 117:
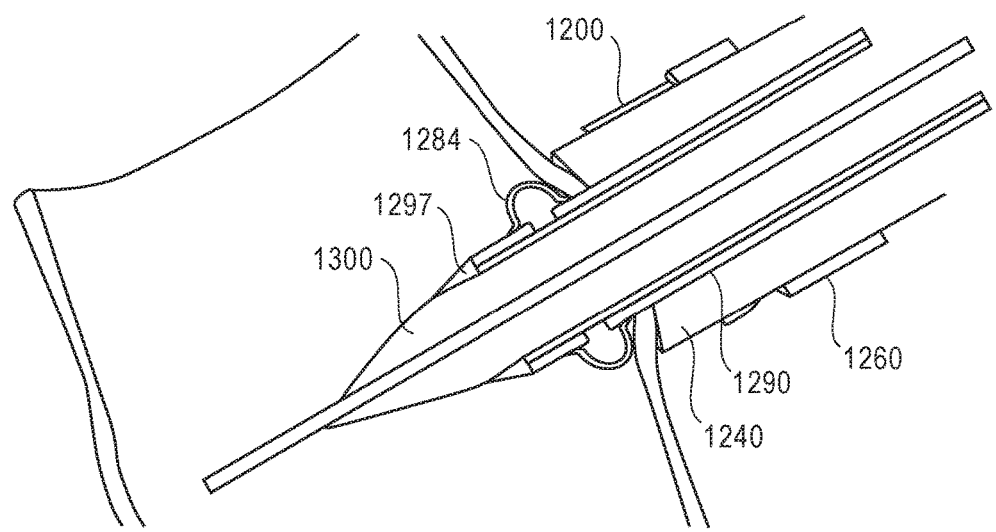
Figure 118:
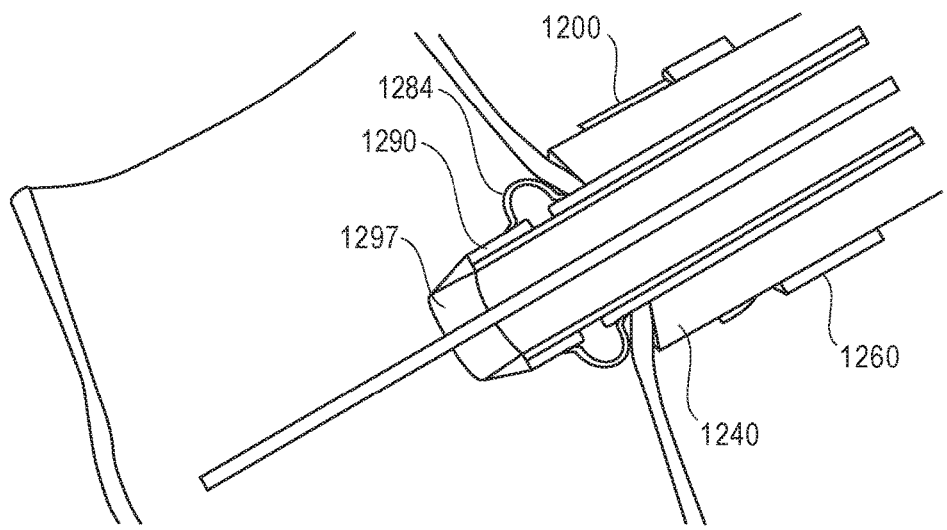

As shown in FIG. 117, the carrier 1240 can then be advanced distally until the distal end 1241 of the carrier 1240 contacts the sidewall of the vessel 1239. By contacting the luminal side of the vessel 1239 with the inflated balloon 1284, and the exterior side of the vessel 1239 with the distal end 1241 of the carrier 1240, a seal is formed around the sidewall of the vessel to reduce or prevent leakage of fluid (e.g., blood) from the vessel, and to support the sidewall of the vessel when the anchors 1209 of the sealing device 1200 are inserted into the sidewall.

Figure 119:
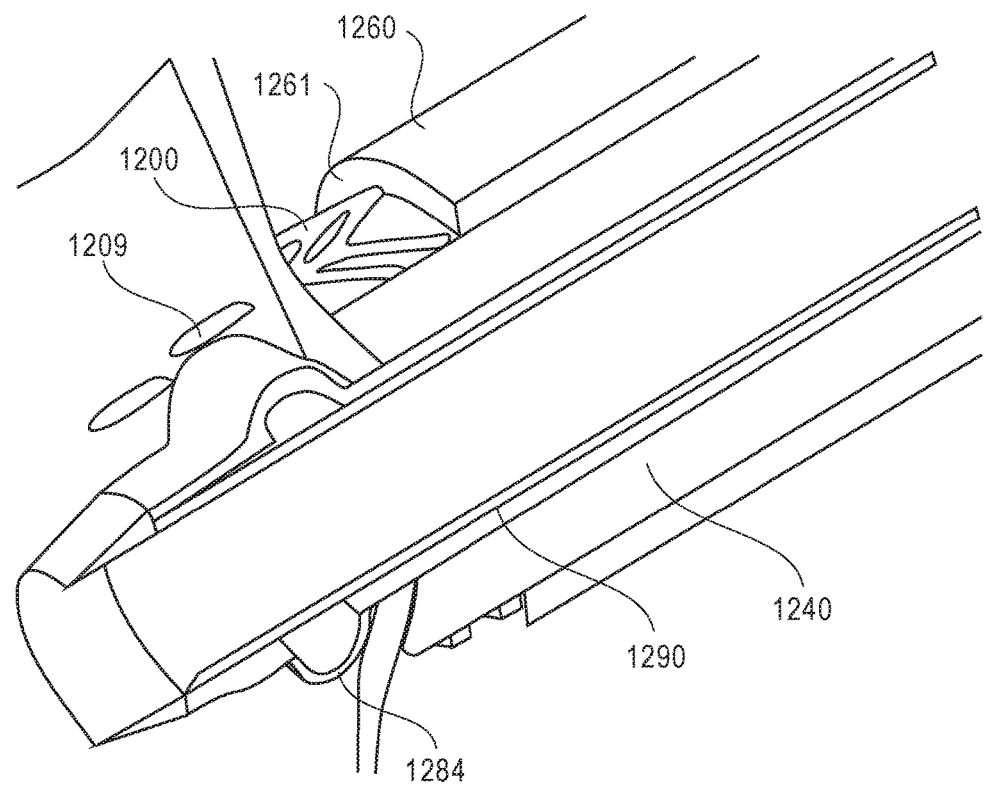
Figure 120:
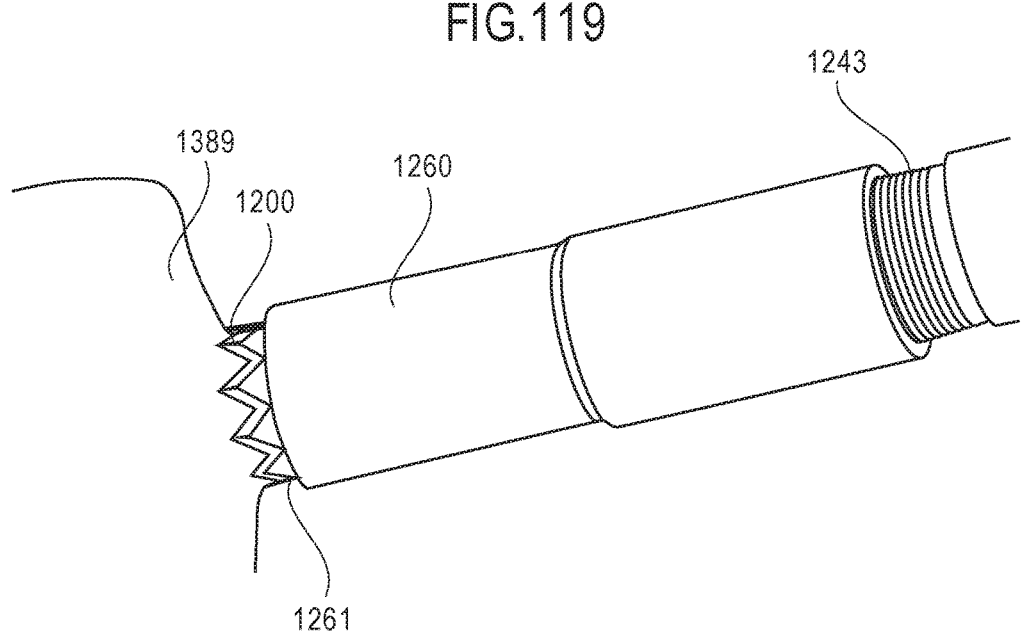
Figure 121:
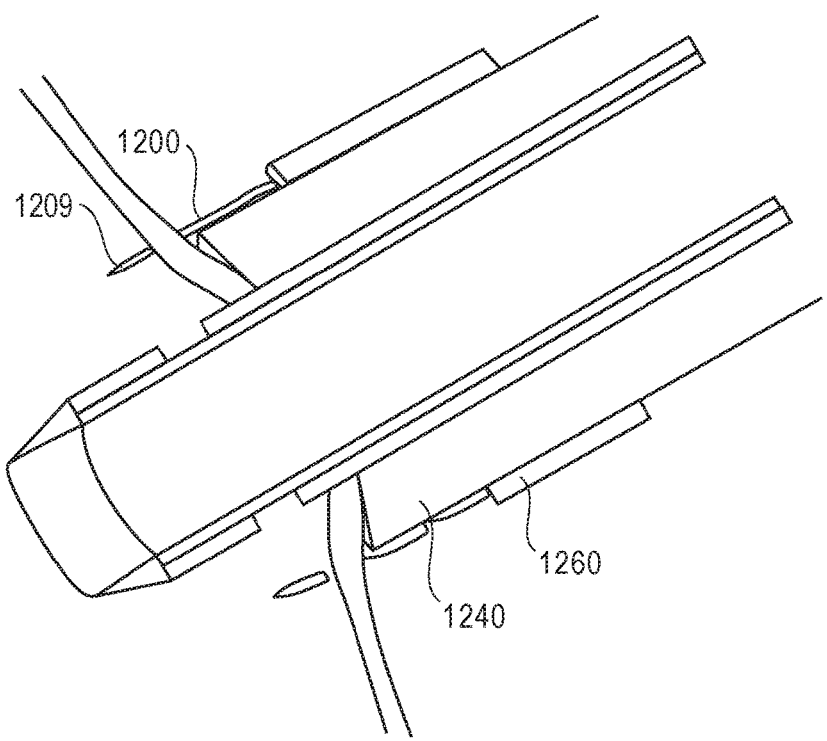
Figure 122:
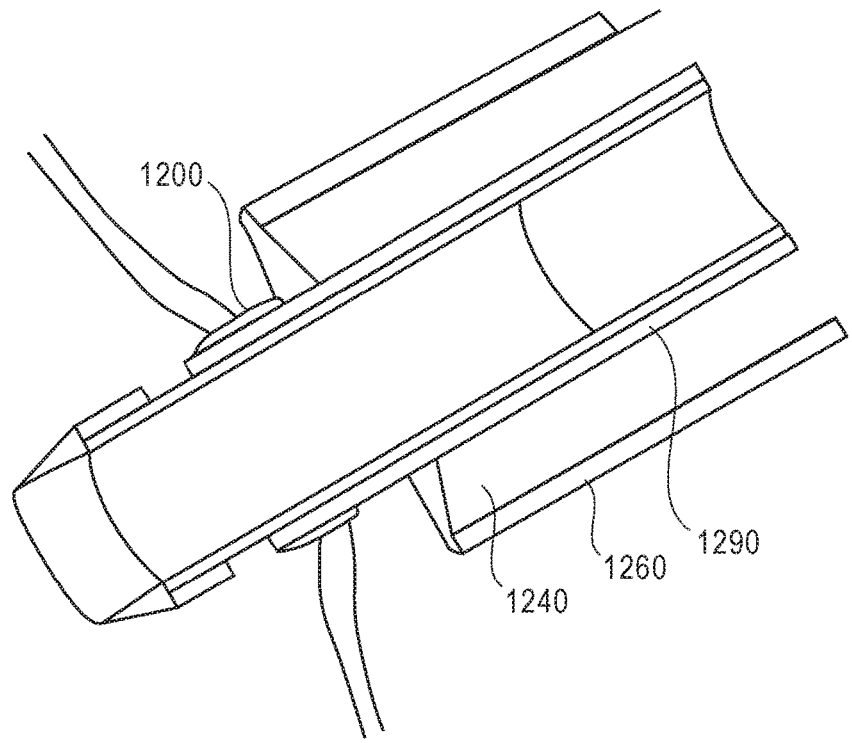
Figure 123:
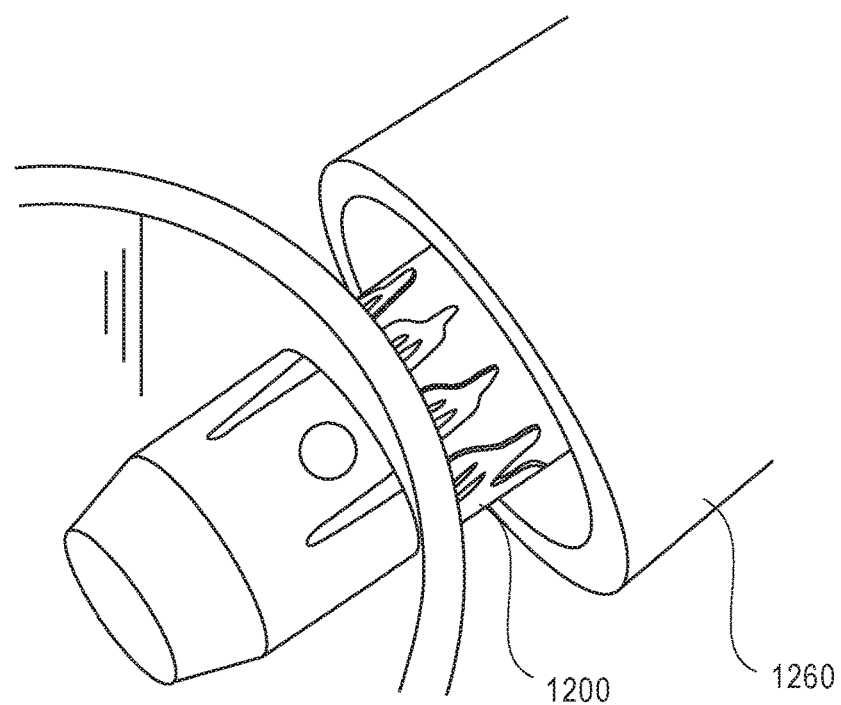

The dilator 1300 can then be retracted proximally and temporarily removed from the delivery assembly 1230 (FIG. 118), and the endoluminal procedure can then be performed In the illustrated embodiment of the method, the pusher 1260 is then rotated, which moves the pusher distally because of the carrier-pusher connection at threads 1243 and 1263. Distal movement of the pusher 1240 pushes the anchors 1209 of the sealing device 1200 past the distal end of the carrier 1240, thereby inserting the anchors 1209 into the sidewall of the vessel 1239 (FIGS. 119 and 120).

The balloon 1284 can then be deflated (FIG. 121) and the carrier 1240 can be retracted proximally (FIG. 122) by rotating the carrier while holding the pusher in place. Holding the pusher in place stabilizes the sealing device against the sidewall of the vessel 1239 while the carrier is retracted. As the carrier is retracted, the anchors 1209 of the sealing device 1200 will remain secured to the sidewall of the vessel 1239. The carrier 1240 is retracted proximally until the distal end 1241 of the carrier 1240 passes proximally beyond the proximal end of the sealing device 1200. The sealing device 1200 will then tighten around the duel lumen balloon assembly 1270 (FIG. 123), thereby providing hemostasis or a seal that reduces and/or prevents bleeding between the duel lumen balloon assembly 1270 and the aperture 1238.

Figure 124:
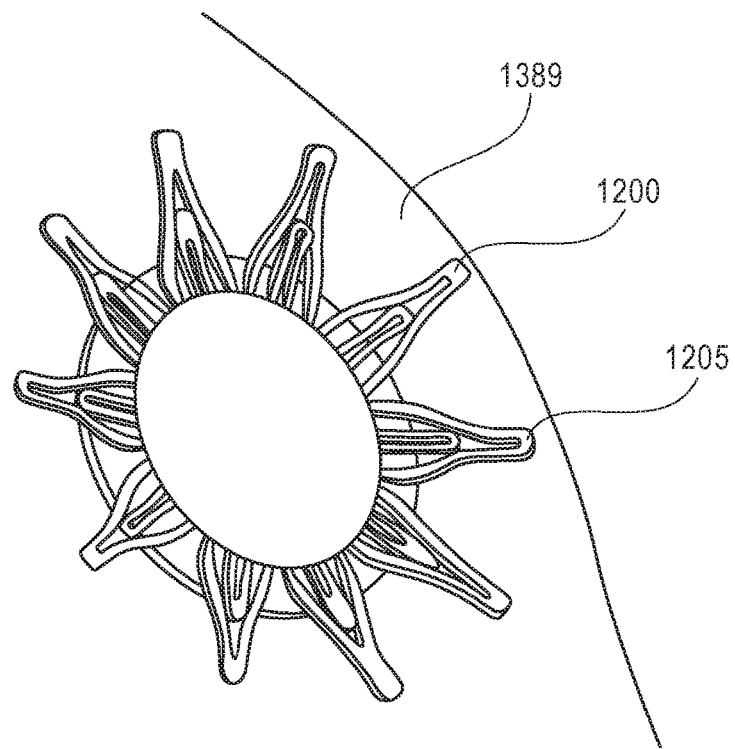

The duel lumen balloon assembly 1270 can then be retracted proximally while the carrier 1240 is held in place to stabilize the sealing device 1200 while the duel lumen balloon assembly 1270 is retracted. As the duel lumen balloon assembly 1270 is retracted from the aperture 1238, the sealing device 1200 shifts to the sealed configuration 1205 (FIG. 124).

In the illustrated embodiment, the sealing device 1200 is deployed into the sidewall of the vessel 1239 after performance of the endoluminal procedure. In alternate embodiments, the sealing device 1200 can be deployed into the sidewall of the vessel 1239 before performance of the endoluminal procedure.

N. Exemplary Delivery Apparatus 1330 for Implanting Sealing Device 1200

Figure 125:
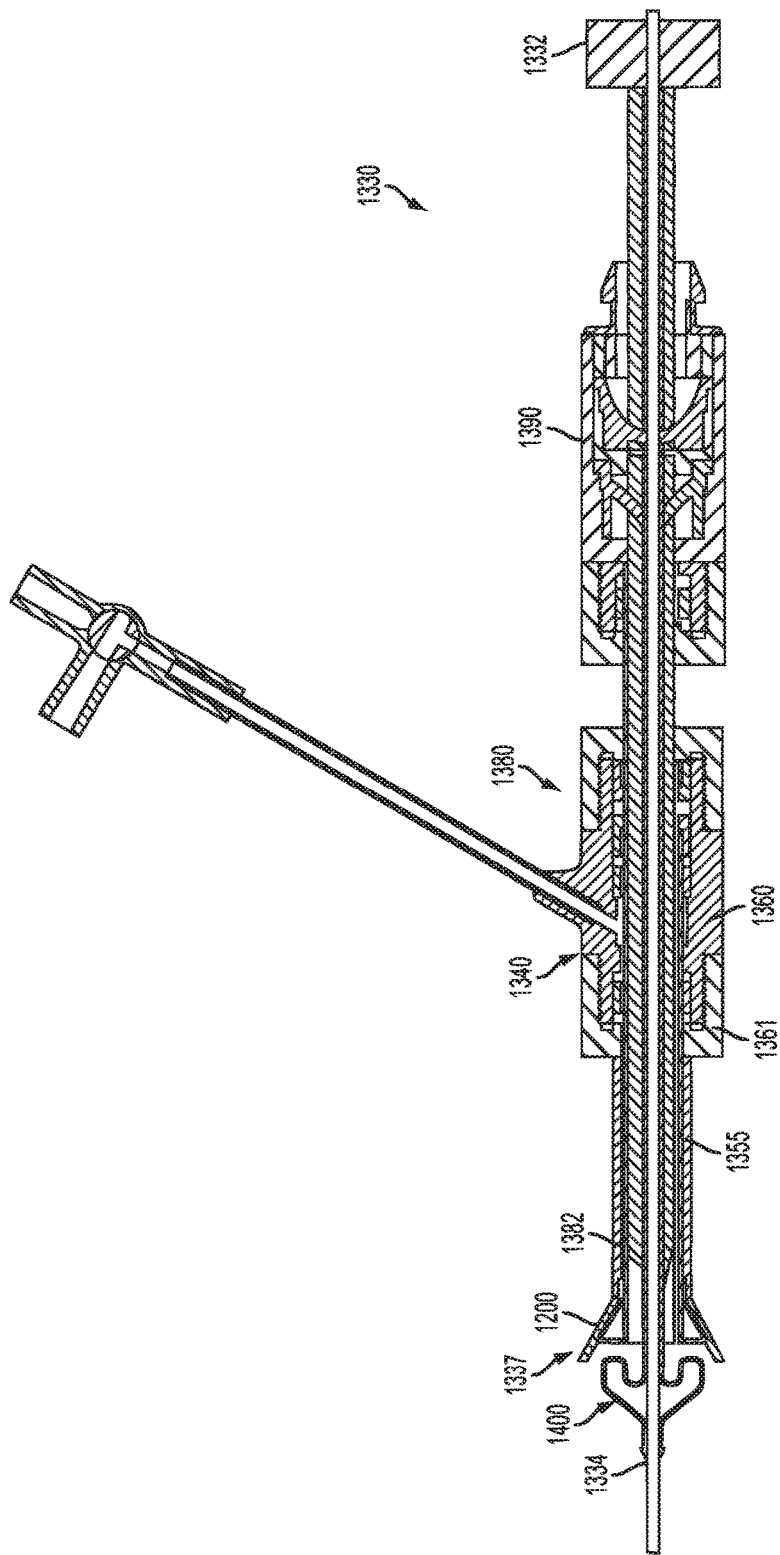
FIG. 125 is a cross-sectional view of a delivery apparatus for implantation of a vessel sealing device into a patient, with the sealing device 1200 loaded onto the delivery apparatus.

FIG. 125 illustrates another delivery apparatus 1330 that can be used for surgical procedures (e.g., implantation of a prosthetic heart valve) that involve opening an aperture in a vessel sidewall (e.g., a sidewall of the aorta) and then sealing that aperture with a sealing device, such as the sealing device 1200. As illustrated in FIGS. 139-150, the delivery apparatus 1330 can be used to open an aperture 1338 in a sidewall of vessel 1339 for intra-luminal access, and then seal the aperture 1338 with sealing device 1200. The delivery apparatus 1330 includes a proximal end 1332 and a distal end 1334, and includes a number of coaxial sleeves which are relatively axially slidable and angularly rotatable along a longitudinal axis extending from the proximal end to the distal end of the deliverer apparatus. Preferably, the sleeves are actuatable by the physician from the proximal end portion of the instrument.

As shown in FIG. 125, the delivery apparatus 1330 generally includes a balloon sheath and filling port subassembly 1340, on which a sealing device (such as the sealing device 1200) can be mounted, and an introducer sheath 1380, and a luminal support and dilator subassembly 1400.

In the illustrated embodiment (and for ease of illustration), the delivery apparatus 1330 is in a straight configuration. However, the delivery apparatus can include a curved or angled configuration to facilitate access to a vessel if needed.

Figure 137:
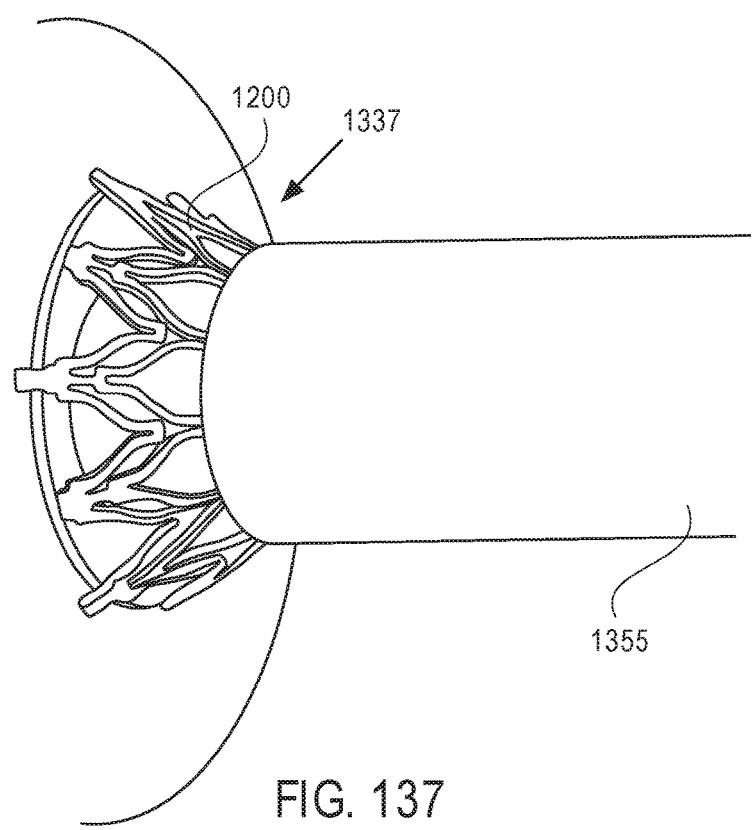
FIG. 137 is a perspective view of the delivery apparatus of FIG. 125, showing operation of the pusher to insert the anchors of the sealing device 1200 into a vessel sidewall.

FIG. 125 shows a cross-sectional view of the delivery apparatus 1330, and illustrates the delivery apparatus in an insertion configuration 1337. In the insertion configuration, the anchors 1209 of the sealing device 1200 extend distally beyond a distal end 1341 of the balloon sheath and filling port subassembly 1340. In a retracted configuration 1336, the anchors 1209 of the sealing device 1200 do not extend distally beyond the distal end 1341 of the balloon sheath and filling port subassembly 1340. The delivery apparatus 1330 can be moved from the retracted configuration 1336 to the insertion configuration 1337 by moving a pusher 1360 distally, thereby pushing the sealing device 1200 distally, and the anchors 1209 of the sealing device 1200 beyond the distal end 1341 of the balloon sheath and filling port subassembly 1340 (see FIG. 137). When used in a surgical procedure, the distal end 1341 of the balloon sheath and filling port subassembly 1340 can be placed against the vessel sidewall. Thus, when the anchors 1209 are pushed distally beyond the distal end 1341, the anchors insert can penetrate into the vessel sidewall and are held in place by the barbs 1216 of the sealing device (see FIG. 137).

The components of the delivery apparatus 1330, such as the balloon sheath and filling port subassembly 1340, the introducer sheath 1380, and the luminal support and dilator subassembly 1400, can include one or more locking mechanisms to releasably secure the position of the components with respect to each other and/or with respect to the sidewall of the vessel, for example, as described herein or as known in the art. The components of the delivery apparatus can be manufactured from any of various suitable materials known in the art, such as any of various metals or polymers, and combinations thereof.

Figure 126:
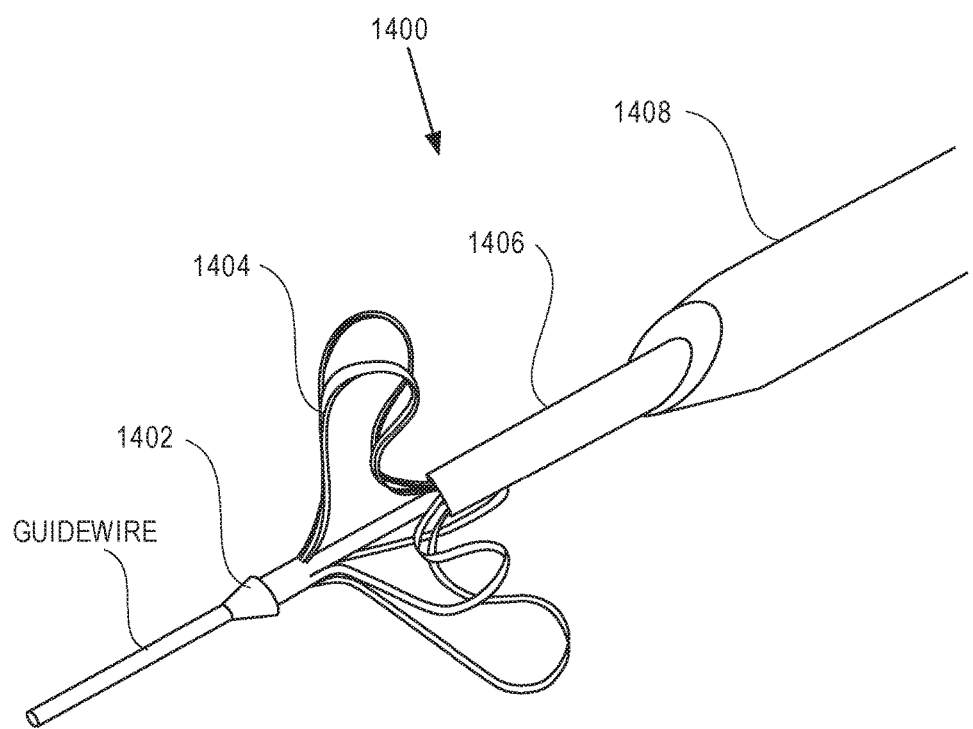
FIG. 126 is a perspective view of a distal portion of the dilator and support structure subassembly of the delivery apparatus of FIG. 125.

Referring to FIG. 126, the luminal support and dilator subassembly 1400 includes multiple sub-components, including a piercing tip 1402, a luminal support structure 1404, a support sheath 1406, and a dilator 1408.

The piercing tip 1402 is attached at the distal end of the luminal support structure 1404, and facilitates insertion of the sub-assembly 1400 through the sidewall of the vessel 1339. The support tip can be made of any suitable material, such as stainless steel, Nitinol or polymer, and secured (e.g., by press-fitting) to the distal end of the luminal support structure 1404. As shown in FIGS. 128 and 129, the piercing tip 1402 includes an inner lumen 1409 suitably sized for passage of a hypodermic needle or guide wire, such as guide wire 1410 (shown in FIG. 127). The piercing tip 1402 includes a distal portion 1412 and proximal portion 1414. The distal portion 1412 can have a conical shape that facilitates insertion of the sub-assembly 1400 through the sidewall of the vessel 1339. The proximal portion 1414 can be suitably sized (e.g., tubular) for press fitting in an accepter lumen 1416 at a distal end 1418 of the luminal support structure 1404 (see FIG. 131). As shown in FIG. 129, the piercing tip 1402 can include a ledge 1411 that extends radially relative to the longitudinal axis of the piercing tip, and which can serves as a hard stop for a distal end 1418 of the luminal support structure 1404, and the support sheath 1406 when the luminal support structure 1404 is crimped inside the support sheath (discussed below).

The luminal support structure 1404 provides support from the luminal side of the vessel 1389 during use of the delivery apparatus 1330. The luminal support structure 1404 can be made of a shape memory material with super-elastic properties, such as a nickel-titanium (e.g., Nitinol), nickel-titanium cobalt, or nickel-titanium chromium alloy.

Figure 130:
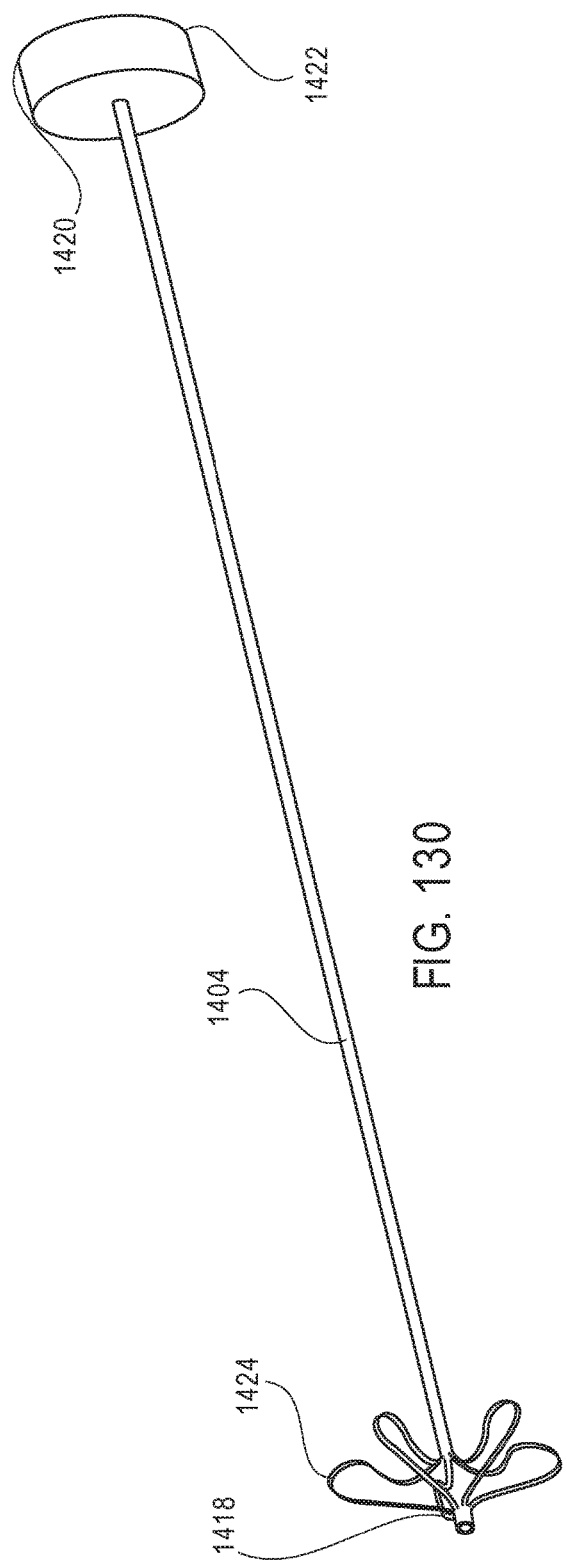
FIGS. 130 and 131 are perspective views of the support structure of the delivery apparatus of FIG. 125.
Figure 131:
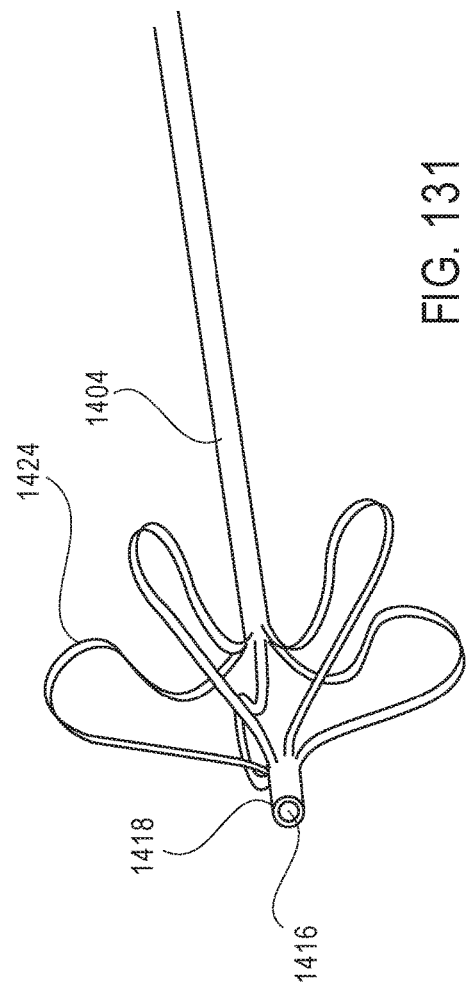

Referring to FIGS. 130 and 131, the distal portion of the luminal support structure 1404 includes a plurality of petal-shaped projections 1424 that extend radially outwardly relative to the longitudinal axis of the support structure. In some embodiments, the balloon 1284 can extend by about up to 15 mm. In some embodiments, each projection can extend by about 10-15 mm from the longitudinal axis of the support structure. The projections can be formed by making longitudinal cuts in a tube of the shape memory material, and then treating the material to set the memory shape of the projections 1424 as that shown in FIGS. 130 and 131. In the illustrated embodiment, the support structure includes five projections 1404; however, more or fewer projections can be used. The memory shape of the projections 1424 can be any shape that allows the projections to provide support on the luminal side of a vessel during a procedure using the delivery apparatus 1330. In several embodiments, the memory shape of the projections 1424 can include an angle or slope towards the proximal end 1420 of the support structure (as shown in FIGS. 130 and 131).

Referring to FIG. 130, the proximal end 1420 of the luminal support structure 1404 can optionally include a handle or other large diameter shape 1422 that allows easier gripping and handling of the support structure.

Referring to FIGS. 126 and 127, the support sheath 1406 provides radial constraint to the luminal support structure 1404 while distal end of the piercing tip 1402 is inserted through the sidewall of the vessel 1339. The support sheath can be made of any suitable sheath material, such as a polymer material to provide flexibility. Referring to FIG. 132, the support sheath can include a distal end 1421 and a proximal end 1423, and the proximal end 1423 can optionally include a handle or other large diameter shape 1425 that allows easier gripping and handling of the support structure.

With reference to FIG. 133, the dilator 1408 can include a distal portion 1426 and a proximal portion 1428. The distal portion of the dilator includes a nose cone portion 1427, which can be tapered or conical to facilitate insertion into an aperture in the side wall of the vessel 1339. The dilator 1408 can optionally include extendable and retractable cutting members (e.g., blades) on the nose cone portion 1427 of the dilator, and proximal to the distal tip of the dilator, that are substantially similar to dilator 1080 (discussed above). The dilator includes a lumen 1429 configured to allow passage of the subassembly 1400. In some embodiments, the distal tip of the dilator can be shaped at an angle (e.g., as shown in FIG. 133) such that the initial dilator contact with tissue is as sharp as possible to aid during the insertion of the dilator through the sidewall of the vessel 1339.

In particular embodiments, the guide wire 1410 can be inserted through the sidewall of the vessel 1339, and the piercing tip 1402 can be used to expand the puncture site from the diameter of the guide wire to about the diameter of the support sheath 1406. The nose cone of the dilator 1408 can then be used to expand the puncture site from the diameter of the support sheath 1406 to about the diameter of the sleeve of the dilator 1408.

Figure 134:
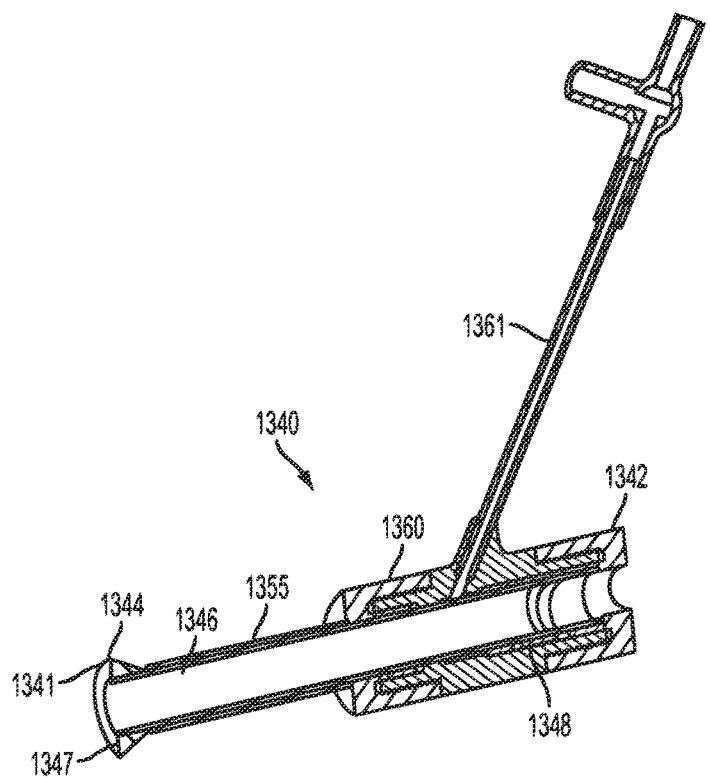
FIGS. 134-136 are cross-sectional views of the balloon sheath and filling port subassembly of the delivery apparatus of FIG. 125.

FIG. 134 shows an embodiment of the balloon sheath and filling port subassembly 1340. The balloon sheath and filling port subassembly 1340 includes a balloon sheath 1346 (which also functions as a carrier for the sealing device 1200) extending from a housing 1360, a pusher 1355 mounted on the sheath 1346, and a balloon 1344, which can be inflated or deflated by injecting or suctioning fluid through an inter-sleeve lumen between the introducer sheath and the balloon sheath.

Figure 135:
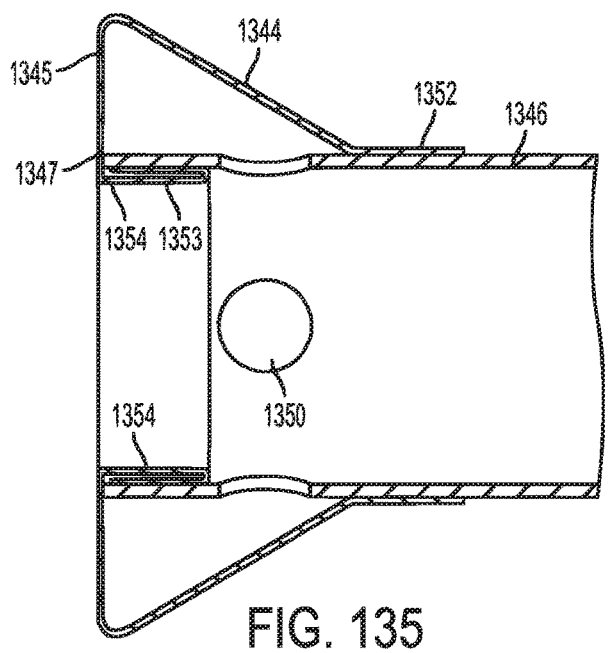
Figure 136:
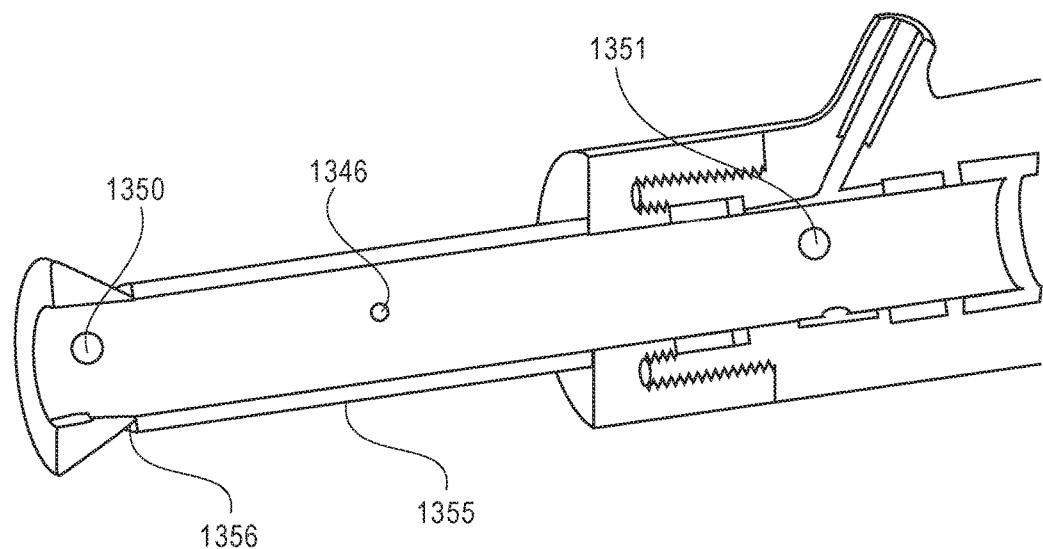

The balloon sheath 1346 in the illustrated embodiment comprises a coaxial sleeve that is positioned between the introducer sheath 1380 and the pusher 1355 on delivery assembly 1330 (see FIGS. 125 and 136). The balloon sheath 1346 includes a distal end 1347 and a proximal end 1348 and can be axially slidable and angularly rotatable relative to the introducer sheath 1380 and the pusher 1355. An inter-sheath lumen can be located between the introducer sheath 1380 and the balloon sheath 1346, and extends at least from a proximal opening 1351 in the balloon sheath (FIG. 136) to a distal opening 1350 in the balloon sheath (FIG. 135).

Referring to FIG. 135, the balloon 1344 is secured to the distal portion of the balloon sheath. A proximal portion 1352 of the balloon 1344 is secured to the outer surface of the balloon sheath 1346, a distal portion 1353 of the balloon 1344 is secured to the inner surface of the balloon sheath 1346, with an inflatable portion 1345 of the balloon in between the proximal and distal portions. The balloon can be secured to the balloon sheath by any suitable means known in the art, for example by adhesive bonding. In some embodiments, the distal portion 1353 of the balloon is folded back upon itself before securing it to the inner surface of the balloon sheath 1346. This additional fold can provide a seal between the balloon sheath and the introducer sheath 1380, thereby allowing rotational and longitudinal movement of the introducer sheath 1380 relative to the balloon sheath 1346 and providing a seal that prevents any balloon filling fluid from leaking from the distal end 1341 of the balloon sheath and filling port subassembly. In some such embodiments, the balloon can be made of silicone.

The inflatable portion 1345 of the balloon can be located in fluid communication with the distal opening 1350 in the balloon sheath which is in fluid communication via the inter-sheath lumen 1354 to the proximal opening 1351 in the balloon sheath. The proximal opening in the balloon sheath can be located in fluid communication with one or more ports on the housing 1360. Thus, inflation and deflation of the balloon can be accomplished by altering the pressure of fluid (e.g., liquid or gas) within the inter-sleeve lumen by injecting or suctioning liquid or gas through an inflation port on the housing 1360. When inflated, the balloon 1344 extends radially outwardly from the balloon sheath. In some embodiments, the balloon 1344 can extend by about up to mm from the outer surface of the balloon sheath.

Once inflated, the balloon can provide a seal against the exterior side of the vessel to reduce or prevent leakage of blood or other fluids from the vessel. In several embodiments, the sealing device 1200 is mounted over the balloon on the balloon sheath. Therefore, inflating the balloon will cause an increase in the diameter of sealing device (FIGS. 125 and 137), which allow the sealing device to engage a larger diameter of tissue when inserted in the vessel sidewall.

Referring to FIGS. 134 and 136, the proximal end 1348 of the balloon sheath is secured within the housing 1360, which can house one or more seals (such as an O-ring) configured to seal against the outer surface of the balloon sheath 1346. Further, proximate its proximal end, the filling port 1360 can include a seal (such as an O-ring) that provides a proximal seal between the balloon sheath and a sleeve 1382 of the introducer sheath 1382, while allowing relative axial movement of the sleeve 1382 and the balloon sheath 1346.

The pusher 1355 in the illustrated embodiment comprises a coaxial sleeve that is positioned radially outwardly from the balloon sheath 1346. The pusher 1355 can be axially slidable and angularly rotatable relative to the balloon sheath 1346.

The pusher 1355 can be coupled to the balloon sheath by any suitable means. For example, in the illustrated embodiment, the pusher 1355 is co-axially mounted on the sheath 1346 and has a proximal end that can abut or be connected to a rotatable knob 1361 of the housing. The distal end 1356 of the pusher is configured to contact the proximal end of the sealing device 1200 when it is mounted on the balloon sheath 1346. When the pusher 1355 is moved distally, such as by rotating knob 1361, the distal end 1356 of the pusher contacts that proximal end of the sealing device 1200 and pushes the sealing device into the deployed configuration 1337 of the delivery apparatus 1330.

In some embodiments, the balloon sheath can be coupled to the pusher by use of interlocking threads on the outer surface of the balloon sheath that engage with threads on the inner surface of the pusher (for example, as described above for the carrier and pusher 1240 and 1260 of delivery apparatus 1230).

Figure 138:
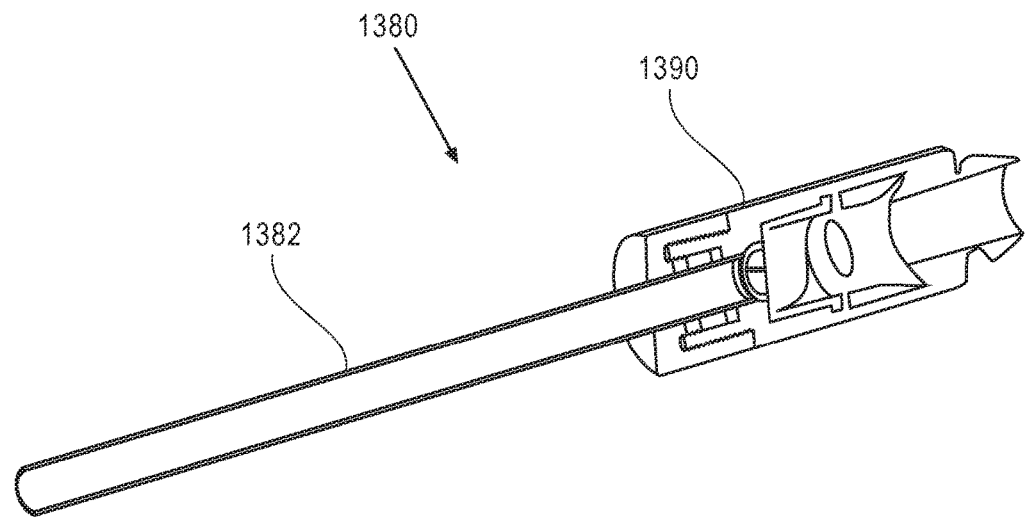
FIG. 138 is a cross-sectional view of the introducer sheath of the delivery apparatus of FIG. 125.

FIG. 138 shows an embodiment of the introducer sheath 1380. The assembly 1380 comprises a sheath or sleeve 1382 extending from a housing 1390. The sleeve 1382 can be positioned axially inwardly from, and can be axially slidable and angularly rotatable relative to, the balloon sheath 1346. Further, the sleeve 1382 can be positioned radially outwardly from, and can be axially slidable and angularly rotatable relative to, the dilator subassembly 1400. The introducer sheath 1380 is configured to allow the dilator to through the sheath assembly 1380, and be removable therefrom. An inner diameter of the introducer sheath can vary based on the intended use, and can be suitably sized to allow access to the intraluminal space of the vessel 1339 via the introducer sheath 1382 by a treating physician, for example, for implantation of a heart valve. In several embodiments, the introducer sheath 1380 is designed for delivery of a prosthetic heart valve to a subject in need thereof. The introducer sheath 1380 can be substantially the same as other embodiments of introducer sheaths described herein or known in the art. An example of a suitable introducer sheath assembly includes the Edwards Ascendra® introducer sheath.

The housing 1390, can house one or more seals configured to seal against the outer surface of a prosthetic-device-delivery-apparatus that is inserted through the introducer sheath 1380, as known in the art. Additionally, the housing can include one or more flush/suction ports for use during surgery as needed.

O. Exemplary Method of Implanting Sealing Device 1200 Using Apparatus 1330

FIGS. 139-150 illustrate an exemplary method of using the delivery apparatus 1330 for accessing the lumen of a vessel 1339 (such as the aorta) to perform an endoluminal procedure via an aperture 1338 in the sidewall of a vessel, and then sealing the aperture following the endoluminal procedure with a sealing device such as sealing device 1200. The illustrated method utilizes the delivery apparatus 1330 and the sealing device 1200; however, other embodiments of a sealing device and/or a delivery apparatus (for example, as described herein) can be used to perform the disclosed method. In several embodiments, the disclosed method is used to create and seal the aperture 1338 in a sidewall of the aorta in a patient during a surgical procedure, such as implantation of a prosthetic heart valve.

Prior to initiation of the method, the sealing device 1200 is loaded onto the delivery apparatus 1330, with the sealing device mounted on the distal portion of the balloon sheath 1346. The sealing device 1200 is mounted such that the anchors 1209 of the sealing device do not extend distally beyond the distal end 1341 of the balloon sheath 1346.

Figure 139:
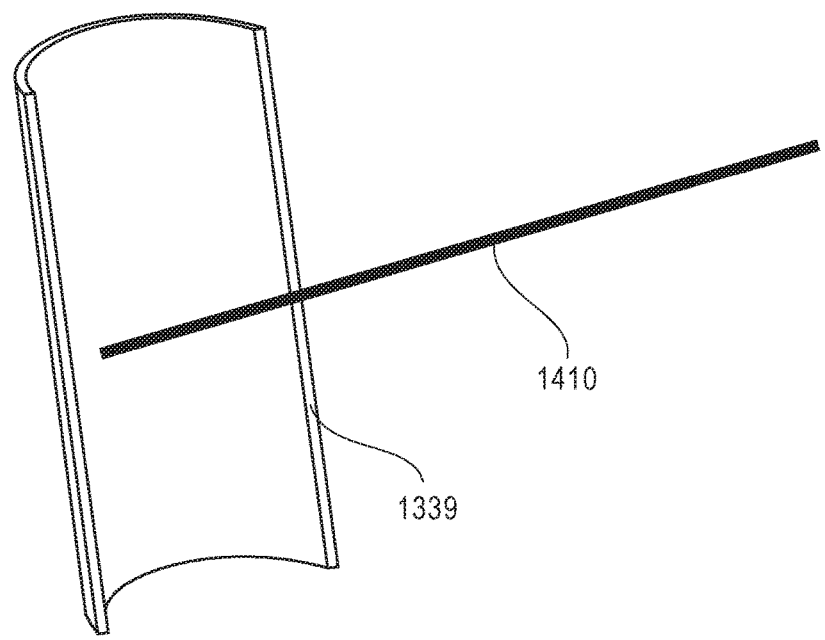
FIGS. 139-150 illustrate an exemplary method of using a disclosed vessel opening and sealing device and a delivery apparatus for accessing the lumen of a vessel for performance of an endoluminal procedure via an aperture in the sidewall of the vessel, and then sealing the aperture following the endoluminal procedure.
Figure 140:
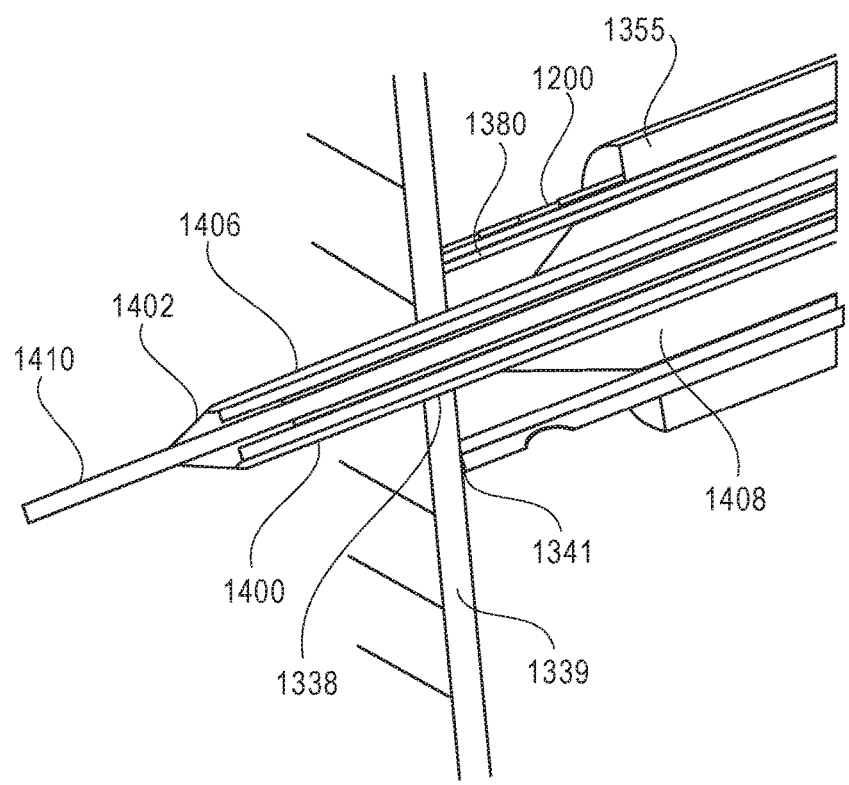

In the illustrated embodiment of the method, a hypodermic needle can be advanced through the lumen of the support structure 1404 and the piercing tip 1402 of the luminal support and dilator subassembly 1400 and inserted through the sidewall of the vessel 1339. The guide wire 1410 can then be inserted through the hypodermic needle and into the lumen of the vessel 1339, and placed as needed for the endoluminal procedure. After placement of the guide wire, the hypodermic needle can be retracted from the sidewall of the vessel, leaving the guide wire in place (FIG. 139). After placement of the guide wire, the delivery apparatus 1330 can be advanced distally until the distal end 1341 of the balloon sheath contacts the exterior wall of the vessel 1339. The piercing tip 1402, and a distal portion of the support sheath 1406 and support structure 1404 of the luminal support and dilator subassembly 1400 can then be advanced distally to traverse the sidewall of the vessel 1239 and form the aperture 1338 (FIG. 140).

Figure 141:
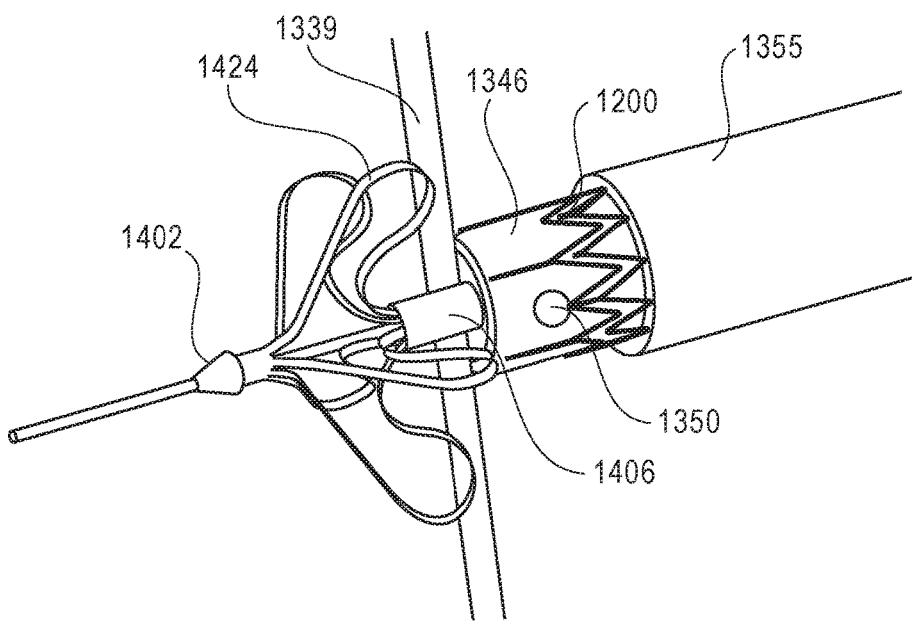

As shown in FIG. 141, the support sheath 1406 is then retracted proximally, to release the projections 1424 of the support structure 1404 in the lumen of the vessel 1339. Because the support structure 1404 is made of shape memory material, the projections 1424 expand radially to their memory shape, as shown in FIG. 141. In some embodiments, the projections can be initially extended in a position where they do not engage the luminal side of the vessel 1339, after which the support structure can be moved proximally to engage the projections 1424 with the luminal side of the vessel wall.

Figure 142:
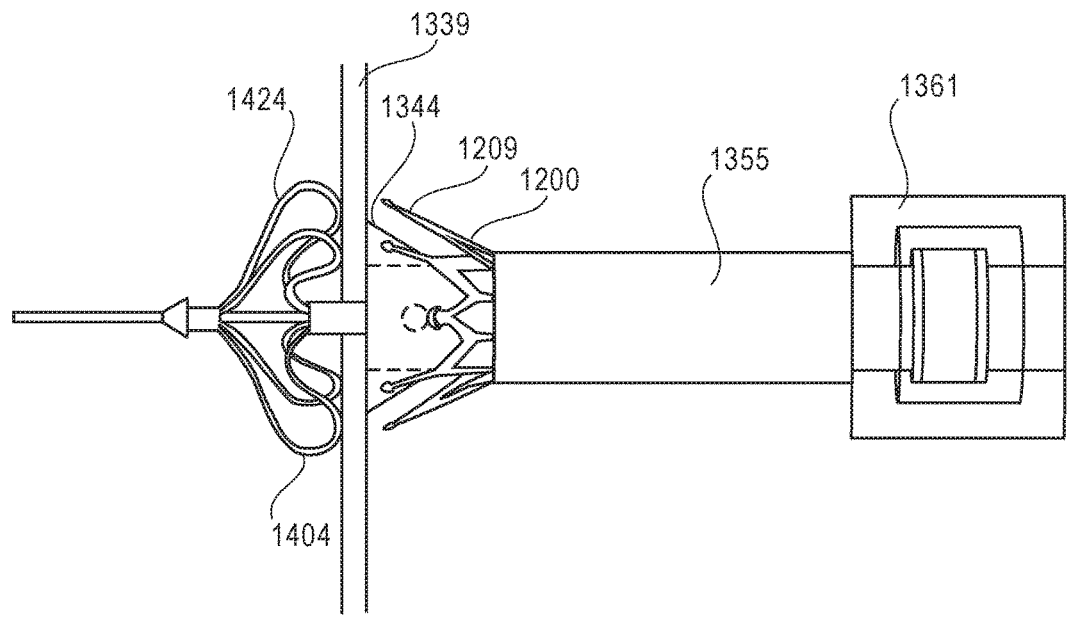

As shown in FIG. 142, the balloon 1344 is then inflated by injecting fluid into the balloon as previously described. By contacting the luminal side of the vessel 1339 with the projections 1424 of the support structure 1404, and the exterior side of the vessel 1339 with the inflated balloon 1344, a seal is formed around the sidewall of the vessel to reduce or prevent leakage of fluid (e.g., blood) from the vessel, and to support the sidewall of the vessel when the anchors 1209 of the sealing device 1200 are inserted into the sidewall.

Figure 143:
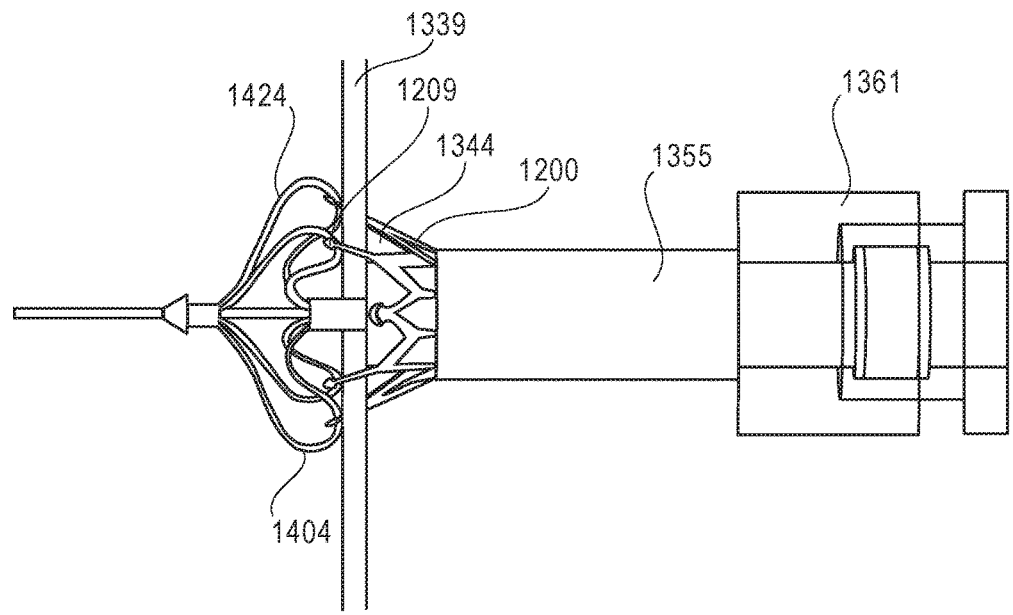

In the illustrated embodiment of the method, the pusher 1355 is then moved distally to push the anchors 1209 of the sealing device 1200 past the distal end of the balloon sheath 1355, such as by rotating knob 1361, thereby inserting the anchors 1109 into the sidewall of the vessel 1339 (FIG. 143).

Figure 144:
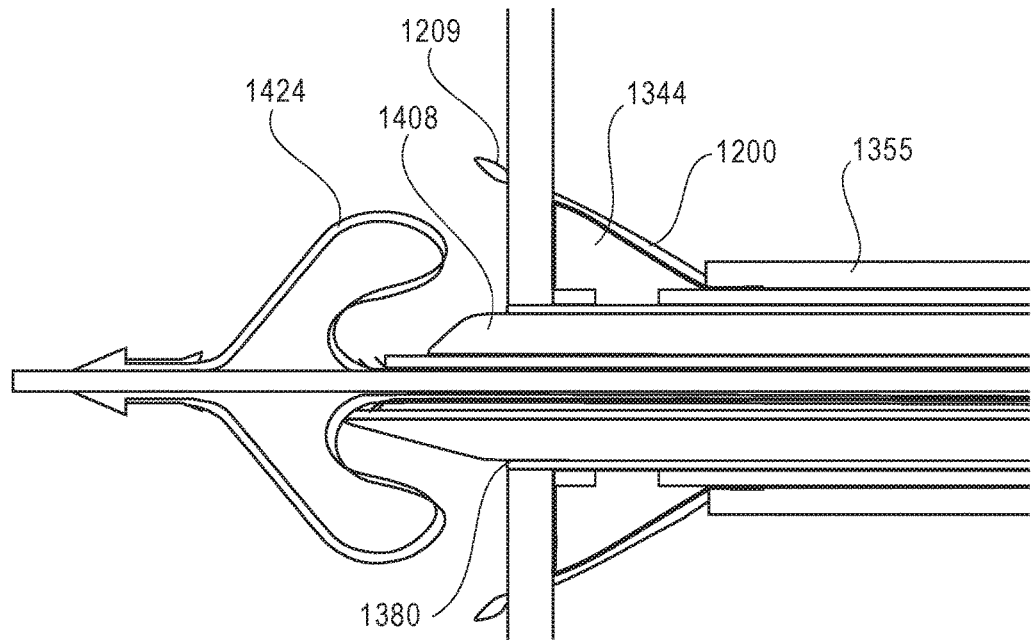
Figure 145:
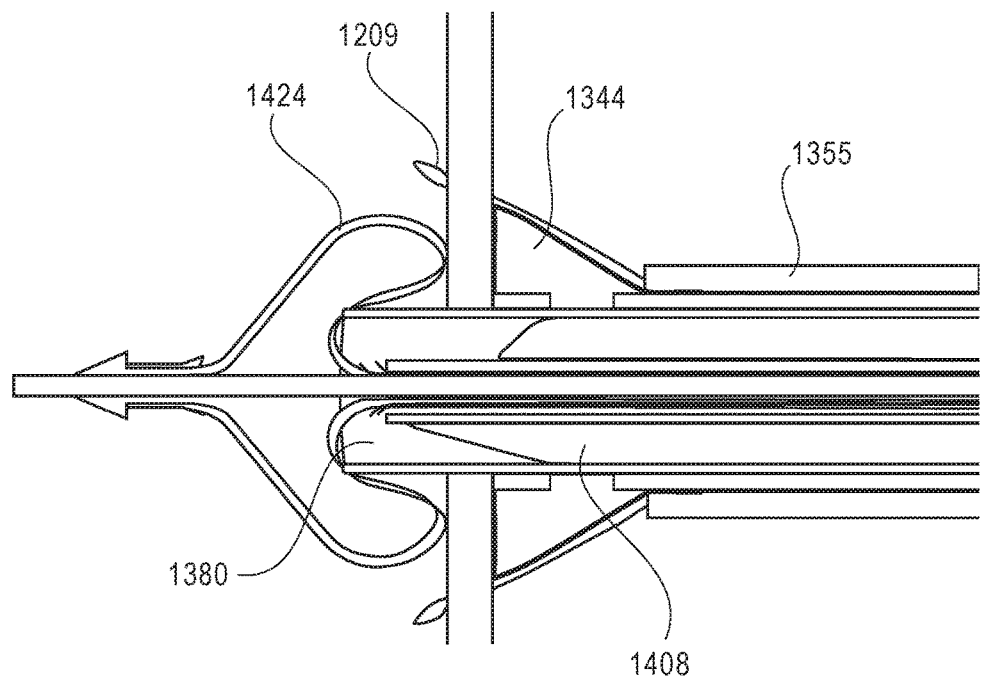
Figure 146:
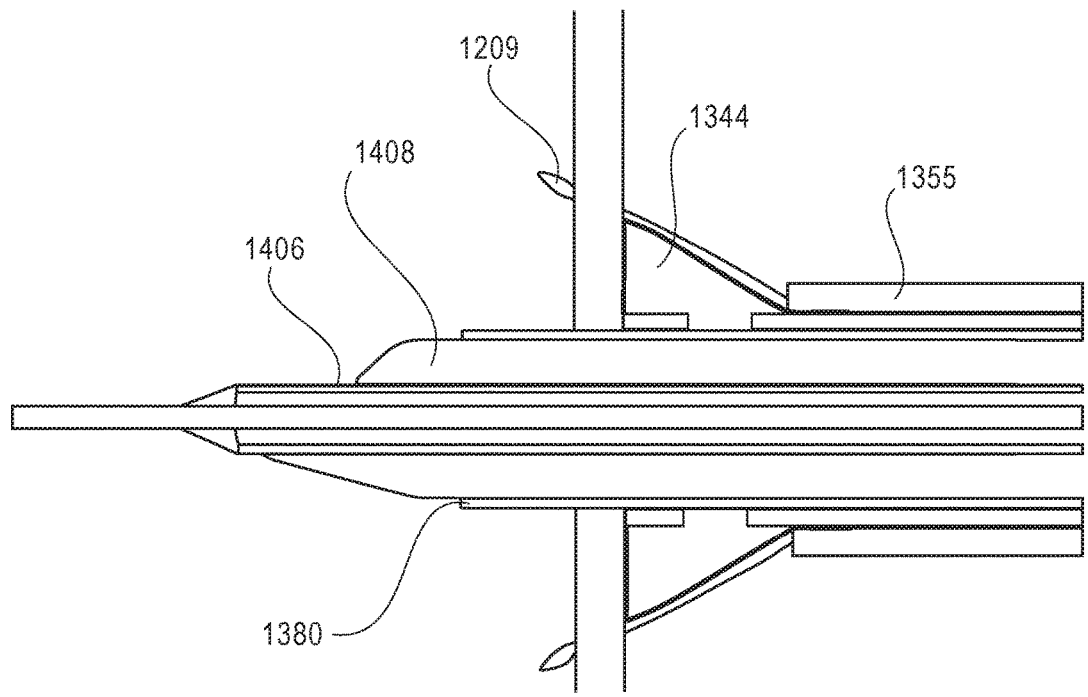
Figure 147:
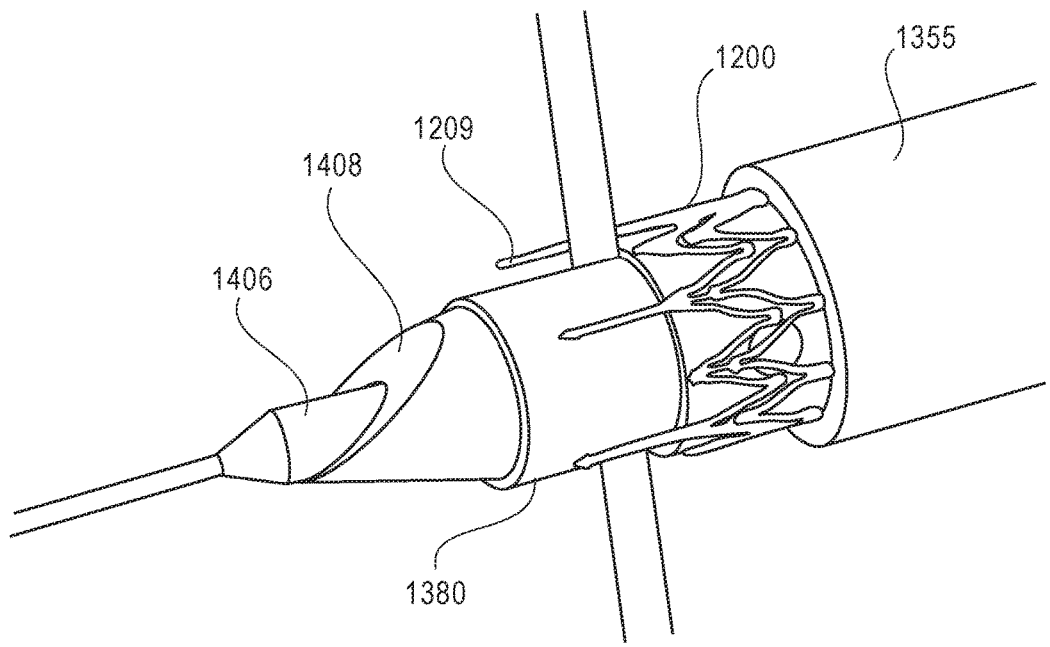
Figure 148:
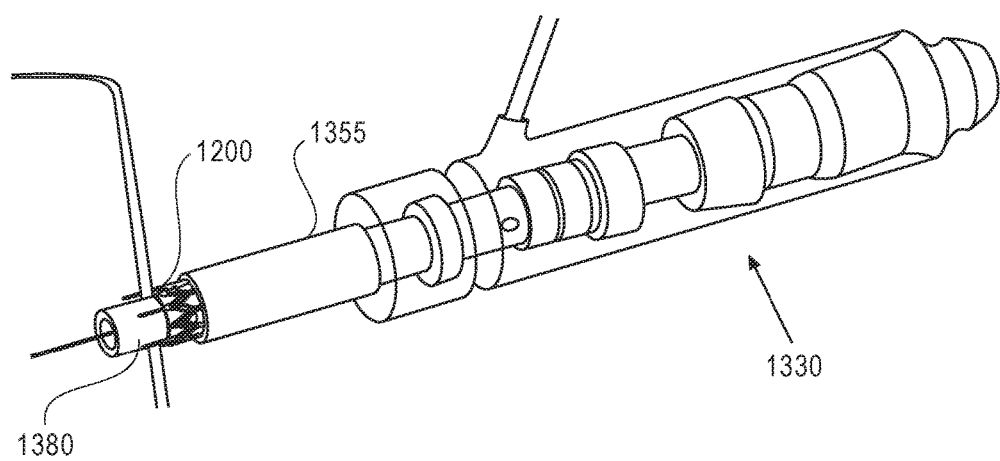

With reference to FIG. 144, the dilator 1408 and introducer sheath 1380 can then be moved distally to traverse the sidewall of vessel 1339, thereby widening the aperture 1338 in the sidewall to about the diameter of the introducer sheath. The introducer sheath can be further inserted into the lumen of the vessel 1339, and the dilator can be retracted inside of the introducer sheath (FIG. 145). Next, the support structure 1404 can be retracted to recapture the projections 1424 of the support structure within the support sheath 1406 (FIG. 146), and the balloon 1344 can be deflated (FIG. 147). The sealing device 1200 will then cause vessel tissue to tighten around the introducer sheath 1380, thereby providing hemostasis or a seal that reduces and/or prevents bleeding between the sleeve and the aperture 1338.

The dilator 1300 can then be retracted proximally and removed from the delivery assembly 1330 (FIG. 148), and the endoluminal procedure can be performed.

Figure 149:
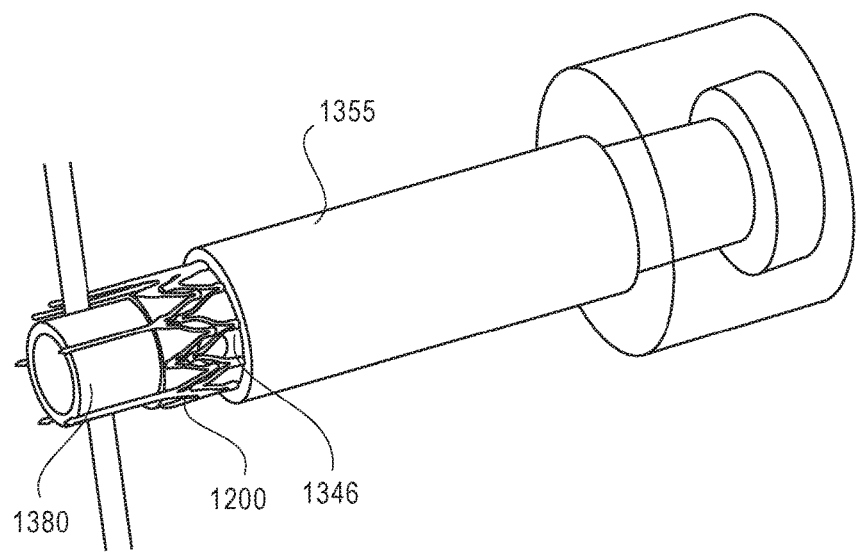

The pusher and balloon sheath can then be retracted proximally until the distal end of the balloon sheath 1346 passes proximally beyond the proximal end of the sealing device 1200 and the sealing device contracts around the outer surface of the introducer sheath 1382 (FIG. 149).

Figure 150:
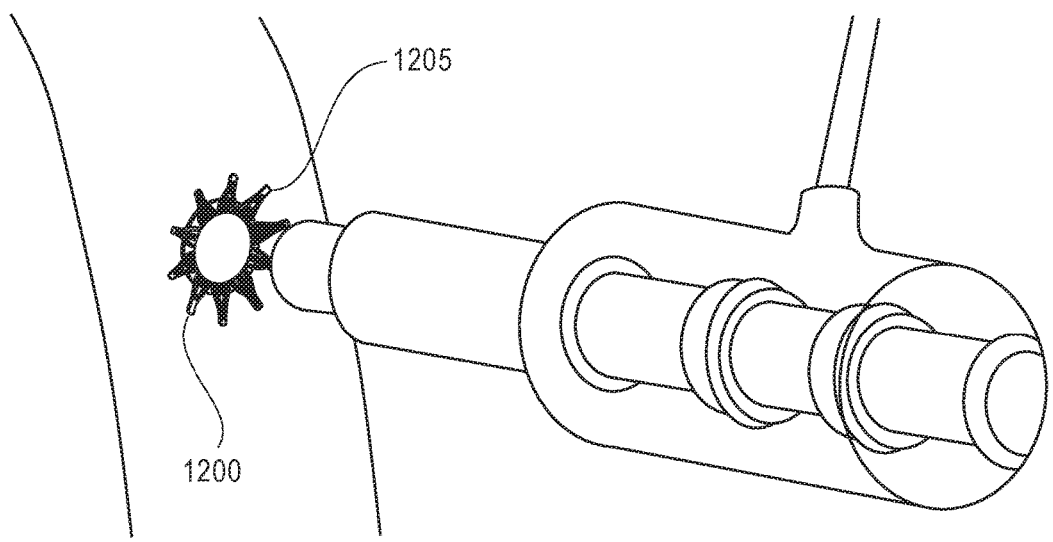

The introducer sheath 1380 can then be retracted proximally from the aperture 1338 in the vessel 1339. As the introducer sheath is retracted from the aperture 1338, the sealing device 1200 shifts to the sealed configuration 1205 (FIG. 150).

In the illustrated embodiment, the sealing device 1200 is deployed into the sidewall of the vessel 1239 before performance of the endoluminal procedure. In alternate embodiments, the sealing device 1200 can be deployed into the sidewall of the vessel 1239 after performance of the endoluminal procedure.

P. Exemplary Delivery Apparatus 1430 for Implanting Sealing Device 1200

Figure 151:
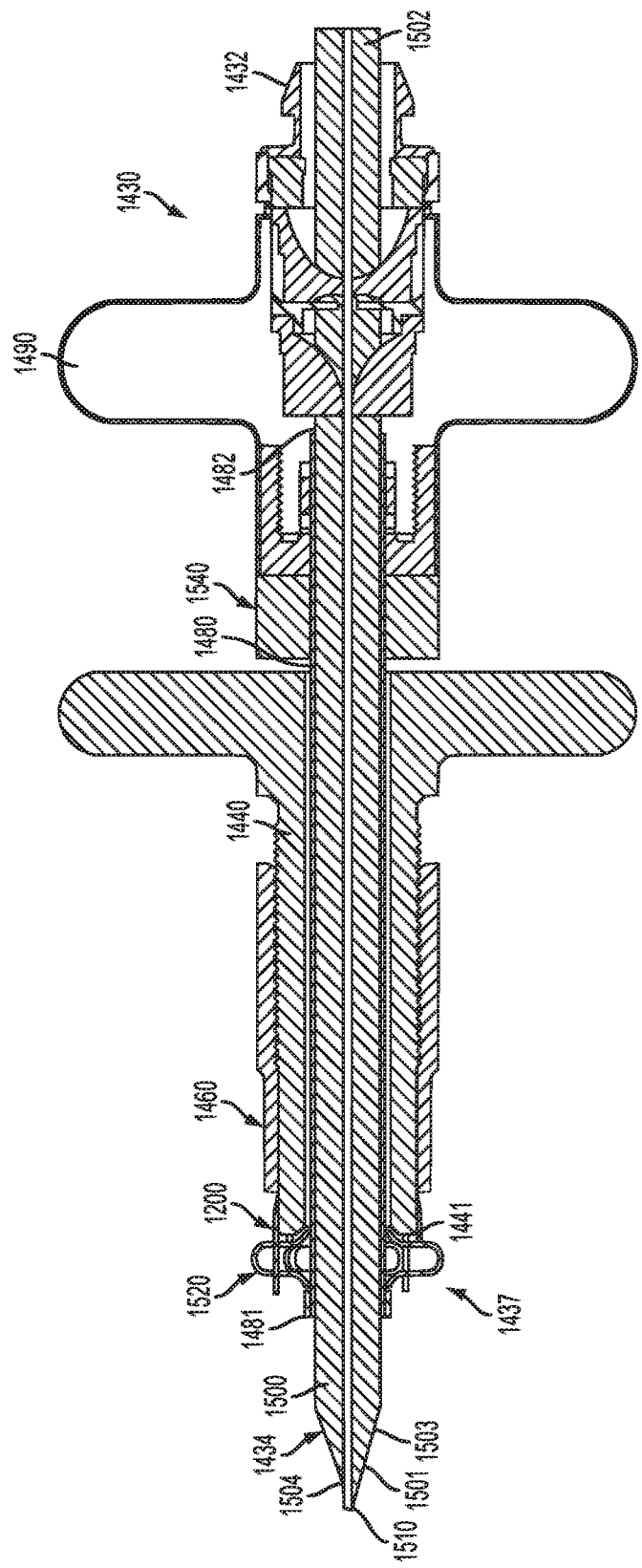
FIG. 151 is a cross-sectional view of a delivery apparatus for implantation of a vessel sealing device into a patient, with the sealing device 1200 loaded onto the delivery apparatus.

FIG. 151 illustrates another delivery apparatus 1430 that can be used for surgical procedures (e.g., implantation of a prosthetic heart valve) that involve opening an aperture in a vessel sidewall (e.g., a sidewall of the aorta) and then seal that aperture with a sealing device, such as the sealing device 1200. In the illustrated embodiment (and for ease of illustration), the delivery apparatus 1430 is in a straight configuration. However, the delivery apparatus can include a curved or angled configuration to facilitate access to a vessel if needed.

As illustrated in FIGS. 160-170, the delivery apparatus 1430 can be used to open an aperture 1438 in a sidewall of vessel 1439 for intra-luminal access, and then seal the aperture 1438 with sealing device 1200. The delivery apparatus 1430 includes a proximal end 1432 and a distal end 1434, and includes a number of coaxial sleeves or shafts which are relatively axially slidable and angularly rotatable along a longitudinal axis extending from the proximal end to the distal end of the deliverer apparatus. Preferably, the sleeves are actuatable by the physician from the proximal end portion of the instrument. As shown in FIG. 151, the delivery apparatus 1430 generally includes a sealing device carrier 1440 upon which the sealing device 1200 can be mounted, a pusher 1460, an introducer sheath 1480 comprising a sleeve or shaft 1484 coupled to an introducer housing 1490 (also referred to as an hemostasis valve assembly), a dilator 1500 with a guide wire lumen, a luminal support structure 1520, and optionally can include a spacer 1540.

FIG. 151 shows a cross-sectional view of the delivery apparatus 1430, and illustrates the delivery apparatus in an insertion configuration 1437. In the insertion configuration, the anchors 1209 of the sealing device 1200 extend distally beyond the distal end 1441 of the sealing device carrier 1440. In a retracted configuration 1436, the anchors 1209 of the sealing device 1200 do not extend distally beyond the distal end 1441 of the sealing device carrier 1440. The delivery apparatus 1430 can be moved from the retracted configuration 1436 to the insertion configuration by moving a pusher 1460 distally, thereby pushing the sealing device 1200 distally, and the anchors 1209 of the sealing device 1200 beyond the distal end 1441 of the sealing device carrier 1440. When used in a surgical procedure, the distal end 1441 of the sealing device carrier 1440 can be placed against the vessel sidewall; thus, when the anchors 1209 are pushed distally beyond the distal end 1441, the anchors can penetrate into the vessel sidewall and are held in place by the barbs 1216 of the sealing device (see FIG. 166).

The components of the delivery apparatus 1430, such as the sealing device carrier 1440, the pusher 1460, the introducer sheath 1480, the introducer housing 1490, the dilator 1500, and the a luminal support structure 1520, can include one or more locking mechanisms to releasably secure the position of the components with respect to each other and/or with respect to the sidewall of the vessel, for example, as described herein or as known in the art. The components of the delivery apparatus can be manufactured from any of various suitable materials known in the art, such as any of various metals or polymers, and combinations thereof.

Figure 152:
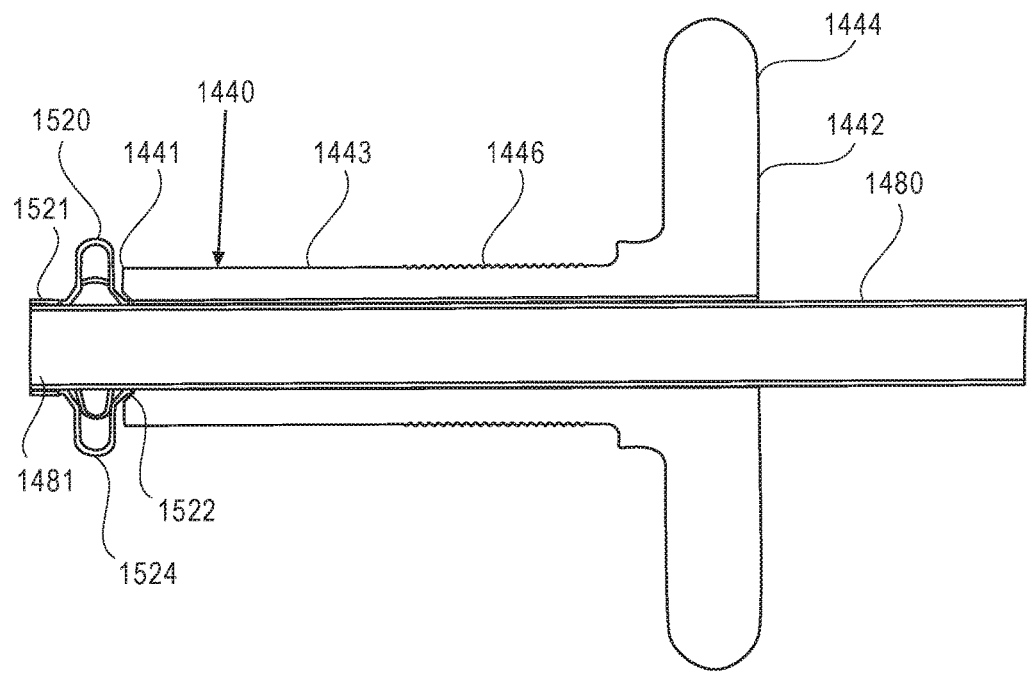
FIG. 152 is a cross-sectional view of the sealing device carrier, support structure and introducer sheath of the delivery apparatus of FIG. 151.
Figure 157:
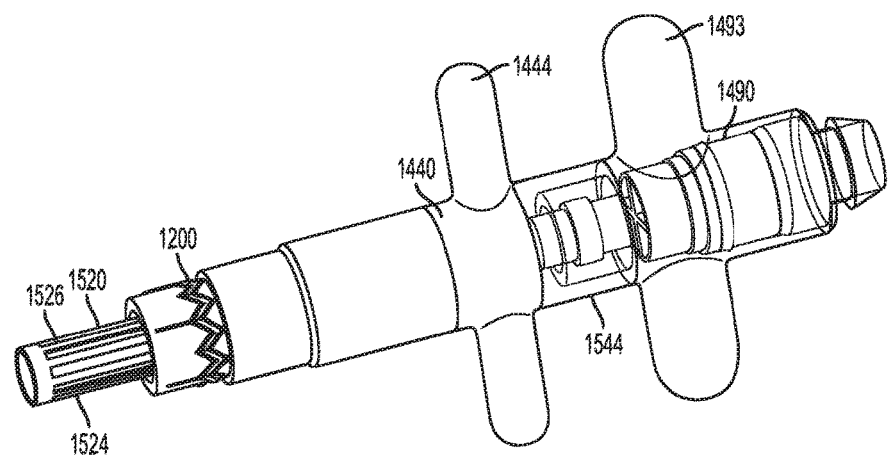
FIGS. 157 and 158 are perspective views of the delivery apparatus of FIG. 151, with the support structure in constrained and non-constrained states, respectively.
Figure 158:
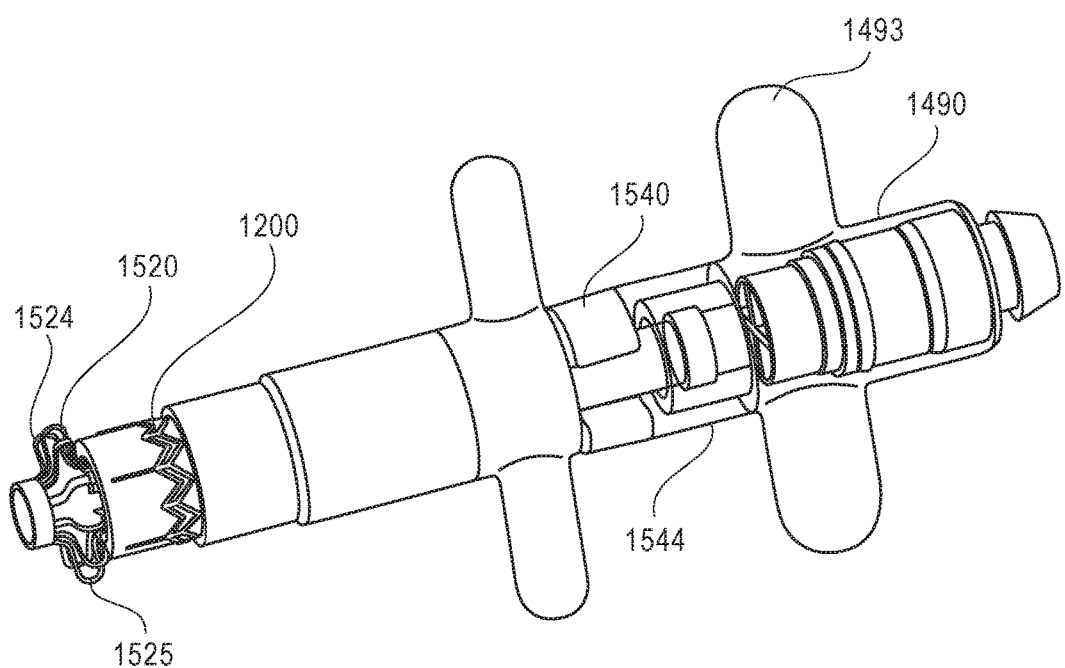
Figure 159:
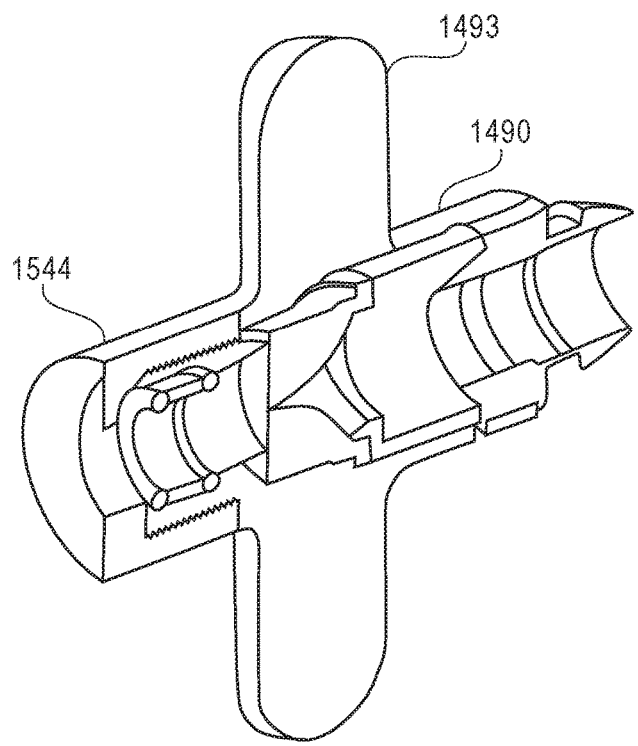
FIG. 159 is a cross-sectional view of the hemostasis valve assembly of the delivery apparatus of FIG. 151.
Figure 160:
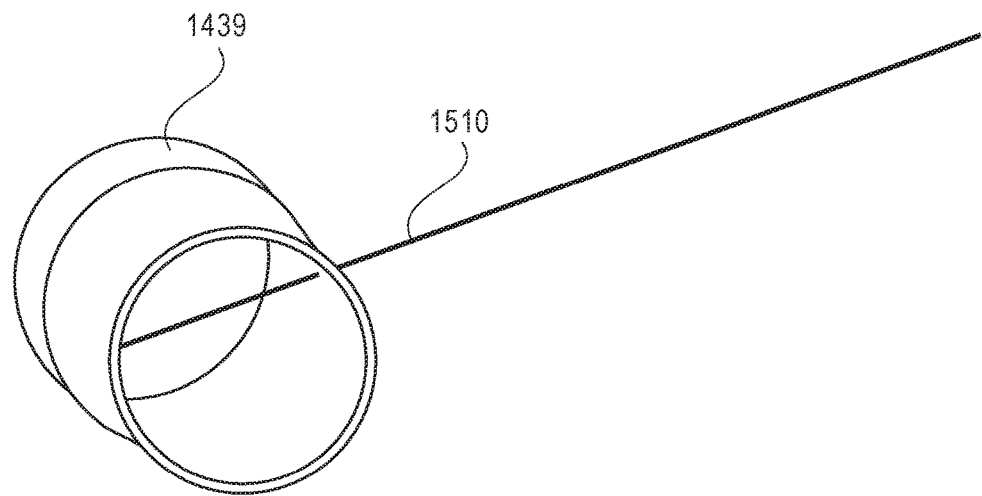

Referring to FIG. 152, the sealing device carrier 1440 includes a distal end 1441 and a proximal end 1442 and a coaxial sleeve or shaft 1443 that is positioned between the sleeve 1484 of the introducer sheath 1480 and the pusher 1460 on delivery assembly 1430. The sealing device carrier 1440 can be axially slidable and angularly rotatable relative to the introducer sheath 1480 and the pusher 1460. The distal end 1441 of the carrier is suitably shaped for contact with the exterior side of the vessel 1439. The outer diameter of the distal portion of the carrier is suitably sized for mounting of the sealing device 1200 in an expanded state on the distal portion of the carrier, for example as shown in FIGS. 157 and 158.

Referring to FIG. 152, at least the distal end 1441 of the carrier 1440 is coupled to the proximal end of the support structure 1520 (described in more detail below). In some embodiments, the carrier 1440 can optional include a handle 1444 to facilitate movement of the carrier by a user, such as a treating physician.

Figure 153:
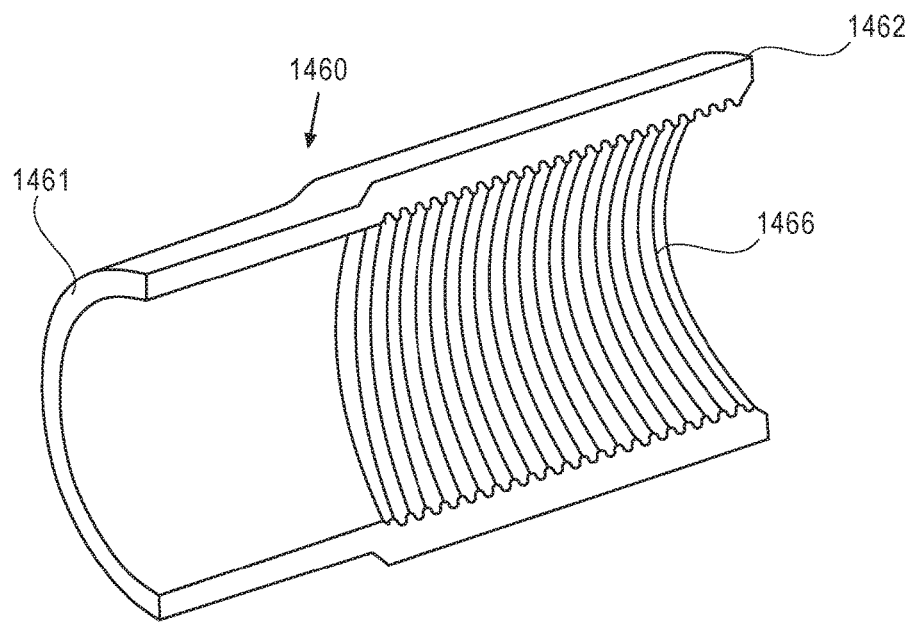
FIG. 153 is a cross-sectional view of the pusher of the delivery apparatus of FIG. 151.

Referring to FIG. 153, the pusher 1460 in the illustrated embodiment comprises a coaxial sleeve that is positioned radially outwardly from the sealing device carrier 1440. The pusher 1460 can be axially slidable and angularly rotatable relative to the sealing device carrier 1440. The pusher includes a distal end 1461 and a proximal end 1462. The pusher 1460 can be secured to the sealing device carrier by any suitable means. For example, in some embodiments, the pusher can be secured to the sealing device carrier by use of internal threads 1446 on the outer surface of the sealing device carrier that engage with external threads 1466 on the inner surface of the pusher (see FIGS. 152-153). The distal end 1461 of the pusher is configured to contact the proximal end of the sealing device 1200 when it is mounted on the carrier 1440. When the pusher 1460 is moved distally, such as by rotating the pusher relative to the carrier, the distal end 1461 of the pusher contacts the proximal end of the sealing device 1200 and pushes the sealing device distally, placing the delivery apparatus into the deployed configuration 1437.

The sleeve 1484 of the introducer sheath 1480 can be positioned radially inwardly from, and can be axially slidable and angularly rotatable relative to, the sealing device carrier 1440. Further, the sleeve 1484 can be positioned radially outwardly from, and can be axially slidable and angularly rotatable relative to, the dilator 1500. The introducer sheath 1480 is configured to allow the dilator to slide inside the introducer sheath, and be removable therefrom. An inner diameter of the introducer sheath can vary based on the intended use, and can be suitably sized to allow access to the intraluminal space of the vessel 1439 via the introducer sheath 1480 by a treating physician, for example, for implantation of a heart valve. The introducer sheath includes a distal end 1481 and a proximal end 1482 (see FIG. 151). In several embodiments, the introducer sheath 1480 is designed for delivery of a prosthetic heart valve to a subject in need thereof. The introducer sheath 1480 and corresponding housing 1490 can be substantially the same as other embodiments of introducer sheaths described herein or known in the art. An example of a suitable introducer sheath includes the Edwards Ascendra® introducer sheath.

As shown in FIG. 151, the proximal end 1482 of the introducer sheath can be secured within the housing 1490. The housing can house one or more seals configured to seal against the outer surface of a prosthetic-device-delivery-apparatus that is inserted through the introducer sheath 1480, as known in the art. The housing 1490 can include one or more flush/suction ports for use during surgery as needed.

Figure 166:
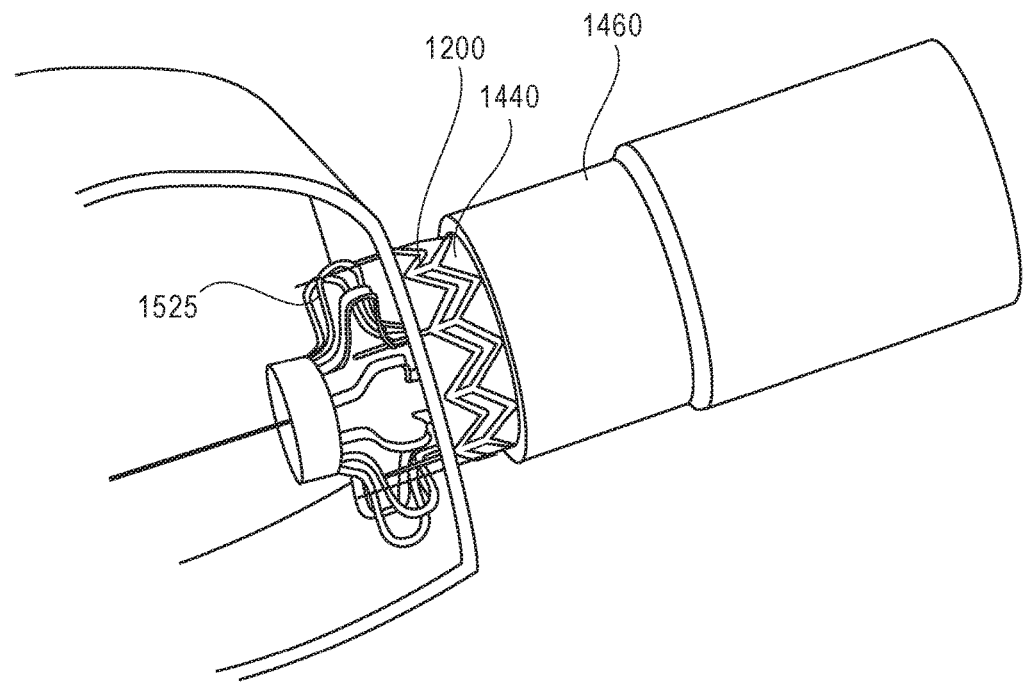

The support structure 1520 includes a plurality of expandable projections 1524 that extend radially outwardly relative to the longitudinal axis of the support structure to provide support from the luminal side of the vessel 1489 during use of the delivery apparatus 1430 (see FIG. 166). The support structure 1520 can be made of a shape memory material with super-elastic properties, such as a nickel-titanium (e.g., nitinol), nickel-titanium cobalt, or nickel-titanium chromium alloy.

In some embodiments, each projection 1524 can extend radially outwardly from the outer surface of the sleeve 1484 about 10-15 mm. The projections can be formed by making longitudinal cuts in a tube of the shape memory material, and then treating the material to set the memory shape of the projections 1524 as that shown in FIGS. 151-154. In the illustrated embodiment, the support structure includes ten projections 1524; however, more or fewer projections can be used. The memory shape of the projections 1524 can be any shape that allows the projections to provide support on the luminal side of a vessel during a procedure using the delivery apparatus 1430.

In some embodiments, the projections 1524 can have a non-constrained memory shape 1525 that extends radially in a direction substantially perpendicular to the longitudinal axis of the delivery apparatus 1430 (as shown in FIGS. 151-154). In other embodiments, the projections 1524 can have a non-constrained memory shape that extends radially at an angle or slope towards the proximal end 1520 of the support structure. In the non-constrained state, the projections 1524 provide support to the luminal side of the vessel wall.

Figure 155:
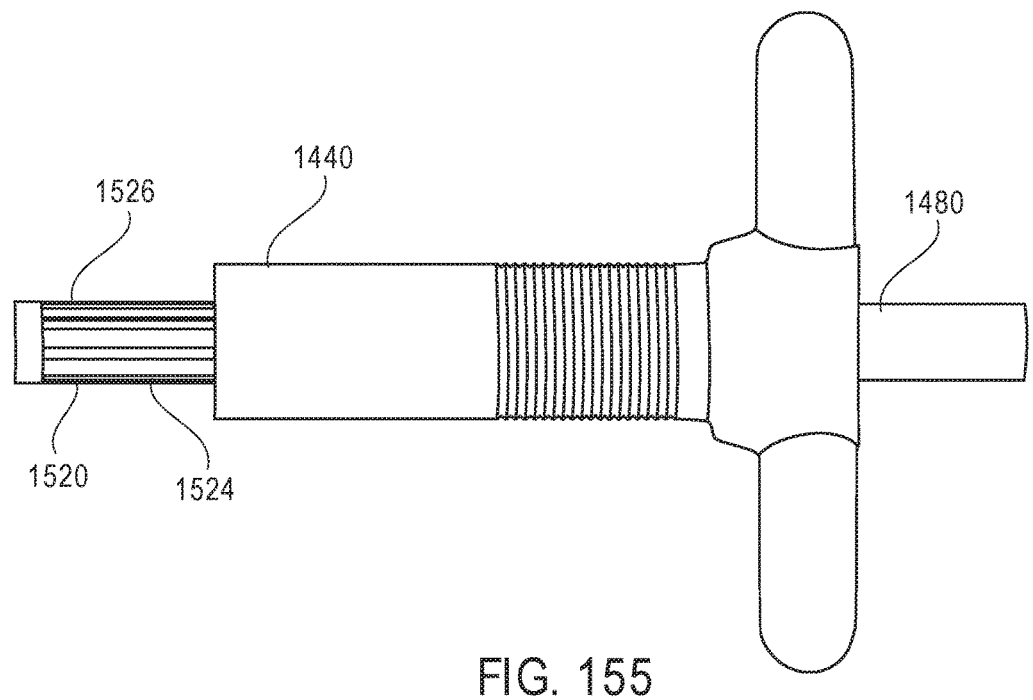

As shown in FIGS. 155 and 157, the projections 1524 are moveable to a constrained state 1526 that is substantially cylindrical, wherein the constrained or flattened projections lie flat against the outer surface of the sleeve 1484. In constrained state 1526, the support structure 1520 is in a configuration that can pass through the aperture 1438 in the side wall of the vessel 1439. Following insertion into the vessel lumen, the support structure is moved to unconstrained state 1525, where the proximal surfaces of the projections 1524 can contact the luminal side of the vessel, thereby supporting the sidewall of the vessel during operation of the delivery apparatus 1430 and insertion of the anchors 1209 of closing device 1200 into the sidewall of the vessel.

Figure 154:
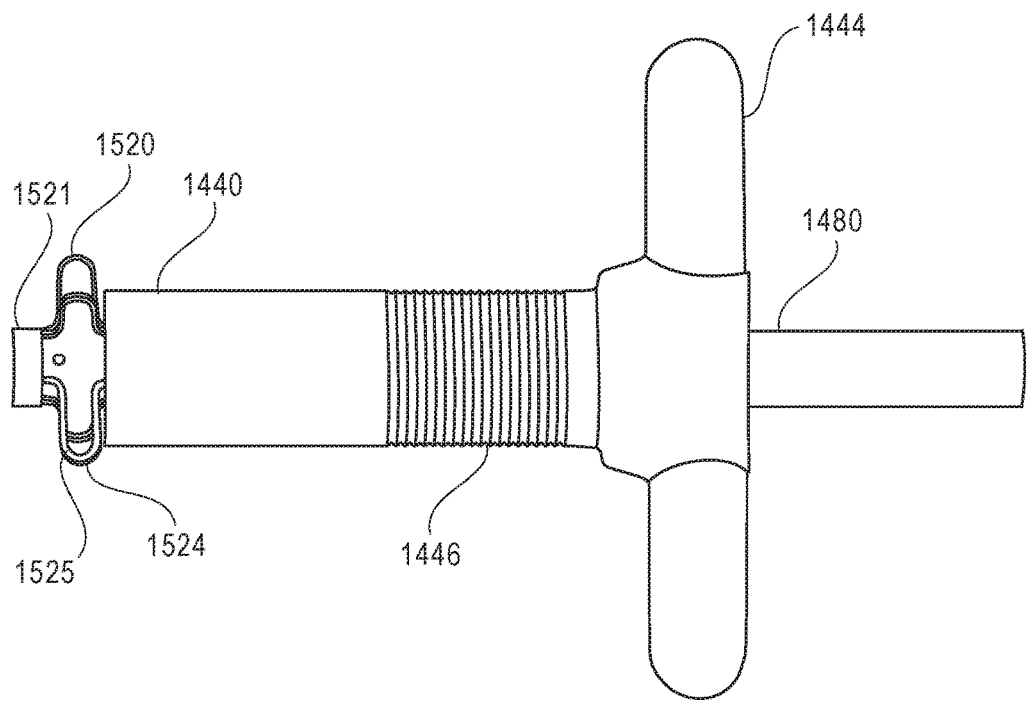
FIGS. 154 and 155 are side views of the sealing device carrier, support structure and introducer sheath of the delivery apparatus of FIG. 151, with the support structure in non-constrained or constrained states, respectively.

Referring to FIGS. 152 and 154, the distal end 1521 of the support structure can be secured to the introducer sheath 1480 at or near the distal end 1481 of the sleeve 1484, and a portion 1522 of the support structure 1520 can be secured to the carrier 1440. Thus, movement of the projections 1524 between the non-constrained state 1525 and constrained state 1536 can be accomplished by moving the carrier 1440 proximally or distally along the longitudinal axis relative to the position of the introducer sheath 1480. Moving the carrier 1440 proximally relative to the introducer sheath 1480 causes longitudinal extension of the support structure and deformation of the support projections 1524 to the constrained state 1526, wherein the support projections 1524 lie flat against the outer surface of the sleeve 1484. Conversely, moving the carrier 1440 distally relative to the introducer sheath 1480 allows longitudinal contraction of the support structure and radial outward extension of the support projections 1524 towards their memory shape.

As discussed above, the introducer sheath 1480 can have a housing 1490. Therefore, movement of the housing relative to the carrier 1440 can cause radial extension or contraction of the support projections 1524 of the support structure 1520. To facilitate such movement, the handle 1444 of the carrier 1440 and/or a handle 1493 of the introducer housing 1490 can be used (FIG. 157). Additionally, in some embodiments, the delivery apparatus 1430 can include one or more spacers 1540 or moveable nuts or knobs 1544 that can be used to fix and/or adjust the distance between the carrier 1440 and the introducer housing 1490 (FIG. 158).

Figure 156:
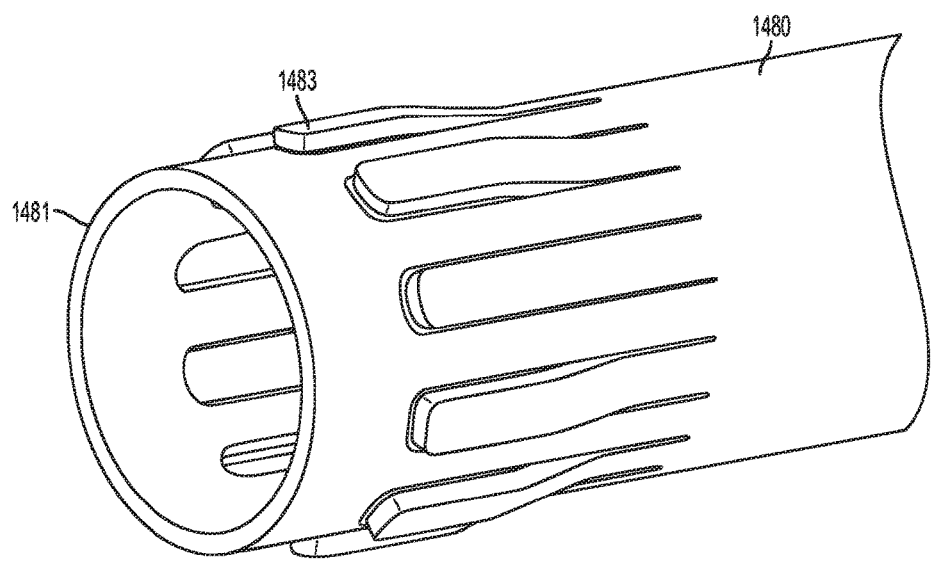
FIG. 156 is a perspective view of the distal portion of the introducer sheath of the delivery apparatus of FIG. 151.

In some embodiments, the sleeve 1484 of introducer sheath can include a plurality of circumferentially spaced tabs 1483 that extend radially outwardly from the sleeve (see FIG. 156). The sleeve desirably includes the same number of tabs as the number of anchors 1209 on the sealing device 1200. The tabs are suitable shaped to fit within the grooves or spaces in between the projections 1524 of the support structure, and thus prevent the tips of the anchors 1209 of the sealing device from catching on the support structure 1520 when the sealing device is inserted into the vessel wall and/or when the delivery apparatus is removed from the aperture in the sidewall of the vessel.

With reference to FIG. 151, the dilator 1500 can include a distal portion 1501 and a proximal portion 1502. The distal portion of the dilator includes a nose cone portion 1503, which can be tapered or conical to facilitate insertion into an aperture in the side wall of the vessel 1439. The dilator 1500 can optionally include extendable and retractable cutting members (e.g., blades) on the nose cone portion 1503 of the dilator, and proximal to the distal tip of the dilator, that are substantially similar to the extendable and retractable cutting members 1082 of dilator 1080 (discussed above), and which can be used to facilitate traversal of the vessel sidewall. Some embodiments of the dilator further comprise a flush/suction port for use during deployment. The distal tip of the dilator includes an aperture 1504 configured to allow passage of the guide wire 1506. In some embodiments, the distal tip of the dilator can be shaped at an angle such that the initial dilator contact with tissue is as sharp as possible to aid during the insertion of the dilator through the sidewall of the vessel 1439.

In particular embodiments, the guide wire 1510 can be inserted through the sidewall of the vessel 1439, and the nose cone 1503 of the dilator can then be used to expand the puncture site to about the diameter of the portion of the dilator 1408 proximal to the nose cone portion.

Q. Exemplary Method of Implanting Sealing Device 1200 with Apparatus 1430

FIGS. 160-168 illustrate an exemplary method of using the delivery apparatus 1430 for accessing the lumen of a vessel 1439 (such as the aorta) to perform an endoluminal procedure via an aperture 1438 in the sidewall of the vessel, and then sealing the aperture following the endoluminal procedure with a sealing device such as sealing device 1200. The illustrated method utilizes the delivery apparatus 1430 and the sealing device 1200; however, other embodiments of a sealing device and/or a delivery apparatus (for example, as described herein) can be used to perform the disclosed method. In several embodiments, the disclosed method is used to create and seal the aperture 1438 in a sidewall of the aorta in a patient during a surgical procedure, such as implantation of a prosthetic heart valve.

Prior to initiation of the method, the sealing device 1200 is loaded onto the delivery apparatus 1430, with the sealing device mounted on the distal portion of the carrier 1440. The sealing device 1200 is mounted such that the anchors 1209 of the sealing device point distally and do not extend distally beyond the distal end 1441 of the carrier.

Figure 161:
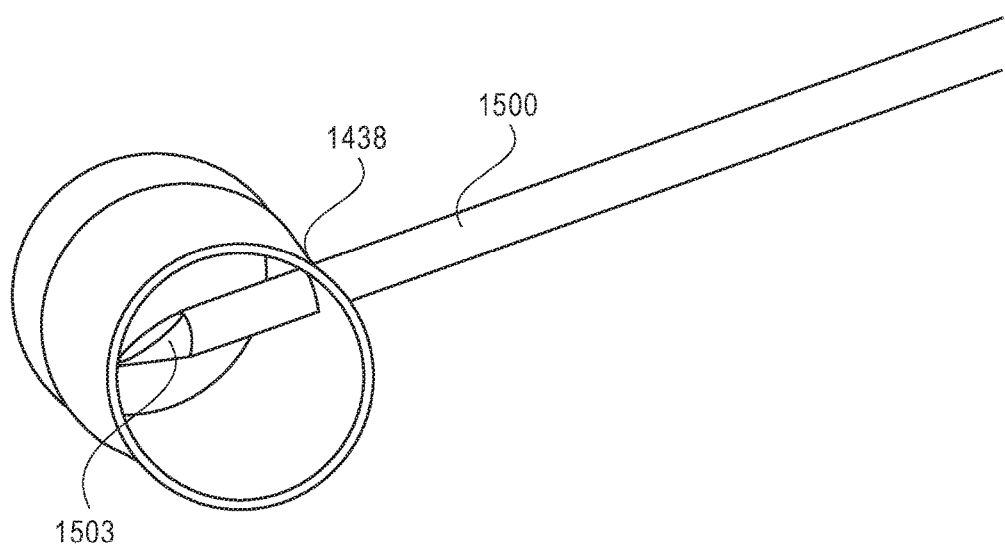
FIGS. 161-168 illustrate an exemplary method of using a disclosed vessel opening and sealing device and a delivery apparatus for accessing the lumen of a vessel for performance of an endoluminal procedure via an aperture in the sidewall of the vessel, and then sealing the aperture following the endoluminal procedure.

In the illustrated embodiment of the method, the delivery apparatus includes the dilator 1500. A hypodermic needle can be advanced through the lumen and aperture at the distal tip of the nose cone of the dilator and inserted through the sidewall of the vessel 1439. The guide wire 1510 can then be inserted through the hypodermic needle and into the lumen of the vessel 1439, and placed as needed for the endoluminal procedure. After placement of the guide wire, the hypodermic needle is retracted from the sidewall of the vessel, leaving the guide wire in place. The delivery apparatus 1430 can then be advanced distally until the distal tip of the nose cone 1503 penetrates and traverses the sidewall of the vessel 1439 (FIG. 161). Optionally, the dilator can include extendable and retractable cutting members, which can be extended from the dilator body to facilitate traversal of the sidewall of the vessel 1439 by the nose cone, for example, as discussed above for cutting members 1082 of dilator 1080. Optionally, an incision in the sidewall of the vessel 1439 can be performed prior to advancing the nose cone through the sidewall of the vessel.

Figure 162:
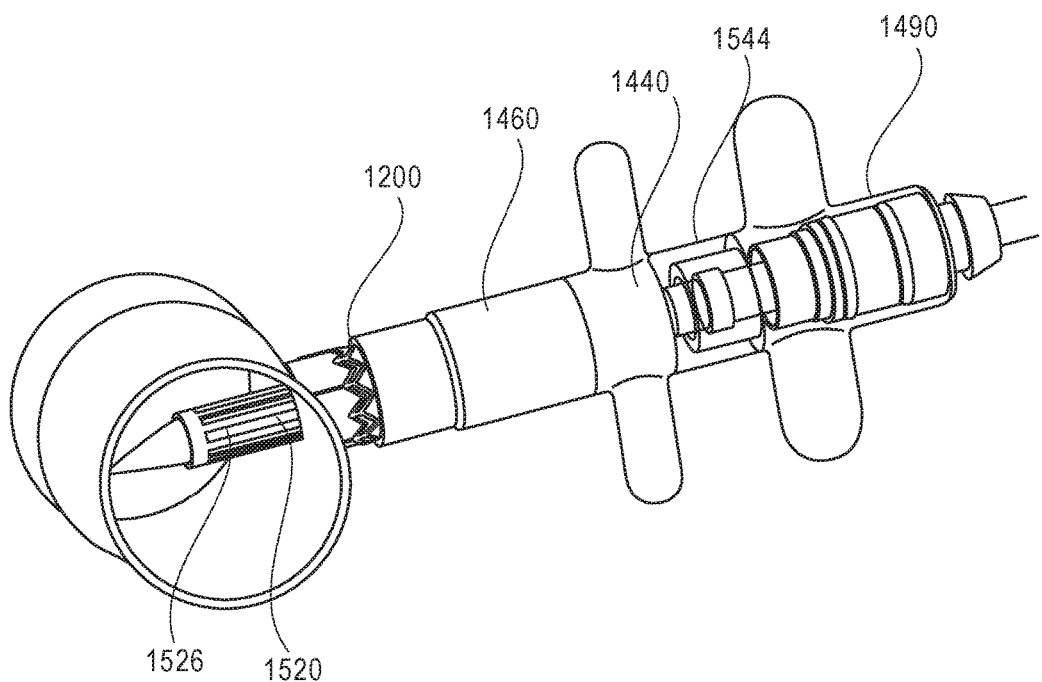

As shown in FIG. 162, the delivery apparatus is moved distally, with the carrier 1440 and introducer housing 1490 pulled towards each other, to place the support structure 1520 in the constrained state 1526. The projections 1524 of the support structure 1520 are in a cylindrical shape and lie flat against the sleeve 1484 of the introducer sheath 1480. In this configuration, the delivery apparatus is moved farther distally until the introducer sheath and constrained support structure traverse the aperture 1438 in the sidewall of the vessel 1339 (FIG. 162).

Figure 163:
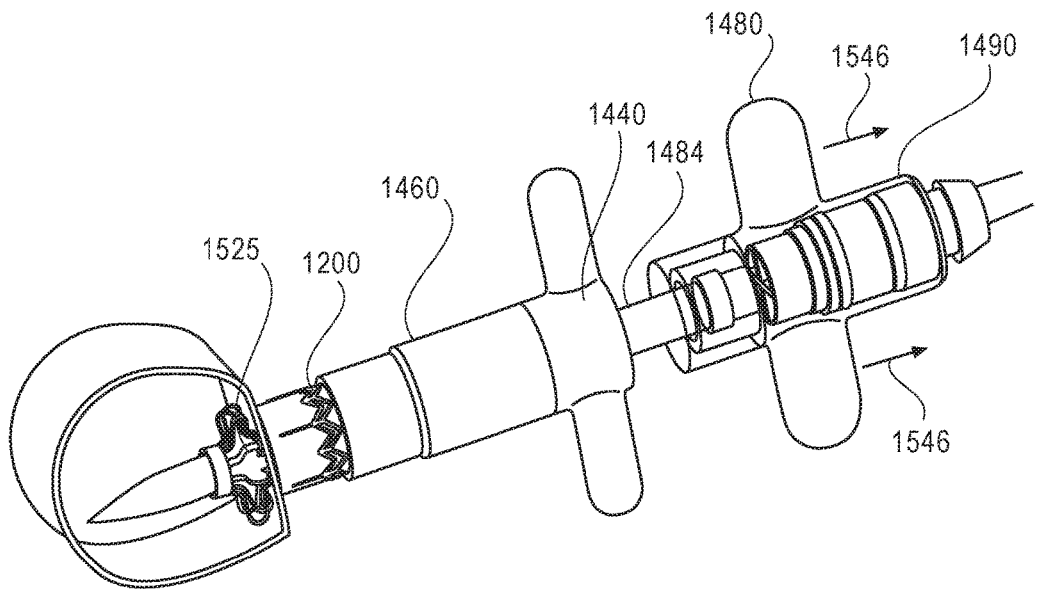

With reference to FIG. 163, the introducer housing is then moved proximally in the direction of arrows 1546, while the carrier 1440 is held stationary. This movement shortens the distance between the distal end of the introducer sheath 1480 (which is secured to the distal end of the support structure 1520) and the distal end of the carrier 1440. Because the support structure 1520 is made of shape memory material, the projections 1424 expand radially outwardly towards their memory shape in the non-constrained state 1525. After expansion of the projections, the support structure 1520 can be moved proximally to engage the projections 1524 with the luminal side of the vessel wall. The sidewall of the vessel 1439 is now "pinched" between the distal end of the carrier 1440 and the proximal surfaces of the support projections 1524, thereby forming a seal around the sidewall of the vessel to reduce or prevent leakage of fluid (e.g., blood) from the vessel, and to support the sidewall of the vessel when the anchors 1209 of the sealing device 1200 are inserted into the sidewall.

Figure 164:
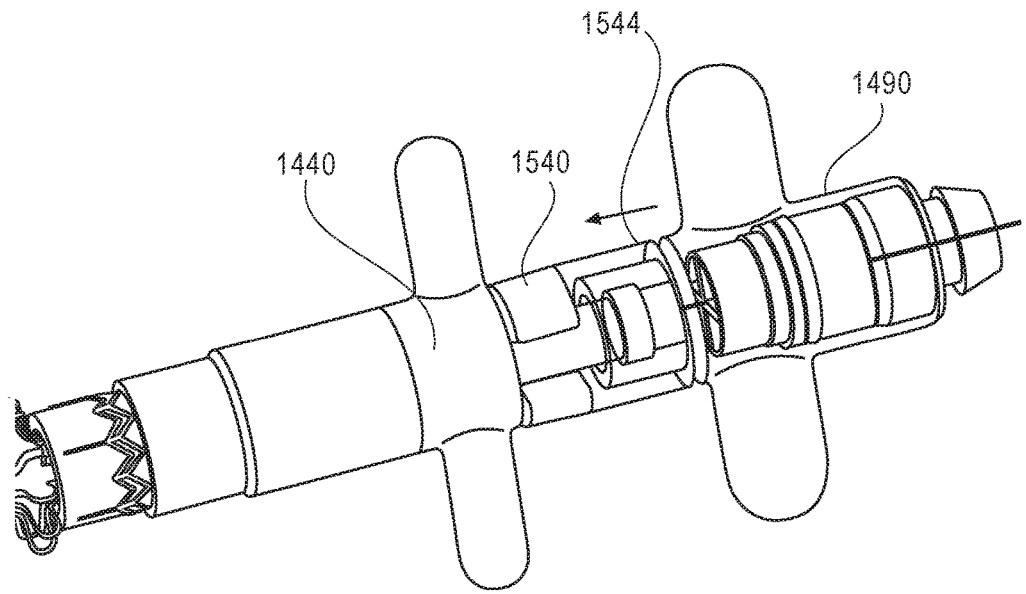

With reference to FIG. 164, the spacer 1540 can optionally be placed between the carrier 1440 and the introducer housing 1490, and the nut 1544 can be moved distally by rotation to set or lock the spacing between the carrier 1440 and the introducer housing 1490.

Figure 165:
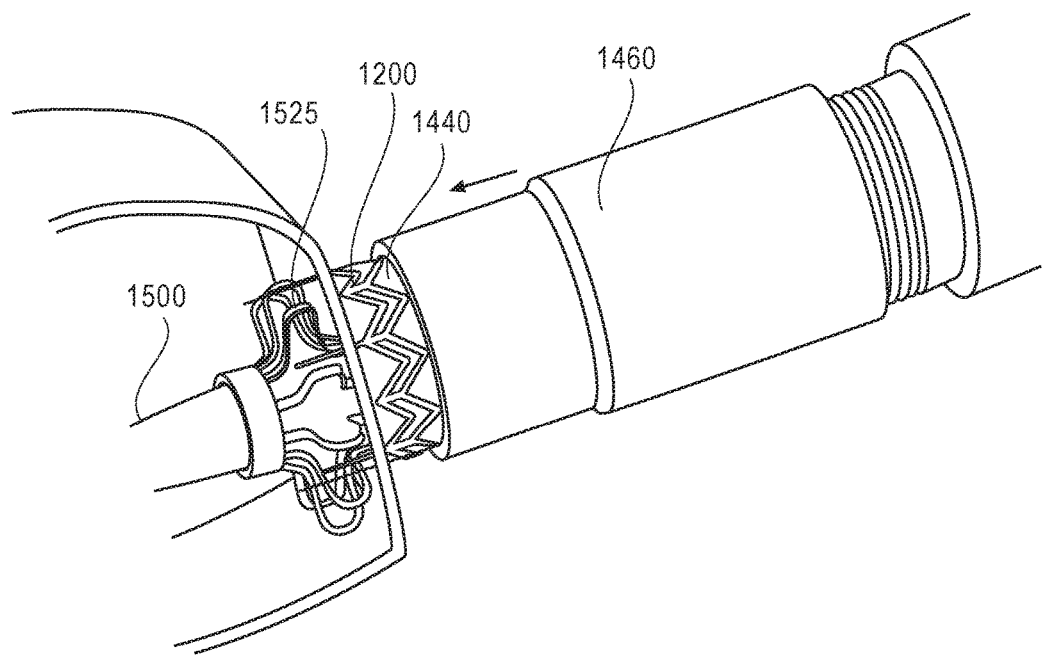

In the illustrated embodiment of the method, the pusher 1460 is then rotated, which moves the pusher distally because of the connection of the pusher to the carrier at threads 1446 and 1466. Distal movement of the pusher 1460 pushes the anchors 1209 of the sealing device 1200 past the distal end of the carrier 1441, thereby inserting the anchors 1109 into the sidewall of the vessel 1439 (FIG. 165).

The dilator 1500 can then be retracted proximally and removed from the delivery assembly 1530 (FIG. 166) and the endoluminal procedure can be performed.

Figure 167:
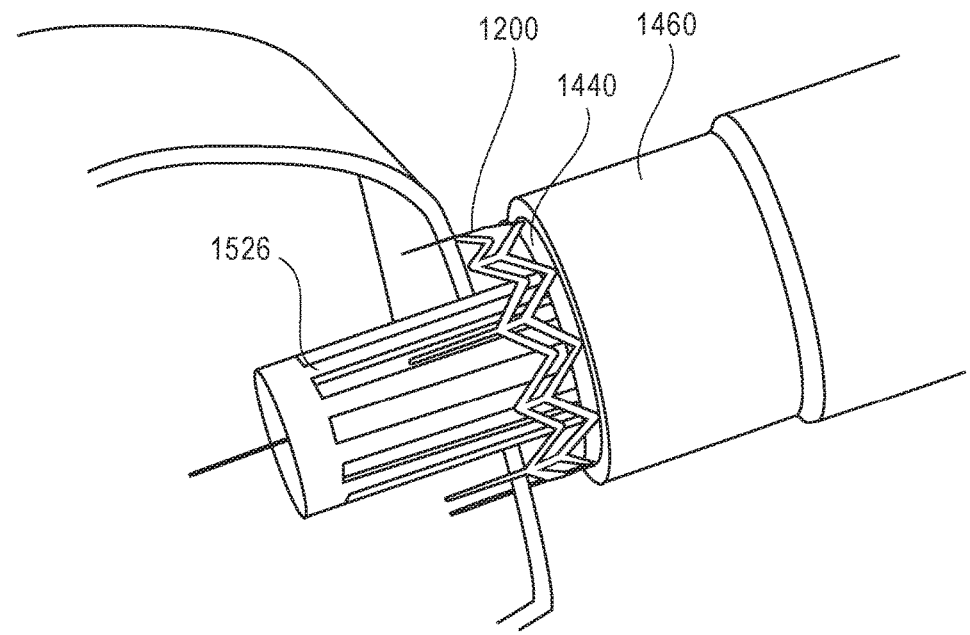
Figure 168:
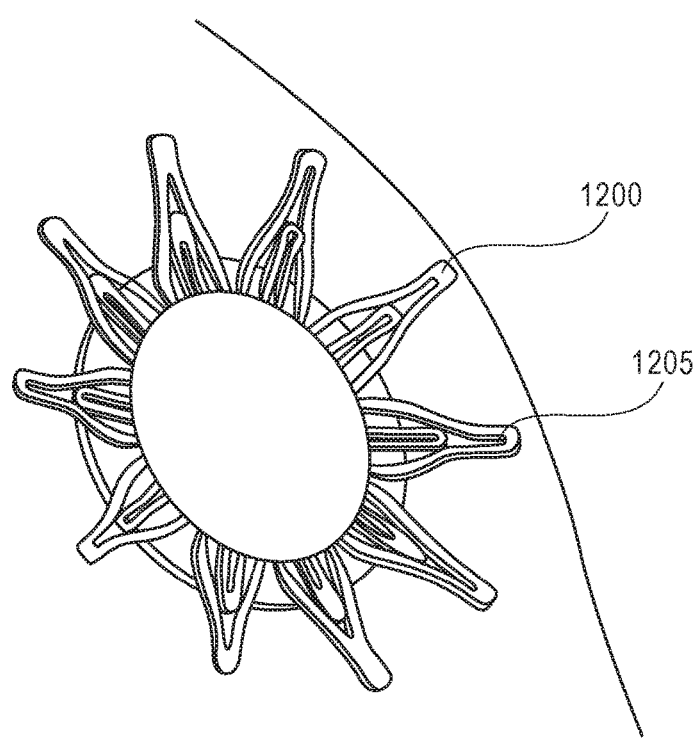
Figure 169:
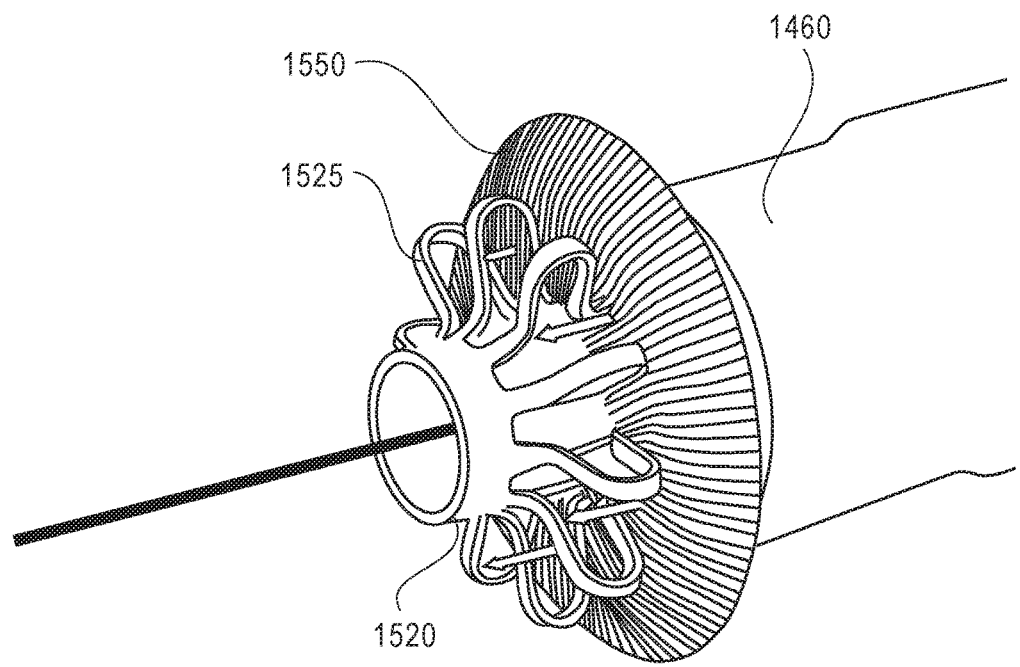
FIG. 169 is a perspective view of the delivery apparatus of FIG. 151 including an absorbent pad at a distal portion of the apparatus, according to one embodiment.

With reference to FIG. 167, the introducer housing 1490 is then moved distally, while the carrier 1440 is held stationery, to move the support structure 1520 to the constrained state 1526 with the projections 1524 of the support structure 1520 in a cylindrical shape and lying flat against the sleeve 1484 of the introducer sheath 1480. In this configuration, the delivery apparatus can be moved proximally to retract the introducer sheath 1480 and constrained support structure 1520 from the vessel, while the pusher 1460 is moved distally by rotation to push the sealing device off of the carrier 1440. As the support structure and introducer sheath are retracted from the aperture 1438, the sealing device 1200 remains anchored in the sidewall of the vessel 1439 and shifts to the sealed configuration 1205 (FIG. 168).

In the illustrated embodiment, the sealing device 1200 is deployed into the sidewall of the vessel 1439 before performance of the endoluminal procedure. In alternate embodiments, the sealing device can be deployed after performance of the endoluminal procedure.

In several embodiments, any of the delivery apparatuses 1230, 1330, 1430 can include an absorbent pad 1550 (such as a pad of CELOX™ gauze, available from Celox Medical, Inc.). For example, with reference to FIG. 169 and delivery apparatus 1430, the absorbent pad 1550 can be placed at the distal end of the carrier of the delivery apparatus. When the expanded support structure 1520 and the distal end of the carrier 1460 are urged against opposite sides of the vessel wall, the absorbent pad 1550 is between the carrier and the vessel wall. The anchors 1209 of the sealing device can penetrate the pad before penetrating the tissue of the vessel wall, which keep the pad in place during the insertion of the sealing device. The properties of the absorbent pad 1550 aids in creating a hemostasis barrier during the endoluminal procedure. Further, at the end of the procedure, the sealing device is deployed along with the absorbent pad 1550. Thus, the absorbent pad 1550 further aids the closure device in the action of sealing the aperture in the vessel wall.

Q. General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

Unless context indicates otherwise, any of the disclosed delivery apparatuses can be used with any of the disclosed devices for sealing an aperture in a vessel sidewall.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

It will be apparent that the precise details of the methods or compositions described may be varied or modified without departing from the spirit of the described embodiments. We claim all such modifications and variations that fall within the scope and spirit of the claims below.

It is claimed:

1. An implantable sealing device delivery assembly for closing an aperture in a vessel sidewall in a medical patient, the assembly comprising:
   an implantable sealing device, the sealing device comprising:
      a puncture frame including a plurality of proximal fingers and a plurality of distal fingers;
      a twisting frame; and
      a flexible tubular sealing member secured between the puncture frame and the twisting frame, wherein the flexible tubular sealing member can be twisted between an open state that allows access through the aperture in the vessel sidewall, and a sealed state in which the vessel sidewall aperture is closed; and
   a delivery assembly comprising:
      a first generally elongate member configured for placement through the vessel aperture to carry the distal fingers of the puncture frame inside of the vessel through the aperture; and
      a second generally elongate member configured for releasable coupling to the twisting frame of the sealing device;
   wherein the proximal fingers of the puncture frame are movable between a retracted configuration in which the proximal fingers are relatively close to the first elongate member of the delivery assembly, and a deployed configuration in which the proximal fingers are engaged with tissue on a proximal side of the vessel sidewall around the vessel aperture;
   wherein the distal fingers of the puncture frame are movable between a retracted configuration in which the distal fingers are relatively close to the first elongate member of the delivery assembly, and a deployed configuration in which the distal fingers are engaged with tissue on a distal side of the vessel sidewall around the vessel aperture and in which the distal fingers and the proximal fingers cooperate to secure the puncture frame in place and against rotation in the vessel aperture;
   wherein the twisting frame is rotatable with respect to the puncture frame by rotation of the second generally elongate member with respect to the vessel sidewall aperture when the puncture frame is secured by the proximal and distal fingers of the puncture frame in place and against rotation in the vessel aperture, to twist the flexible tubular sealing member from its open state to its sealed state, thereby to close the vessel sidewall aperture; and
   wherein the second generally elongate member of the delivery assembly is configured for release from the twisting frame of the sealing device to allow the withdrawal of the first and second generally elongate members of the delivery assembly from the medical patient while leaving the closed sealing device in place in the vessel sidewall aperture.

* * * * *